(12) United States Patent
Sung et al.

(10) Patent No.: US 8,222,248 B2
(45) Date of Patent: Jul. 17, 2012

(54) ORGANIC COMPOUNDS

(75) Inventors: Moo Je Sung, Belmont, MA (US); Gary Mark Coppola, Budd Lake, NJ (US); Taeyoung Yoon, Newton, MA (US); Thomas A. Gilmore, Salem, MA (US)

(73) Assignee: Novartis AG, Basel (CH)

( * ) Notice: Subject to any disclaimer, the term of this patent is extended or adjusted under 35 U.S.C. 154(b) by 88 days.

(21) Appl. No.: 12/446,088

(22) PCT Filed: Oct. 17, 2007

(86) PCT No.: PCT/US2007/081607
§ 371 (c)(1),
(2), (4) Date: Nov. 12, 2010

(87) PCT Pub. No.: WO2008/048991
PCT Pub. Date: Apr. 24, 2008

(65) Prior Publication Data
US 2011/0046133 A1 Feb. 24, 2011

Related U.S. Application Data

(60) Provisional application No. 60/829,980, filed on Oct. 18, 2006, provisional application No. 60/952,341, filed on Jul. 27, 2007.

(51) Int. Cl.
*A61K 31/5377* (2006.01)
*A61K 31/4709* (2006.01)
*A61K 31/4184* (2006.01)
*C07D 413/14* (2006.01)
*C07D 401/12* (2006.01)
*C07D 235/18* (2006.01)

(52) U.S. Cl. ............ 514/235.2; 514/314; 514/394; 544/128; 546/171; 548/310.7

(58) Field of Classification Search ........ 514/235.2, 514/394, 314, 338, 249, 252.06, 255.05, 514/275; 548/310.7, 305.1; 546/171, 273.4; 544/353, 238, 405, 331, 128
See application file for complete search history.

(56) References Cited

U.S. PATENT DOCUMENTS
6,251,689 B1 6/2001 Laborde et al.

FOREIGN PATENT DOCUMENTS
| | | |
|---|---|---|
| EP | 0882718 A | 12/1998 |
| WO | 2002/072090 A | 9/2002 |
| WO | 03/106439 A | 12/2003 |
| WO | 2004/063155 A | 7/2004 |
| WO | 2004/072025 A2 | 8/2004 |
| WO | 2006/044775 A | 4/2006 |
| WO | 2007/056155 A | 5/2007 |

OTHER PUBLICATIONS

Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10), (2004) 2394-2404.*
Kong et al., Studies on Chemical Components of Viscum Coloratum. V, 1989, Chinese Journal of Pharmaceuticals, 20(3), 110-115.*
Database WPI Week 2004 Derwent Publications Ltd., London, GB; AN 2004-142772 XP002477078.
Goker H et al: "Synthesis and antimicrobial activity of some new 2-phenyl-N-substituted carboxamido-1H-benzimidazole derivatives" Archiv Der Pharmazie, VCH, 2001.
Ayhan-Kilcigil G et al: "Synthesis and Antimicrobial Activity of Some New Benzimidazole Carboxylates and Carboxamides" Farmaco, Societa Chimica Italiana, Pavia, 1999.
Behrens C et al: "Synthesis of a Hoechst 32258 Analogue Amino Acid Building Block for Direct Incorporation of a Fluorescent, High-Affinity DNA Binding Motif into Peptides", 2001.
Gao et al: "Research on drugs against hydatidosis: synthesis of benzimidazoles" Zhongguo Yiyao Gongye Zazhi—Chinese Journal of Pharmaceuticals, Shanghai Yiyao Gongye Yanjiuyuan, Shanghai, CN, 1989.

* cited by examiner

*Primary Examiner* — Kamal Saeed
*Assistant Examiner* — Kristin Bianchi
(74) *Attorney, Agent, or Firm* — Joshua Roth

(57) ABSTRACT

The present invention provides compounds of the following structure;

A-L1-B—C-D that are useful for treating or preventing conditions or disorders associated with DGAT1 activity in animals, particularly humans.

11 Claims, No Drawings

ORGANIC COMPOUNDS

This application is the National Stage of Application No. PCT/US2007/081607, filed on Oct. 17, 2007, which claims benefit under 35 U.S.C. §119(e) of U.S. Provisional Application Nos. 60/829,980, filed Oct. 18, 2006, and 60/952,341, filed Jul. 27, 2007, the contents of which are incorporated herein by reference in their entirety.

BACKGROUND OF THE INVENTION

Obesity can be viewed as an energy balance disorder, arising when energy input exceeds energy output, with most of the excess calories converted into triglycerides and stored in the adipose tissue. Medications currently approved for the treatment of obesity attempt to restore energy balance primarily by decreasing energy input by either suppressing appetite or interfering with lipid absorption in the small intestine. Because of the rapid increase in the prevalence of obesity worldwide and the lack of efficacy of current medical therapies, novel pharmacologic therapies for obesity are required.

One potential therapeutic strategy involves inhibiting triglyceride synthesis. Although triglycerides are essential for normal physiology, excess triglyceride accumulation results in obesity and, particularly when it occurs in nonadipose tissues, is associated with insulin resistance. DGAT is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1, see Cases et al, Proc. Natl. Acad. Sci. 95:13018-13023, 1998) and DGAT2 (acyl coA-diacylglycerol acyl transferase 2, see Cases et al, J. Biol. Chem. 276:38870-38876, 2001). DGAT1 and DGAT2 do not share significant protein sequence homology. Importantly, DGAT1 knockout mice are protected from high fat diet-induced weight gain and insulin resistance (Smith et al, Nature Genetics 25:87-90, 2000). The phenotype of the DGAT1 knockout mice suggest that a DGAT1 inhibitor has utility for the treatment of obesity and obesity-associated complications.

The international patent application WO 2004098494 describes compounds, compositions, and methods using substituted indoles for treating fungal infections by modulating kinesin Kip1.

WO 2002072090 describes the preparation of 2-(carboxamidophenyl)benzimidazole-5-carboxamides and analogs as IgE and cell proliferation inhibitors.

WO 2002046168 describes the preparation of Benzimidazoles as selective estrogen receptor-beta ligand WO 9837072 describes substituted benzimidazoles as non-nucleoside inhibitors of reverse transcriptase.

WO 2001014343 describes the preparation of substituted 2-(2,6-difluorophenyl)benzimidazoles as non-nucleoside inhibitors of HIV-1 reverse transcriptase.

WO 9837072 describes substituted benzimidazoles as non-nucleoside inhibitors of reverse transcriptase

BRIEF DESCRIPTION OF THE INVENTION

The present invention provides compounds that are useful for treating or preventing conditions or disorders associated with DGAT activity, especially DGAT1 activity in animals, particularly humans.

The compound provided by the present invention has the following structure

A-L1-B—C-D wherein

A is selected from a substituted or unsubstituted alkyl, substituted or unsubstituted alkoxy, substituted or unsubstituted cycloalkyl, substituted or unsubstituted aryl, and a substituted or unsubstituted heterocyclyl, wherein A linked to L1 via a carbon member of the ring when A is a ring, L1 is selected from the group consisting of:

an amine group of the formula $-(CH_2)_n-(CR_4R_{4'})_p-(CH_2)_m-N(R_3)-$, a thiocarbamoyl group of the formula $-(CH_2)_n-(CR_4R_{4'})_p-(CH_2)_m-N(R_3)-C(S)-$, an amide group of the formula $-C(O)-N(R_3)-(CH_2)_n-(CR_4R_{4'})_p-(CH_2)_m-$, an amidine group of the formula $-C(NH)-N(R_3)-(CH_2)_n-(CR_4R_{4'})_p-(CH_2)_m-$, an amide group of the formula $-(CH_2)_n-(CR_4R_{4'})_p-(CH_2)_m-C(O)-N(R_3)-$, a sulphonamide group of the formula $-(CH_2)_n-(CR_4R_{4'})_p-(CH_2)_m-S(O)_2-N(R_3)-$, a carbamate group of the formula $-(CH_2)_n-(CR_4R_{4'})_p-(CH_2)_m-(O)-C(O)-N(R_3)-$, or a urea group of the formula $-(CH_2)_n-(CR_4R_{4'})_p-(CH_2)_m-N(R_3)-C(O)-N(R_{3A})-$, wherein;

$R_3$ and $R_{3A}$ are, independently from each other, hydrogen or lower alkyl, m, n and p are, independently from each other, an integer from 0 to 2, $R_4$ and $R_{4'}$ are, independently from each other, hydrogen, halogen, hydroxyl, lower alkoxy, lower alkoxycarbonyl, carboxy or lower alkyl, or $R_4$ and $R_{4'}$ are joined together to form a spiro residue of the formula

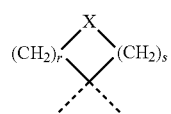

wherein;

X is $NR_{3'}$, O, S or $CR_{3''}R_{4''}$, r and s are, independently from each other, an integer from 0 to 3, $R_{3'}$ is hydrogen or lower alkyl, $R_{3''}$ is hydrogen, halogen, hydroxyl, alkoxy or lower alkyl, $R_{4''}$ is hydrogen or lower alkyl B is a substituted or unsubstituted divalent heteroaryl group selected from one of the groups below:

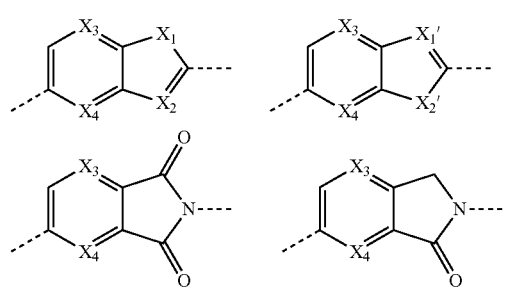

-continued

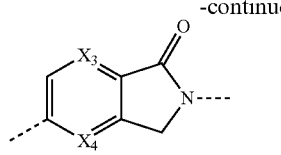

wherein;

$X_1$ and $X_2'$ are independently selected from O, NH, $NR_9$ or S, wherein $R_9$ is selected from lower alkyl, lower alkylamino, lower alkoxyalkyl, lower hydroxyalkyl, $X_1'$, $X_2$, $X_3$ and $X_4$ are independently selected from N, or CH, C is

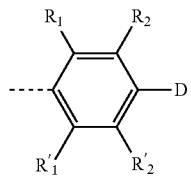

wherein $R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$, $R'_1$, $R_2$ and $R'_2$ are independently selected from hydrogen, halogen, trifluoromethyl, aryloxy, lower alkyl, lower alkoxy, lower alkylamino, lower dialkylamino, and $NO_2$, or C may also be a substituted or unsubstituted bicyclic aryl or heteroaryl group, D is selected from hydrogen, halogen, hydroxyl, cyano, alkanoylamino, carboxy, carbamoyl, —O-$L_2$-E, —S-$L_2$-E', —C(O)—O-$L_2$-E, -$L_2$-E", and —$NR_6$-$L_2$-E', $L_2$ is —$(CH_2)_n$—$(CR_5R_{5'})_p$—$(CH_2)_m$—

E is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —$SO_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is;
  acyl, alkoxycarbonyl, cycloalkoxycarbonyl, aryloxycarbonyl, heterocyclyloxycarbony, carboxy, carbamoyl, sulfonylcarbamoyl, sulfonyl, —$SO_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —$SO_2$—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

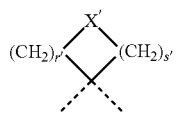

wherein;

X' is $NR_x$, O, S or $CR_xR_{x''}$ r' and s' are, independently from each other, zero or an integer from 1 to 3, $R_x$ is hydrogen or lower alkyl, $R_{x'}$ is hydrogen, halogen, hydroxyl, alkoxy or lower alkyl, $R_{x''}$ is hydrogen or lower alkyl, Unless otherwise indicated, the compounds provided in the formula above are meant to include all pharmaceutically acceptable salts, prodrugs, stereoisomers, crystalline forms, or polymorphs thereof.

The present invention also provides pharmaceutical compositions comprising the compound as defined above and a pharmaceutically acceptable carrier or excipient.

The present invention also provides methods for treating or preventing conditions or disorders associated with DGAT activity preferably DGAT1 activity in animals, particularly humans. Preferably, the disorder is selected from the following: metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris. In yet another aspect, the present invention provides methods of using a compound or composition of the invention as an anorectic.

The present invention also provides the use of a compound having the following structure

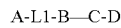

wherein

A is selected from a substituted or unsubstituted alkyl, substituted or unsubstituted alkoxy, substituted or unsubstituted cycloalkyl, substituted or unsubstituted aryl, and a substituted or unsubstituted heterocyclyle, wherein A is linked to L1 via a carbon member of the ring when A is a ring, L1 is selected from the group consisting of:
- an amine group of the formula —$(CH_2)_n$—$(CR_4R_{4'})_p$—$(CH_2)_m$—$N(R_3)$—,
- a thiocarbamoyl group of the formula —$(CH_2)_n$—$(CR_4R_{4'})_p$—$(CH_2)_m$—$N(R_3)$—$C(S)$—,
- an amide group of the formula —$C(O)$—$N(R_3)$—$(CH_2)_n$—$(CR_4R_{4'})_p$—$(CH_2)_m$—,
- an amidine group of the formula —$C(NH)$—$N(R_3)$—$(CH_2)_n$—$(CR_4R_{4'})_p$—$(CH_2)_m$—,
- an amide group of the formula —$(CH_2)_n$—$(CR_4R_{4'})_p$—$(CH_2)_m$—$C(O)$—$N(R_3)$—, or
- a sulphonamide group of the formula —$(CH_2)_n$—$(CR_4R_{4'})_p$—$(CH_2)_mS(O)_2$—$N(R_3)$—,
- a carbamate group of the formula —$(CH_2)_n$—$(CR_4R_{4'})_p$—$(CH_2)_m(O)$—$C(O)$—$N(R_3)$—, or
- a urea group of the formula —$(CH_2)_n$—$(CR_4R_{4'})_p$—$(CH_2)_mN(R_3)$—$C(O)$—$N(R_{3A})$—, wherein;
$R_3$ and $R_{3A}$ are, independently from each other, hydrogen or lower alkyl,
m, n and p are, independently from each other, an integer from 0 to 2,
$R_4$ and $R_{4'}$ are, independently from each other, hydrogen, halogen, hydroxyl, lower alkoxy, lower alkoxycarbonyl, carboxy or lower alkyl, or $R_4$ and $R_{4'}$ are joined together to form a spiro residue of the formula

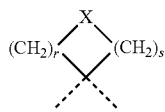

wherein;
X is $NR_{3'}$, O, S or $CR_{3''}R_{4''}$
r and s are, independently from each other, an integer from 0 to 3,
$R_{3'}$ is hydrogen or lower alkyl,
$R_{3''}$ is hydrogen, halogen, hydroxyl, alkoxy, or lower alkyl,
$R_{4''}$ is hydrogen or lower alkyl B is a substituted or unsubstituted divalent heteroaryl group selected from one of the groups below:

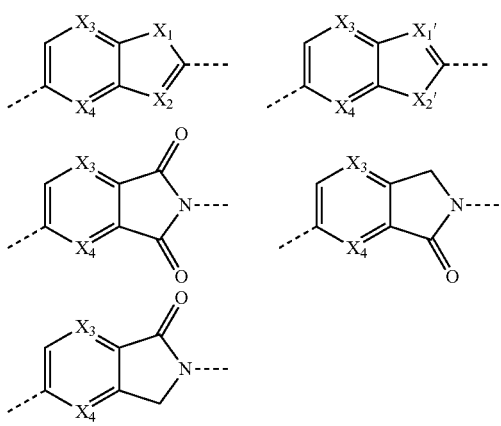

wherein;
$X_1$ and $X_2'$ are independently selected from O, NH, $NR_9$ or S, wherein $R_9$ is selected from lower alkyl, lower alkylamino, lower alkoxyalkyl, lower hydroxyalkyl,
$X_1'$, $X_2$, $X_3$ and $X_4$ are independently selected from N, or CH, C is

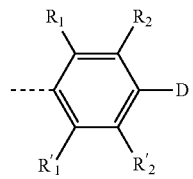

wherein
$R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$,
$R_1'$, $R_2$ and $R_2'$ are independently selected from hydrogen, halogen, trifluoromethyl, aryloxy, lower alkyl, lower alkoxy, lower alkylamino, lower dialkylamino, and $NO_2$, or C may also be a substituted or unsubstituted bicyclic aryl or heteroaryl group, D is selected from hydrogen, halogen, hydroxyl, cyano, alkanoylamino, carboxy, carbamoyl, —$O$-$L_2$-$E$, —$S$-$L_2$-$E'$, —$C(O)$—$O$-$L_2$-$E$, -$L_2$-$E''$, and —$NR_6$-$L_2$-$E'$, $L_2$ is —$(CH_2)_n$—$(CR_5R_{5'})_p$—$(CH_2)_m$—

E is;
alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —$SO_2$—OH, sulfamoyl, sulfonylcarbamoyl, sulfonyloxy, sulfonamido, —$C(O)$—$O$—$R$—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is;
alkyl, acyl, alkoxycarbonyl, cycloalkoxycarbonyl, aryloxycarbonyl, heterocyclyloxycarbony, carboxy, carbamoyl, sulfonylcarbamoyl, sulfonyl, sulfamoyl, sulfonamido, phosphonic acid, phosphonate, sulfonyloxy, —$SO_2$—OH, —$C(O)$—$O$—$R$—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is;
alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —$SO_2$—OH, sulfonylcarbamoyl, —$C(O)$—$O$—$R$—PRO, substituted or unsubstituted aryl, substituted or unsubstituted heterocyclyl, or substituted or unsubstituted heteroaryl, m', n' and p' are, independently from each other, an integer from 0 to 4, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

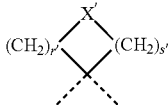

wherein;
X' is $NR_x$, O, S or $CR_x R_{x''}$
r' and s' are, independently from each other, zero or an integer from 1 to 3,
$R_x$ is hydrogen or lower alkyl,
$R_{x'}$ is hydrogen, halogen, hydroxyl, alkoxy, or lower alkyl,
$R_{x''}$ is hydrogen or lower alkyl,
or a prodrug or a pharmaceutically acceptable salt thereof for the manufacture of a medicament for the treatment of DGAT preferably DGAT1 associated disorders.

Unless otherwise indicated, the compounds provided in the formula above are meant to include all pharmaceutically acceptable salts, prodrugs, stereoisomers, crystalline forms, or polymorphs thereof.

The treatment of prevention of the DGAT or DGAT1-related disorders or conditions listed above consists of administering to subject in need thereof a therapeutically effective amount of a compound described in this invention. The treatment may also include co-administration with additional therapeutic agents.

DETAILED DESCRIPTION OF THE INVENTION

Listed below are definitions of various terms used to describe the compounds of the present invention. These definitions apply to the terms as they are used throughout the specification unless they are otherwise limited in specific instances either individually or as part of a larger group, e.g., wherein an attachment point of a certain group is limited to a specific atom within that group.

In general, whenever an alkyl group is referred to as a part of the structure, an optionally substituted alkyl is also intended.

The term "substituted or unsubstituted alkyl" refers to straight- or branched-chain hydrocarbon groups having 1-20 carbon atoms, preferably 1-10 carbon atoms, containing 0 to 3 substituents. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, alkanoyl, alkoxy, alkoxycarbonyl, alkoxycarbonyloxy, alkanoyloxy, thiol, alkylthio, alkylthiono, alkylsulfonyl, sulfamoyl, sulfonamido, carbamoyl, cyano, carboxy, acyl, aryl, alkenyl, alkynyl, aralkyl, aralkanoyl, aralkylthio, arylsulfonyl, arylthio, aroyl, aroyloxy, aryloxycarbonyl, aralkoxy, guanidino, optionally substituted amino, heterocyclyl.

The term "lower alkyl" refers to those alkyl groups as described above having 1-7, preferably 2-4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having 2-4 carbon atoms are preferred.

The term "alkynyl" refers to any of the above alkyl groups having at least two carbon atoms and further containing a carbon to carbon triple bond at the point of attachment. Groups having 2-4 carbon atoms are preferred.

The term "alkylene" refers to a straight-chain bridge of 4-6 carbon atoms connected by single bonds, e.g., $-(CH_2)_x-$, wherein x is 4-6, which may be interrupted with one or more heteroatoms selected from O, S, S(O), $S(O)_2$ or NR, wherein R may be hydrogen, alkyl, cycloalkyl, aryl, heterocyclyl, aralkyl, heteroaralkyl, acyl, carbamoyl, sulfonyl, alkoxycarbonyl, aryloxycarbonyl or aralkoxycarbonyl and the like; and the alkylene may further be substituted with one or more substituents selected from optionally substituted alkyl, cycloalkyl, aryl, heterocyclyl, oxo, halogen, hydroxy, carboxy, alkoxy, alkoxycarbonyl and the like.

The term "cycloalkyl" refers to optionally substituted monocyclic, bicyclic or tricyclic hydrocarbon groups of 3-12 carbon atoms, each of which may contain one or more carbon to carbon double bonds, or the cycloalkyl may be substituted by one or more substituents, such as alkyl, halo, oxo, hydroxy, alkoxy, alkanoyl, acylamino, carbamoyl, alkylamino, dialkylamino, thiol, alkylthio, cyano, carboxy, alkoxycarbonyl, sulfonyl, sulfonamido, sulfamoyl, heterocyclyl and the like.

The term "carboxamide" refers to $-C(O)-NHR_\alpha$, wherein $R_\alpha$ is selected from hydrogen, a $C_1$-$C_8$ alkyl group, a substituted or unsubstituted cycloalkyl group, a substituted or unsubstituted aryl group, a substituted or unsubstituted heterocyclyl group, and carboxamide is preferably $-C(O)-NH_2$.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.
The term "alkanoyl" refers to alkyl-C(O)—.
The term "cycloalkanoyl" refers to cycloalkyl-C(O)—.
The term "alkanoyloxy" refers to alkyl-C(O)—O—.
The terms "alkylamino" and "dialkylamino" refer to alkyl-NH— and $(alkyl)_2N-$, respectively.
The term "alkanoylamino" refers to alkyl-C(O)—NH—.
The term "alkylthio" refers to alkyl-S—.
The term "alkylthiono" refers to alkyl-S(O)—.
The term "alkylsulfonyl" refers to alkyl-$S(O)_2$—.
The term "alkoxycarbonyl" refers to alkyl-O—C(O)—.
The term "alkoxycarbonyloxy" refers to alkyl-O—C(O)O—.

The term "carbamoyl" refers to $H_2NC(O)-$, alkyl-NHC(O)—, $(alkyl)_2NC(O)-$, aryl-NHC(O)—, alkyl(aryl)-NC(O)—, heteroaryl-NHC(O)—, alkyl(heteroaryl)-NC(O)—, aralkyl-NHC(O)—, alkyl(aralkyl)-NC(O)—, heterocyclyl-NHC(O)—, cycloalkyl-NHC(O)—, and the like.

The term "sulfamoyl" refers to $H_2NS(O)_2-$, alkyl-NHS$(O)_2-$, $(alkyl)_2NS(O)_2-$, aryl-$NHS(O)_2$, alkyl(aryl)-NS$(O)_2-$, $(aryl)_2NS(O)_2-$, heteroaryl-NHS$(O)_2-$, aralkyl-NHS$(O)_2-$, heteroaralkyl-NHS$(O)_2-$ and the like.

The term "sulfonylcarbamoyl" refers to sulfonyl-NHC(O)— or HO—$SO_2$—NHC(O)—.

The term "sulfonamido" refers to alkyl-S(O)₂—NH—, aryl-S(O)₂—NH—, aralkyl-S(O)₂—NH—, heteroaryl-S(O)₂—NH—, heteroaralkyl-S(O)₂—NH—, alkyl-S(O)₂—N(alkyl)-, aryl-S(O)₂—N(alkyl)-, aralkyl-S(O)₂—N(alkyl)-, heteroaryl-S(O)₂—N(alkyl)-, heteroaralkyl-S(O)₂—N(alkyl)- and the like.

The term "sulfonyl" refers to alkylsulfonyl, arylsulfonyl, heteroarylsulfonyl, aralkylsulfonyl, heteroaralkylsulfonyl cycloalkylsulfonyl and the like.

The term "sulfonate" or "sulfonyloxy" refers to alkyl-S(O)₂—O—, aryl-S(O)₂—O—, aralkyl-S(O)₂—O—, heteroaryl-S(O)₂—O—, heteroaralkyl-S(O)₂—O— and the like.

The term "optionally substituted amino" refers to a primary or secondary amino group which may optionally be substituted by a substituent such as acyl, sulfonyl, alkoxycarbonyl, cycloalkoxycarbonyl, aryloxycarbonyl, heteroaryloxycarbonyl, aralkoxycarbonyl, heteroaralkoxycarbonyl, carbamoyl and the like.

The term "aryl" refers to monocyclic or bicyclic aromatic hydrocarbon groups having 6-14 or 6-12 carbon atoms in the ring portion, such as phenyl, biphenyl, naphthyl, anthryl, and tetrahydronaphthyl, each of which may optionally be substituted by 1-4 substituents, such as optionally substituted alkyl, trifluoromethyl, optionally substituted cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like.

The term "monocyclic aryl" refers to optionally substituted phenyl as described under aryl.

The term "aralkyl" refers to an aryl group bonded directly through an alkyl group, such as benzyl.

The term "aralkanoyl" refers to aralkyl-C(O)—.

The term "aralkylthio" refers to aralkyl-S—.

The term "aralkoxy" refers to an aryl group bonded directly through an alkoxy group.

The term "arylsulfonyl" refers to aryl-S(O)₂—.

The term "arylthio" refers to aryl-S—.

The term "aroyl" refers to aryl-C(O)—.

The term "aroyloxy" refers to aryl-C(O)—O—.

The term "aroylamino" refers to aryl-C(O)—NH—.

The term "aryloxycarbonyl" refers to aryl-O—C(O)—.

The term "cycloalkoxycarbonyl" refers to cycloalkyl-O—C(O)—.

The term "heterocyclyloxycarbonyl" refers to heterocyclyl-O—C(O)—.

The term "heterocyclyl" or "heterocyclo" refers to an optionally substituted, fully saturated or unsaturated, aromatic or nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2, 3 or 4 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyridyl N-oxide, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, 1,3-dioxo-1,3-dihydroisoindol-2-yl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 substituents. Exemplary substituents include, but are not limited to, the following:

(a) optionally substituted alkyl;
(b) hydroxyl (or protected hydroxyl);
(c) halo (halogen) e.g. Cl, F, Br;
(d) oxo, i.e., =O;
(e) optionally substituted amino;
(f) alkoxy;
(g) cycloalkyl;
(h) carboxy;
(i) heterocyclooxy;
(j) alkoxycarbonyl, such as unsubstituted lower alkoxycarbonyl;
(k) mercapto;
(l) nitro;
(m) cyano;
(n) sulfamoyl;
(o) alkanoyloxy;
(p) aroyloxy;
(q) arylthio;
(r) aryloxy;
(s) alkylthio;
(t) formyl;
(u) carbamoyl;
(v) aralkyl; or
(w) aryl optionally substituted with alkyl, cycloalkyl, alkoxy, hydroxyl, amino, acylamino, alkylamino, dialkylamino or halo.

The term "heterocyclooxy" denotes a heterocyclic group bonded through an oxygen bridge.

The terms "saturated or unsaturated heterocycloalkyl" or "heterocycloalkyl" refers to nonaromatic heterocyclic or heterocyclyl groups as described above.

The term "heteroaryl" refers to an aromatic heterocycle, e.g., monocyclic or bicyclic aryl, such as pyrrolyl, pyrazolyl, imidazolyl, triazolyl, oxazolyl, isoxazolyl, thiazolyl, tetrazol, isothiazolyl, furyl, thienyl, pyridyl, pyridyl N-oxide, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)₂—.

The term "phosphonic acid" refers to —P(O₂)—OH

The term "phosphonate" refers to —P(O$_2$)—R, wherein R is selected from a C$_1$-C$_8$, alkyl group, a cycloalkyl group, a substituted or unsubstituted aryl group, preferably a substituted or unsubstituted phenyl, a substituted or unsubstituted heterocyclyl group, or a carboxylic acid ester group. Preferably the phenyl group R is unsubstituted or substituted by a halogen or a lower alkyl (e.g. 4-Me-phenyl-).

The term "heteroaroyl" refers to heteroaryl-C(O)—.

The term "heteroaroylamino" refers to heteroaryl-C(O)NH—.

The term "heteroaralkyl" refers to a heteroaryl group bonded through an alkyl group.

The term "heteroaralkanoyl" refers to heteroaralkyl-C(O)—.

The term "heterocyclyloyl" refers to heterocyclyl-C(O)—.

The term "heteroaralkanoylamino" refers to heteroaralkyl-C(O)NH—.

The term "acyl" refers to alkanoyl, cycloalkanoyl, aroyl, heteroaroyl, aralkanoyl, heteroaralkanoyl, heterocyclyloyl and the like.

The term "acylamino" refers to alkanoylamino, aroylamino, heteroaroylamino, aralkanoylamino, heteroaralkanoylamino and the like.

The term "divalent" refers to a residue linked to at least two residues and optionally having further substituents. As an example, within the context of the present invention the expression "substituted or unsubstituted divalent phenyl residue" is considered to be equivalent to the expression "substituted or unsubstituted phenylene residue".

For the carboxyl group derivatives —C(O)—O—R—PRO, the term "R—PRO" refers to the common ester derivatives that can serve as a prodrug. Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

The present invention provides a compound having the following structure

A-L1-B—C-D and pharmaceutically acceptable salts, and prodrugs thereof, wherein

A is selected from a substituted or unsubstituted alkyl, substituted or unsubstituted alkoxy, substituted or unsubstituted cycloalkyl, substituted or unsubstituted aryl, and a substituted or unsubstituted heterocyclyle, wherein A is linked to L1 via a carbon member of the ring when A is a ring, L1 is selected from the group consisting of:
an amine group of the formula —(CH$_2$)$_n$—(CR$_4$R$_{4'}$)$_p$—(CH$_2$)$_m$—N(R$_3$)—,
a thiocarbamoyl group of the formula —(CH$_2$)$_n$—(CR$_4$R$_{4'}$)$_p$—(CH$_2$)$_m$—N(R$_3$)—C(S)—,
an amide group of the formula —C(O)—N(R$_3$)—(CH$_2$)$_n$—(CR$_4$R$_{4'}$)$_p$—(CH$_2$)$_m$—,
an amidine group of the formula —C(NH)—N(R$_3$)—(CH$_2$)$_n$—(CR$_4$R$_{4'}$)$_p$—(CH$_2$)$_m$—,
an amide group of the formula —(CH$_2$)$_n$—(CR$_4$R$_{4'}$)$_p$—(CH$_2$)$_m$—C(O)—N(R$_3$)—,
a sulphonamide group of the formula —(CH$_2$)$_n$—(CR$_4$R$_{4'}$)$_p$—(CH$_2$)$_m$ S(O)$_2$—N(R$_3$)—,
a carbamate group of the formula —(CH$_2$)$_n$—(CR$_4$R$_{4'}$)$_p$—(CH$_2$)$_m$ (O)—C(O)—N(R$_3$)—, or
a urea group of the formula —(CH$_2$)$_n$—(CR$_4$R$_{4'}$)$_p$—(CH$_2$)$_m$ N(R$_3$)—C(O)—N(R$_{3A}$)—, wherein;

R$_3$ and R$_{3A}$ are, independently from each other, hydrogen or lower alkyl, m, n and p are, independently from each other, an integer from 0 to 2, R$_4$ and R$_{4'}$ are, independently from each other, hydrogen, halogen, hydroxyl, lower alkoxy, lower alkoxycarbonyl, carboxy or lower alkyl, or R$_4$ and R$_{4'}$ are joined together to form a spiro residue of the formula

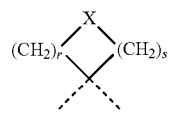

wherein;

X is NR$_{3'}$, O, S or CR$_{3''}$R$_{4''}$ r and s are, independently from each other, zero or an integer from 1 to 3, R$_{3'}$ is hydrogen or lower alkyl, R$_{3''}$ is hydrogen, halogen, hydroxyl, alkoxy, or lower alkyl, R$_{4''}$ is hydrogen or lower alkyl, B is a substituted or unsubstituted divalent heteroaryl group selected from one of the groups below:

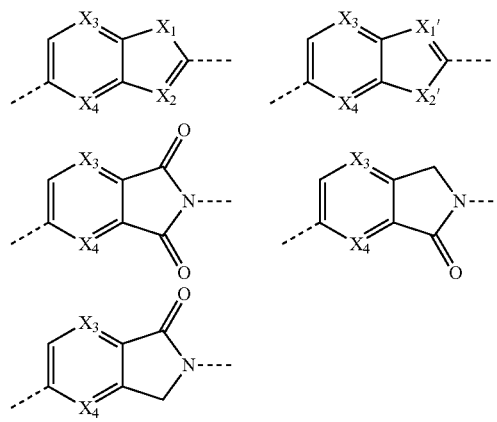

wherein;

X$_1$ and X$_2'$ are independently selected from O, NH, NR$_9$ or S, wherein R$_9$ is selected from lower alkyl, lower alkylamino, lower alkoxyalkyl, lower hydroxyalkyl, X$_1'$, X$_2$, X$_3$ and X$_4$ are independently selected from N, or CH, C is

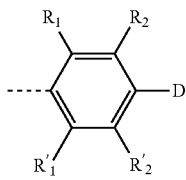

wherein
R₁ is selected from hydrogen, cyano, lower alkylsulfonylamino, alkanoylamino, halogen, lower alkyl, trifluoromethyl, lower alkoxy, lower alkylamino, lower dialkylamino, and NO₂, R'₁, R₂ and R'₂ are independently selected from hydrogen, halogen, trifluoromethyl, aryloxy, lower alkyl, lower alkoxy, lower alkylamino, lower dialkylamino, and NO₂, or C may also be a substituted or unsubstituted bicyclic aryl or heteroaryl group, D is selected from hydrogen, halogen, hydroxyl, cyano, alkanoylamino, carboxy, carbamoyl, —O-L₂-E, —S-L₂-E', —C(O)—O-L₂-E, -L₂-E", and —NR₆-L₂-E', L₂ is —(CH₂)ₙ—(CR₅R₅')ₚ—(CH₂)ₘ—

E is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO₂—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is;
  alkyl, acyl, alkoxycarbonyl, cycloalkoxycarbonyl, aryloxycarbonyl, heterocyclyloxycarbony, carboxy, carbamoyl, sulfonylcarbamoyl, sulfonyl, sulfamoyl, sulfonamido, phosphonic acid, phosphonate, sulfonyloxy, —SO₂—OH, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —SO₂—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, R₅ and R₅' are, independently from each other, hydrogen, halogen, hydroxyl, lower alkoxy, or lower alkyl, or R₅ and R₅' are joined together to form a spiro residue of the formula

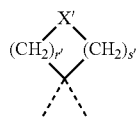

wherein;
X' is NR$_x$, O, S or CR$_x$R$_{x''}$
r' and s' are, independently from each other, zero or an integer from 1 to 3,
R$_x$ is hydrogen or lower alkyl,
R$_{x'}$ is hydrogen, halogen, hydroxyl, alkoxy, or lower alkyl,
R$_{x''}$ is hydrogen or lower alkyl, Unless otherwise indicated, the compounds provided in the formula above are meant to include all pharmaceutically acceptable salts, prodrugs, stereoisomers, crystalline forms, or polymorphs thereof.

In a preferred embodiment, the moiety A is selected from the group consisting of a substituted or unsubstituted 6-membered monocyclic aryl group, a substituted or unsubstituted 9 or 10-membered bicyclic aryl group, a substituted or unsubstituted biphenyl, a substituted or unsubstituted 5 or 6-membered monocyclic heterocyclyl, or a 9 or 10-membered bicyclic heterocyclyl group.

When the moiety A is a substituted or unsubstituted alkyl group it is in a first preferred embodiment lower alkyl group.

When the moiety A is a substituted or unsubstituted alkoxy group it is in a first preferred embodiment lower alkoxy group.

When the moiety A is a substituted or unsubstituted cycloalkyl group it is in a first preferred embodiment a substituted or unsubstituted 5 or 6-membered monocyclic cycloalkyl group or substituted or unsubstituted adamantyl group.

In a preferred embodiment, the moiety A is selected from the group consisting of a substituted or unsubstituted aryl group preferably phenyl, or naphthyl, and a substituted or unsubstituted monocyclic or bicyclic heterocyclyl group. Preferred substituents of the moiety A are halogen, alkyl, phenyl, cycloalkyl, cyano, trifluoromethyl, alkoxy, hydroxyl, optionally substituted amino, acyl, alkanoyloxy, aryloxy, alkylthio, arylthio, oxo, nitro, carboxy, alkoxycarbonyl, carbamoyl, alkylthiono, sulfonyl, sulfonamido, and heterocyclyl. More preferably, the substituents of moiety A are selected from halogen, unsubstituted or substituted lower alkyl, alkanoyl, —C(O)—NHalkyl, —C(O)—N(alkyl)₂, —C(O)—NHphenyl, cycloalkyl, cyano, oxo, trifluoromethyl, unsubstituted or substituted lower alkoxy, unsubstituted or substituted phenyl, unsubstituted or substituted phenoxy, aryloxy, hydroxyl, unsubstituted or substituted 5-membered monocyclic heteraryl, 5 or 6-membered monocyclic heterocyclyloyl, carbamoyl, optionally substituted amino.

When the moiety A is a substituted or unsubstituted aryl group, it is in a first preferred embodiment a substituted or unsubstituted phenyl, a substituted or unsubstituted naphthyl or a substituted or unsubstituted biphenyl.

Other substituents of moiety A are independently from each other selected from, hydrogen, optionally substituted alkyl; hydroxyl (or protected hydroxyl); halo (halogen) e.g. Cl, F, Br; oxo, i.e. =O; optionally substituted amino; alkoxy; cycloalkyl; carboxy; heterocyclooxy; alkoxycarbonyl, such as unsubstituted lower alkoxycarbonyl; mercapto; nitro; cyano; sulfamoyl; alkanoyloxy; aroyloxy; arylthio; aryloxy; alkylthio; formyl; carbamoyl; aralkyl; or aryl optionally substituted with alkyl, cycloalkyl, alkoxy, hydroxyl, amino, acylamino, alkylamino, dialkylamino or halo, trifluoromethyl, acyl, alkanoyl, thiol, alkylthio, arylthio, carbamoyl, alkylthiono, sulfonyl, sulfonamido, heterocyclyl and the like.

When the moiety A is a monocyclic heterocyclyl, it is in a first preferred embodiment a substituted or unsubstituted 5 or 6-membered monocyclic heteroaryl.

When the moiety A is a monocyclic heteroaryl, it preferably is a substituted or unsubstituted imidazole, pyrazole, triazole, thiazole, pyridine, pyridine N-oxide, pyridazine, pyrimidine, triazine or pyrazine residue.

When the moiety A is a 6-membered monocyclic heteroaryl, it preferably is a substituted or unsubstituted pyridine, pyrimidine, pyridazine, pyridine N-oxide or pyrazine residue.

When the moiety A is a bicyclic heterocyclyl, it preferably is a substituted or unsubstituted 9 or 10-membered bicyclic heterocyclyl, preferably selected from substituted or unsubstituted benzimidazole, benzopyrrole, benzoxazole, benzothiazole, oxazolopyridine, thiazolopyridine, imidazolopyridine, indole, quinoline, isoquinoline, benzofuran, benzothiophene, indazole, cinnoline, quinazoline, coumarin, quinoxaline or phthalazine residue. More preferably, the bicyclic heterocyclyl group is selected from a substituted or unsubstituted benzimidazole, benzoxazole, quinoline, isoquinoline, benzothiazole, oxazolopyridine, thiazolopyridine or imidazolopyridine group.

In a further preferred embodiment, the moiety A is a substituted or unsubstituted benzothiazole.

In a preferred embodiment, the moiety A is a substituted or unsubstituted aryl group, or a substituted or unsubstituted monocyclic or bicyclic heterocyclyl group, selected from the group consisting of:

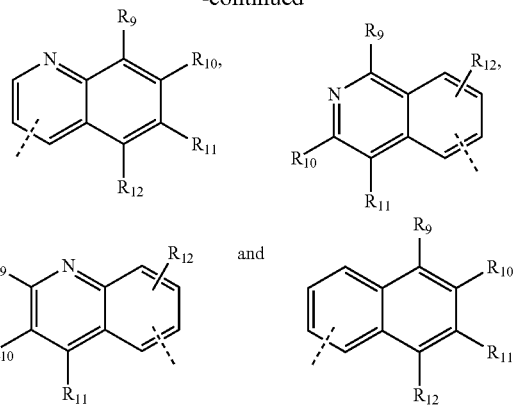

wherein, $R_7$, $R'_7$ and $R''_7$ are, independently from each other selected from hydrogen, optionally substituted alkyl; hydroxyl (or protected hydroxyl); halo (halogen) e.g. Cl, F, Br; oxo, i.e. =O; optionally substituted amino; alkoxy; cycloalkyl; carboxy; heterocyclooxy; alkoxycarbonyl, such as unsubstituted lower alkoxycarbonyl; mercapto; nitro; cyano; sulfamoyl; alkanoyloxy; aroyloxy; arylthio; optionally substituted aryloxy; alkylthio; formyl; carbamoyl; optionally substituted aralkyl; optionally substituted phenyl or optionally substituted aryl e.g. optionally substituted with alkyl, cycloalkyl, alkoxy, hydroxyl, amino, acylamino, alkylamino, dialkylamino or halo, preferably only one or two of the substituents $R_7$, $R'_7$ and $R''_7$ is not hydrogen, and $R_8$, $R'_8$ and $R''_8$ are, independently from each other selected from, hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl, and preferably only one or two of the substituents $R_8$, $R'_8$ and $R''_8$ is not hydrogen.

and $R_9$, $R_{10}$, $R_{11}$ and $R_{12}$ are, independently from each other selected from, hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl.

In a preferred embodiment, the moiety A is a substituted or unsubstituted aryl group, or a substituted or unsubstituted monocyclic or bicyclic heterocyclyl group, selected from the group consisting of:

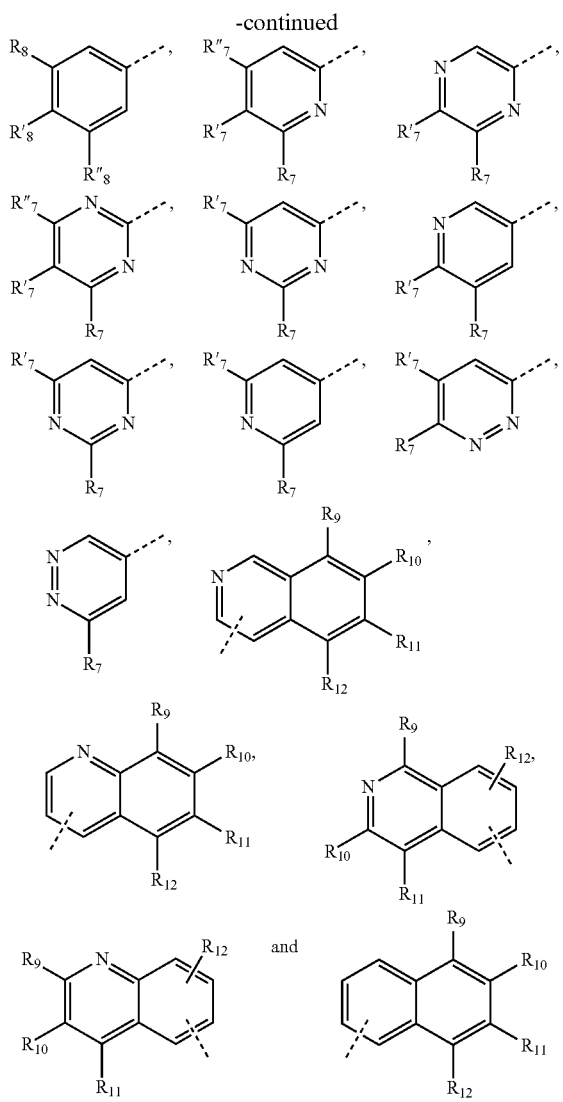

wherein,

R$_7$, R'$_7$ and R"$_7$ are, independently from each other selected from, hydrogen, halo, optionally substituted lower alkyl; trifluoromethyl, preferably only one or two of the substituents R$_7$, R'$_7$ and R"$_7$ is not hydrogen, and R$_8$, R'$_8$ and R"$_8$ are, independently from each other selected from, hydrogen, optionally substituted alkyl, trifluoromethyl, trifluoromethoxy, halo, hydroxy, optionally substituted alkoxy, acyl, alkanoyl, optionally substituted phenyloxy, optionally substituted aryloxy, optionally substituted phenyl, cyano, carbamoyl, and preferably only one or two of the substituents R$_8$, R'$_8$ and R"$_8$ is not hydrogen.

and

R$_9$, R$_{10}$, R$_{11}$ and R$_{12}$ are, independently from each other selected from, hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl.

The amine group representing L1 can have the following orientations:
a) A←(CH$_2$)$_n$—(CR$_4$R$_{4'}$)$_p$—(CH$_2$)$_m$—N(R$_3$)→B, or
b) B←(CH$_2$)$_n$—(CR$_4$R$_{4'}$)$_p$—(CH$_2$)$_m$—N(R$_3$)→A The amide group representing L1 can have the following orientations:
c) A←C(O)—N(R$_3$)—(CH$_2$)$_n$—(CR$_4$R$_{4'}$)$_p$—(CH$_2$)$_m$→B, or
d) B←C(O)—N(R$_3$)—(CH$_2$)$_n$—(CR$_4$R$_{4'}$)$_p$—(CH$_2$)$_m$→A The sulphonamide group representing L1 can have the following orientations:
e) A←(CH$_2$)$_n$—(CR$_4$R$_{4'}$)$_p$—(CH$_2$)$_m$—S(O)$_2$—N(R$_3$)→B, or
f) B←(CH$_2$)$_n$—(CR$_4$R$_{4'}$)$_p$—(CH$_2$)$_m$—S(O)$_2$—N(R$_3$)→A The thiocarbamoyl group representing L1 can have the following orientations:
g) A←(CH$_2$)$_n$—(CR$_4$R$_{4'}$)$_p$—(CH$_2$)$_m$—N(R$_3$)—C(S)→B, or
h) B←(CH$_2$)$_n$—(CR$_4$R$_{4'}$)$_p$—(CH$_2$)$_m$—N(R$_3$)—C(S)→A The amidine group representing L1 can have the following orientations:
i) A←C(NH)—N(R$_3$)—(CH$_2$)$_n$—(CR$_4$R$_{4'}$)$_p$—(CH$_2$)$_m$→B, or
j) B←C(NH)—N(R$_3$)—(CH$_2$)$_n$—(CR$_4$R$_{4'}$)$_p$—(CH$_2$)$_m$→A The amide group representing L1 can have the following orientations:
k) A←(CH$_2$)$_n$—(CR$_4$R$_{4'}$)$_p$—(CH$_2$)$_m$—C(O)—N(R$_3$)→B, or
l) B←(CH$_2$)$_n$—(CR$_4$R$_{4'}$)$_p$—(CH$_2$)$_m$—C(O)—N(R$_3$)→A, The carbamate group representing L1 can have the following orientations:
m) A←(CH$_2$)$_n$—(CR$_4$R$_{4'}$)$_p$—(CH$_2$)$_m$—OC(O)—N(R$_3$)→B, or
n) B←(CH$_2$)$_n$—(CR$_4$R$_{4'}$)$_p$—(CH$_2$)$_m$—OC(O)—N(R$_3$)→A, The urea group representing L1 can have the following orientations:
o) A←(CH$_2$)$_n$—(CR$_4$R$_{4'}$)$_p$—(CH$_2$)$_m$—N(R$_3$)—C(O)—N(R$_{3A}$)→B, or
p) B←(CH$_2$)$_n$—(CR$_4$R$_{4'}$)$_p$—(CH$_2$)$_m$—N(R$_3$)—C(O)—N(R$_{3A}$)→A, In a first embodiment, L1 can have the following orientations:
a) A←(CH$_2$)$_n$—(CR$_4$R$_{4'}$)$_p$—(CH$_2$)$_m$—N(R$_3$)→B,
d) B←C(O)—N(R$_3$)—(CH$_2$)$_n$—(CR$_4$R$_{4'}$)$_p$—(CH$_2$)$_m$→A,
f) B←(CH$_2$)$_n$—(CR$_4$R$_{4'}$)$_p$—(CH$_2$)$_m$—S(O)$_2$—N(R$_3$)→A,
g) A←(CH$_2$)$_n$—(CR$_4$R$_{4'}$)$_p$—(CH$_2$)$_m$—N(R$_3$)—C(S)→B,
j) B←C(NH)—N(R$_3$)—(CH$_2$)$_n$—(CR$_4$R$_{4'}$)$_p$—(CH$_2$)$_m$→A,
k) A←(CH$_2$)$_n$—(CR$_4$R$_{4'}$)$_p$—(CH$_2$)$_m$—C(O)—N(R$_3$)→B,
m) A←(CH$_2$)$_n$—(CR$_4$R$_{4'}$)$_p$—(CH$_2$)$_m$—OC(O)—N(R$_3$)→B, or
o) A←(CH$_2$)$_n$—(CR$_4$R$_{4'}$)$_p$—(CH$_2$)$_m$—N(R$_3$)—C(O)—N(R$_{3A}$)→B In a first embodiment L1 group is:
an amine group of the formula —(CH$_2$)$_n$—(CR$_4$R$_{4'}$)$_p$—(CH$_2$)$_m$—N(R$_3$)—,
a thiocarbamoyl group of the formula —(CH$_2$)$_n$—(CR$_4$R$_{4'}$)$_p$—(CH$_2$)$_m$—N(R$_3$)—C(S)—,
an amide group of the formula —C(O)—N(R$_3$)—(CH$_2$)$_n$—(CR$_4$R$_{4'}$)$_p$—(CH$_2$)$_m$—,
an amide group of the formula —(CH$_2$)$_n$—(CR$_4$R$_{4'}$)$_p$—(CH$_2$)$_n$—C(O)—N(R$_3$)—,
an amidine group of the formula —C(NH)—N(R$_3$)—(CH$_2$)$_n$—(CR$_4$R$_{4'}$)$_p$—(CH$_2$)$_m$—,
a sulphonamide group of the formula —(CH$_2$)$_n$—(CR$_4$R$_{4'}$)$_p$—(CH$_2$)$_m$—S(O)$_2$—N(R$_3$)—,
a carbamate group of the formula —(CH$_2$)$_n$—(CR$_4$R$_{4'}$)$_p$—(CH$_2$)$_m$—(O)—C(O)—N(R$_3$)—, or
a urea group of the formula —(CH$_2$)$_n$—(CR$_4$R$_{4'}$)$_p$—(CH$_2$)$_m$—N(R$_3$)—C(O)—N(R$_{3A}$)—, wherein;
R₃ and R₃ₐ are, independently from each other, hydrogen or lower alkyl,
m, n and p are, independently from each other, an integer from 0 to 2,
R₄ and R₄' are, independently from each other, hydrogen, halogen, hydroxyl, lower alkoxy, lower alkoxycarbonyl, lower alkoxycarbonyl, carboxy or lower alkyl, or R₄ and R₄' are joined together to form a spiro residue of the formula

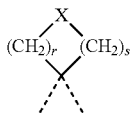

wherein;
X is NR₃', O, S or CR₃''R₄'''
r and s are, independently from each other, zero or an integer from 1 to 3, preferably 1 or 2,
R₃' is hydrogen or lower alkyl,
R₃'' is hydrogen, halogen, hydroxyl, alkoxy, or lower alkyl,
R₄'' is hydrogen or lower alkyl.

In a second embodiment L1 group is:
an amine group of the formula —(CH₂)ₙ—(CR₄R₄')ₚ—(CH₂)ₘ—N(R₃)—,
a thiocarbamoyl group of the formula —(CH₂)ₙ—(CR₄R₄')ₚ—(CH₂)ₘ—N(R₃)—C(S)—,
an amide group of the formula —C(O)—N(R₃)—(CH₂)ₙ—(CR₄R₄')ₚ—(CH₂)ₘ—,
an amide group of the formula —(CH₂)ₙ—(CR₄R₄')ₚ—(CH₂)ₘ—C(O)—N(R₃)—,
an amidine group of the formula —C(NH)—N(R₃)—(CH₂)ₙ—(CR₄R₄')ₚ—(CH₂)ₘ—,
a sulphonamide group of the formula (CH₂)ₙ—(CR₄R₄')ₚ—(CH₂)ₘ—S(O)₂—N(R₃)—,
a carbamate group of the formula —(CH₂)ₙ—(CR₄R₄')ₚ—(CH₂)ₘ—(O)—C(O)—N(R₃)—, or
a urea group of the formula —(CH₂)ₙ—(CR₄R₄')ₚ—(CH₂)ₘ—N(R₃)—C(O)—N(R₃ₐ)—,
wherein;
R₃ or R₃ₐ is hydrogen,
m, n and p are, independently from each other, an integer from 0 to 2,
R₄ and R₄' are, independently from each other, hydrogen, halogen, hydroxyl, lower alkoxy, lower alkoxycarbonyl, lower alkoxycarbonyl, carboxy or lower alkyl.

In a preferred embodiment L1 group is:
an amine group of the formula —(CH₂)ₙ—(CR₄R₄')ₚ—(CH₂)ₘ—N(R₃)—,
a thiocarbamoyl group of the formula —(CH₂)ₙ—(CR₄R₄')ₚ—(CH₂)ₘ—N(R₃)—C(S)—,
an amide group of the formula —C(O)—N(R₃)—(CH₂)ₙ—(CR₄R₄')ₚ—(CH₂)ₘ—,
an amide group of the formula —(CH₂)ₙ—(CR₄R₄')ₚ—(CH₂)ₘ—C(O)—N(R₃)—,
an amidine group of the formula —C(NH)—N(R₃)—(CH₂)ₙ—(CR₄R₄')ₚ—(CH₂)ₘ—,
a sulphonamide group of the formula —(CH₂)ₙ—(CR₄R₄')ₚ—(CH₂)ₘ S(O)₂—N(R₃)—,
a carbamate group of the formula —(CH₂)ₙ—(CR₄R₄')ₚ—(CH₂)ₘ—(O)—C(O)—N(R₃)—, or
a urea group of the formula —(CH₂)ₙ—(CR₄R₄')ₚ—(CH₂)ₘ—N(R₃)—C(O)—N(R₃ₐ)—, wherein;
R₃ or R₃ₐ is hydrogen,
m, n and p are, independently from each other, an integer from 0 to 2,
m+n+p is between 0 and 6, preferably 0, 1 or 2,
R₄ and R₄' are, independently from each other, hydrogen.

In a preferred embodiment L1 group is an amide or thiocarbamoyl group wherein the carbonyl or thiocarbamoyl carbon atom is attached to the moiety B.

In a preferred embodiment L1 group is an amide group of the formula;

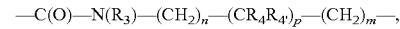

wherein;
R₃ is hydrogen,
m, n and p are, independently from each other, an integer from 0 to 2,
m+n+p is between 0 and 6, preferably 0, 1 or 2,
R₄ and R₄' are, independently from each other, hydrogen;
wherein the L1 group can have the following orientation,
B←C(O)—N(R₃)—(CH₂)ₙ—(CR₄R₄')ₚ—(CH₂)ₘ→A.

According to the present invention, the moiety B is a substituted or unsubstituted, bicyclic, 9-membered heteroaryl group. As explained above, the term "divalent" refers to a residue being attached to at least two further residues.

Besides the moieties A-L1- and —C-D to which it is attached, the moiety B can optionally have from 1 to 4, preferably 0, 1 or 2, additional substituents as described herein above for the heterocyclyl groups. Preferred substituents comprise halogen, alkyl, cycloalkyl, cyano, trifluoromethyl, alkoxy, hydroxyl, and optionally substituted amino.

Preferably, the moiety B can have the following orientation

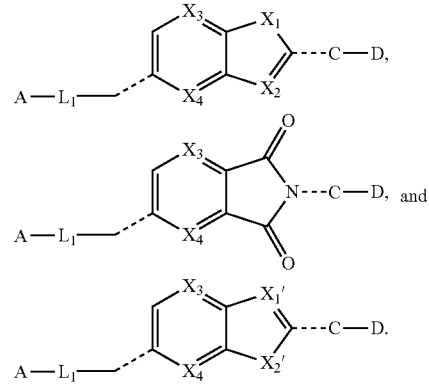

Preferably, the moiety B is selected from the group consisting of a substituted or unsubstituted, bicyclic, 9-membered heteroaryl group as herein described, wherein;
X₁, X₂' are independently selected from O, NH, NR₉ or S, wherein R₉ is selected from lower alkyl, lower alkylamino, lower alkoxyalkyl, lower hydroxyalkyl,
X₁', X₂, X₃, X₄ are independently selected from N or CH.

In a preferred embodiment, the moiety B is a substituted or unsubstituted, bicyclic, 9-membered heteroaryl group as herein described, wherein the 5-membered ring is linked to the moiety C.

Preferably, the moiety B is selected from the group consisting of a substituted or unsubstituted, bicyclic, 9-membered heteroaryl group as herein described, wherein;
X₁, X₂' are independently selected from O or NH,
X₁', X₂, are independently selected from N or CH, and
X₃, X₄ are CH.

In a preferred embodiment, the moiety B is selected from;
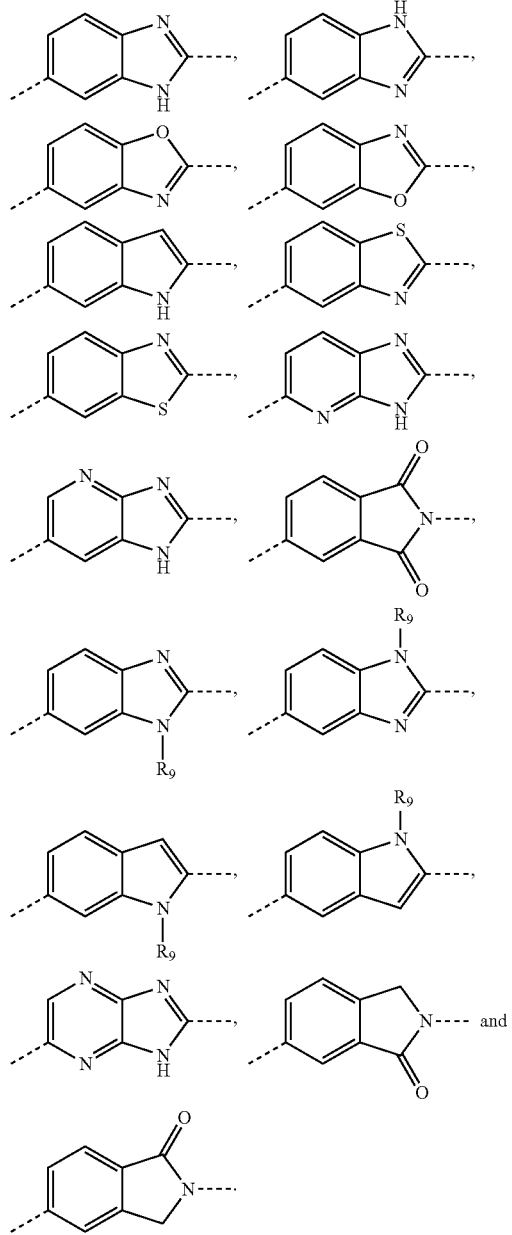
In a preferred embodiment, the moiety B is a substituted or unsubstituted, bicyclic, 9-membered heteroaryl group as herein described, wherein the 5-membered ring is linked to the moiety C i.e.
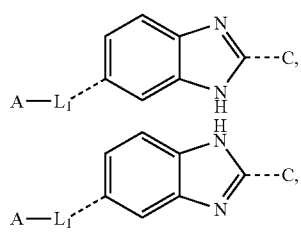
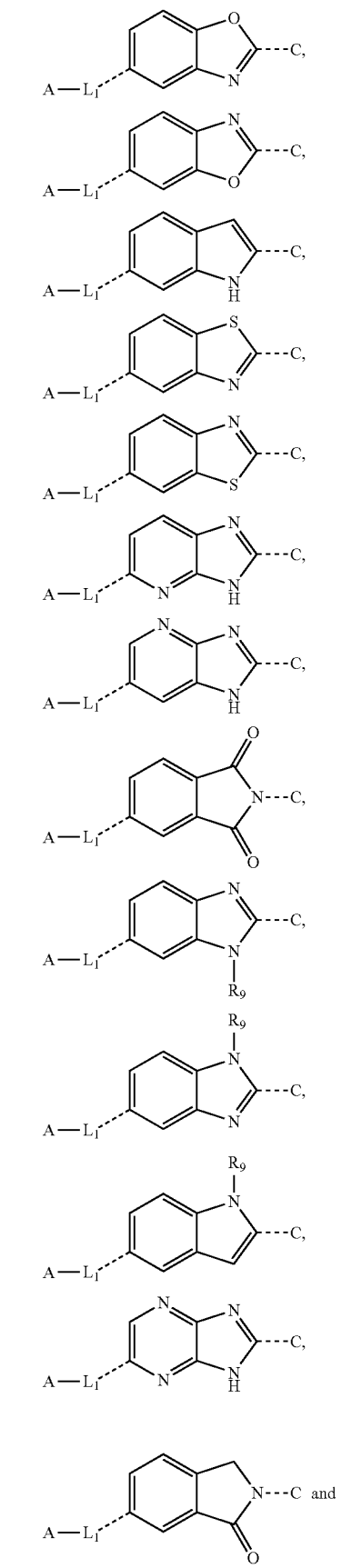

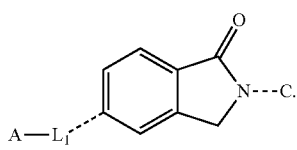

In a preferred embodiment, the moiety B is a substituted or unsubstituted, bicyclic heteroaryl group selected from;

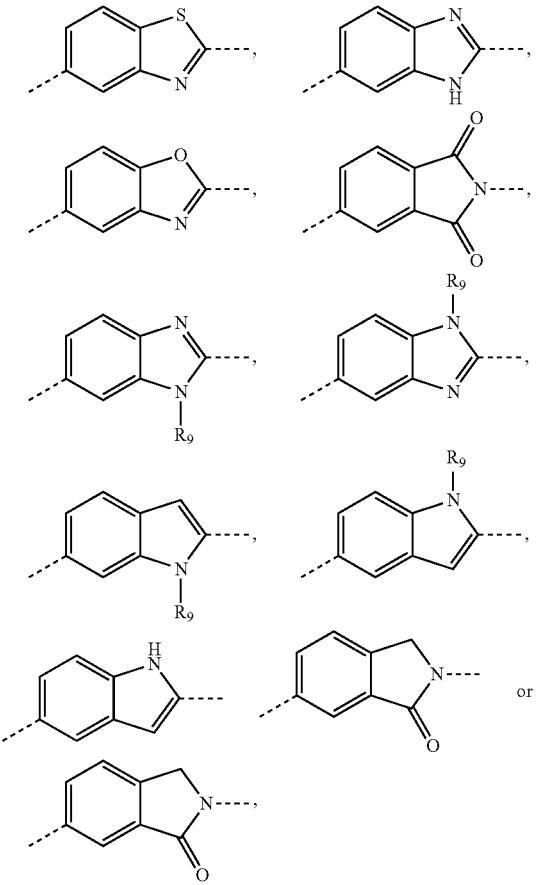

most preferably wherein the 5-membered ring is linked to the moiety C as described above.

In an other preferred embodiment, the moiety B is a substituted or unsubstituted, bicyclic heteroaryl group selected from;

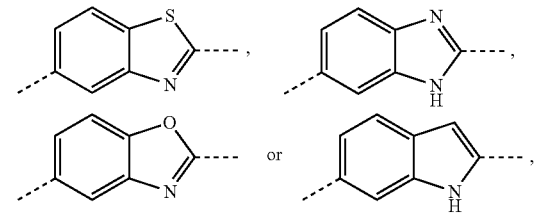

most preferably wherein the 5-membered ring is linked to the moiety C as described above.

In the herein specification, the below two moieties B should be considered as equivalent

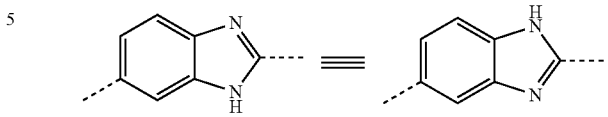

Preferably, the moiety B is selected from the group consisting of a substituted or unsubstituted, bicyclic heteroaryl group as herein described, wherein the optionally 1 to 4 substituents are selected from the substituents described herein above for the heterocyclyl groups, and preferably selected from halogen, substituted or unsubstituted lower alkyl, lower alkoxy, cyano, nitro, optionally substituted amino. Substituted lower alkyl is for example substituted by hydroxyl.

In a preferred embodiment the moiety C is;

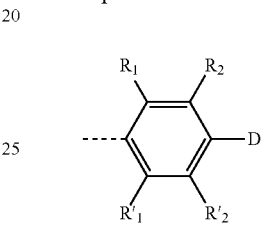

wherein
$R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$,
$R'_1$, $R_2$ and $R'_2$ are independently selected from hydrogen, halogen, trifluoromethyl, aryloxy, lower alkyl, lower alkoxy, lower alkylamino, lower dialkylamino, and $NO_2$,
or
$R'_1$ and $R'_2$ are joined together to form a substituted or unsubstituted 5 to 7-membered monocyclic aryl, substituted or unsubstituted 5 to 7-membered monocyclic heterocyclyl, or substituted or unsubstituted 5 to 7-membered monocyclic cycloalkyl group,
or
$R_1$ and $R_2$ are joined together to form a substituted or unsubstituted 5 to 7-membered monocyclic aryl, substituted or unsubstituted 5 to 7-membered monocyclic heterocyclyl, or substituted or unsubstituted 5 to 7-membered monocyclic cycloalkyl group.

In a preferred embodiment the moiety C is;

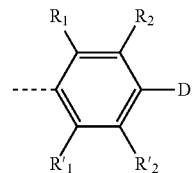

wherein
$R_1$ is selected from hydrogen, cyano, lower alkylsulfonylamino, alkanoylamino, halogen, lower alkyl, trifluoromethyl, lower alkoxy, lower alkylamino, lower dialkylamino, and $NO_2$,
$R'_1$, $R_2$ and $R'_2$ are independently selected from hydrogen, halogen, trifluoromethyl, aryloxy, lower alkyl, lower alkoxy, lower alkylamino, lower dialkylamino, and $NO_2$, or R'₁ and R'₂ are joined together to form a substituted or unsubstituted 6-membered aryl.

In a preferred embodiment the moiety C is;

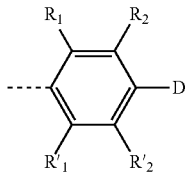

wherein

R₁ is selected from halogen, cyano, lower alkylsulfonylamino, alkanoylamino, lower alkyl, trifluoromethyl, lower alkoxy, lower alkylamino, lower dialkylamino, and NO₂, R'₁ is selected from hydrogen, halogen, lower alkyl, trifluoromethyl, lower alkoxy, lower alkylamino, lower dialkylamino, and NO₂, R₂ and R'₂ are hydrogen.

In another preferred embodiment the moiety C is;

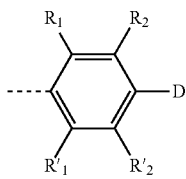

wherein

R₁ is selected from halogen, trifluoromethyl, and lower alkyl,

R'₁ is selected from hydrogen, nitro, halogen, trifluoromethyl and lower alkyl,

R₂ and R'₂ are hydrogen.

In another preferred embodiment the moiety C is;

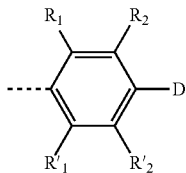

wherein

R₁ is selected from halogen, trifluoromethyl and lower alkyl,

R'₁ is selected from nitro, halogen, trifluoromethyl and lower alkyl,

R₂ and R'₂ are hydrogen.

In a preferred embodiment the moiety D is selected from hydrogen, hydroxyl, cyano, alkanoylamino, carboxy, carbamoyl, —O-L₂-E, —S-L₂-E', —C(O)—O-L₂-E, -L₂-E", and —NR₆-L₂-E', wherein;

L2 is —(CH₂)ₙ—(CR₅R₅')ₚ—(CH₂)ₘ—,

E is;
alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO₂—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy, or sulfonamido, E' is;
alkyl, acyl, alkoxycarbonyl, cycloalkoxycarbonyl, aryloxycarbonyl, heterocyclyloxycarbony, carboxy, carbamoyl, substituted or unsubstituted aryl, sulfonylcarbamoyl, sulfonyl, sulfamoyl, sulfonamido, phosphonic acid, phosphonate, sulfonyloxy, —SO₂—OH, —C(O)—O—R—PRO, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy, E" is;
alkyl, acyl, alkoxycarbonyl, phosphonic acid, phosphonate, cycloalkoxycarbonyl, aryloxycarbonyl, heterocyclyloxycarbony, carbamoyl, sulfonyl, sulfamoyl, sulfonyloxy, sulfonamido, —SO₂—OH, sulfonylcarbamoyl, —C(O)—O—R—PRO, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, preferably 0, 1, 2, 3 or 4, R₅ and R₅' are, independently from each other, hydrogen, halogen, hydroxyl, lower alkoxy, or lower alkyl, or R₅ and R₅' are joined together to form a spiro residue of the formula

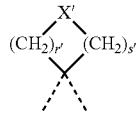

wherein;

X' is NRₓ, O, S or CRₓ'Rₓ"

r' and s' are, independently from each other, an integer from 0 to 3,

Rₓ is hydrogen or lower alkyl,

Rₓ' is hydrogen, halogen, hydroxyl, alkoxy, or lower alkyl,

Rₓ" is hydrogen or lower alkyl;

In a further preferred embodiment the moiety D is selected from hydrogen, halogen, hydroxyl, cyano, alkanoylamino, carboxy, —O-L₂-E, -L₂-E", —C(O)—O-L₂-E and —NR₆-L₂-E', wherein, L₂ is —(CH₂)ₙ—(CR₅R₅')ₚ—(CH₂)ₘ—

E is; alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO₂—OH, —C(O)—O—R—PRO, substituted or unsubstituted aryl, substituted or unsubstituted heterocyclyl, or substituted or unsubstituted heteroaryl, E' is; alkyl, acyl, alkoxycarbonyl, cycloalkoxycarbonyl, aryloxycarbonyl, heterocyclyloxycarbony, carboxy, carbamoyl, sulfonyl, —SO₂—OH, —C(O)—O—R—PRO, substituted or unsubstituted aryl, substituted or unsubstituted heterocyclyl, or substituted or unsubstituted heteroaryl, E" is; alkyl, acyl, alkoxycarbonyl, phosphonic acid, phosphonate, cycloalkoxycarbonyl, aryloxycarbonyl, heterocyclyloxycarbony, carboxy, sulfonyloxy, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

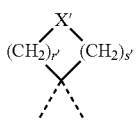

wherein;

X' is $NR_x$, O, S or $CR_xR_{x''}$ r' and s' are, independently from each other, an integer from 0 to 3, $R_x$ is hydrogen or lower alkyl, $R_{x'}$ is hydrogen, halogen, hydroxyl, alkoxy, or lower alkyl, $R_{x''}$ is hydrogen or lower alkyl.

In a further preferred embodiment the moiety D is selected from hydrogen, halogen, hydroxyl, cyano, alkanoylamino, carboxy, —O-$L_2$-E, -$L_2$-E", —C(O)—O-$L_2$-E and —$NR_6$-$L_2$-E', wherein, $L_2$ is —$(CH_2)_n$—$(CR_5R_{5'})_p$—$(CH_2)_m$—

E is; alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl, E' is; alkyl, acyl, alkoxycarbonyl, cycloalkoxycarbonyl, aryloxycarbonyl, heterocyclyloxycarbony, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl, E" is; alkyl, acyl, alkoxycarbonyl, phosphonic acid, phosphonate, cycloalkoxycarbonyl, aryloxycarbonyl, heterocyclyloxycarbony, carboxy, sulfonyloxy, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, $R_5$ and $R_{5'}$ are, independently from each other, hydrogen, halogen, hydroxyl, lower alkoxy, or lower alkyl, $R_6$ is hydrogen or lower alkyl.

In a second further preferred embodiment the moiety D is selected from;

hydrogen, halogen, hydroxyl, cyano, alkanoylamino, carboxy, carbamoyl, -$L_2$-(substituted or unsubstituted lower alkyl), -$L_2$-alkoxycarbonyl, -$L_2$-acyl, -$L_2$-(substituted or unsubstituted heteroaryl) or —O-$L_2$-E, wherein;

$L_2$ is —$(CH_2)_n$—$(CR_5R_{5'})_p$—$(CH_2)_m$—

E is a substituted or unsubstituted lower alkyl, acyl, a substituted or unsubstituted lower alkoxycarbonyl, phosphonic acid, phosphonate, cycloalkoxycarbonyl, aryloxycarbonyl, heterocyclyloxycarbony, carboxy, carbamoyl, sulfonyl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, $R_5$ and $R_{5'}$ are, independently from each other, hydrogen.

Preferably, the divalent residue -$L_2$- has the following orientation:

—O—$(CH_2)_n$—$(CR_5R_{5'})_p$—$(CH_2)_{m'}$→E, —S—$(CH_2)_n$—$(CR_5R_{5'})_p$—$(CH_2)_{m'}$→E', —C(O)—O—$(CH_2)_n$—$(CR_5R_{5'})_p$—$(CH_2)_{m'}$→E', —$(CH_2)_n$—$(CR_5R_{5'})_p$—$(CH_2)_{m'}$→E", —$NR_6$—$(CH_2)_n$—$(CR_5R_{5'})_p$—$(CH_2)_{m'}$→E".

When E is a sulphonic acid group or a derivative thereof, it is preferably selected from a —S(O)$_2$—OH group, a —S(O)$_2$—$NHR^{10}$ group, or —S(O)$_2$—$R^{10}$ group, wherein $R^{10}$ is selected from hydrogen, a $C_1$-$C_8$ alkyl group, a cycloalkyl group, a substituted or unsubstituted aryl group, preferably a substituted or unsubstituted phenyl, a substituted or unsubstituted heterocyclyl group, or a carboxylic acid ester group. Most preferably E is selected from a —S(O)$_2$—OH group, or —S(O)$_2$—$R^{10}$ group. Preferably the phenyl group $R^{10}$ is unsubstituted or substituted by a halogen or a lower alkyl (e.g. 4-Me-phenyl-)

The sulphonic acid group or derivative thereof can be attached to the moiety L2 via its sulphur atom or via its nitrogen atom. Preferably, it is attached to the moiety L2 via its sulphur atom.

Chemical formulas of preferred embodiments are also shown below:

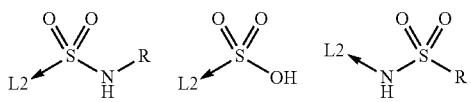

wherein R has the same meaning as $R^{10}$ defined above.

When E is an acyl, it is preferably a heterocyclyloyl or an alkanoyl which are unsubstituted or substituted as defined hereinabove. Preferred substituent is one or more substituents e.g. 1, 2, 3, 4 or 5 substituents, selected from an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E is a "heterocyclyloyl" i.e. heterocyclyl —C(O)—, preferably the carbonyl moiety "—C(O)—" is linked to, a substituted or unsubstituted, monocyclic 5 or 6-membered heterocyclyl group, or bicyclic 9 or 10-membered heterocyclyl group, via a ring member amino. The "heterocyclyloyl group" can be unsubstituted or substituted as defined herein for heterocyclyl rings. Preferred substituent is one or more substituents, e.g. 1, 2, 3, 4 or 5 substituents, selected from an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

In an embodiment the "heterocyclyloyl group" contains a fully saturated heterocyclyl. Examples of preferred heterocloyl groups, which can be substituted or unsubstituted are;

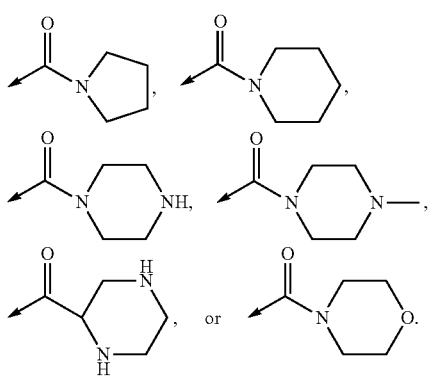

When E is an alkanoyl, the alkyl moiety is preferably a substituted or unsubstituted lower alkyl. The preferred substitutents e.g. 1, 2, 3, 4 or 5 substituents, are selected from —$CF_3$, halogen, hydroxyl, cycloalkyl, aryl, heterocyclyl, nitro, optionally substituted amino, cyano, carboxy, and/or a thiol group.

When E is carbamoyl, the alkyl moiety is preferably a substituted or unsubstituted lower alkyl, the aryl moiety is preferably substituted or unsubstituted phenyl, the heterocyclyl moiety is preferably a substituted or unsubstituted 6 or 5-membered heterocyclyl, or a substituted or unsubstituted 9 or 10-membered heterocyclyl.

A preferred carbamoyl is —C(O)—NRaRb, wherein Ra and Rb are independently selected from hydrogen and a substituted or unsubstituted lower alkyl.

When E is an alkoxycarbonyl, the alkyl moiety is preferably a substituted or unsubstituted lower alkyl. The preferred substitutents e.g. 1, 2, 3, 4 or 5 substituents, are —$CF_3$, halogen, hydroxyl, cycloalkyl, aryl, heterocyclyl, nitro, optionally substituted amino, cyano, carboxy, and/or a thiol group.

When E contains an aryl group e.g. "E" is aryl, or aryloxycarbonyl, the aryl is substituted or unsubstituted and is preferably phenyl. Preferred substituent is one or more substituents, e.g. 1, 2, 3, 4 or 5 substituents, selected from a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E contains a heterocyclyl group e.g. "E" is a heterocyclyl, heterocyclyl-NHC(O)—, or heterocyclyloxycarbony, the heterocyclyl moiety is optionally substituted. Preferred substituent is one or more substituents, e.g. 1, 2, 3, 4 or 5 substituents, selected from, an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E is a substituted or unsubstituted heterocyclyl, it is preferably a 5-membered heterocyclyl residue, and preferably selected from the group consisting of:
a tetrazole residue,
a triazole residue,
an oxadiazole residue,
a thiadiazole residue,
a diazole residue,
an oxazole residue,
a thiazole residue,
an oxathiadiazole residue,
a tetrahydropyrrol (pyrrolidin).

Preferred substituent is one or more substituents, e.g. 1, 2, 3, 4 or 5 substituents, selected from, an oxo group, a hydroxyl group, a substituted or unsubstituted lower alkyl group, a substituted or unsubstituted lower alkoxy group, trifluoromethyl, a halogen, nitro, optionally substituted amino, cyano, carboxy, and/or a thiol group.

When E is a 5-membered heterocyclyl residue, representing moiety E are also shown below:

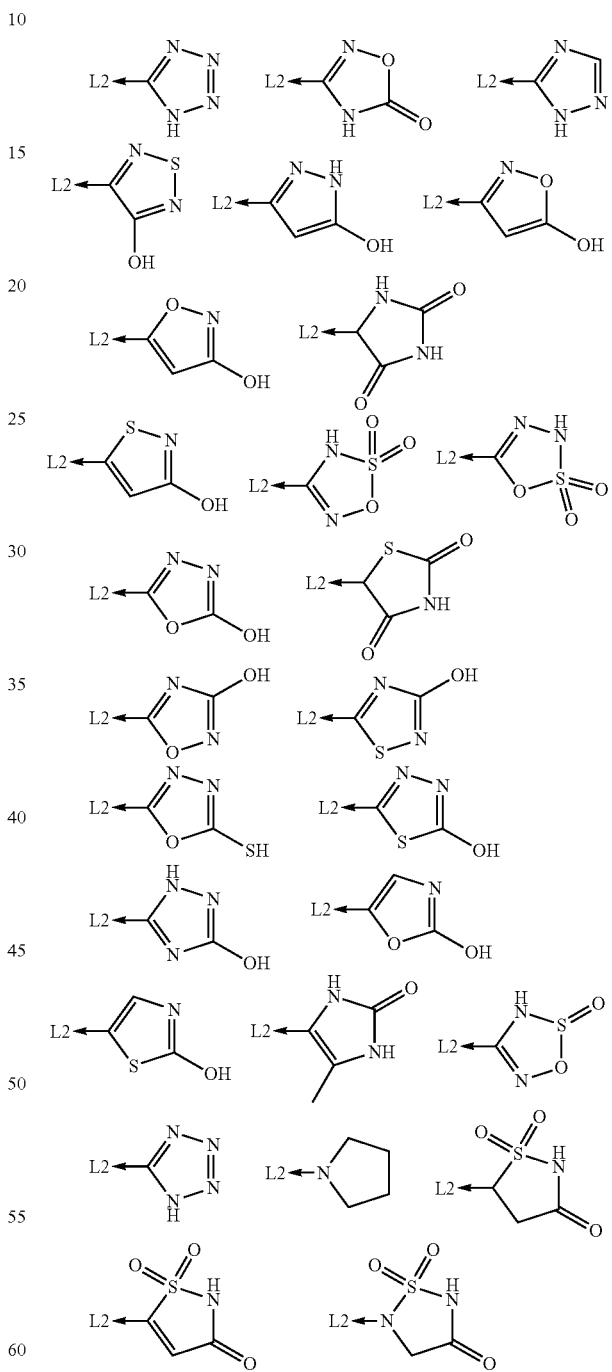

In a further embodiment, the moiety E is selected from phosphonic acid, —P($O_2$)— (substituted or unsubstituted lower alkyl), —P($O_2$)— (substituted or unsubstituted phenyl), carboxy, —S($O$)$_2$—OH, —S($O$)$_2$-(substituted or unsubstituted lower alkyl), —S($O$)$_2$-(substituted or unsubstituted phenyl), —S(O)$_2$-trifluoromethyl, a substituted or unsubstituted lower alkyl, a substituted or unsubstituted heterocyclolyl, a substituted or unsubstituted alkanoyl, a substituted or unsubstituted alkoxycarbonyl, a substituted or unsubstituted phenyloxycarbonyl, —C(O)—NH-(substituted or unsubstituted lower alkyl), —C(O)—N(substituted or unsubstituted lower alkyl)$_2$, —C(O)—NH$_2$, a substituted or unsubstituted 5-membered monocyclic heterocyclyl.

In a further embodiment, the moiety D is hydrogen, lower alkanoylamino, or carboxy.

Preferred are the compounds of formula (I)

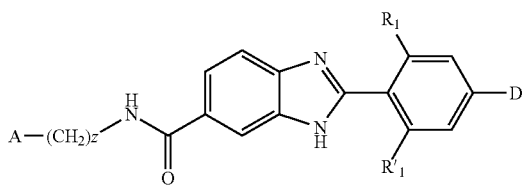

designated as the ALPHA group,
or the compounds of formula (II)

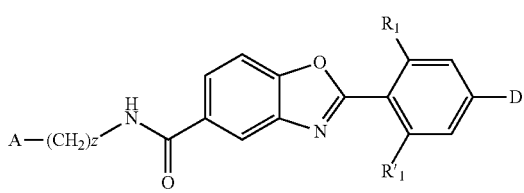

designated as the BETA group,
or the compounds of formula (III)

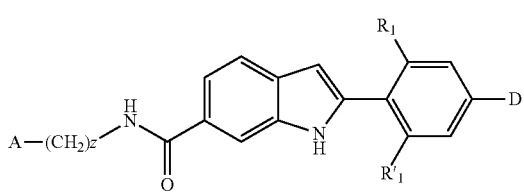

designated as the GAMMA group,
or the compounds of formula (IV)

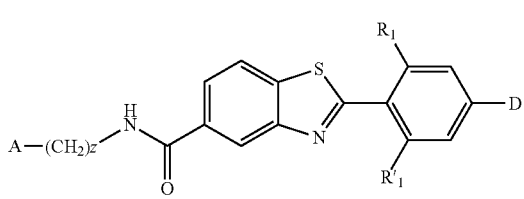

designated as the OMEGA group,
wherein
A is selected from the group consisting of a substituted or unsubstituted aryl group, preferably a phenyl group, and a substituted or unsubstituted monocyclic or bicyclic heterocyclyl group, wherein A is linked to —(CH$_2$)z- via a carbon member of the ring,
Z is an integer from 0 to 2, R$_1$ is selected from hydrogen, cyano, lower alkylsulfonylamino, alkanoylamino, halogen, lower alkyl, trifluoromethyl, lower alkoxy, lower alkylamino, lower dialkylamino, and NO$_2$, R'$_1$, R$_2$ and R'$_2$ are independently selected from hydrogen, halogen, trifluoromethyl, aryloxy, lower alkyl, lower alkoxy, lower alkylamino, lower dialkylamino, and NO$_2$, or R'$_1$ and R'$_2$ are joined together to form a substituted or unsubstituted 6-membered aryl, D is selected from hydrogen, halogen, hydroxyl, cyano, alkanoylamino, carboxy, carbamoyl, —O-L$_2$-E, —S-L$_2$-E', —C(O)—O-L$_2$-E, -L$_2$-E'', and —NR$_6$-L$_2$-E', L2 is —(CH$_2$)$_n$—(CR$_5$R$_5$)$_p$—(CH$_2$)$_m$—

E is;
 alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, substituted or unsubstituted aryl, substituted or unsubstituted heterocyclyl, or substituted or unsubstituted heteroaryl, and when n'+m'+p' is equal to zero, E is not sulfonyloxy or sulfonamido, E' is;
 alkyl, acyl, alkoxycarbonyl, cycloalkoxycarbonyl, aryloxycarbonyl, heterocyclyloxycarbony, carboxy, sulfonyl, —SO$_2$—OH, sulfonyl, sulfamoyl, sulfonamido, phosphonic acid, phosphonate, sulfonyloxy, carbamoyl, substituted or unsubstituted aryl, substituted or unsubstituted heterocyclyl, or substituted or unsubstituted heteroaryl, and when n'+m'+p' is equal to zero, E' is not sulfonyl, sulfamoyl, sulfonamido, phosphonic acid, phosphonate, or sulfonyloxy, E'' is;
 alkyl, acyl, alkoxycarbonyl, cycloalkoxycarbonyl, phosphonic acid, phosphonate, aryloxycarbonyl, heterocyclyloxycarbony, carboxy, carbamoyl, sulfonyl, sulfamoyl, sulfonyloxy, sulfonamido, substituted or unsubstituted aryl, substituted or unsubstituted heterocyclyl, or substituted or unsubstituted heteroaryl, m', n' and p' are, independently from each other, an integer from 0 to 4, m'+n'+p' is between 0 and 12, preferably 0, 1, 2, 3 or 4, R$_5$ and R$_{5'}$ are, independently from each other, hydrogen, halogen, hydroxyl, lower alkoxy, or lower alkyl, or R$_5$ and R$_{5'}$ are joined together to form a spiro residue of the formula

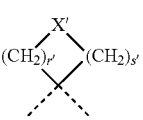

wherein;
X' is NR$_x$, O, S or CR$_x$R$_{x''}$
r' and s' are, independently from each other, an integer from 0 to 3,
R$_x$ is hydrogen or lower alkyl,
R$_{x'}$ is hydrogen, halogen, hydroxyl, alkoxy, or lower alkyl,
R$_{x''}$ is hydrogen or lower alkyl;

Preferred are the compounds in the ALPHA, BETA, GAMMA or OMEGA groups wherein;
$R_1$ is selected from halogen, lower alkyl, trifluoromethyl, lower alkoxy, lower alkylamino, lower dialkylamino, and $NO_2$,
$R'_1$ is selected from hydrogen, halogen, lower alkyl, trifluoromethyl, lower alkoxy, lower alkylamino, lower dialkylamino, and $NO_2$.

Preferred are the compounds in the ALPHA, BETA, GAMMA or OMEGA groups wherein;
D is selected from hydrogen, halogen, hydroxyl, cyano, alkanoylamino, carboxy, carbamoyl, -$L_2$-(substituted or unsubstituted lower alkyl), -$L_2$-alkoxycarbonyl, acyl, -$L_2$-(substituted or unsubstituted heteroaryl) or —O-$L_2$-E,
L2 is —$(CH_2)_n$—$(CR_5R_{4'})_{p'}$—$(CH_2)_m$—
E is;
alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, substituted or unsubstituted aryl, substituted or unsubstituted heterocyclyl, or substituted or unsubstituted heteroaryl, and when n'+m'+p' is equal to zero, E is not sulfonyloxy or sulfonamido,
m', n' and p' are, independently from each other, an integer from 0 to 4,
m'+n'+p' is between 0 and 12, preferably 0, 1, 2, 3 or 4,
$R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

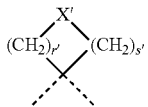

wherein;
X' is $NR_x$, O, S or $CR_xR_{x''}$
r' and s' are, independently from each other, zero or an integer from 1 to 3,
$R_x$ is hydrogen or lower alkyl,
$R_{x'}$ is hydrogen, halogen, hydroxyl, alkoxy, or lower alkyl,
$R_{x''}$ is hydrogen or lower alkyl;

Other preferred are the compounds in the ALPHA, BETA, GAMMA or OMEGA groups wherein;
D is selected from hydrogen, halogen, hydroxyl, cyano, alkanoylamino, carboxy, carbamoyl, -$L_2$-(substituted or unsubstituted lower alkyl), -$L_2$-alkoxycarbonyl, -$L_2$-acyl, -$L_2$-(substituted or unsubstituted heteroaryl) or —O-$L_2$-E,
L2 is —$(CH_2)_n$—$(CR_5R_{5'})_{p'}$—$(CH_2)_m$—
E is;
alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, substituted or unsubstituted aryl, substituted or unsubstituted heterocyclyl, or substituted or unsubstituted heteroaryl, and when n'+m'+p' is equal to zero, E is not sulfonyloxy or sulfonamido,
m', n' and p' are, independently from each other, an integer from 0 to 2,
m'+n'+p' is 0, 1, 2, 3 or 4, or preferably 0, 1 or 2, $R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

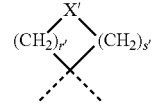

wherein;
X' is $NR_x$, O, S or $CR_xR_{x''}$
r' and s' are, independently from each other, zero or an integer from 1 to 3,
$R_x$ is hydrogen or lower alkyl,
$R_{x'}$ is hydrogen, halogen, hydroxyl, alkoxy, or lower alkyl,
$R_{x''}$ is hydrogen or lower alkyl;

Other preferred are the compounds in the ALPHA, BETA, GAMMA or OMEGA groups wherein;
D is selected from hydrogen, halogen, hydroxyl, cyano, alkanoylamino, carboxy, —O-$L_2$-E, -$L_2$-E", and —$NR_6$-$L_2$-E',
L2 is —$(CH_2)_n$—$(CR_5R_{5'})_{p'}$—$(CH_2)_m$—,
E or E' is; alkyl, acyl, alkoxycarbonyl, cycloalkoxycarbonyl, aryloxycarbonyl, heterocyclyloxycarbony, carboxy, carbamoyl, sulfonyl, —$SO_2$—OH, —C(O)—O—R—PRO, substituted or unsubstituted aryl, substituted or unsubstituted heterocyclyl, or substituted or unsubstituted heteroaryl,
E" is; alkyl, acyl, alkoxycarbonyl, cycloalkoxycarbonyl, aryloxycarbonyl, heterocyclyloxycarbony, carboxy, sulfonyloxy, substituted or unsubstituted aryl, substituted or unsubstituted heterocyclyl, or substituted or unsubstituted heteroaryl,
m', n' and p' are, independently from each other, an integer from 0 to 4,
m'+n'+p' is between 0 and 12, or is 0, 1, 2, 3 or 4, or preferably 0, 1 or 2,
$R_5$ and $R_{5'}$ are, independently from each other, hydrogen, halogen, hydroxyl, lower alkoxy, or lower alkyl, or $R_5$ and $R_{5'}$ are joined together to form a spiro residue of the formula

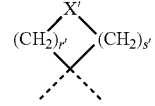

wherein;
X' is $NR_x$, O, S or $CR_xR_{x''}$
r' and s' are, independently from each other, zero or an integer from 1 to 3,
$R_x$ is hydrogen or lower alkyl,
$R_{x'}$ is hydrogen, halogen, hydroxyl, alkoxy, or lower alkyl,
$R_{x''}$ is hydrogen or lower alkyl;

Other preferred are the compounds in the ALPHA, BETA, GAMMA or OMEGA groups wherein $R_5$ and $R_{5'}$ are not joined together to form a spiro residue.

Other preferred are the compounds in the ALPHA, BETA, GAMMA or OMEGA groups wherein;
D is selected from;
hydrogen, halogen, hydroxyl, cyano, alkanoylamino, carboxy, carbamoyl, -$L_2$-(substituted or unsubstituted lower alkyl), -L$_2$-alkoxycarbonyl, -L$_2$-acyl, -L$_2$-(substituted or unsubstituted heteroaryl) or —O-L$_2$-E, wherein;

L$_2$ is —(CH$_2$)$_n$—(CR$_5$R$_5$')$_p$—(CH$_2$)$_m$—

E is a substituted or unsubstituted lower alkyl, acyl, a substituted or unsubstituted lower alkoxycarbonyl, cycloalkoxycarbonyl, aryloxycarbonyl, heterocyclyloxycarbony, carboxy, carbamoyl, sulfonyl, substituted or unsubstituted heterocyclyl, or substituted or unsubstituted heteroaryl, m', n' and p' are, independently from each other, an integer from 0 to 4, m'+n'+p' is between 0 and 12, or is 0, 1, 2, 3 or 4, or preferably 0, 1 or 2, R$_5$ and R$_5$' are, independently from each other, hydrogen.

Preferred are the compounds in the ALPHA, BETA, GAMMA or OMEGA groups wherein;

A is a substituted or unsubstituted phenyl group, or a substituted or unsubstituted monocyclic or bicyclic heterocyclyl group, selected from the group consisting of:

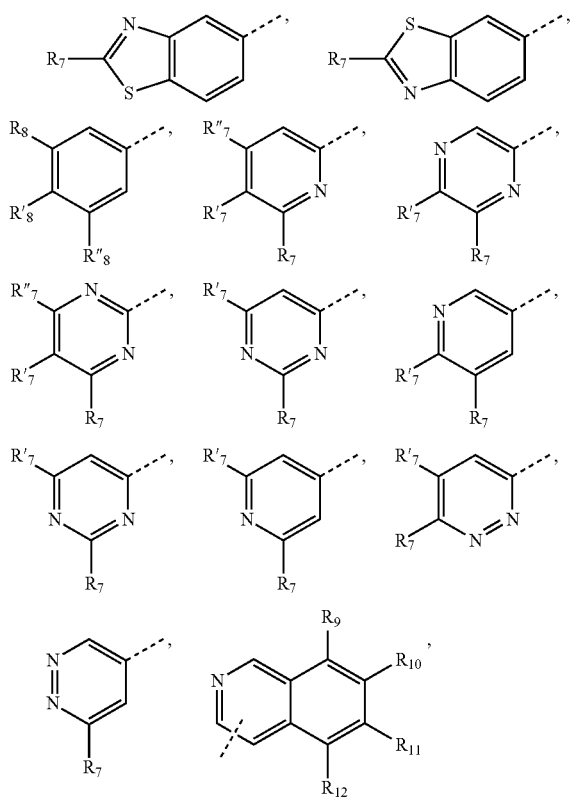

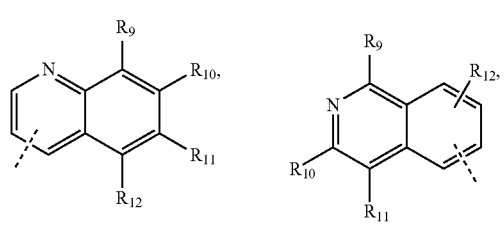

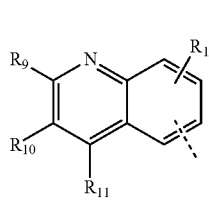

wherein,

R$_7$, R'$_7$ and R"$_7$ are, independently from each other selected from, hydrogen, optionally substituted alkyl; hydroxyl (or protected hydroxyl); halo (halogen) e.g. Cl, F, Br; oxo, i.e., =O; optionally substituted amino; optionally substituted alkoxy; cycloalkyl; carboxy; heterocyclooxy; alkoxycarbonyl, such as unsubstituted lower alkoxycarbonyl; mercapto; nitro; cyano; sulfamoyl; alkanoyloxy; aroyloxy; arylthio; optionally substituted aryloxy; alkylthio; formyl; carbamoyl; aralkyl; or aryl optionally substituted with alkyl, cycloalkyl, alkoxy, hydroxyl, amino, acylamino, alkylamino, dialkylamino or halo, and preferably only one or two of the substituents R$_7$, R'$_7$ and R"$_7$ is not hydrogen, and R$_8$, R'$_8$ and R"$_8$ are, independently from each other selected from, hydrogen, optionally substituted alkyl, trifluoromethyl, trifluoromethoxy, cycloalkyl, halo, hydroxy, optionally substituted alkoxy, acyl, alkanoyloxy, alkanoyl, optionally substituted aryloxy, optionally substituted amino, optionally substituted phenyl, thiol, alkylthio, arylthio, nitro, cyano, carboxy, alkoxycarbonyl, carbamoyl, alkylthiono, sulfonyl, sulfonamido, optionally substituted heterocyclyl and the like, and preferably only one or two of the substituents R$_8$, R'$_8$ and R$_8$'' is not hydrogen.

and

R$_9$, R$_{10}$, R$_{11}$ and R$_{12}$ are, independently from each other selected from, hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl.

Preferred are the compounds in the ALPHA, BETA, GAMMA or OMEGA groups wherein;

A is a substituted or unsubstituted phenyl group, or a substituted or unsubstituted monocyclic or bicyclic heterocyclyl group, selected from the group consisting of:

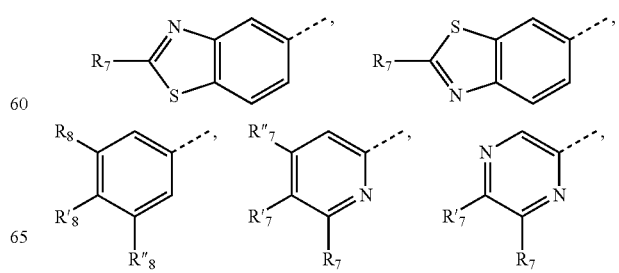

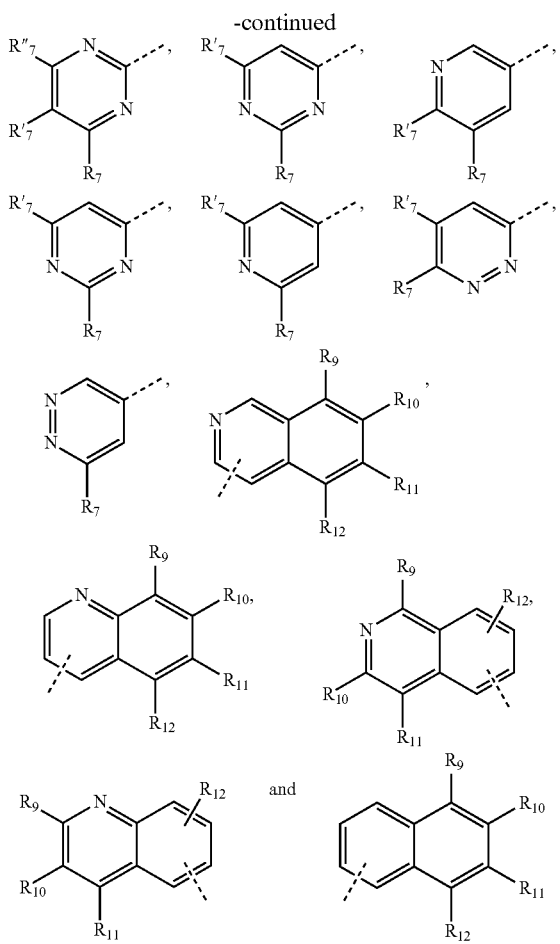

wherein,

R$_7$, R$_7'$ and R$_{7''}$ are, independently from each other selected from, hydrogen, optionally substituted lower alkyl; trifluoromethyl, preferably two of the substituents R$_7$, R$'_7$ and R$''_7$ are hydrogen,
and R$_8$, R$'_8$ and R$_{8''}$ are, independently from each other selected from, hydrogen, optionally substituted alkyl, trifluoromethyl, trifluoromethoxy, halo, hydroxy, optionally substituted alkoxy, acyl, alkanoyl, optionally substituted aryloxy, optionally substituted phenyl, cyano, carbamoyl, and preferably only one or two of the substituents R$_8$, R$'_5$ and R$_{8''}$ is not hydrogen.
and R$_9$, R$_{10}$, R$_{11}$ and R$_{12}$ are, independently from each other selected from, hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, optionally substituted heterocyclyl and the like e.g. preferably a 5-membered monocyclic heteroaryl.

Preferred are the compounds in the ALPHA, BETA, GAMMA or OMEGA groups wherein;
the moiety E is selected from phosphonic acid, —P(O$_2$)-(substituted or unsubstituted lower alkyl), —P(O$_2$)-(substituted or unsubstituted phenyl), carboxy, —S(O)$_2$—OH, —S(O)$_2$-(substituted or unsubstituted lower alkyl), —S(O)$_2$-(substituted or unsubstituted phenyl), —S(O)$_2$-trifluoromethyl, a substituted or unsubstituted lower alkyl, a substituted or unsubstituted heterocyclolyl, a substituted or unsubstituted alkanoyl, a substituted or unsubstituted alkoxycarbonyl, a substituted or unsubstituted phenyloxycarbonyl, —C(O)—NH-(substituted or unsubstituted lower alkyl), —C(O)—N(substituted or unsubstituted lower alkyl)$_2$, —C(O)—NH$_2$, a substituted or unsubstituted 5-membered monocyclic heterocyclyl, or
the moiety D is hydrogen, lower alkanoylamino, or carboxy.

The present invention also provides the herein described compounds ALPHA, BETA, GAMMA or OMEGA, wherein the amide linker L1

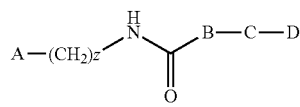

is replaced by the following amide linker

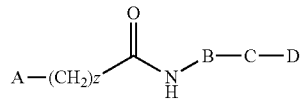

to form the compounds ALPHA', BETA', GAMMA' or OMEGA'.

Any of the herein described compounds wherein;
m'+n'+p' is 0, 1 or 2, and/or
m+n+p is 0, 1, 2 or 3.

The present invention also provides a pharmaceutical composition comprising the compound as defined above and a pharmaceutically acceptable carrier or excipient.

According to a further aspect, the present invention provides use of a compound having the following chemical structure

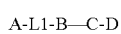

wherein
A is selected from a substituted or unsubstituted alkyl, substituted or unsubstituted alkoxy, substituted or unsubstituted cycloalkyl, substituted or unsubstituted aryl, and a substituted or unsubstituted heterocyclyle, wherein A is linked to L1 via a carbon member of the ring when A is a ring,
L1 is selected from the group consisting of:
an amine group of the formula —(CH$_2$)$_n$—(CR$_4$R$_{4'}$)$_p$—(CH$_2$)$_m$—N(R$_3$)—,
a thiocarbamoyl group of the formula —(CH$_2$)$_n$—(CR$_4$R$_{4'}$)$_p$—(CH$_2$)$_m$—N(R$_3$)—C(S)—,
an amide group of the formula —C(O)—N(R$_3$)—(CH$_2$)$_n$—(CR$_4$R$_{4'}$)$_p$—(CH$_2$)$_m$—,
an amidine group of the formula —C(NH)—N(R$_3$)—(CH$_2$)$_n$—(CR$_4$R$_{4'}$)$_p$—(CH$_2$)$_m$—,
an amide group of the formula —(CH$_2$)$_n$—(CR$_4$R$_{4'}$)$_p$—(CH$_2$)$_m$—C(O)—N(R$_3$)—,
a sulphonamide group of the formula —(CH$_2$)$_n$—(CR$_4$R$_{4'}$)$_p$—(CH$_2$)$_m$—S(O)$_2$—N(R$_3$)—,
a carbamate group of the formula —(CH$_2$)$_n$—(CR$_4$R$_{4'}$)$_p$—(CH$_2$)$_m$—(O)—C(O)—N(R$_3$)—, or
a urea group of the formula —(CH$_2$)$_n$—(CR$_4$R$_{4'}$)$_p$—(CH$_2$)$_m$—N(R$_3$)—C(O)—N(R$_{3A}$)—, wherein;
R$_3$ and R$_{3A}$ are, independently from each other, hydrogen or lower alkyl,
m, n and p are, independently from each other, zero or an integer from 1 to 2,
m+m+p is between 0 and 6, and is preferably 0, 1, 2 or 3
R$_4$ and R$_{4'}$ are, independently from each other, hydrogen, halogen, hydroxyl, lower alkoxy, lower alkoxycarbonyl, carboxy or lower alkyl, or R$_4$ and R$_{4'}$ are joined together to form a spiro residue of the formula

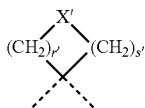

wherein;
X is NR$_{3''}$, O, S or CR$_{3''}$R$_{4''}$
r and s are, independently from each other, zero or an integer from 1 to 3,
R$_{3'}$ is hydrogen or lower alkyl,
R$_{3''}$ is hydrogen, halogen, hydroxyl, alkoxy, or lower alkyl,
R$_{4''}$ is hydrogen or lower alkyl;
B is a substituted or unsubstituted divalent heteroaryl group selected from one of the groups below:

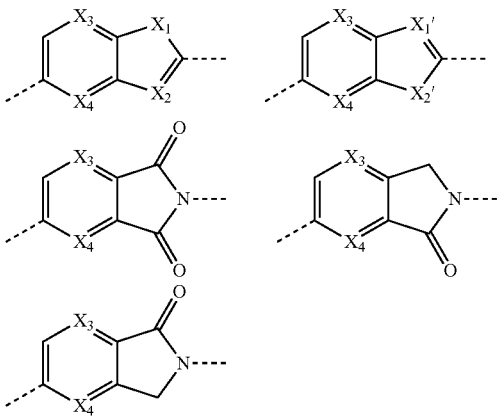

wherein;
X$_1$ and X$_2'$ are independently selected from O, NH, NR$_9$ or S, wherein R$_9$ is selected from lower alkyl, lower alkylamino, lower alkoxyalkyl, lower hydroxyalkyl,
X$_1'$, X$_2$, X$_3$ and X$_4$ are independently selected from N, or CH,
C is

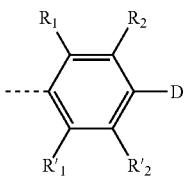

wherein
R$_1$ is selected from hydrogen, cyano, lower alkylsulfonylamino, alkanoylamino, halogen, lower alkyl, trifluoromethyl, lower alkoxy, lower alkylamino, lower dialkylamino, and NO$_2$, R$'_1$, R$_2$ and R$'_2$ are independently selected from hydrogen, halogen, trifluoromethyl, aryloxy, lower alkyl, lower alkoxy, lower alkylamino, lower dialkylamino, and NO$_2$,
or
C may also be a substituted or unsubstituted bicyclic aryl or heteroaryl group,
D is selected from hydrogen, halogen, hydroxyl, cyano, alkanoylamino, carboxy, carbamoyl, —O-L$_2$-E, —S-L$_2$-E', —C(O)—O-L$_2$-E, -L$_2$-E", and —NR$_6$-L$_2$-E',
L$_2$ is —(CH$_2$)$_n$—(CR$_5$R$_{5'}$)$_p$—(CH$_2$)$_m$—
E is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO$_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido,
E' is;
  alkyl, acyl, alkoxycarbonyl, cycloalkoxycarbonyl, aryloxycarbonyl, heterocyclyloxycarbony, carboxy, carbamoyl, sulfonylcarbamoyl, sulfonyl, —SO$_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy,
E" is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —SO$_2$—OH, sulfonylcarbamoyl, —C(O)—O—R—PRO, substituted or unsubstituted aryl, substituted or unsubstituted heterocyclyl, or substituted or unsubstituted heteroaryl,
m', n' and p' are, independently from each other, an integer from 0 to 4,
m'+n'+p' is between 0 and 12, and is preferably 0, 1, 2, 3 or 4,
R$_5$ and R$_{5'}$ are, independently from each other, hydrogen, halogen, hydroxyl, lower alkoxy, or lower alkyl, or R$_5$ and R$_{5'}$ are joined together to form a spiro residue of the formula

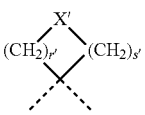

wherein;
X' is NR$_{x'}$, O, S or CR$_{x'}$R$_{x''}$
r' and s' are, independently from each other, zero or an integer from 1 to 3,
R$_{x'}$ is hydrogen or lower alkyl,
R$_{x'}$ is hydrogen, halogen, hydroxyl, alkoxy, or lower alkyl,
R$_{x''}$ is hydrogen or lower alkyl;

or a prodrug or a pharmaceutically acceptable salt thereof for the manufacture of a medicament for the treatment of DGAT especially DGAT1 associated disorders.

In a preferred embodiment, the compound used for the manufacture of the medicament is one of those as defined herein or as defined in claims 1 to 30, especially the herein specifically described compounds.

Among the preferred DGAT especially DGAT1 associated disorders, the following can be mentioned:
Metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

Preferably, the DGAT1 associated disorder is impaired glucose tolerance, Type 2 diabetes and obesity.

In yet another aspect, the present invention provides methods of using the compound or composition of the invention as an anorectic.

The compounds of the invention depending on the nature of the substituents possess one or more stereogenic centers. The resulting diastereoisomers, optical isomers, i.e., enantiomers, and geometric isomers, and mixtures thereof, are encompassed by the instant invention.

A compound as described herein above, wherein in a preferred embodiment, the moiety A is a substituted or unsubstituted phenyl group, a substituted or unsubstituted naphthyl group or a substituted or unsubstituted 6-membered heteroaryl group comprising one or two nitrogen atoms in the ring, or a substituted or unsubstituted 9-membered heteroaryl group comprising one nitrogen in the ring and optionally a second heteroatom selected from O, N or S, L1 is —NH—C(O)—, the moiety B is a substituted or unsubstituted divalent 9-membered heteroaryl selected from benzothiazole, benzoxazole, benzopyrrole or benzimidazole residue, the moiety C is selected from a substituted or unsubstituted divalent phenyl group, the moiety D is selected from hydrogen, halogen, hydroxyl, cyano, alkanoylamino, carboxy, carbamoyl, -$L_2$-(substituted or unsubstituted lower alkyl), -$L_2$-alkoxycarbonyl, -$L_2$-acyl, -$L_2$-(substituted or unsubstituted heteroaryl) or —O-$L_2$-E, wherein L2 is selected from a divalent $C_1$-$C_4$ alkyl group or a single bound, and E is selected from; phosphonic acid, —P($O_2$)-(substituted or unsubstituted lower alkyl), —P($O_2$)-(substituted or unsubstituted phenyl), carboxy, sulfonyl (preferably —S(O)$_2$—OH, —S(O)$_2$-(substituted or unsubstituted lower alkyl), —S(O)$_2$-(substituted or unsubstituted phenyl), or —S(O)$_2$-trifluoromethyl), a substituted or unsubstituted lower alkyl, a substituted or unsubstituted heterocyclolyl, a substituted or unsubstituted alkanoyl, a substituted or unsubstituted alkoxycarbonyl, a substituted or unsubstituted phenyloxycarbonyl, carbamoyl (preferably; —C(O)—NH-(substituted or unsubstituted lower alkyl), —C(O)—N(substituted or unsubstituted lower alkyl)$_2$, or —C(O)—NH$_2$), or a substituted or unsubstituted 5-membered monocyclic heterocyclyl. Preferred substituents are as previously described hereinabove e.g. for the ALPHA, BETA, GAMMA or OMEGA compounds.

A compound as described herein above, wherein in a preferred embodiment, the moiety A is a substituted or unsubstituted phenyl group or a substituted or unsubstituted 6-membered heteroaryl group comprising one or two nitrogen atoms in the ring, or a substituted or unsubstituted 9-membered heteroaryl group comprising one nitrogen in the ring and optionally a second heteroatom selected from O, N or S, L1 is —(CH$_2$)$_z$—NH—C(O)—, Z is 1 or 2, the moiety B is a substituted or unsubstituted divalent 9-membered heteroaryl selected from benzothiazole, benzoxazole, benzopyrrole or benzimidazole residue, the moiety C is selected from a substituted or unsubstituted divalent phenyl group, the moiety D is selected from hydrogen, halogen, hydroxyl, cyano, alkanoylamino, carboxy, carbamoyl, -$L_2$-(substituted or unsubstituted lower alkyl), -$L_2$-alkoxycarbonyl, -$L_2$-acyl, -$L_2$-(substituted or unsubstituted heteroaryl) or —O-$L_2$-E, wherein L2 is selected from a divalent $C_1$-$C_4$ alkyl group or a single bound, and E is selected from phosphonic acid, —P($O_2$)-(substituted or unsubstituted lower alkyl), —P($O_2$)-(substituted or unsubstituted phenyl), carboxy, sulfonyl (preferably —S(O)$_2$—OH, —S(O)$_2$-(substituted or unsubstituted lower alkyl), —S(O)$_2$-(substituted or unsubstituted phenyl), or —S(O)$_2$-trifluoromethyl), a substituted or unsubstituted lower alkyl, a substituted or unsubstituted heterocyclolyl, a substituted or unsubstituted alkanoyl, a substituted or unsubstituted alkoxycarbonyl, a substituted or unsubstituted phenyloxycarbonyl, carbamoyl (preferably; —C(O)—NH-(substituted or unsubstituted lower alkyl), —C(O)—N(substituted or unsubstituted lower alkyl)$_2$, or —C(O)—NH$_2$), or a substituted or unsubstituted 5-membered monocyclic heterocyclyl. Preferred substituents are as previously described hereinabove e.g. for the ALPHA, BETA, GAMMA or OMEGA compounds.

A compound as described herein above, wherein in a preferred embodiment, the moiety A is a substituted or unsubstituted phenyl group or a substituted or unsubstituted 6-membered heteroaryl group comprising one or two nitrogen atoms in the ring, or a substituted or unsubstituted 9-membered heteroaryl group comprising one nitrogen in the ring and optionally a second heteroatom selected from O, N or S, L1 is —NH—C(O)—(CH$_2$)$_z$, Z is 0, 1 or 2, the moiety B is a substituted or unsubstituted divalent 9-membered heteroaryl selected from benzothiazole, benzoxazole, benzopyrrole or benzimidazole residue, the moiety C is selected from a substituted or unsubstituted divalent phenyl group, the moiety D is selected from hydrogen, halogen, hydroxyl, cyano, alkanoylamino, carboxy, carbamoyl, -$L_2$-(substituted or unsubstituted lower alkyl), -$L_2$-alkoxycarbonyl, -$L_2$-acyl, -$L_2$-(substituted or unsubstituted heteroaryl) or —O-$L_2$-E, wherein L2 is selected from a divalent $C_1$-$C_4$ alkyl group or a single bound, and E is selected from phosphonic acid, —P($O_2$)-(substituted or unsubstituted lower alkyl), —P($O_2$)-(substituted or unsubstituted phenyl), carboxy, sulfonyl (preferably —S(O)$_2$—OH, —S(O)$_2$-(substituted or unsubstituted lower alkyl), —S(O)$_2$-(substituted or unsubstituted phenyl), or —S(O)$_2$-trifluoromethyl), a substituted or unsubstituted lower alkyl, a substituted or unsubstituted heterocyclolyl, a substituted or unsubstituted alkanoyl, a substituted or unsubstituted alkoxycarbonyl, a substituted or unsubstituted phenyloxycarbonyl, carbamoyl (preferably; —C(O)—NH-(substituted or unsubstituted lower alkyl), —C(O)—N(substituted or unsubstituted lower alkyl)$_2$, or —C(O)—NH$_2$), or a substituted or unsubstituted 5-membered monocyclic heterocyclyl. Preferred substituents are as previously described hereinabove e.g. for the ALPHA, BETA, GAMMA or OMEGA compounds.

A compound as described herein above, wherein in a preferred embodiment, the moiety A is a substituted or unsubstituted phenyl group or a substituted or unsubstituted 6-membered heteroaryl group comprising one or two nitrogen atoms in the ring, or a substituted or unsubstituted 9-membered heteroaryl group comprising one nitrogen in the ring and optionally a second heteroatom selected from O, N or S, L1 is —NH—C(O)—, the moiety B is a substituted or unsubstituted divalent 9-membered heteroaryl selected from benzothiazole, benzoxazol, benzopyrrol or benzimidazole residue, the moiety C is selected from a substituted or unsubstituted divalent phenyl group, the moiety D is selected from hydrogen, halogen, —O-L2-E, or -L2-E, wherein L2 is selected from a divalent $C_1$-$C_4$ alkyl group or a single bond, and wherein E is selected from hydrogen, a substituted or unsubstituted 5-membered heterocyclyl comprising at least one N (i.e. —N— or —NH—) preferably 1, 2, 3 or 4, as heteroatom member of the ring, a substituted or unsubstituted lower alkoxycarbonyl, —S(O)$_2$—R$_{10}$, wherein R$_{10}$ is selected from a substituted or unsubstituted lower alkyl and a substituted or unsubstituted phenyl, —C(O)—R$_{11}$ wherein R$_{11}$ is a substituted or unsubstituted 6 or 5-membered heterocyclyl, preferably fully saturated, comprising at least one N (i.e. —N— or —NH—), preferably 1, 2, 3 or 4, as heteroatom member of the ring and wherein a R$_{11}$ ring member N is linked to the carbonyl function (i.e. E is —C(O)→N(ring member of R$_{11}$). Preferred substituents are as previously described hereinabove e.g. for the ALPHA and BETA compounds.

In an embodiment, the moiety A is a substituted or unsubstituted phenyl group or a substituted or unsubstituted 6-membered heteroaryl group comprising one or two nitrogen atoms in the ring, or a substituted or unsubstituted 9-membered heteroaryl group comprising one nitrogen in the ring and optionally a second heteroatom selected from O, N or S, L1 is —(CH$_2$)$_z$—NH—C(O)—, Z is 1 or 2, the moiety B is a substituted or unsubstituted divalent 9-membered heteroaryl selected from benzothiazole, benzoxazole, benzopyrrole or benzimidazole residue, the moiety C is selected from a substituted or unsubstituted divalent phenyl group, the moiety D is selected from hydrogen, halogen, —O-L2-E, or -L2-E, wherein L2 is selected from a divalent $C_1$-$C_4$ alkyl group or a single bond, and wherein E is selected from hydrogen, a substituted or unsubstituted 5-membered heterocyclyl comprising at least one N (i.e. —N— or —NH—) preferably 1, 2, 3 or 4, as heteroatom member of the ring, a substituted or unsubstituted lower alkoxycarbonyl, —S(O)$_2$—R$_{10}$, wherein R$_{10}$ is selected from a substituted or unsubstituted lower alkyl and a substituted or unsubstituted phenyl, —C(O)—R$_{11}$ wherein R$_{11}$ is a substituted or unsubstituted 6 or 5-membered heterocyclyl, preferably fully saturated, comprising at least one N (i.e. —N— or —NH—), preferably 1, 2, 3 or 4, as heteroatom member of the ring and wherein a R$_{11}$ ring member N is linked to the carbonyl function (i.e. E is —C(O)→N(ring member of R$_{11}$). Preferred substituents are as previously described hereinabove e.g. for the ALPHA and BETA compounds.

In another embodiment, the moiety A is selected from a substituted or unsubstituted phenyl group (preferred substituents are as described hereinabove), a substituted or unsubstituted 6-membered heteroaryl group selected from pyridinyl, pyrazinyl and pyrimidinyl (preferred substituents are as described hereinabove), and a substituted or unsubstituted 9-membered heteroaryl group selected from benzothiazol (preferred substituents are as described hereinabove), L1 is —(CH$_2$)$_z$—NH—C(O)—, Z is 0, 1 or 2, the moiety B is a substituted or unsubstituted divalent 9-membered heteroaryl selected from benzothiazole, benzoxazol, benzopyrrol or benzimidazole residue (preferred substituents are as described hereinabove), the moiety C is selected from a substituted or unsubstituted divalent phenyl group (preferred substituents are as described hereinabove), the moiety D is selected from hydrogen, halogen, —O-L2-E, or -L2-E, wherein L2 is selected from a divalent $C_1$-$C_4$ alkyl group or a single bond, and wherein E is selected from hydrogen, a substituted or unsubstituted 5-membered heterocyclyl comprising at least one N (i.e. —N— or —NH—) preferably 1, 2, 3 or 4, as heteroatom member of the ring, a substituted or unsubstituted lower alkoxycarbonyl, —S(O)$_2$—R$_{10}$, wherein R$_{10}$ is selected from a substituted or unsubstituted lower alkyl and a substituted or unsubstituted phenyl, —C(O)—R$_{11}$ wherein R$_{11}$ is a substituted or unsubstituted 6 or 5-membered heterocyclyl, preferably fully saturated, comprising at least one N (i.e. —N— or —NH—), preferably 1, 2, 3 or 4, as heteroatom member of the ring and wherein a R$_{11}$ ring member N is linked to the carbonyl function (i.e. E is —C(O)→N (ring member of R$_{11}$).

Preferred substituents are as previously described hereinabove e.g. for the ALPHA BETA, GAMMA and OMEGA compounds.

Particular embodiments of the invention are:

[2-(2-Chloro-phenyl)-3H-benzoimidazol-5-yl]-carbamic acid ethyl ester

[2-(4-Methoxy-2-methyl-phenyl)-3H-benzoimidazol-5-yl]-carbamic acid ethyl ester

[2-(2,6-Dimethyl-phenyl)-3H-benzoimidazol-5-yl]-carbamic acid ethyl ester

[2-(2,4-Dichloro-phenyl)-3H-benzoimidazol-5-yl]-carbamic acid ethyl ester

[2-(2,3-Dichloro-phenyl)-3H-benzoimidazol-5-yl]-carbamic acid ethyl ester

N-[2-(2,6-Dichloro-phenyl)-3H-benzoimidazol-5-yl]-butyramide

N-[2-(2,6-Dichloro-phenyl)-3H-benzoimidazol-5-yl]-3-methyl-butyramide

N-[2-(2,6-Dichloro-phenyl)-3H-benzoimidazol-5-yl]-2-ethoxy-acetamide

N-[2-(2,6-Dichloro-phenyl)-3H-benzoimidazol-5-yl]-2-phenyl-acetamide

N-[2-(2,6-Dichloro-phenyl)-3H-benzoimidazol-5-yl]-3-methyl-benzamide

N-[2-(2,6-Dichloro-phenyl)-3H-benzoimidazol-5-yl]-2,4,6-trimethyl-benzenesulfonamide 2-(2,6-Dichloro-phenyl)-3H-benzoimidazole-5-carboxylic acid propylamide 2-(2,6-Dichloro-phenyl)-3H-benzoimidazole-5-carboxylic acid butylamide 2-(2,6-Dichloro-phenyl)-3H-benzoimidazole-5-carboxylic acid benzylamide 2-(2,6-Dichloro-phenyl)-3H-benzoimidazole-5-carboxylic acid (2-methoxy-ethyl)-amide 2-(2,6-Dichloro-phenyl)-3H-benzoimidazole-5-carboxylic acid isopropylamide 2-(2,6-Dichloro-phenyl)-3H-benzoimidazole-5-carboxylic acid cyclohexylamide 2-(2,6-Dichloro-phenyl)-3H-benzoimidazole-5-carboxylic acid isobutyl-methyl-amide 2-(2,6-Dichloro-phenyl)-3H-benzoimidazole-5-carboxylic acid diethylamide 2-(2,6-Dichloro-phenyl)-3H-benzoimidazole-5-carboxylic acid benzyl-methyl-amide 2-(2,6-Dichloro-phenyl)-3H-benzoimidazole-5-carboxylic acid ((R)-1-phenyl-ethyl)-amide
2-(2,6-Dichloro-phenyl)-3H-benzoimidazole-5-carboxylic acid ((S)-1-phenyl-ethyl)-amide
2-(2,6-Dichloro-phenyl)-3H-benzoimidazole-5-carboxylic acid (1,2,3,4-tetrahydro-naphthalen-1-yl)-amide
2-(2,6-Dichloro-phenyl)-3H-benzoimidazole-5-carboxylic acid (Rindan-1-ylamide
2-(2,6-Dichloro-phenyl)-3H-benzoimidazole-5-carboxylic acid (biphenyl-3-ylmethyl)-amide
2-(2,6-Dichloro-phenyl)-3H-benzoimidazole-5-carboxylic acid (biphenyl-4-ylmethyl)-amide
2-(2,6-Dichloro-phenyl)-3H-benzoimidazole-5-carboxylic acid 2-methyl-benzylamide
2-(2,6-Dichloro-phenyl)-3H-benzoimidazole-5-carboxylic acid phenethyl-amide
2-(2,6-Dichloro-phenyl)-3H-benzoimidazole-5-carboxylic acid (2-o-tolyl-ethyl)-amide
2-(2,6-Dichloro-phenyl)-3H-benzoimidazole-5-carboxylic acid phenylamide
2-(2,6-Dichloro-phenyl)-3H-benzoimidazole-5-carboxylic acid o-tolylamide
2-(2,6-Dichloro-phenyl)-3H-benzoimidazole-5-carboxylic acid (3-chloro-phenyl)-amide
2-(2,6-Dichloro-phenyl)-3H-benzoimidazole-5-carboxylic acid (4-chloro-phenyl)-amide
2-(2,6-Dichloro-phenyl)-3H-benzoimidazole-5-carboxylic acid (4-dimethylcarbamoyl-phenyl)-amide
2-(2,6-Dichloro-phenyl)-3H-benzoimidazole-5-carboxylic acid (3-methoxy-phenyl)-amide
2-(2,6-Dichloro-phenyl)-3H-benzoimidazole-5-carboxylic acid (4-methoxy-phenyl)-amide
2-(2,6-Dichloro-phenyl)-3H-benzoimidazole-5-carboxylic acid (3-isopropoxy-phenyl)-amide
2-(2,6-Dichloro-phenyl)-3H-benzoimidazole-5-carboxylic acid (3-ethoxy-phenyl)-amide
2-(2,6-Dichloro-phenyl)-3H-benzoimidazole-5-carboxylic acid (3,4-dimethyl-phenyl)-amide
2-(2,6-Dichloro-phenyl)-3H-benzoimidazole-5-carboxylic acid (3,5-dimethyl-phenyl)-amide
2-(2,6-Dichloro-phenyl)-3H-benzoimidazole-5-carboxylic acid p-tolylamide
2-(2,6-Dichloro-phenyl)-3H-benzoimidazole-5-carboxylic acid (3-cyano-phenyl)-amide
2-(2,6-Dichloro-phenyl)-3H-benzoimidazole-5-carboxylic acid (3-acetyl-phenyl)-amide
2-(2,6-Dichloro-phenyl)-3H-benzoimidazole-5-carboxylic acid (4-fluoro-phenyl)-amide
2-(2,6-Dichloro-phenyl)-3H-benzoimidazole-5-carboxylic acid (4-cyano-phenyl)-amide
2-(2,6-Dichloro-phenyl)-3H-benzoimidazole-5-carboxylic acid (3-chloro-4-fluoro-phenyl)-amide
2-(2,6-Dichloro-phenyl)-3H-benzoimidazole-5-carboxylic acid (3,4-dichloro-phenyl)-amide
2-(2,6-Dichloro-phenyl)-3H-benzoimidazole-5-carboxylic acid (4-fluoro-3-methyl-phenyl)-amide
2-(2,6-Dichloro-phenyl)-3H-benzoimidazole-5-carboxylic acid (3-chloro-4-methyl-phenyl)-amide
2-(2,6-Dichloro-phenyl)-3H-benzoimidazole-5-carboxylic acid (3,4-difluoro-phenyl)-amide
2-(2,6-Dichloro-phenyl)-3H-benzoimidazole-5-carboxylic acid (3,4-dimethoxy-phenyl)-amide
2-(2,6-Dichloro-phenyl)-3H-benzoimidazole-5-carboxylic acid (1H-indazol-5-yl)-amide
2-(2,6-Dichloro-phenyl)-3H-benzoimidazole-5-carboxylic acid (1H-indazol-6-yl)-amide
2-(2,6-Dichloro-phenyl)-3H-benzoimidazole-5-carboxylic acid (2-methyl-benzothiazol-6-yl)-amide
2-(2,6-Dichloro-phenyl)-3H-benzoimidazole-5-carboxylic acid (2-methyl-benzothiazol-5-yl)-amide
2-(2,6-Dichloro-phenyl)-3H-benzoimidazole-5-carboxylic acid quinoli6-ylamide
2-(2,6-Dichloro-phenyl)-1H-benzoimidazole-5-carboxylic acid pyridin-2-ylamide
2-(2,6-Dichloro-phenyl)-1H-benzoimidazole-5-carboxylic acid (6-chloro-pyridin-2-yl)-amide
2-(2,6-Dichloro-phenyl)-1H-benzoimidazole-5-carboxylic acid (6-methyl-pyridin-2-yl)-amide
2-(2,6-Dichloro-phenyl)-1H-benzoimidazole-5-carboxylic acid quinoxalin-6-ylamide
2-(2,6-Dichloro-phenyl)-1H-benzoimidazole-5-carboxylic acid (6-chloro-pyridin-3-yl)-amide
2-(2,6-Dichloro-phenyl)-1H-benzoimidazole-5-carboxylic acid pyridin-3-ylamide
2-(2,6-Dichloro-phenyl)-1H-benzoimidazole-5-carboxylic acid (5-chloro-pyridin-2-yl)-amide
2-(2,6-Dichloro-phenyl)-1H-benzoimidazole-5-carboxylic acid (5-methyl-pyridin-2-yl)-amide
2-(2,6-Dichloro-phenyl)-1H-benzoimidazole-5-carboxylic acid (4-methyl-pyridin-2-yl)-amide
2-(2,6-Dichloro-phenyl)-1H-benzoimidazole-5-carboxylic acid (6-chloro-pyridazin-3-yl)-amide
2-(2,6-Dichloro-phenyl)-1H-benzoimidazole-5-carboxylic acid pyrazin-2-ylamide
2-(2,6-Dichloro-phenyl)-1H-benzoimidazole-5-carboxylic acid (4-methyl-pyrimidin-2-yl)-amide
2-(2,6-Dichloro-phenyl)-1H-benzoimidazole-5-carboxylic acid pyridazin-3-ylamide
2-(2,6-Dichloro-phenyl)-1H-benzoimidazole-5-carboxylic acid (6-chloro-pyrazin-2-yl)-amide
2-(2,6-Dichloro-phenyl)-1H-benzoimidazole-5-carboxylic acid (5-chloro-pyrimidin-2-yl)-amide
2-(2,6-Dichloro-phenyl)-1H-benzoimidazole-5-carboxylic acid pyrimidin-4-ylamide
2-(2,6-Dichloro-phenyl)-1H-benzoimidazole-5-carboxylic acid [3-(2H-tetrazol-5-yl)-phenyl]-amide
2-(2,6-Dichloro-phenyl)-3H-benzoimidazole-5-carboxylic acid [2-(3-chloro-phenyl)-ethyl]-amide
2-(2,6-Dichloro-phenyl)-3H-benzoimidazole-5-carboxylic acid [2-(4-bromo-phenyl)-ethyl]-amide
2-(2,6-Dichloro-phenyl)-3H-benzoimidazole-5-carboxylic acid [2-(4-fluoro-phenyl)-ethyl]-amide
2-(2,6-Dichloro-phenyl)-3H-benzoimidazole-5-carboxylic acid [2-(3,4-dimethyl-phenyl)-ethyl]-amide
2-(2,6-Dichloro-phenyl)-3H-benzoimidazole-5-carboxylic acid [2-(3-ethoxy-phenyl)-ethyl]-amide
2-(2,6-Dichloro-phenyl)-3H-benzoimidazole-5-carboxylic acid [2-(4-methoxy-phenyl)-ethyl]-amide
2-(2,6-Dichloro-phenyl)-3H-benzoimidazole-5-carboxylic acid [2-(2-methoxy-phenyl)-ethyl]-amide
2-(2,6-Dichloro-phenyl)-3H-benzoimidazole-5-carboxylic acid [2-(3-fluoro-phenyl)-ethyl]-amide
2-(2,6-Dichloro-phenyl)-3H-benzoimidazole-5-carboxylic acid [2-(2,4-dichloro-phenyl)-ethyl]-amide
2-(2,6-Dichloro-phenyl)-3H-benzoimidazole-5-carboxylic acid [2-(2-ethoxy-phenyl)-ethyl]-amide
2-(2,6-Dichloro-phenyl)-3H-benzoimidazole-5-carboxylic acid [2-(4-ethyl-phenyl)-ethyl]-amide
2-(2,6-Dichloro-phenyl)-3H-benzoimidazole-5-carboxylic acid [2-(2,4-dimethyl-phenyl)-ethyl]-amide
2-(2,6-Dichloro-phenyl)-3H-benzoimidazole-5-carboxylic acid ((R)-2-phenyl-propyl)-amide 2-(2,6-Dichloro-phenyl)-3H-benzoimidazole-5-carboxylic acid [2-(3,4-dimethoxy-phenyl)-ethyl]-amide
2-(2,6-Dichloro-phenyl)-3H-benzoimidazole-5-carboxylic acid [2-(3-bromo-4-methoxy-phenyl)-ethyl]-amide
2-(2,6-Dichloro-phenyl)-3H-benzoimidazole-5-carboxylic acid [2-(2-fluoro-phenyl)-ethyl]-amide
2-(2,6-Dichloro-phenyl)-3H-benzoimidazole-5-carboxylic acid [2-(2,5-dimethoxy-phenyl)-ethyl]-amide
2-(2,6-Dichloro-phenyl)-3H-benzoimidazole-5-carboxylic acid [2-(4-phenoxy-phenyl)-ethyl]-amide
2-(2,6-Dichloro-phenyl)-3H-benzoimidazole-5-carboxylic acid [2-(4-ethoxy-3-methoxy-phenyl)-ethyl]-amide
2-(2,6-Dichloro-phenyl)-3H-benzoimidazole-5-carboxylic acid [2-(4-ethoxy-phenyl)-ethyl]-amide
2-(2,6-Dichloro-phenyl)-3H-benzoimidazole-5-carboxylic acid [2-(2,6-dichloro-phenyl)-ethyl]-amide
2-(2,6-Dichloro-phenyl)-3H-benzoimidazole-5-carboxylic acid [2-(4-hydroxy-phenyl)-ethyl]-amide
2-(2,6-Dichloro-phenyl)-3H-benzoimidazole-5-carboxylic acid [2-(2,5-dimethyl-phenyl)-ethyl]-amide
2-(2,6-Dichloro-phenyl)-3H-benzoimidazole-5-carboxylic acid (5-chloro-benzo[b]thiophen-3-ylmethyl)-amide
2-(2,6-Dichloro-phenyl)-1H-benzoimidazole-5-carboxylic acid (2-pyridin-2-yl-ethyl)-amide
2-(2,6-Dichloro-phenyl)-1H-benzoimidazole-5-carboxylic acid (2-pyridin-3-yl-ethyl)-amide
2-(2,6-Dichloro-phenyl)-1H-benzoimidazole-5-carboxylic acid (2-pyridin-4-yl-ethyl)-amide
2-(2,6-Dichloro-phenyl)-3H-benzoimidazole-5-carboxylic acid (3-chloro-phenyl)-methyl-amide
2-(2,6-Dichloro-phenyl)-3H-benzoimidazole-5-sulfonic acid (3,4-dimethyl-phenyl)-amide
2-(2,6-Dichloro-phenyl)-3H-benzoimidazole-5-sulfonic acid (2-methyl-benzothiazolyl-5-yl)-amide
2-(2,6-Dimethyl-phenyl)-3H-benzoimidazole-5-carboxylic acid (3-chloro-phenyl)-amide
2-o-Tolyl-3H-benzoimidazole-5-carboxylic acid (3-chloro-phenyl)-amide
{4-[6-(3-Chloro-phenylcarbamoyl)-1H-benzoimidazol-2-yl]-3,5-dimethyl-phenoxy}-acetic acid ethyl ester
{4-[6-(3-Chloro-phenylcarbamoyl)-1H-benzoimidazol-2-yl]-3,5-dimethyl-phenoxy}-acetic acid
{4-[6-(3-Chloro-phenylcarbamoyl)-1H-benzoimidazol-2-yl]-3-methyl-phenyl}-carbamic acid ethyl ester
2-Phenyl-3H-benzoimidazole-5-carboxylic acid (3-chloro-phenyl)-amide
2-(2-Chloro-phenyl)-3H-benzoimidazole-5-carboxylic acid (3-chloro-phenyl)-amide
2-(3-Chloro-phenyl)-3H-benzoimidazole-5-carboxylic acid (3-chloro-phenyl)-amide
2-(4-Chloro-phenyl)-3H-benzoimidazole-5-carboxylic acid (3-chloro-phenyl)-amide
2-(2-Chloro-6-nitro-phenyl)-3H-benzoimidazole-5-carboxylic acid (3-chloro-phenyl)-amide
2-(2-Methoxy-naphthalen-1-yl)-3H-benzoimidazole-5-carboxylic acid (3-chloro-phenyl)-amide
2-(2-Methoxy-phenyl)-3H-benzoimidazole-5-carboxylic acid (3-chloro-phenyl)-amide
2-(2-Trifluoromethyl-phenyl)-3H-benzoimidazole-5-carboxylic acid (3-chloro-phenyl)-amide
2-(2-Fluoro-phenyl)-3H-benzoimidazole-5-carboxylic acid (3-chloro-phenyl)-amide
2-(2-Cyano-phenyl)-3H-benzoimidazole-5-carboxylic acid (3-chloro-phenyl)-amide
2-(2-Chloro-6-fluoro-phenyl)-3H-benzoimidazole-5-carboxylic acid (3-chloro-phenyl)-amide
2-(2,3-Dichloro-phenyl)-3H-benzoimidazole-5-carboxylic acid (3-chloro-phenyl)-amide
2-(2,5-Dichloro-phenyl)-3H-benzoimidazole-5-carboxylic acid (3-chloro-phenyl)-amide
2-(2,4-Dichloro-phenyl)-3H-benzoimidazole-5-carboxylic acid (3-chloro-phenyl)-amide
2-(4-Methoxy-naphthalen-1-yl)-3H-benzoimidazole-5-carboxylic acid (3-chloro-phenyl)-amide
2-(4-Acetylamino-phenyl)-3H-benzoimidazole-5-carboxylic acid (3-chloro-phenyl)-amide
2-(3-Phenoxy-phenyl)-3H-benzoimidazole-5-carboxylic acid (3-chloro-phenyl)-amide
2-Naphthalen-1-yl-3H-benzoimidazole-5-carboxylic acid (3-chloro-phenyl)-amide
4-[6-(3-Chloro-phenylcarbamoyl)-1H-benzoimidazol-2-yl]-benzoic acid methyl ester
2-(4-Cyano-phenyl)-3H-benzoimidazole-5-carboxylic acid (3-chloro-phenyl)-amide
2-(2,6-Dimethoxy-phenyl)-3H-benzoimidazole-5-carboxylic acid (3-chloro-phenyl)-amide
2-(4-tert-Butyl-phenyl)-3H-benzoimidazole-5-carboxylic acid (3-chloro-phenyl)-amide
2-(2,6-Dinitro-phenyl)-3H-benzoimidazole-5-carboxylic acid (3-chloro-phenyl)-amide
2-(2,6-Difluoro-phenyl)-3H-benzoimidazole-5-carboxylic acid (3-chloro-phenyl)-amide
2-(2-Fluoro-6-methoxy-phenyl)-3H-benzoimidazole-5-carboxylic acid (3-chloro-phenyl)-amide
2-(2-Fluoro-6-trifluoromethyl-phenyl)-3H-benzoimidazole-5-carboxylic acid (3-chloro-phenyl)-amide
2-(2-Chloro-6-methanesulfonylamino-phenyl)-3H-benzoimidazole-5-carboxylic acid (3-chloro-phenyl)-amide
2-(2-Acetylamino-6-chloro-phenyl)-3H-benzoimidazole-5-carboxylic acid (3-chloro-phenyl)-amide
4-[6-(3-Chloro-phenylcarbamoyl)-1H-benzoimidazol-2-yl]-3-methyl-benzoic acid
4-[6-(3-Chloro-phenylcarbamoyl)-1H-benzoimidazol-2-yl]-3-methyl-benzoic acid methyl ester
2-(4-Acetylamino-2,6-dimethyl-phenyl)-3H-benzoimidazole-5-carboxylic acid (3,4-dimethyl-phenyl)-amide
2-[2,6-dimethyl-4-(2-oxo-2-pyrrolidin-1-yl-ethoxy)-phenyl]-3H-benzoimidazole-5-carboxylic acid (3,4-dimethyl-phenyl)-amide
Toluene-4-sulfonic acid 4-[6-(3,4-dimethyl-phenylcarbamoyl)-1H-benzoimidazol-2-yl]-3,5-dimethyl-phenyl ester
2-[2,6-dimethyl-4-(2-pyrrolidin-1-yl-ethoxy)-phenyl]-3H-benzoimidazole-5-carboxylic acid (3,4-dimethyl-phenyl)-amide
2-[2,6-Dimethyl-4-(1H-tetrazol-5-yl-methoxy)-phenyl]-3H-benzoimidazole-5-carboxylic acid (3,4-dimethyl-phenyl)-amide
{4-[6-(3,4-Dimethyl-phenylcarbamoyl)-1H-benzoimidazol-2-yl]-3,5-dimethyl-phenoxy}-acetic acid ethyl ester
2-(4-Cyano-2,6-dimethyl-phenyl)-3H-benzoimidazole-5-carboxylic acid (3,4-dimethyl-phenyl)-amide
Trifluoro-methanesulfonic acid 4-[6-(3,4-dimethyl-phenylcarbamoyl)-1H-benzoimidazol-2-yl]-3,5-dimethyl-phenyl ester
2-(2,6-Dimethyl-phenyl)-3H-benzoimidazole-5-carboxylic acid (3,4-dimethyl-phenyl)-amide
2-(4-Hydroxy-2,6-dimethyl-phenyl)-3H-benzoimidazole-5-carboxylic acid (3,4-dimethyl-phenyl)-amide
2-(4-Methoxy-2,6-dimethyl-phenyl)-3H-benzoimidazole-5-carboxylic acid (3,4-dimethyl-phenyl)-amide
2-(4-Carbamoylmethoxy-2,6-dimethyl-phenyl)-3H-benzoimidazole-5-carboxylic acid (3,4-dimethyl-phenyl)-amide 2-(2,6-Dimethyl-4-methylcarbamoylmethoxy-phenyl)-3H-benzoimidazole-5-carboxylic acid (3,4-dimethyl-phenyl)-amide
2-(4-Dimethylcarbamoylmethoxy-2,6-dimethyl-phenyl)-3H-benzoimidazole-5-carboxylic acid (3,4-dimethyl-phenyl)-amide
Methanesulfonic acid 4-[6-(3,4-dimethyl-phenylcarbamoyl)-1H-benzoimidazol-2-yl]-3,5-dimethyl-phenyl ester
{4-[6-(3,4-Dimethyl-phenylcarbamoyl)-1H-benzoimidazol-2-yl]-3,5-dimethyl-phenoxy}-acetic acid
2-{2,6-Dimethyl-4-[2-(4-methyl-piperazin-1-yl)-2-oxo-ethoxy]-phenyl}-3H benzoimidazole-5-carboxylic acid (3,4-dimethyl-phenyl)-amide
4-[6-(3,4-Dimethyl-phenylcarbamoyl)-1H-benzoimidazol-2-yl]-3,5-dimethyl-benzoic acid
2-[2,6-dimethyl-4-(4-methyl-piperazine-1-carbonyl)-phenyl]-3H-benzoimidazole-5-carboxylic acid (3,4-dimethyl-phenyl)-amide
2-[2,6-Dimethyl-4-(2H-tetrazol-5-yl)-phenyl]-3H-benzoimidazole-5-carboxylic acid (3,4-dimethyl-phenyl)-amide
[2-(2,6-Dichloro-phenyl)-3H-benzoimidazol-5-ylmethyl]-(3,4-dimethyl-phenyl)-amine
2-(4-Carbamoylmethoxy-2,6-dimethyl-phenyl)-3H-benzoimidazole-5-carboxylic acid (2-methyl-benzothiazol-5-yl)-amide
2-(2,6-Dimethyl-4-methylcarbamoylmethoxy-phenyl)-3H-benzoimidazole-5-carboxylic acid (2-methyl-benzothiazol-5-yl)-amide
2-(4-Dimethylcarbamoylmethoxy-2,6-dimethyl-phenyl)-3H-benzoimidazole-5-carboxylic acid (2-methyl-benzothiazol-5-yl)-amide
2-[2,6-Dimethyl-4-(2-oxo-2-pyrrolidin-1-yl-ethoxy)-phenyl]-3H-benzoimidazole-5-carboxylic acid (2-methyl-benzothiazol-5-yl)-amide
Trifluoro-methanesulfonic acid 3,5-dimethyl-4-[6-(2-methyl-benzothiazol-5-ylcarbamoyl)-1H-benzoimidazol-2-yl]-phenyl ester
Methanesulfonic acid 3,5-dimethyl-4-[6-(2-methyl-benzothiazol-5-ylcarbamoyl)-1H-benzoimidazol-2-yl]-phenyl ester
Toluene-4-sulfonic acid 3,5-dimethyl-4-[6-(2-methyl-benzothiazol-5-ylcarbamoyl)-1H-benzoimidazol-2-yl]-phenyl ester
{3,5-Dimethyl-4-[6-(2-methyl-benzothiazol-5-ylcarbamoyl)-1 Hbenzoimidazol-2-yl]-phenoxy}-acetic acid ethyl ester
{3,5-dimethyl-4-[6-(2-methyl-benzothiazol-5-ylcarbamoyl)-1H-benzoimidazol-2-yl]-phenoxy}-acetic acid
2-(2,6-Dichlorophenyl)-3H-benzoimidazole-5-carboxylic acid (3,5-dimethoxyphenyl)-amide
2-(2,6-Dichlorophenyl)-3H-benzoimidazole-5-carboxylic acid benzo[1,3]dioxol-5-ylamide
2-(2,6-Dichlorophenyl)-3H-benzoimidazole-5-carboxylic acid (3-chloro-4-methoxyphenyl)-amide
2-(2,6-Dichlorophenyl)-3H-benzoimidazole-5-carboxylic acid (3-trifluoromethylphenyl)-amide
2-(2,6-Dichlorophenyl)-3H-benzoimidazole-5-carboxylic acid (4-trifluoromethylphenyl)-amide
2-(2,6-Dichlorophenyl)-3H-benzoimidazole-5-carboxylic acid (3-trifluoromethoxyphenyl)-amide
2-(2,6-Dichlorophenyl)-3H-benzoimidazole-5-carboxylic acid (4-fluoro-3-trifluoromethylphenyl)-amide
2-(2,6-Dichlorophenyl)-3H-benzoimidazole-5-carboxylic acid (3,5-difluorophenyl)-amide
2-(2,6-Dichlorophenyl)-3H-benzoimidazole-5-carboxylic acid (4-nitrophenyl)-amide
2-(2,6-Dichlorophenyl)-3H-benzoimidazole-5-carboxylic acid (2,4-dichlorophenyl)-amide
2-(2,6-Dichlorophenyl)-3H-benzoimidazole-5-carboxylic acid (3,5-dichlorophenyl)-amide
2-(2,6-Dichlorophenyl)-3H-benzoimidazole-5-carboxylic acid (2-fluorophenyl)-amide
2-(2,6-Dichlorophenyl)-3H-benzoimidazole-5-carboxylic acid (4-chloro-2-fluorophenyl)-amide
2-(2,6-Dichlorophenyl)-3H-benzoimidazole-5-carboxylic acid biphenyl-4-ylamide
2-(2,6-Dichlorophenyl)-3H-benzoimidazole-5-carboxylic acid (4-phenoxyphenyl)-amide
2-(2,6-Dichlorophenyl)-3H-benzoimidazole-5-carboxylic acid (2-methoxyphenyl)-amide
2-(2,6-Dichlorophenyl)-3H-benzoimidazole-5-carboxylic acid (4-methanesulfonylphenyl)-amide
2-(2,6-Dichlorophenyl)-3H-benzoimidazole-5-carboxylic acid m-tolylamide
2-(2,6-Dichlorophenyl)-3H-benzoimidazole-5-carboxylic acid (3-phenoxyphenyl)-amide
2-(2,6-Dichlorophenyl)-3H-benzoimidazole-5-carboxylic acid (3-cyano-4-methylphenyl)-amide
2-(2,6-Dichlorophenyl)-3H-benzoimidazole-5-carboxylic acid (4-tert-butylphenyl)-amide
2-(2,6-Dichlorophenyl)-3H-benzoimidazole-5-carboxylic acid (3,5-di-tert-butylphenyl)-amide
3-{[2-(2,6-Dichlorophenyl)-3H-benzoimidazole-5-carbonyl]-amino}-benzoic acid methyl ester
2-(2,6-Dichlorophenyl)-3H-benzoimidazole-5-carboxylic acid (3-dimethylaminophenyl)-amide
2-(2,6-Dichlorophenyl)-3H-benzoimidazole-5-carboxylic acid (3-phenylpropyl)-amide
2-(2,6-Dichlorophenyl)-3H-benzoimidazole-5-carboxylic acid (3-oxazol-5-yl-phenyl)-amide
2-(2,6-Dichlorophenyl)-3H-benzoimidazole-5-carboxylic acid (4-oxazol-5-yl-phenyl)-amide
2-(2,6-Dichlorophenyl)-3H-benzoimidazole-5-carboxylic acid naphthalen-2-ylamide
2-(2,6-Dichlorophenyl)-3H-benzoimidazole-5-carboxylic acid (5-oxo-5,6,7,8-tetrahydronaphthalen-2-yl)-amide
2-(2,6-Dichlorophenyl)-3H-benzoimidazole-5-carboxylic acid indan-5-ylamide
2-(2,6-Dichlorophenyl)-3H-benzoimidazole-5-carboxylic acid (2-oxo-4-trifluoromethyl-2H-chromen-7-yl)-amide
2-(2,6-Dichlorophenyl)-3H-benzoimidazole-5-carboxylic acid (4-methylthiazol-2-O-amide
2-(2,6-Dichlorophenyl)-3H-benzoimidazole-5-carboxylic acid (4,5-dimethylthiazol-2-yl)-amide
2-(2,6-Dichlorophenyl)-3H-benzoimidazole-5-carboxylic acid (5,6,7,8-tetrahydronaphthalen-2-yl)-amide
2-(2,6-Dichlorophenyl)-3H-benzoimidazole-5-carboxylic acid (8-oxo-5,6,7,8-tetrahydronaphthalen-2-yl)-amide
2-(2,6-Dichlorophenyl)-3H-benzoimidazole-5-carboxylic acid (8-hydroxy-5,6,7,8-tetrahydronaphthalen-2-yl)-amide
2-(2,6-Dichlorophenyl)-3H-benzoimidazole-5-carboxylic acid (4-phenylbutyl)-amide
2-(2,6-Dichlorophenyl)-3H-benzoimidazole-5-carboxylic acid endo-bicyclo[2.2.1]hept-2-ylamide
2-(2,6-Dichlorophenyl)-3H-benzoimidazole-5-carboxylic acid exo-bicyclo[2.2.1]hept-2-ylamide
2-(2,6-Dichlorophenyl)-3H-benzoimidazole-5-carboxylic acid adamantan-2-ylamide
2-(2,6-Dichlorophenyl)-3H-benzoimidazole-5-carboxylic acid (4-methyl-2-oxo-2H-chromen-7-yl)-amide
2-(2,6-Dichlorophenyl)-3H-benzoimidazole-5-carboxylic acid (2,3-dihydrobenzo[1,4]dioxin-6-yl)-amide 2-(2,6-Dichlorophenyl)-3H-benzoimidazole-5-carboxylic acid [2-(pyrrolidine-1-carbonyl)-phenyl]-amide
2-(2,6-Dichlorophenyl)-3H-benzoimidazole-5-carboxylic acid (4-butylphenyl)-amide
2-(2,6-Dichlorophenyl)-3H-benzoimidazole-5-carboxylic acid (4-cyclohexylphenyl)-amide
2-(2,6-Dichlorophenyl)-3H-benzoimidazole-5-carboxylic acid (4-tert-butylcyclohexyl)-amide
2-(2,6-Dichlorophenyl)-3H-benzoimidazole-5-carboxylic acid quinolin-7-ylamide
2-(2,6-Dichlorophenyl)-3H-benzoimidazole-5-carboxylic acid isoquinolin-3-ylamide
2-(2,6-Dichlorophenyl)-3H-benzoimidazole-5-carboxylic acid (2-methylquinolin-6-yl)-amide
2-(2,6-Dichlorophenyl)-3H-benzoimidazole-5-carboxylic acid (4-methoxynaphthalen-2-yl)-amide
2-(2,6-Dichlorophenyl)-3H-benzoimidazole-5-carboxylic acid quinolin-3-ylamide
2-(2,6-Dichlorophenyl)-3H-benzoimidazole-5-carboxylic acid (4-methoxymethyl-2-oxo-2H-chromen-7-yl)-amide
2-(2,6-Dichlorophenyl)-3H-benzoimidazole-5-carboxylic acid quinolin-2-ylamide
2-(2,6-Dichlorophenyl)-3H-benzoimidazole-5-carboxylic acid anthracen-2-ylamide
(E)-3-(4-{[2-(2,6-Dichlorophenyl)-3H-benzoimidazole-5-carbonyl]-amino}-phenyl)-acrylic acid ethyl ester
2-(2,6-Dichlorophenyl)-3H-benzoimidazole-5-carboxylic acid (4-ethylphenyl)-amide
2-(2,6-Dichlorophenyl)-3H-benzoimidazole-5-carboxylic acid (4-isopropylphenyl)-amide
2-(2,6-Dichlorophenyl)-3H-benzoimidazole-5-carboxylic acid (2,6-dimethoxyphenyl)-amide
2-(2,6-Dichlorophenyl)-3H-benzoimidazole-5-carboxylic acid (2,5-di-tert-butylphenyl)-amide
2-(2,6-Dichlorophenyl)-3H-benzoimidazole-5-carboxylic acid (2,6-diisopropylphenyl)-amide
2-(2,6-Dichlorophenyl)-3H-benzoimidazole-5-carboxylic acid (3-phenylcarbamoylphenyl)-amide
2-(2,6-Dichlorophenyl)-3H-benzoimidazole-5-carboxylic acid [2-(4-fluorophenoxy)-pyridin-3-yl]-amide
2-(2,6-Dichlorophenyl)-3H-benzoimidazole-5-carboxylic acid (4-chloro-3-trifluoromethylphenyl)-amide
2-(2,6-Dichlorophenyl)-3H-benzoimidazole-5-carboxylic acid (4-sec-butylphenyl)-amide
2-(2,6-Dichlorophenyl)-3H-benzoimidazole-5-carboxylic acid (2-phenyl-2H-pyrazol-3-yl)-amide
2-(2,6-Dichlorophenyl)-3H-benzoimidazole-5-carboxylic acid (2-methyl-5-phenyl-2H-pyrazol-3-yl)-amide
2-(2,6-Dichlorophenyl)-3H-benzoimidazole-5-carboxylic acid (8-hydroxyquinolin-2-yl)-amide
2-(2,3-Dimethylphenyl)-3H-benzoimidazole-5-carboxylic acid (3,4-dimethylphenyl)-amide
2-(2,6-Dimethylphenyl)-3H-benzoimidazole-5-carboxylic acid naphthalen-2-ylamide
2-(2,6-Dimethylphenyl)-3H-benzoimidazole-5-carboxylic acid (4-methyl-2-oxo-2H-chromen-7-yl)-amide
2-(4-Chloro-phenyl)-3-(2-hydroxy-ethyl)-3H-benzoimidazole-5-carboxylic acid (3,4-dimethyl-phenyl)-amide
2-(2,6-Dichloro-phenyl)-3-(2-hydroxy-ethyl)-3H-benzoimidazole-5-carboxylic acid (3,4-dimethyl-phenyl)-amide
2-(2-Chloro-6-nitro-phenyl)-3-(2-hydroxy-ethyl)-3H-benzoimidazole-5-carboxylic acid (3,4-dimethyl-phenyl)-amide
2-(2,6-Dimethyl-phenyl)-3-(2-hydroxy-ethyl)-3H-benzoimidazole-5-carboxylic acid (3,4-dimethyl-phenyl)-amide
2-(2,6-Dimethoxy-phenyl)-3-(2-hydroxy-ethyl)-3H-benzoimidazole-5-carboxylic acid (3,4-dimethyl-phenyl)-amide
2-(2-Chloro-phenyl)-3-(2-hydroxy-ethyl)-3H-benzoimidazole-5-carboxylic acid (3,4-dimethyl-phenyl)-amide
2-(4-Chloro-phenyl)-3-methyl-3H-benzoimidazole-5-carboxylic acid (3,4-dimethyl-phenyl)-amide
2-(2,6-Dichloro-phenyl)-3-methyl-3H-benzoimidazole-5-carboxylic acid (3,4-dimethyl-phenyl)-amide
2-(2-Chloro-6-nitro-phenyl)-3-methyl-3H-benzoimidazole-5-carboxylic acid (3,4-dimethyl-phenyl)-amide
2-(2,6-Dimethyl-phenyl)-3-methyl-3H-benzoimidazole-5-carboxylic acid (3,4-dimethyl-phenyl)-amide
2-(2,6-Dimethoxy-phenyl)-3-methyl-3H-benzoimidazole-5-carboxylic acid (3,4-dimethyl-phenyl)-amide
2-(2-Chloro-phenyl)-3-methyl-3H-benzoimidazole-5-carboxylic acid (3,4-dimethyl-phenyl)-amide
2-(2,6-Dichlorophenyl)-1-methyl-1H-benzoimidazole-5-carboxylic acid (3,4-dimethylphenyl)-amide
2-(2,6-dichloro-phenyl)-1H-indole-5-carboxylic acid (2-methyl-benzothiazol-5-yl)-amide
2-(2,6-Dichloro-phenyl)-1H-indole-5-carboxylic acid (3,4-dimethyl-phenyl)-amide
2-(2,6-Dichloro-phenyl)-1H-indole-5-carboxylic acid (3-chloro-phenyl)-amide
2-(2,6-dichloro-phenyl)-benzooxazole-6-carboxylic acid (2-o-tolyl-ethyl)-amide
2-(2,6-Dichloro-phenyl)-benzooxazole-6-carboxylic acid (3-chloro-phenyl)-amide
2-(2,6-Dichloro-phenyl)-benzooxazole-6-carboxylic acid (3,4-dimethyl-phenyl)-amide
2-(2,6-Dichloro-phenyl)-benzooxazole-6-carboxylic acid (3,5-dimethyl-phenyl)-amide
2-(2,6-Dichloro-phenyl)-benzooxazole-6-carboxylic acid p-tolylamide
2-(2,6-Dichloro-phenyl)-benzooxazole-6-carboxylic acid (3-chloro-4-methyl-phenyl)-amide
2-(2,6-Dichloro-phenyl)-benzooxazole-6-carboxylic acid (4-fluoro-3-methyl-phenyl)-amide
2-(2,6-Dichloro-phenyl)-benzooxazole-6-carboxylic acid (2-methyl-benzothiazol-6-yl)-amide
2-(2,6-Dichloro-phenyl)-benzooxazole-6-carboxylic acid (1H-indazol-5-yl)-amide
2-(2,6-Dichloro-phenyl)-benzooxazole-6-carboxylic acid (1H-indazol-6-yl)-amide
2-(2,6-Dichloro-phenyl)-benzooxazole-6-carboxylic acid [2-(2-methoxy-phenyl)-ethyl]-amide
2-(2,6-Dichloro-phenyl)-benzooxazole-6-carboxylic acid [2-(3-fluoro-phenyl)-ethyl]-amide
2-(2,6-Dichloro-phenyl)-benzooxazole-6-carboxylic acid [2-(4-fluoro-phenyl)-ethyl]-amide
2-(2,6-Dichloro-phenyl)-benzooxazole-6-carboxylic acid benzylamide
2-(2,6-Dichloro-phenyl)-benzooxazole-6-carboxylic acid 2-methyl-benzylamide
2-(2,6-Dichloro-phenyl)-benzooxazole-6-carboxylic acid 2-chloro-benzylamide
2-(2,6-Dichloro-phenyl)-benzooxazole-6-carboxylic acid 3-methoxy-benzylamide
2-(2,6-Dichloro-phenyl)-benzooxazole-6-carboxylic acid 4-methoxy-benzylamide
2-(2,6-Dichlorophenyl)-benzooxazole-5-carboxylic acid (3,4-dimethylphenyl)-amide
2-(2,6-Dichlorophenyl)-benzooxazole-5-carboxylic acid (2-methylbenzothiazol-5-yl)-amide
2-(2,6-Dichlorophenyl)-benzooxazole-5-carboxylic acid [2-(4-ethylphenyl)-ethyl]-amide 2-(2,6-Dichlorophenyl)-benzooxazole-5-carboxylic acid (3-phenylpropyl)-amide
2-(4-Dimethylcarbamoylmethoxy-2,6-dimethylphenyl)-benzooxazole-5-carboxylic acid (3,4-dimethylphenyl)-amide
{4-[5-(3,4-Dimethyl-phenylcarbamoyl)-1H-benzoimidazol-2-yl]-3,5-dimethyl-phenylamino}-acetic acid methyl ester
{4-[5-(3,4-Dimethylphenylcarbamoyl)-1H-benzoimidazol-2-yl]-3,5-dimethylphenylamino}-acetic acid
2-[4-(2-Hydroxyethylamino)-2,6-dimethylphenyl]-1H-benzoimidazole-5-carboxylic acid (3,4-dimethyl-phenyl)-amide
3-{4-[5-(3,4-Dimethylphenylcarbamoyl)-1H-benzoimidazol-2-yl]-3,5-dimethylphenyl}-propionic acid tert-butyl ester
3-{4-[5-(3,4-dimethylphenylcarbamoyl)-1H-benzoimidazol-2-yl]-3,5-dimethylphenyl}-propionic acid
2-(2,6-Dimethylphenyl)-1,3-dioxo-2,3-dihydro-1H-isoindole-5-carboxylic acid (3,4-dimethylphenyl)-amide
2-(2,6-Dichlorophenyl)-1,3-dioxo-2,3-dihydro-1H-isoindole-5-carboxylic acid (3,4-dimethylphenyl)-amide
2-(2,6-Dichlorophenyl)-3H-benzoimidazole-5-carboxylic acid isoquinolin-1-ylamide
2-(2,6-Dichlorophenyl)-3H-benzoimidazole-5-carboxylic acid (4-vinylphenyl)-amide
2-(2,6-Dichlorophenyl)-3H-benzoimidazole-5-carboxylic acid (4-cyanophenyl)-amide
3-(4-{[2-(2,6-Dichlorophenyl)-3H-benzoimidazole-5-carbonyl]-amino}-phenyl)-propionic acid
3-(4-{[2-(2,6-Dichlorophenyl)-3H-benzoimidazole-5-carbonyl]-amino}-phenyl)-propionic acid ethyl ester
2-(2,6-Dichlorophenyl)-3H-benzoimidazole-5-carboxylic acid (1,1-dimethylindan-5-yl)-amide
2-(2,6-Dichlorophenyl)-3H-benzimidazole-5-carboxylic acid decylamide
2-(2,6-Dichlorophenyl)-3H-benzoimidazole-5-carboxylic acid [2-(4-tert-butylphenyl)-ethyl]amide
2-(2-Chloro-6-methylphenyl)-3H-benzoimidazole-5-carboxylic acid (3,4-dimethylphenyl)-amide
2-(2-Chloro-6-trifluoromethylphenyl)-3H-benzoimidazole-5-carboxylic acid quinolin-2-ylamide
2-(2,4-Dichloro-6-methoxyphenyl)-3H-benzoimidazole-5-carboxylic acid quinolin-2-ylamide
2-(3,5-Dichloro-pyridin-4-yl)-3H-benzoimidazole-5-carboxylic acid quinolin-2-ylamide
2-(2,6-Dichlorophenyl)-3H-benzoimidazole-5-carboxylic acid [2-(4-chlorophenyl)-2-oxo-ethyl]-amide
2-(2,6-Dichlorophenyl)-3H-benzimidazole-5-carboxylic acid [2-(4-chlorophenyl)-1-methyl-2-oxoethyl]-amide
2-(2,6-Dichlorophenyl)-6,7-difluoro-3H-benzoimidazole-5-carboxylic acid quinolin-2-ylamide
N-[2-(2,6-Dichlorophenyl)-3H-benzoimidazol-5-yl]-3,4-dimethylbenzamide
Quinoline-2-carboxylic acid [2-(2,6-dichlorophenyl)-3H-benzimidazol-5-yl]-amide
2-(2,6-Dimethylphenyl)-3H-benzimidazole-5-carboxylic acid (4-tert-butylphenyl)-amide
1-[2-(2,6-Dichlorophenyl)-3H-benzimidazol-5-yl]-3-(3,4-dimethylphenyl)-urea
2-(2,4,6-Trichlorophenyl)-3H-benzoimidazole-5-carboxylic acid quinolin-2-ylamide
2-(2,6-Dimethylphenyl)-1H-indole-6-carboxylic acid (4-tert-butylphenyl)-amide
2-(2,6-Dimethylphenyl)-1H-indole-6-carboxylic acid (3,4-dimethylphenyl)-amide
2-(2,6-Dichlorophenyl)-1H-indole-6-carboxylic acid quinolin-2-ylamide
2-(2,6-Dimethylphenyl)-1H-indole-6-carboxylic acid quinolin-2-ylamide
2-(2,6-Dichlorophenyl)-1H-Indole-6-carboxylic acid (6-trifluoromethylpyridin-3-yl)-amide
2-(2,6-Dichlorophenyl)-1-ethoxy-1H-indole-6-carboxylic acid (3,4-dimethylphenyl)-amide
2-(2,6-Dichlorophenyl)-1H-indole-6-carboxylic acid (3,4-dimethylphenyl)-amide
2-(2,6-Dichlorophenyl)-1H-indole-6-carboxylic acid thiazolo[5,4-b]pyridin-2-ylamide
2-(2,6-Dichlorophenyl)-1H-indole-6-carboxylic acid (5-bromothiazolo[5,4-b]pyridin-2-yl)-amide
2-(2,6-Dichloro-4-morpholin-4-yl-phenyl)-1H-indole-6-carboxylic acid quinolin-2-ylamide
3-{3,5-Dimethyl-4-[6-(quinolin-2-ylcarbamoyl)-1H-indol-2-yl]-phenyl}-propionic acid methyl ester
3-{3,5-Dimethyl-4-[6-(quinolin-2-ylcarbamoyl)-1H-indol-2-yl]-phenyl}-propionic acid
3-{4-[6-(4-tert-Butylphenylcarbamoyl)-1H-indol-2-yl]-3,5-dimethylphenyl}-propionic acid
3-{3,5-Dichloro-4-[6-(quinolin-2-ylcarbamoyl)-1H-indol-2-yl]-phenyl}-propionic acid hydrochloride salt
2-(2,6-Dichloro-4-hydroxyphenyl)-1H-indole-6-carboxylic acid quinolin-2-ylamide
3-{4-[5-(3,4-Dimethylphenylcarbamoyl)-1H-benzoimidazol-2-yl]-3,5-dimethylphenyl}-propionic acid
3-{4-[6-(3,4-Dimethylphenylcarbamoyl)-1H-benzoimidazol-2-yl]-3,5-dimethylphenyl}-propionic acid methyl ester
3-{4-[6-(5,6-Dimethylpyridin-2-ylcarbamoyl)-1H-benzimidazol-2-yl]-3,5-dimethylphenyl}-propionic acid
{3,5-Dichloro-4-[6-(3,4-dimethylphenylcarbamoyl)-1H-benzoimidazol-2-yl]-phenoxy}-acetic acid methyl ester
{3,5-Dichloro-4-[6-(3,4-dimethyl-phenylcarbamoyl)-1H-benzoimidazol-2-yl]-phenoxy}-acetic acid
{3-Chloro-4-[6-(3,4-dimethylphenylcarbamoyl)-1H-benzoimidazol-2-yl]-phenoxy}-acetic acid methyl ester
{3-Chloro-4-[6-(3,4-dimethylphenylcarbamoyl)-1H-benzoimidazol-2-yl]-phenoxy}-acetic acid
{3,5-Dimethyl-4-[6-(quinolin-2-ylcarbamoyl)-1H-benzoimidazol-2-yl]-phenoxy}-acetic acid methyl ester
{3,5-Dimethyl-4-[6-(quinolin-2-ylcarbamoyl)-1H-benzoimidazol-2-yl]-phenoxy}-acetic acid
2-[4-((R)-2,2-Dimethyl-[1,3]dioxolan-4-ylmethoxy)-2,6-dimethylphenyl]-3H-benzoimidazole-5-carboxylic acid (3,4-dimethylphenyl)-amide
2-[4-((S)-2,3-Dihydroxy-propoxy)-2,6-dimethylphenyl]-3H-benzoimidazole-5-carboxylic acid (3,4-dimethylphenyl)-amide
2-[4-((S)-2,2-Dimethyl-[1,3]dioxolan-4-ylmethoxy)-2,6-dimethylphenyl]-3H-benzoimidazole-5-carboxylic acid (3,4-dimethylphenyl)-amide
2-[4-((R)-2,3-Dihydroxy-propoxy)-2,6-dimethylphenyl]-3H-benzoimidazole-5-carboxylic acid (3,4-dimethylphenyl)-amide
2-[4-((R)-2,2-Dimethyl-[1,3]dioxolan-4-ylmethoxy)-2,6-dimethylphenyl]-3H-benzoimidazole-5-carboxylic acid quinolin-2-ylamide
2-[4-((S)-2,3-Dihydroxypropoxy)-2,6-dimethylphenyl]-3H-benzoimidazole-5-carboxylic acid quinolin-2-ylamide
3-{4-[6-(Quinolin-2-ylcarbamoyl)-1H-benzoimidazol-2-yl]-phenyl}-propionic acid
3-{3,5-Dimethyl-4-[6-(naphthalen-2-ylcarbamoyl)-1H-benzoimidazol-2-yl]-phenyl}-propionic acid
3-{4-[6-(Isoquinolin-1-ylcarbamoyl)-1H-benzoimidazol-2-yl]-3,5-dimethylphenyl}-propionic acid {3,5-Dichloro-4-[6-(quinolin-2-ylcarbamoyl)-1H-benzoimidazol-2-yl]-phenoxy}-acetic acid methyl ester
{3,5-Dichloro-4-[6-(quinolin-2-ylcarbamoyl)-1H-benzoimidazol-2-yl]-phenoxy}-acetic acid
2-(2,6-Dichloro-4-dimethylcarbamoylmethoxyphenyl)-3H-benzoimidazole-5-carboxylic acid quinolin-2-ylamide
{3,5-Dichloro-4-[6-(quinolin-2-ylcarbamoyl)-1H-benzoimidazol-2-yl]-phenoxymethyl}-phosphonic acid diethylester
{3,5-Dichloro-4-[6-(quinolin-2-ylcarbamoyl)-1H-benzoimidazol-2-yl]-phenoxymethyl}-phosphonic acid
3-{3,5-Dichloro-4-[6-(quinolin-2-ylcarbamoyl)-1H-benzoimidazol-2-yl]-phenyl}-propionic acid
3-{4-[6-(4-tert-Butylphenylcarbamoyl)-1H-benzimidazol-2-yl]-3,5-dimethylphenyl}-propionic acid
(E)-3-{4-[6-(4-tert-Butylphenylcarbamoyl)-1H-benzimidazol-2-yl]-3,5-dimethylphenyl}-acrylic acid
{4-[6-(4-tert-Butylphenylcarbamoyl)-1H-benzoimidazol-2-yl]-3,5-dimethylphenoxy}-acetic acid
3-{4-[6-(4-tert-Butylphenylcarbamoyl)-1H-benzoimidazol-2-yl]-3,5-dimethylphenyl}-2,2-dimethylpropionic acid
3-{3,5-Dimethyl-4-[6-(quinolin-2-ylcarbamoyl)-1H-benzoimidazol-2-yl]-phenyl}-2,2-dimethyl-propionic acid
3-{3,5-Dimethyl-4-[5-(6-trifluoromethyl-pyridin-3-ylcarbamoyl)-1H-benzoimidazol-2-yl]-phenyl}-2,2-dimethyl-propionic acid
(2-{3,5-Dimethyl-4-[6-(quinolin-2-ylcarbamoyl)-1H-benzoimidazol-2-yl]-phenyl}-ethyl)-phosphonic acid
(3-{3,5-Dimethyl-4-[6-(quinolin-2-ylcarbamoyl)-1H-benzoimidazol-2-yl]-phenyl}-propyl)-phosphonic acid diethyl ester
(3-{3,5-Dimethyl-4-[6-(quinolin-2-ylcarbamoyl)-1H-benzoimidazol-2-yl]-phenyl}-propyl)-phosphonic acid
(3-{3,5-Dimethyl-4-[6-(quinolin-2-ylcarbamoyl)-1H-benzoimidazol-2-yl]-phenyl}-propyl)-phosphonic acid monoethyl ester
(3-{3,5-Dimethyl-4-[6-(6-trifluoromethyl-pyridin-3-ylcarbamoyl)-1H-benzoimidazol-2-yl]-phenyl}-propyl)-phosphonic acid
(3-{4-[6-(4-tert-Butyl-phenylcarbamoyl)-1H-benzoimidazol-2-yl]-3,5-dimethyl-phenyl}-propyl)-phosphonic acid
3-{3,5-Dichloro-4-[6-(6-trifluoromethylpyridin-3-ylcarbamoyl)-1H-benzoimidazol-2-yl]-phenyl}-propionic acid
(3,4-Dimethylphenyl)-{1-[2-(2,6-dimethylphenyl)-3H-benzoimidazol-5-yl]-2,2,2-trifluoroethyl}-amine
3-{3,5-Dimethyl-4-[6-(quinolin-2-ylcarbamoyl)-1H-benzoimidazol-2-yl]-phenyl}-propionic acid
or any pharmaceutically acceptable salt or prodrug thereof.

The processes described herein for the preparation of compounds above may be conducted under inert atmosphere, preferably under nitrogen atmosphere.

In starting compounds and intermediates which are converted to the compounds of the present invention in a manner described herein, functional groups present, such as amino, thiol, carboxyl and hydroxyl groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably, such as are inert to the reagents and are solvents thereof, of catalysts, condensing or said other agents, respectively and/or inert atmospheres, at low temperatures, RT or elevated temperatures, preferably at or near the boiling point of the solvents used, and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials, intermediates and processes for their manufacture.

Depending on the choice of starting materials and methods, the new compounds may be in the form of one of the possible isomers or mixtures thereof, for example, as substantially pure geometric (cis or trans) isomers, diastereomers, optical isomers (antipodes), racemates or mixtures thereof. The aforesaid possible isomers or mixtures thereof are within the purview of this invention.

Any resulting mixtures of isomers can be separated on the basis of the physicochemical differences of the constituents, into the pure geometric or optical isomers, diastereomers, racemates, for example, by chromatography and/or fractional crystallization.

Finally, compounds of the invention are either obtained in the free form, or in a salt form thereof, preferably, in a pharmaceutically acceptable salt form thereof, or as a prodrug derivative thereof.

Compounds of the instant invention which contain acidic groups may be converted into salts with pharmaceutically acceptable bases. Such salts include alkali metal salts, like sodium, lithium and potassium salts; alkaline earth metal salts, like calcium and magnesium salts; ammonium salts with organic bases, e.g., trimethylamine salts, diethylamine salts, tris(hydroxymethyl)methylamine salts, dicyclohexylamine salts and N-methyl-D-glucamine salts; salts with amino acids like arginine, lysine and the like. Salts may be formed using conventional methods, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention, in general, may be converted into acid addition salts, especially pharmaceutically acceptable salts. These are formed, e.g., with inorganic acids, such as mineral acids, e.g., sulfuric acid, phosphoric or hydrohalic acid, or with organic carboxylic acids, such as ($C_1$-$C_4$)-alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid, or with organic sulfonic acids, such as $(C_1-C_4)$-alkylsulfonic acids, e.g., methanesulfonic acid; or arylsulfonic acids which are unsubstituted or substituted (for example by halogen). Preferred are salts formed with hydrochloric acid, maleic acid and methanesulfonic acid.

Prodrug derivatives of any compound of the invention are derivatives of said compounds which following administration release the parent compound in vivo via some chemical or physiological process, e.g., a prodrug on being brought to the physiological pH or through enzyme action is converted to the parent compound. Exemplary prodrug derivatives are, e.g., esters of free carboxylic acids and S-acyl and O-acyl derivatives of thiols, alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the prodrug derivatives and the compounds in the form of their salts, whenever a compound is referred to in this context, a prodrug derivative and a corresponding salt is also intended, provided such is possible or appropriate under the circumstances.

The compounds, including their salts, can also be obtained in the form of their hydrates, or include other solvents used for their crystallization.

As described herein above, the compounds of the present invention may be employed for the treatment of conditions mediated by DGAT especially DGAT1 activity. Such compounds may thus be employed therapeutically for the treatment of impaired glucose tolerance, Type 2 diabetes and obesity.

In yet another aspect, the present invention provides methods of using a compound or composition of the invention to treat or prevent a disease or condition associated with DGAT especially DGAT1. Disease and conditions associated with lipid metabolism and cell proliferation, and complications thereof, may be treated with the subject compounds and compositions. In one group of embodiments, diseases and conditions, including chronic diseases, of humans and other species that can be treated with inhibitors of DGAT especially DGAT1 function include, but are not limited to, metabolic disorders such as obesity, diabetes, anorexia nervosa, bulimia, cachexia, syndrome X, insulin resistance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (for example, esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

In yet another aspect, the present invention provides methods of using a compound or composition of the invention as an anorectic.

The present invention further provides pharmaceutical compositions comprising a therapeutically effective amount of a pharmacologically active compound of the instant invention, alone or in combination with one or more pharmaceutically acceptable carriers.

The pharmaceutical compositions according to the invention are those suitable for enteral, such as oral or rectal; transdermal and parenteral administration to mammals, including man, for the treatment of conditions mediated by DGAT especially DGAT1 activity. Such conditions include impaired glucose tolerance, Type 2 diabetes and obesity.

Thus, the pharmacologically active compounds of the invention may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Accordingly, the present invention provides pharmaceutical compositions as described above for the treatment of conditions mediated by DGAT especially DGAT1 activity, preferably, impaired glucose tolerance, Type 2 diabetes and obesity.

The pharmaceutical compositions may contain a therapeutically effective amount of a compound of the invention as defined above, either alone or in a combination with another therapeutic agent, e.g., each at an effective therapeutic dose as reported in the art. Such therapeutic agents include:

a) antidiabetic agents, such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1B (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;
c) anti-obesity agents such as orlistat or rimonabant; and
d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.
e) agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof.

In each case in particular in the compound claims and the final products of the working examples, the subject matter of the final products, the pharmaceutical preparations and the claims are hereby incorporated into the present application by reference to these publications and patent applications.

Other specific anti-diabetic compounds are described by Patel Mona in *Expert Opin Investig Drugs,* 2003, 12(4), 623-633, in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications). The corresponding content thereof is hereby incorporated by reference.

Accordingly, the present invention provides pharmaceutical compositions comprising a therapeutically effective amount of a compound of the invention in combination with a therapeutically effective amount of another therapeutic agent, preferably selected from anti-diabetics, hypolipidemic agents, anti-obesity agents or anti-hypertensive agents, most preferably from antidiabetics or hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by DGAT activity preferably DGAT1 activity, preferably, impaired glucose tolerance, Type 2 diabetes and obesity.

Thus, the present invention also relates to a compound as defined in the claims and described above for use as a medicament; to the use of a compound as defined in the claims and described above for the preparation of a pharmaceutical composition for the prevention and/or treatment of conditions mediated by DGAT activity preferably DGAT1 activity, and to a pharmaceutical composition for use in conditions mediated by DGAT activity preferably DGAT1 activity comprising a compound as defined in the claims and described above, or a pharmaceutically acceptable salt thereof, in association with a pharmaceutically acceptable diluent or carrier therefore.

The present invention further provides a method for the prevention and/or treatment of conditions mediated by DGAT activity preferably DGAT1 activity, which comprises administering a therapeutically effective amount of a compound of the present invention.

A unit dosage for a mammal of about 50-70 kg may contain between about 1 mg and 1000 mg, advantageously between about 5-500 mg of the active ingredient. The therapeutically effective dosage of active compound is dependent on the species of warm-blooded animal (mammal), the body weight, age and individual condition, on the form of administration, and on the compound involved.

In accordance with the foregoing the present invention also provides a therapeutic combination, e.g., a kit, kit of parts, e.g., for use in any method as defined herein, comprising a compound as defined in the claims and described above, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents and anti-hypertensive agents, or a pharmaceutically acceptable salt thereof. The kit may comprise instructions for its administration.

Similarly, the present invention provides a kit of parts comprising: (i) a pharmaceutical composition of the invention; and (ii) a pharmaceutical composition comprising a compound selected from an anti-diabetic, a hypolipidemic agent, an anti-obesity agent and an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound as defined in the claims and described above, or a pharmaceutically acceptable salt thereof, and a second drug substance, said second drug substance being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to modulation of the DGAT especially DGAT1 activity.

Preferably, the condition associated with DGAT especially DGAT1 activity is selected from impaired glucose tolerance, Type 2 diabetes and obesity.

Finally, the present invention provides a method or use which comprises administering a compound as defined in the claims and described above in combination with a therapeutically effective amount of an anti-diabetic agent, a hypolipidemic agent, an anti-obesity agent or an anti-hypertensive agent.

Ultimately, the present invention provides a method or use which comprises administering a compound as defined in the claims and described above in the form of a pharmaceutical composition as described herein.

As used throughout the specification and in the claims, the term "treatment" embraces all the different forms or modes of treatment as known to those of the pertinent art and in particular includes preventive, curative, delay of progression and palliative treatment.

The above-cited properties are demonstrable in vitro and in vivo tests using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-2}$ molar and $10^{-9}$ molar concentrations. A therapeutically effective amount in vivo may range depending on the route of administration, between about 0.1 mg/kg and 1000 mg/kg, preferably between about 1 mg/kg and 100 mg/kg.

The activity of compounds according to the invention may be assessed by the following methods or methods well-described in the art:

The enzyme preparation used in this assay is a membrane preparation from Sf9 cells overexpressing human $(His)_6DGAT1$. During all steps samples were chilled to 4° C. Sf9 cells expressing human $(His)_6DGAT1$ were thawed at RT and re-suspended at a 10:1 ratio (mL buffer/g of cells) in 50 mM HEPES, 1× Complete Protease Inhibitor, pH 7.5.

The re-suspended pellet was homogenized for 1 min using a Brinkman PT 10/35 homogenizer with a 20 mm generator. Cells were lysed using Avestin Emulsiflex (chilled to 4° C.) at 10000-15000 psi. Lysate was centrifuged at 100,000×g for 1 h at 4° C. Supernatant was removed and pellets were re-suspended in 50 mM HEPES, 1× Complete Protease Inhibitor, pH 7.5 at ⅙ the volume of supernatant. Re-suspended pellets were pooled and homogenized with 10 strokes of a Glas-Col motor driven teflon pestle on setting 70. The protein concentration of the membrane preparation was quantified using BCA protein assay with 1% SDS. The membrane preparation was aliquoted, frozen on dry ice, and stored at −80° C.

For 50 mL, 25 mL of 0.2 M HEPES stock buffer, 0.5 mL of 1 M $MgCl_2$ (5 mM final concentration), and 24.5 mL of milli-Q $H_2O$ are added to the 55 mL Wheaton Potter-Elve-hjem homogenizer. Enzyme preparation (0.1 mL) is added to buffer and the mixture is homogenized with 5 strokes on ice using the Glas-Col variable speed homogenizer system on setting 70.

For 50 mL, 0.5 mL 10 mM diolein is added to 9.5 mL of EtOH in a 50 mL Falcon screw cap conical centrifuge tube. Five mL of 10 mM sodium acetate pH 4.5 is added followed by 0.5 mL of 10 mM oleoyl-CoA. Finally, the remaining 4.5 mL of 10 mM sodium acetate pH 4.5 is added followed by 30 mL of milli-Q $H_2O$. The solution should be gently agitated by hand to induce mixing. The final concentrations of EtOH and sodium acetate are 20% and 2 mM, respectively.

Dry compounds are dissolved in the appropriate volume of DMSO to a final concentration of 10 mM. A 10-point, 3-fold dose response is used to evaluate compound potency. All dilutions are performed in DMSO in a Greiner 384-well microplate.

1. 2 µL of compound in DMSO is added to the appropriate wells. 2 µL of DMSO is added to 100% activity and 100% inhibition controls.
2. 25 µL of enzyme mix is added to all wells and plate(s) are incubated for 10 min at RT.
3. 10 µL of 20% acetic acid quench is added to 100% inhibition control wells. Plate(s) are vortexed using Troemner multi-tube vortexer (setting 7 for 10 sec).
4. 25 µL of substrate mix is added to all wells. Plate(s) are vortexed using Troemner multi-tube vortexer (setting 7 for 10 sec). Plate(s) are incubated for 30 min at RT.
5. 10 µL of 20% acetic acid quench is added to all wells. Plate(s) are vortexed using Troemner multi-tube vortexer (setting 7 for 10 sec).
6. 50 µL of 1-butanol w/glyceryl tripalmitoleate internal standard is added to all wells.
7. Plate(s) are sealed with super pierce strong plate sealer using the thermo-sealer.
8. Plate(s) are vortexed using Troemner multi-tube vortexer (setting 10 for 5 min).
9. Plate(s) are centrifuged at 162×g (1000 rpm for GH-3.8 rotor) for 5 min using Beckman GS-6R tabletop centrifuge.

Samples were analyzed by LC/MS/MS using a Waters 1525 µLC and Quattro Micro API MS. Where indicated, tripalmitolein was used as an internal standard to control for instrument variation.

Data is converted to % inhibition prior to curve fitting using the following equation:

$$\% \text{ Inhibition} = \frac{(\text{response compound} - \text{response 100\% inhibition control})}{(\text{response 100\% activity control} - \text{response 100\% inhibition control})} \times 100$$

Using the method described above, the compounds of the present invention were shown to possess inhibitory activity with IC50 values ranging from 0.001 uM to 100 uM.

Table 1 shows the inhibitory activity ($IC_{50}$ values) of representative compounds to human DGAT1.

| Example | $IC_{50}$ (µM) |
| --- | --- |
| 1-6 | between 1 and 30 |
| 1-82 | less than 1 |
| 3-1 | between 1 and 30 |
| 4-11 | between 30 and 100 |

The activity on DGAT2 receptors can be assessed as described in the International patent application WO03/053363.

Methods of Preparation:

In the below description of general Methods of Preparation and Synthesis;

Ar can represent D-C— wherein D and C are as hereinabove defined.

ArCHO can represent D-C—CHO, wherein D and C are as hereinabove defined.

$RNH_2$ can represent $H_2N-(CH_2)_n-(CR_4R_{4'})_p-(CH_2)_m-A$ or $A-(CH_2)_n-(CR_4R_{4'})_p-(CH_2)_m-NH_2$ wherein A, $R_4$, $R_{4'}$, p, n and m have the same definition as for L1 which are hereinabove defined.

RCOCl can represent $Cl-C(O)-(CH_2)_n-(CR_4R_{4'})_p-(CH_2)_m-A$ or $A-(CH_2)_n-(CR_4R_{4'})_p-(CH_2)_m-C(O)-Cl$ wherein A, $R_4$, $R_{4'}$, p, n and m have the same definition as for L1 which are hereinabove defined.

$RSO_2Cl$ can represent $Cl-SO_2-(CH_2)_n-(CR_4R_{4'})_p-(CH_2)_m-A$ or $A-(CH_2)_n-(CR_4R_{4'})_p-(CH_2)_m-SO_2-Cl$ wherein A, $R_4$, $R_{4'}$, p, n and m have the same definition as for L1 which are hereinabove defined.

Y can represent A-L1-.

$R_2$ can represent a hereinabove defined heterocyclyl substituent.

≡≡≡—Ar can represent ≡≡≡—C-D wherein D and C are as hereinabove defined.

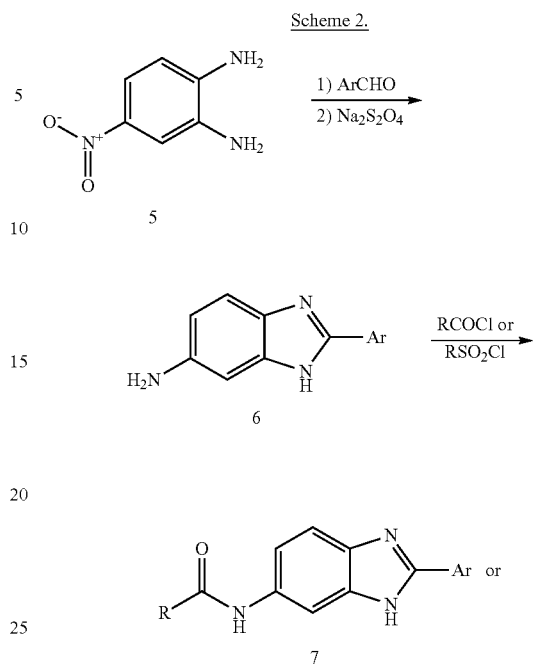

Scheme 2.

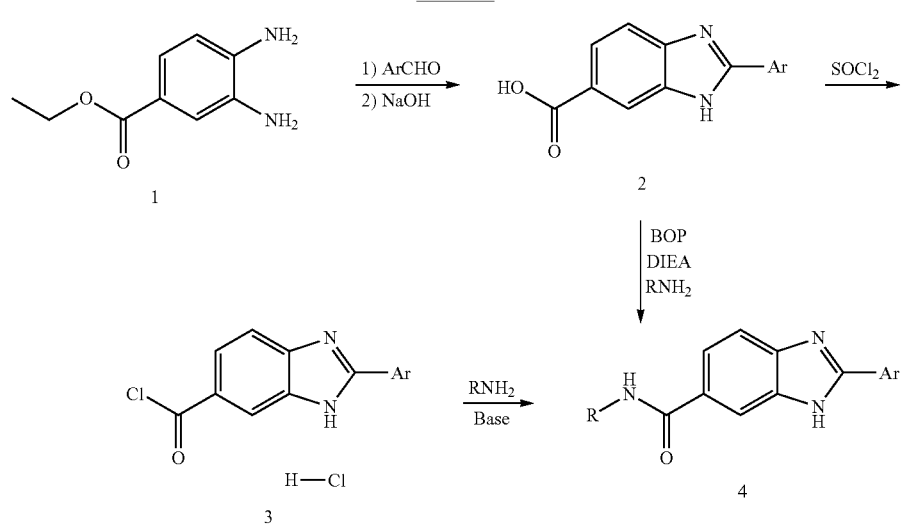

Scheme 1.

Oxidative cyclocondensation of 3,4-diamino-benzoic acid ethyl ester with substituted benzaldehyde provides the benzimidazole core. The reaction is carried out in the open air in oxidizing media, such as DMSO or nitrobenzene, preferably the former, in the presence of a catalyst such as FeCl3, Sc(OTf)3/Cu(OTf)2, or Yb(OTf)3/Cu(OTf)2. After saponification of the ethyl ester, resulting carboxylic acid is converted to acid chloride by the action of SOCl2 and ensuing amidation with a variety of alkyl, aryl, or heteroarylamine in the presence of base such as, but not limited to, DIPEA, pyridine, or Na2CO3, affords compounds 4. In addition, amidation of compound 2 by using an coupling reagent such as, but not limited to, BOP and EDCl with aryl, heteroarylamine in an inert solvent can provides compounds 4.

-continued

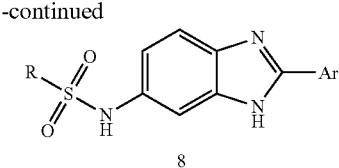

In the similar fashion, 4-nitrophenylenediamine is converted to 2-aryl-5-nitro-3H-benzoimidazole, which, upon reduction of the nitro group, give rise to aerobically unstable 5-aminobenzimidazole core. Amidation or sulfonylation of the latter provides a variety of 2-aryl-3H-benzoimidazol-5-amine carboxamides 7 and sulfonamides 8.

Scheme 3.

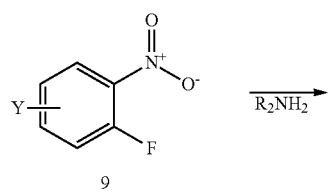

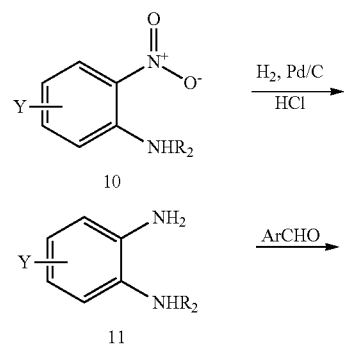

In another form of synthesis, the cyclocondensation can be carried out at the last stage, with the eventual 5-substituent pre-installed on the ring.

Scheme 4.

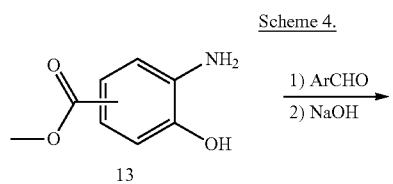

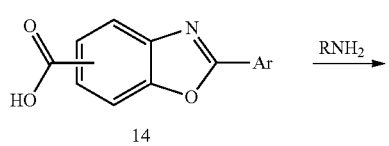

Oxidative cyclocondensation of compound 13 and subsequent hydrolysis can provide compound 14. The amidation of compound 14 by using an coupling reagent can afford compound 15.

Scheme 5.

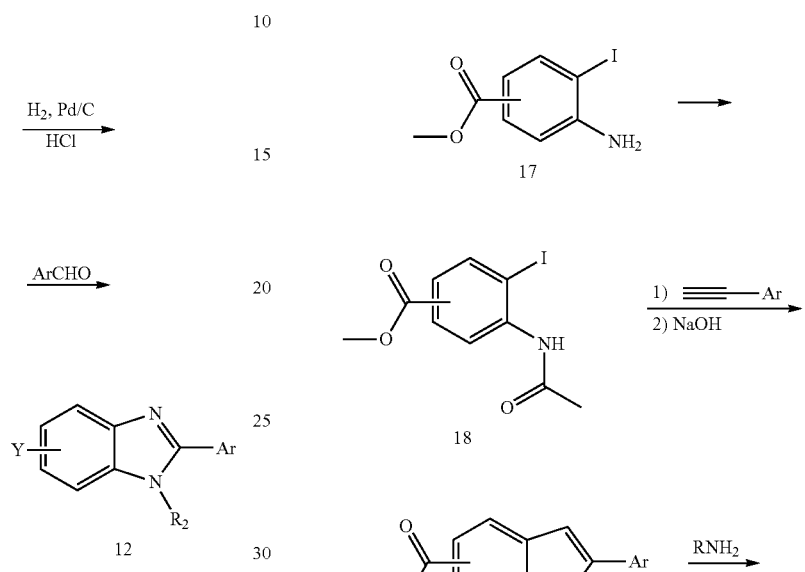

Compound 19, useful for the preparation of compound 20 can be prepared by employing the palladium-catalyzed coupling of alkynes with iodoanilines in the present of TMG (tetramethylguanidine).

HPLC Method 10: 4.6 mm×5 cm Inersil C8-3 reverse phase, 3.0 μm particle size running a gradient of 10-90% MeCN/water (5 mM ammonium formate) over a period of 2 min at a flow rate of 4 mL/min at 50° C. DAD-UV detection, 220-600 nm.

EXAMPLES

The following Examples are intended to illustrate the invention and are not to be construed as being limitations thereon. If not mentioned otherwise, all evaporations are performed under reduced pressure, preferably between about 50 mmHg and 100 mmHg. The structure of final products, intermediates and starting materials is confirmed by standard analytical methods, e.g., microanalysis, melting point (m.p.) and spectroscopic characteristics, e.g., MS, IR and NMR. Abbreviations used are those conventional in the art.

Example 1-1

[2-(2-Chloro-phenyl)-3H-benzoimidazol-5-yl]-carbamic acid ethyl ester

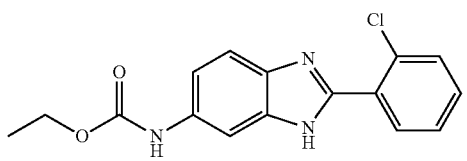

To a solution of 4-nitro-benzene-1,3-diamine (1.6 g) in acetonitrile (20 mL) was added NaHCO$_3$ (1 g) and ethyl chloroformate (1.0 mL). The mixture was heated at 75° C. with stirring overnight. Cooled to ambient temperature, the mixture was diluted by water and extracted twice with ethyl acetate. Combined organics were dried over Na$_2$SO$_4$, filtered, and concentrated to give crude yellow solid. Trituration from dichloromethane afforded (3-amino-4-nitro-phenyl)-carbamic acid ethyl ester: 1H NMR (400 MHz, CD$_3$OD) 7.9 (d, 1H), 7.3 (s, 1H), 6.5 (d, 1H), 4.2 (q, 2H), 1.3 (t, 3H).

A solution of (3-amino-4-nitro-phenyl)-carbamic acid ethyl ester (1.2 g) in ethyl acetate (40 mL) was placed in a Parr shaker bottle and 10% Pd/C (200 mg) was added. The mixture was hydrogenated at 50 psi H$_2$ for 20 h. The mixture was filtered on Celite and the filtrated was treated with 4 M HCl in dioxane (5 mL). Resulting precipitate was filtered and washed with ethyl acetate before it was vacuum-dried to give (3,4-diamino-phenyl)-carbamic acid ethyl ester di-hydrochloride salt as a purple solid: 1H NMR (400 MHz, DMSO-d6) 9.5 (s, 1H), 7.1 (s, 1H), 7.0 (d, 1H), 6.8 (d, 1H), 4.1 (q, 2H), 1.3 (t, 3H).

A freshly prepared solution of (3,4-diamino-phenyl)-carbamic acid ethyl ester in DMSO (0.2 M, 0.10 mL) was placed in a vial. To it was added 2-chloro-benzaldehyde (0.2 M in toluene, 0.12 mL), followed by FeCl$_3$ (0.02 M in THF, 0.050 mL). The mixture was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give [2-(2-chloro-phenyl)-3H-benzoimidazol-5-yl]-carbamic acid ethyl ester: MS (m/z) 315.97 (M+1).

In a multiple parallel fashion, the following compounds was prepared in the same way as described for Example 1-1:

| Example | Structure | Chemical Name | MS found (M + 1) |
|---|---|---|---|
| 1-2 | 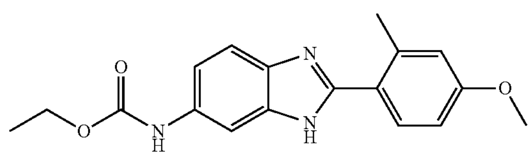 | [2-(4-Methoxy-2-methyl-phenyl)-3H-benzoimidazol-5-yl]-carbamic acid ethyl ester | 326.04 |
| 1-3 | 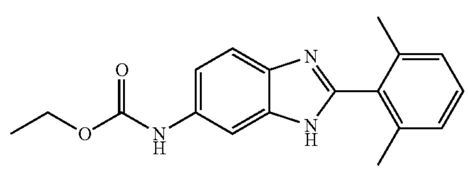 | [2-(2,6-Dimethyl-phenyl)-3H-benzoimidazol-5-yl]-carbamic acid ethyl ester | 310.04 |
| 1-4 | 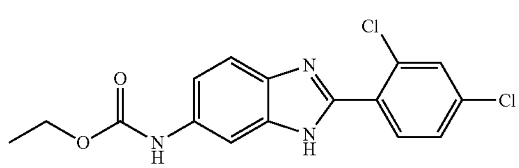 | [2-(2,4-Dichloro-phenyl)-3H-benzoimidazol-5-yl]-carbamic acid ethyl ester | 349.9 |
| 1-5 | 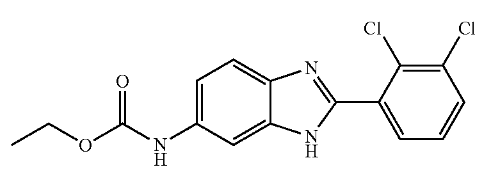 | [2-(2,3-Dichloro-pheny])-3H-benzoimidazol-5-yl]-carbamic acid ethyl ester | 349.9 |

Example 1-6

N-[2-(2-Chloro-phenyl)-3H-benzoimidazol-5-yl]-acetamide

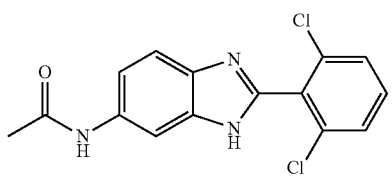

To a solution of 4-nitro-benzene-1,2-diamine (1.5 g) and 2,6-dichloro-benzaldehyde (1.7 g) in DMSO (20 mL) was added a catalytic amount of $FeCl_3$ and the mixture was stirred in an open flask at ambient temperature overnight. Resulting solution was diluted by aqueous $NH_4Cl$ and extracted twice with ethyl acetate. Combined organics were dried over $Na_2SO_4$, filtered, and concentrated in vacuo. The residue was taken up in THF (10 mL) and mixed with conc $NH_4OH$ (5 mL). To the solution was added $Na_2S_2O_4$ (2 g) as a solid and the mixture was stirred at ambient temperature for 24 h. After usual aqueous workup, the crude product obtained was purified by column chromatography on silica gel to give aerobically unstable 2-(2,6-dichloro-phenyl)-3H-benzoimidazol-5-ylamine: 1H NMR (CDCl3, 400 MHz) 7.4 (app d, 2H), 7.3 (m, 1H), 7.2 (m, 2H), 7.1 (app d, 1H), 6.7 (br, 1H), 3.7 (br, 2H).

To a vial containing a solution of 2-(2,6-dichloro-phenyl)-3H-benzoimidazol-5-ylamine in dioxane (0.2 M, 0.10 mL) was added DIPEA (0.5 M in toluene, 0.050 mL) and acetic acid (0.2 M in toluene, 0.12 mL), followed by BOP reagent (0.2 M in DMF, 0.15 mL). After overnight at ambient temperature, the mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to N-[2-(2-Chloro-phenyl)-3H-benzoimidazol-5-yl]-acetamide: MS (m/z) 320.02 (M+1).

In a multiple parallel fashion, the following compounds was prepared in the same way as described for Example 1-6:

| Example | Structure | Chemical Name | MS found (M + 1) |
|---|---|---|---|
| 1-7 | 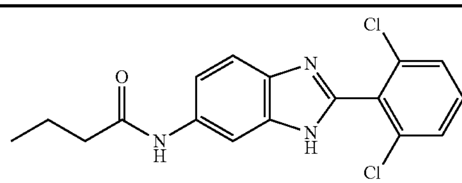 | N-[2-(2,6-Dichloro-phenyl)-3H-benzoimidazol-5-yl]-butyramide | 348.02 |
| 1-8 | 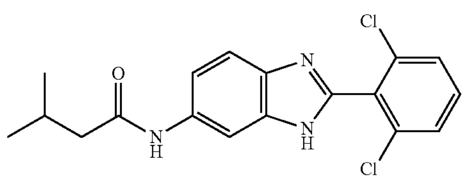 | N-[2-(2,6-Dichloro-phenyl)-3H-benzoimidazol-5-yl]-3-methyl-butyramide | 362.08 |
| 1-9 | 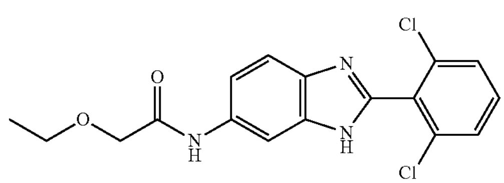 | N-[2-(2,6-Dichloro-phenyl)-3H-benzoimidazol-5-yl]-2-ethoxy-acetamide | 364.02 |
| 1-10 | 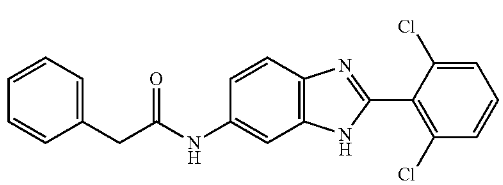 | N-[2-(2,6-Dichloro-phenyl)-3H-benzoimidazol-5-yl]-2-phenyl-acetamide | 396.04 |
| 1-11 | 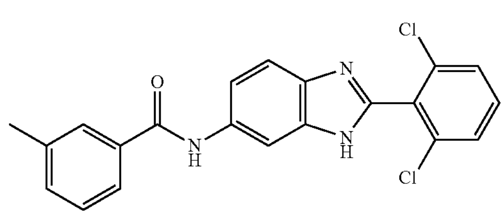 | N-[2-(2,6-Dichloro-phenyl)-3H-benzoimidazol-5-yl]-3-methyl-benzamide | 396.04 |

Example 1-12

N-[2-(2,6-Dichloro-phenyl)-3H-benzoimidazol-5-yl]-2,4,6-trimethyl-benzenesulfonamide

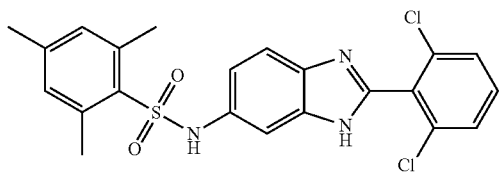

To a vial containing a solution of 2-(2,6-dichloro-phenyl)-3H-benzoimidazol-5-ylamine, prepared as described in Example 1-6, in dioxane (0.2 M, 0.10 mL) was added DIPEA (0.5 M in toluene, 0.050 mL), followed by 2,4,6-trimethyl-benzenesulfonyl chloride (0.2 M in toluene, 0.12 mL). After overnight at ambient temperature, solid phase extraction (SPE) by strong cation exchange (SCX) was followed by silica gel column chromatography to give N-[2-(2,6-Dichloro-phenyl)-3H-benzoimidazol-5-yl]-2,4,6-trimethyl-benzenesulfonamide: MS (m/z) 460.06 (M+1).

Example 1-13

2-(2,6-Dichloro-phenyl)-3H-benzoimidazole-5-carboxylic acid propylamide

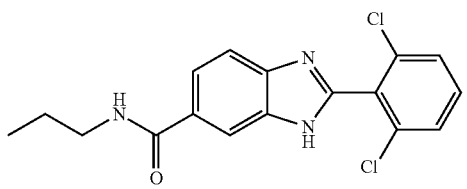

To a solution of 3,4-diamino-benzoic acid ethyl ester (0.9 g) and 2,6-dichlorobenzaldehyde (1.2 g) in DMSO (20 mL) was added Sc(OTf)$_3$ (0.1 g) and Cu(OTf)$_2$ (0.07 g). The mixture was stirred in an open flask at ambient temperature overnight, before it was poured into aqueous NH$_4$OH. Resulting precipitate was collected by filtration and the wet solid was dissolved in MeOH (20 mL). To it was added 1N NaOH (12 mL) and the mixture was heated to reflux overnight, when it was cooled to ambient temperature, diluted by water, and washed with ether. The aqueous phase was then carefully acidified to pH 3-4 and resulting precipitate was filtered and air dried to give crude 2-(2,6-dichloro-phenyl)-3H-benzoimidazole-5-carboxylic acid as tan solid: 1H NMR (400 MHz, CD3OD) 8.4 (br s, 1H), 8.0 (d, 1H), 7.7 (s, 1H), 7.6 (m, 3H).

The acid from above (1.0 g) was added to SOCl$_2$ (5 mL), a catalytic amount of DMF (0.05 mL) was added, and the mixture was stirred at ambient temperature overnight. Resulting slurry was diluted with toluene (20 mL), stirred vigorously for 1 h, filtered, and washed successively with toluene and dichloromethane to afford 2-(2,6-dichloro-phenyl)-3H-benzoimidazole-5-carbonyl chloride hydrochloride salt as a pale yellow solid.

A suspension of 2-(2,6-dichloro-phenyl)-3H-benzoimidazole-5-carbonyl chloride hydrochloride salt in acetonitrile (0.2 M, 0.10 mL) was added to a vial containing n-propylamine (0.2 M in toluene, 0.11 mL) and DIPEA (0.5M in toluene, 0.10 mL). After incubation on a shaker at ambient temperature overnight, the mixture was diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et$_3$N) and, after evaporation of volatiles, the crude was further purified by silica gel column chromatography to give 2-(2,6-dichloro-phenyl)-3H-benzoimidazole-5-carboxylic acid propylamide: MS (m/z) 347.95 (M+1).

In a multiple parallel fashion, the following compounds was prepared in the same way as described for Example 1-13:

| Example | Structure | Chemical Name | MS found (M + 1) |
|---|---|---|---|
| 1-14 | 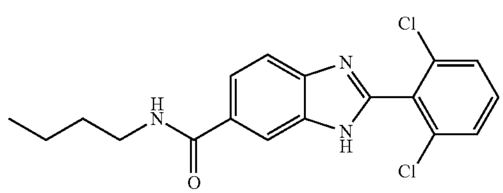 | 2-(2,6-Dichloro-phenyl)-3H-benzoimidazole-5-carboxylic acid butylamide | 361.93 |
| 1-15 | 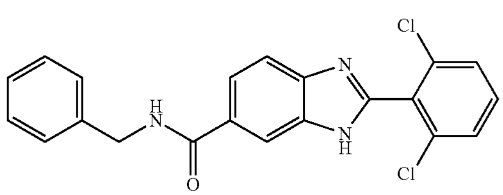 | 2-(2,6-Dichloro-phenyl)-3H-benzoimidazole-5-carboxylic acid benzylamide | 395.94 |

-continued

| Example | Structure | Chemical Name | MS found (M + 1) |
|---|---|---|---|
| 1-16 | 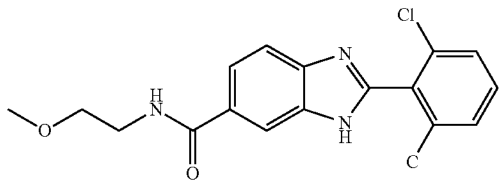 | 2-(2,6-Dichloro-phenyl)-3H-benzoimidazole-5-carboxylic acid (2-methoxy-ethyl)-amide | 363.94 |
| 1-17 | 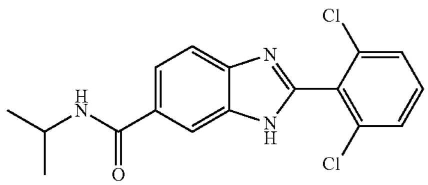 | 2-(2,6-Dichloro-phenyl)-3H-benzoimidazole-5-carboxylic acid isopropylamide | 347.95 |
| 1-18 | 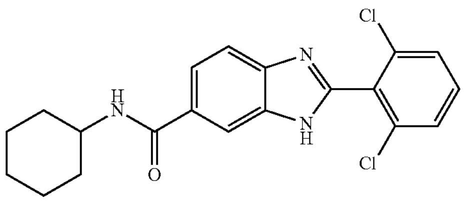 | 2-(2,6-Dichloro-phenyl)-3H-benzoimidazole-5-carboxylic acid cyclohexylamide | 387.94 |
| 1-19 | 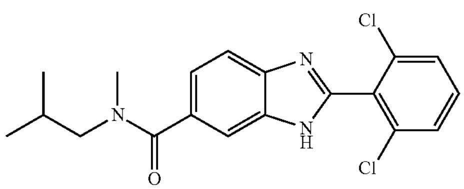 | 2-(2,6-Dichloro-phenyl)-3H-benzoimidazole-5-carboxylic acid isobutyl-methyl-amide | 375.97 |
| 1-20 | 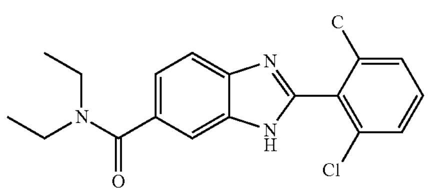 | 2-(2,6-Dichloro-phenyl)-3H-benzoimidazole-5-carboxylic acid diethylamide | 361.93 |
| 1-21 | 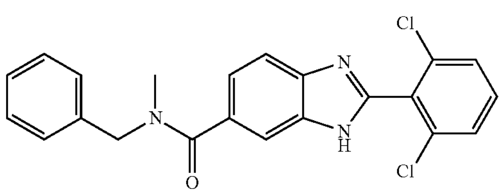 | 2-(2,6-Dichloro-phenyl)-3H-benzoimidazole-5-carboxylic acid benzyl-methyl-amide | 409.92 |
| 1-25 | 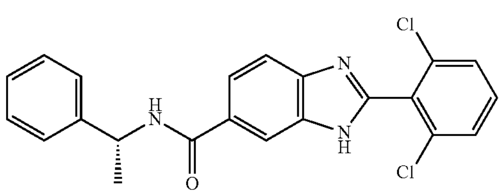 | 2-(2,6-Dichloro-phenyl)-3H-benzoimidazole-5-carboxylic acid ((R)-1-phenyl-ethyl)-amide | 409.97 |
| 1-26 | 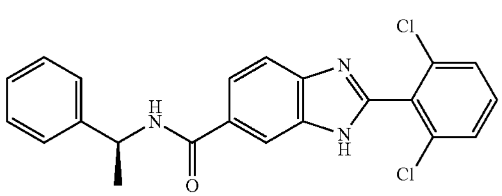 | 2-(2,6-Dichloro-phenyl)-3H-benzoimidazole-5-carboxylic acid ((S)-1-phenyl-ethyl)-amide | 409.97 |

-continued

| Example | Structure | Chemical Name | MS found (M + 1) |
|---|---|---|---|
| 1-27 | 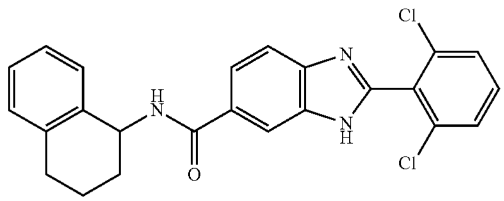 | 2-(2,6-Dichloro-phenyl)-3H-benzoimidazole-5-carboxylic acid (1,2,3.4-tetrahydro-naphthalen-1-yl)-amide | 436.03 |
| 1-28 | 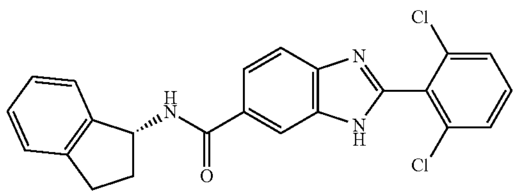 | 2-(2,6-Dichloro-phenyl)-3H-benzoimidazole-5-carboxylic acid (Rindan-1-ylamide | 421.96 |
| 1-29 | 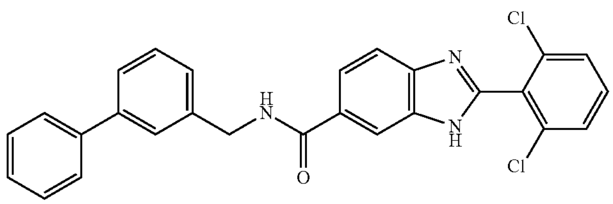 | 2-(2,6-Dichloro-phenyl)-3H-benzoimidazole-5-carboxylic acid (biphenyl-3-ylmethyl)-amide | 472.02 |
| 1-30 | 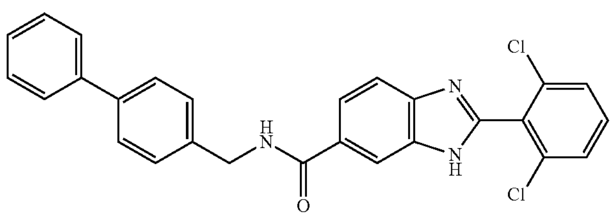 | 2-(2,6-Dichloro-phenyl)-3H-benzoimidazole-5-carboxylic acid (biphenyl-4-ylmethyl)-amide | 472.02 |
| 1-31 | 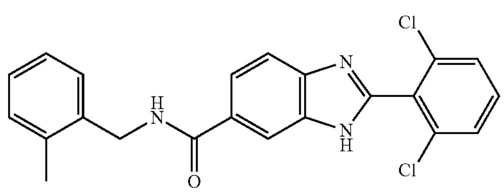 | 2-(2,6-Dichloro-phenyl)-3H-benzoimidazole-5-carboxylic acid 2-methyl-benzylamide | 409.97 |
| 1-32 | 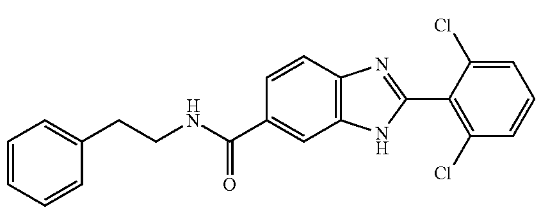 | 2-(2,6-Dichloro-phenyl)-3H-benzoimidazole-5-carboxylic acid phenethyl-amide | 409.97 |
| 1-33 | 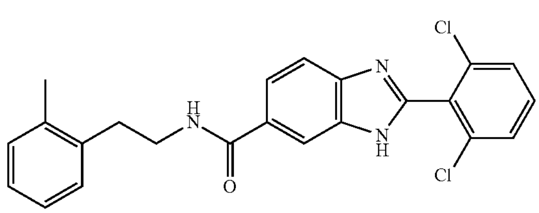 | 2-(2,6-Dichloro-phenyl)-3H-benzoimidazole-5-carboxylic acid (2-o-tolyl-ethyl)-amide | 424.01 |

-continued

| Example | Structure | Chemical Name | MS found (M + 1) |
|---|---|---|---|
| 1-34 | 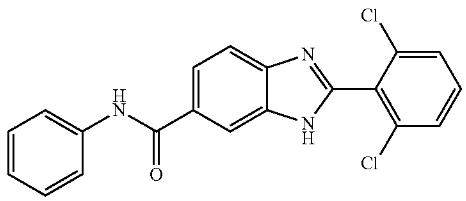 | 2-(2,6-Dichloro-phenyl)-3H-benzoimidazole-5-carboxylic acid phenylamide | 381.95 |
| 1-35 | 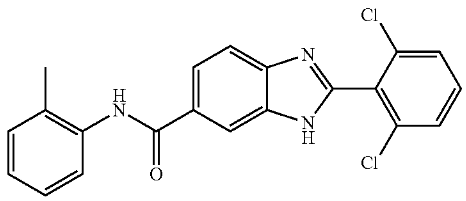 | 2-(2,6-Dichloro-phenyl)-3H-benzoimidazole-5-carboxylic acid o-tolylamide | 395.97 |
| 1-36 | 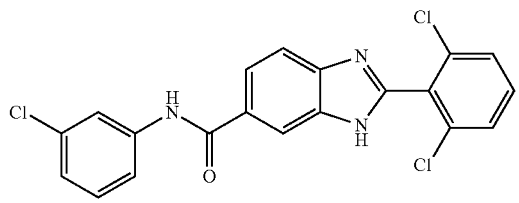 | 2-(2,6-Dichloro-phenyl)-3H-benzoimidazole-5-carboxylic acid (3-chloro-phenyl)-amide | 415.93 |
| 1-37 | 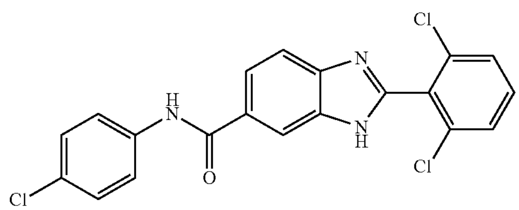 | 2-(2,6-Dichloro-phenyl)-3H-benzoimidazole-5-carboxylic acid (4-chloro-phenyl)-amide | 415.93 |
| 1-38 | 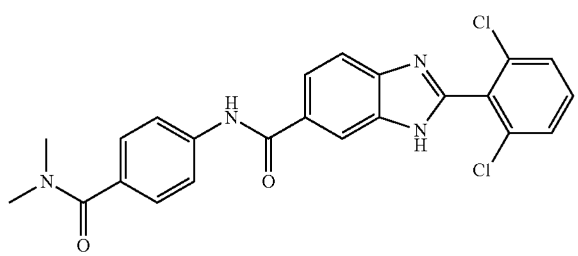 | 2-(2,6-Dichloro-phenyl)-3H-benzoimidazole-5-carboxylic acid (4-dimethylcarbamoyl-phenyl)-amide | 453.02 |
| 1-39 | 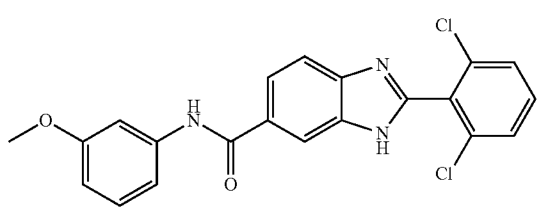 | 2-(2,6-Dichloro-phenyl)-3H-benzoimidazole-5-carboxylic acid (3-methoxy-phenyl)-amide | 411.98 |
| 1-40 | 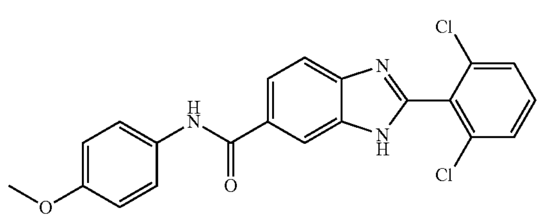 | 2-(2,6-Dichloro-phenyl)-3H-benzoimidazole-5-carboxylic acid (4-methoxy-phenyl)-amide | 411.98 |

-continued

| Example | Structure | Chemical Name | MS found (M + 1) |
|---|---|---|---|
| 1-41 | 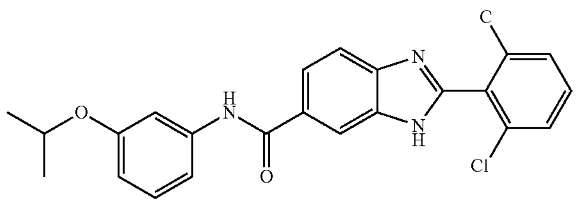 | 2-(2,6-Dichloro-phenyl)-3H-benzoimidazole-5-carboxylic acid (3-isopropoxy-phenyl)-amide | 440.06 |
| 1-42 | 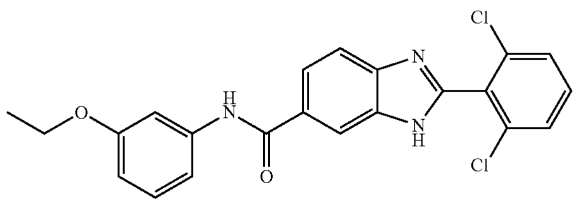 | 2-(2,6-Dichloro-phenyl)-3H-benzoimidazole-5-carboxylic acid (3-ethoxy-phenyl)-amide | 426 |
| 1-43 | 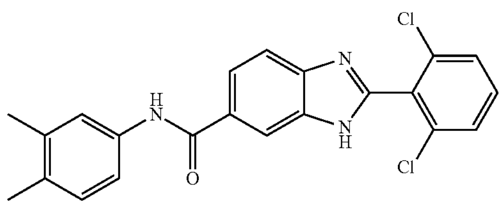 | 2-(2,6-Dichloro-phenyl)-3H-benzoimidazole-5-carboxylic acid (3,4-dimethyl-phenyl)-amide | 410.04 |
| 1-44 | 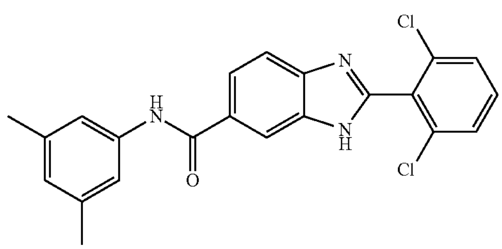 | 2-(2,6-Dichloro-phenyl)-3H-benzoimidazole-5-carboxylic acid (3,5-dimethyl-phenyl)-amide | 410.04 |
| 1-45 | 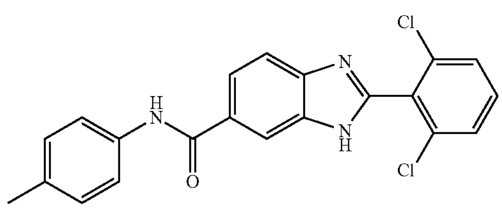 | 2-(2,6-Dichloro-phenyl)-3H-benzoimidazole-5-carboxylic acid p-tolylamide | 396.03 |
| 1-46 | 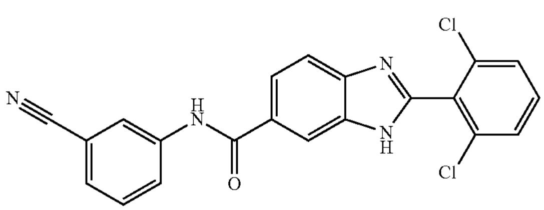 | 2-(2,6-Dichloro-phenyl)-3H-benzoimidazole-5-carboxylic acid (3-cyano-phenyl)-amide | 406.99 |
| 1-47 | 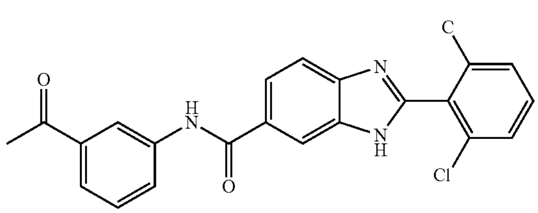 | 2-(2,6-Dichloro-phenyl)-3H-benzoimidazole-5-carboxylic acid (3-acetyl-phenyl)-amide | 424.01 |

| Example | Structure | Chemical Name | MS found (M + 1) |
|---|---|---|---|
| 1-48 | 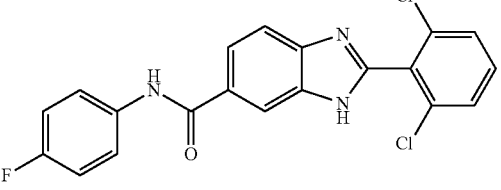 | 2-(2,6-Dichloro-phenyl)-3H-benzoimidazole-5-carboxylic acid (4-fluoro-phenyl)-amide | 399.99 |
| 1-49 | 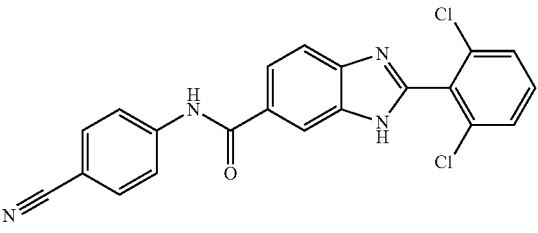 | 2-(2,6-Dichloro-phenyl)-3H-benzoimidazole-5-carboxylic acid (4-cyano-phenyl)-amide | 406.99 |
| 1-50 | 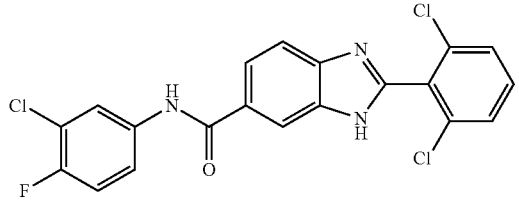 | 2-(2,6-Dichloro-phenyl)-3H-benzoimidazole-5-carboxylic acid (3-chloro-4-fluoro-phenyl)-amide | 433.96 |
| 1-51 | 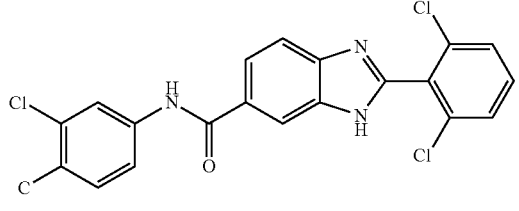 | 2-(2,6-Dichloro-phenyl)-3H-benzoimidazole-5-carboxylic acid (3,4-dichloro-phenyl)-amide | 449.94 |
| 1-52 | 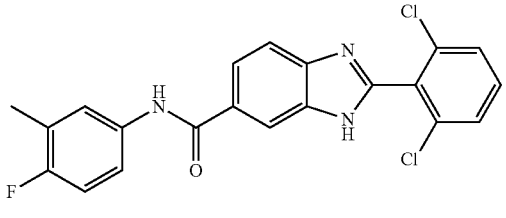 | 2-(2,6-Dichloro-phenyl)-3H-benzoimidazole-5-carboxylic acid (4-fluoro-3-methyl-phenyl)-amide | 413.99 |
| 1-53 | 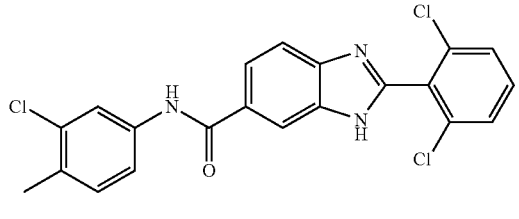 | 2-(2,6-Dichloro-phenyl)-3H-benzoimidazole-5-carboxylic acid (3-chloro-4-methyl-phenyl)-amide | 430 |
| 1-54 | 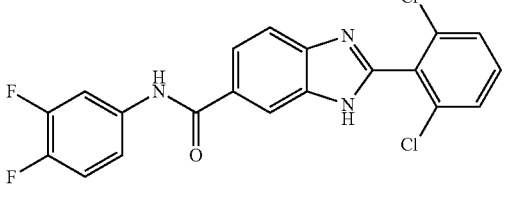 | 2-(2,6-Dichloro-phenyl)-3H-benzoimidazole-5-carboxylic acid (3,4-difluoro-phenyl)-amide | 417.98 |

-continued

| Example | Structure | Chemical Name | MS found (M + 1) |
|---|---|---|---|
| 1-55 | 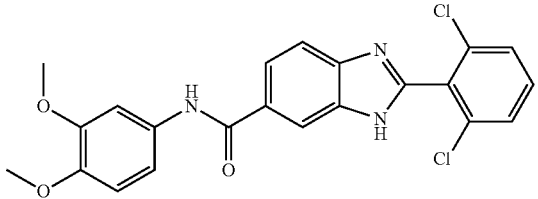 | 2-(2,6-Dichloro-phenyl)-3H-benzoimidazole-5-carboxylic acid (3,4-dimethoxy-phenyl)-amide | 440.06 |
| 1-56 | 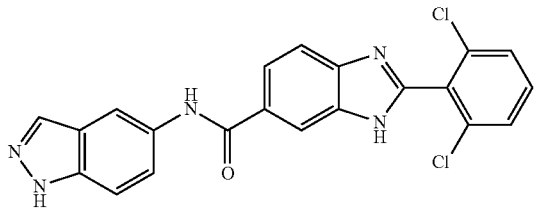 | 2-(2,6-Dichloro-phenyl)-3H-benzoimidazole-5-carboxylic acid (1H-indazol-5-yl)-amide | 422.03 |
| 1-57 | 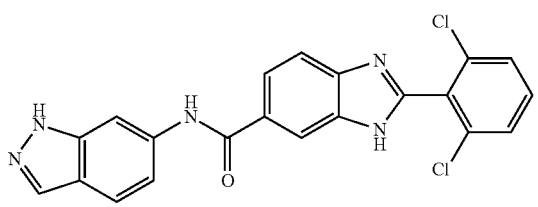 | 2-(2,6-Dichloro-phenyl)-3H-benzoimidazole-5-carboxylic acid (1H-indazol-6-yl)-amide | 422.03 |
| 1-58 | 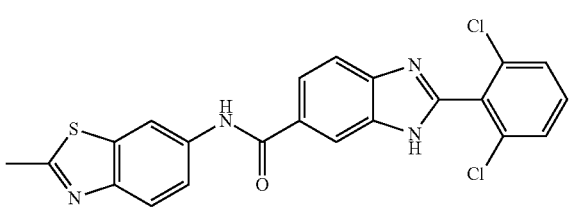 | 2-(2,6-Dichloro-phenyl)-3H-benzoimidazole-5-carboxylic acid (2-methyl-benzothiazol-6-yl)-amide | 453.02 |
| 1-59 | 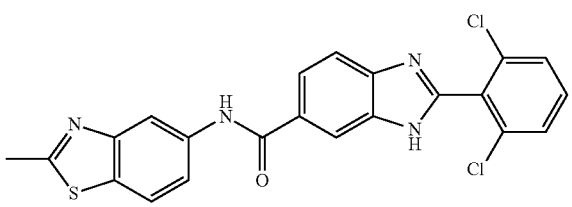 | 2-(2,6-Dichloro-phenyl)-3H-benzoimidazole-5-carboxylic acid (2-methyl-benzothiazol-5-yl)-amide | 453.02 |
| 1-60 | 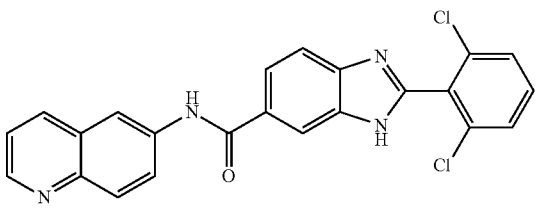 | 2-(2,6-Dichloro-phenyl)-3H-benzoimidazole-5-carboxylic acid quinoli6-ylamide | 433.03 |
| 1-61 | 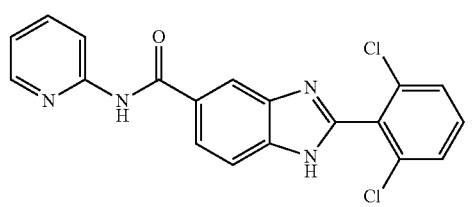 | 2-(2,6-Dichloro-phenyl)-1H-benzoimidazole-5-carboxylic acid pyridin-2-ylamide | 383.1 |

-continued

| Example | Structure | Chemical Name | MS found (M + 1) |
|---|---|---|---|
| 1-62 | 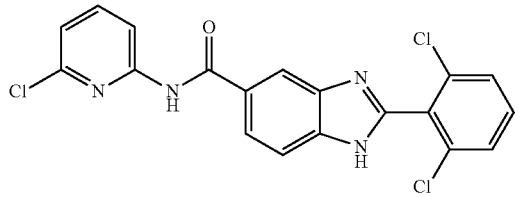 | 2-(2,6-Dichloro-phenyl)-1H-benzoimidazole-5-carboxylic acid (6-chloro-pyridin-2-yl)-amide | 419.1 |
| 1-63 | 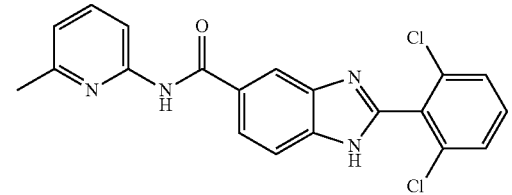 | 2-(2,6-Dichloro-phenyl)-1H-benzoimidazole-5-carboxylic acid (6-methyl-pyridin-2-yl)-amide | 397.1 |
| 1-64 | 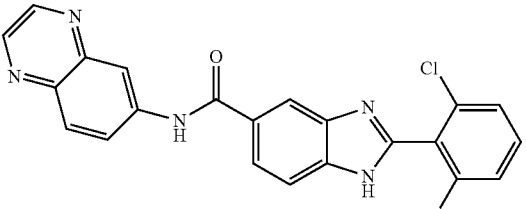 | 2-(2,6-Dichloro-phenyl)-1H-benzoimidazole-5-carboxylic acid quinoxalin-6-ylamide | 434.1 |
| 1-65 | 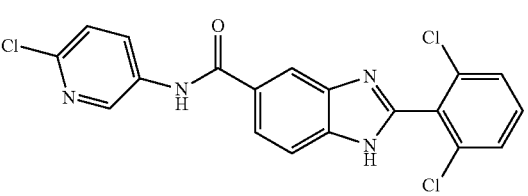 | 2-(2,6-Dichloro-phenyl)-1H-benzoimidazole-5-carboxylic acid (6-chloro-pyridin-3-yl)-amide | 419.1 |
| 1-66 | 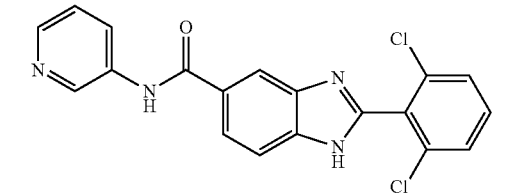 | 2-(2,6-Dichloro-phenyl)-1H-benzoimidazole-5-carboxylic acid pyridin-3-ylamide | 383.1 |
| 1-67 | 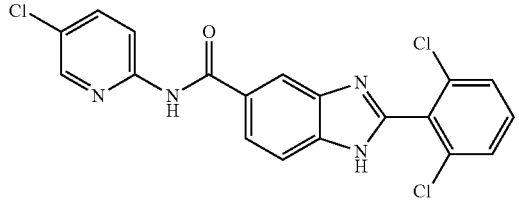 | 2-(2,6-Dichloro-phenyl)-1H-benzoimidazole-5-carboxylic acid (5-chloro-pyridin-2-yl)-amide | 419.1 |
| 1-68 | 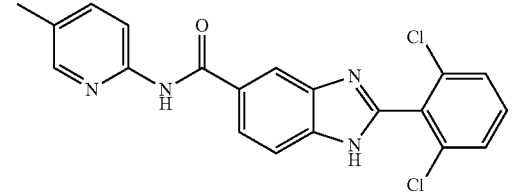 | 2-(2,6-Dichloro-phenyl)-1H-benzoimidazole-5-carboxylic acid (5-methyl-pyridin-2-yl)-amide | 397.1 |

| Example | Structure | Chemical Name | MS found (M + 1) |
|---|---|---|---|
| 1-69 | 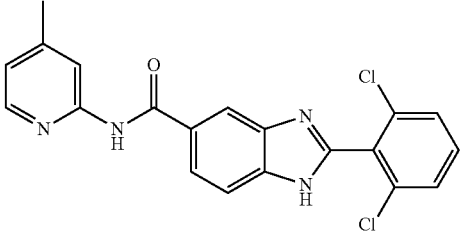 | 2-(2,6-Dichloro-phenyl)-1H-benzoimidazole-5-carboxylic acid (4-methyl-pyridin-2-yl)-amide | 397.1 |
| 1-70 | 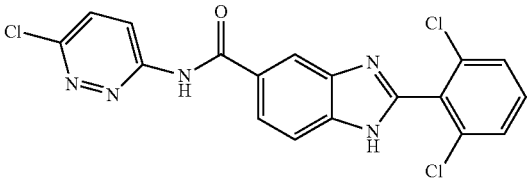 | 2-(2,6-Dichloro-phenyl)-1H-benzoimidazole-5-carboxylic acid (6-chloro-pyridazin-3-yl)-amide | 420.1 |
| 1-71 | 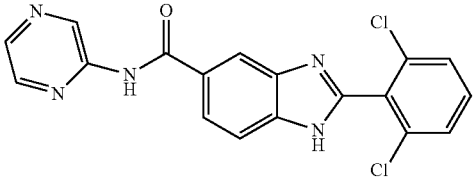 | 2-(2,6-Dichloro-phenyl)-1H-benzoimidazole-5-carboxylic acid pyrazin-2-ylamide | 384.2 |
| 1-72 | 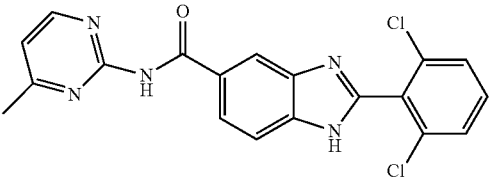 | 2-(2,6-Dichloro-phenyl)-1H-benzoimidazole-5-carboxylic acid (4-methyl-pyrimidin-2-yl)-amide | 398.1 |
| 1-73 | 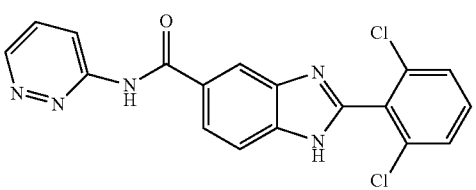 | 2-(2,6-Dichloro-phenyl)-1H-benzoimidazole-5-carboxylic acid pyridazin-3-ylamide | 384.0 |
| 1-74 | 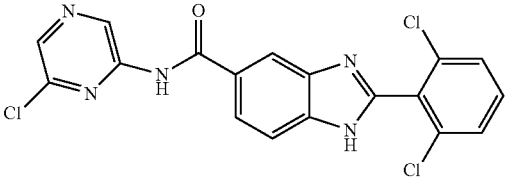 | 2-(2,6-Dichloro-phenyl)-1H-benzoimidazole-5-carboxylic acid (6-chloro-pyrazin-2-yl)-amide | 418.0 |
| 1-75 | 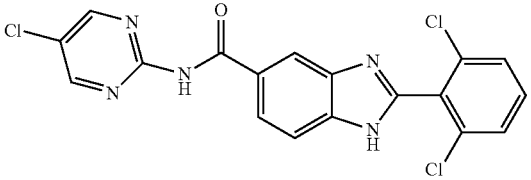 | 2-(2,6-Dichloro-phenyl)-1H-benzoimidazole-5-carboxylic acid (5-chloro-pyrimidin-2-yl)-amide | 418.0 |

| Example | Structure | Chemical Name | MS found (M + 1) |
|---|---|---|---|
| 1-76 | 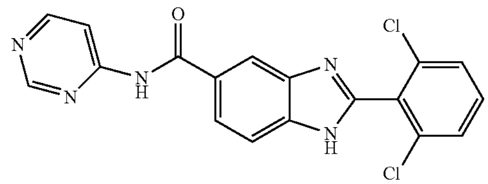 | 2-(2,6-Dichloro-phenyl)-1H-benzoimidazole-5-carboxylic acid pyrimidin-4-ylamide | 384.2 |
| 1-77 | 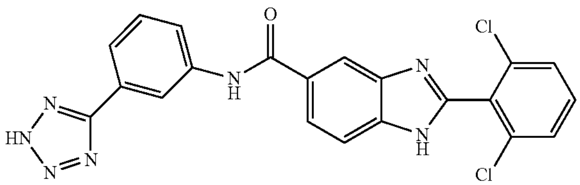 | 2-(2,6-Dichloro-phenyl)-1H-benzoimidazole-5-carboxylic acid [3-(2H-tetrazol-5-yl)-phenyl]-amide | 450.2 |

Example 1-78

2-(2,6-Dichloro-phenyl)-3H-benzoimidazole-5-carboxylic acid [2-(3-chloro-phenyl)-ethyl]-amide

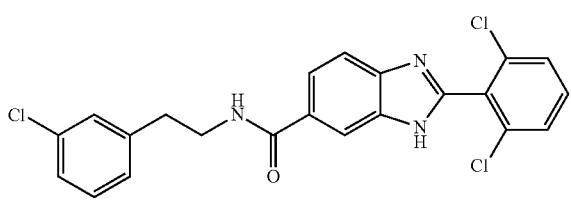

A solution of 2-(2,6-dichloro-phenyl)-3H-benzoimidazole-5-carboxylic acid (107.5 mg), 3-chlorophenethylamine (54.5 mg), BOP (186 mg) and DIEA (0.091 mL) in DMF (1 mL) was stirred at room temperature for 60 h. Then 1N NaOH aqueous solution was added. The aqueous layer was extracted with EtOAc, and the organic extracts were dried over $Na_2SO_4$, filtered and concentrated under reduced pressure. The crude product was purified by column chromatography ($SiO_2$, EtOAc:Hexane=20:80 to 80:10) and prep-HPLC later to give 2-(2,6-dichloro-phenyl)-3H-benzoimidazole-5-carboxylic acid [2-(3-chloro-phenyl)-ethyl]-amide: MS (m/z) 446 (M+1).

By employing the method of Example 1-78, using appropriate starting materials, the following compounds were prepared:

| Example | Structure | Chemical Name | MS found (M + 1) |
|---|---|---|---|
| 1-79 | 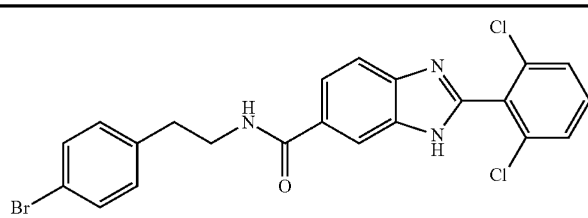 | 2-(2,6-Dichloro-phenyl)-3H-benzoimidazole-5-carboxylic acid [2-(4-bromo-phenyl)-ethyl]-amide | 490 |
| 1-80 | 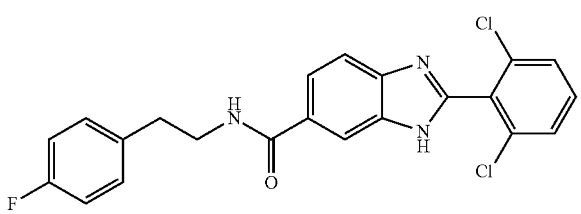 | 2-(2,6-Dichloro-phenyl)-3H-benzoimidazole-5-carboxylic acid [2-(4-fluoro-phenyl)-ethyl]-amide | 428 |
| 1-81 | 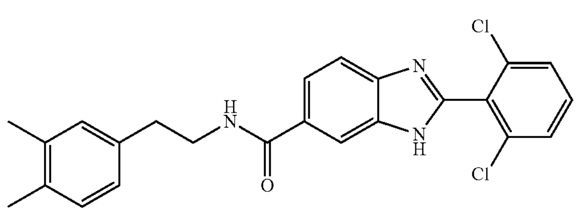 | 2-(2,6-Dichloro-phenyl)-3H-benzoimidazole-5-carboxylic acid [2-(3,4-dimethyl-phenyl)-ethyl]-amide | 438 |

| Example | Structure | Chemical Name | MS found (M + 1) |
|---|---|---|---|
| 1-82 | 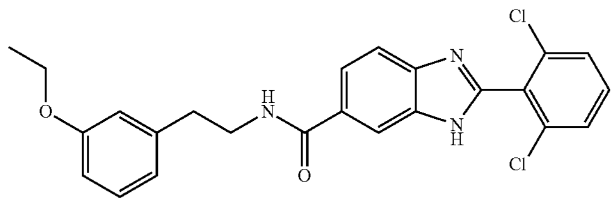 | 2-(2,6-Dichloro-phenyl)-3H-benzoimidazole-5-carboxylic acid [2-(3-ethoxy-phenyl)-ethyl]-amide | 454 |
| 1-83 | 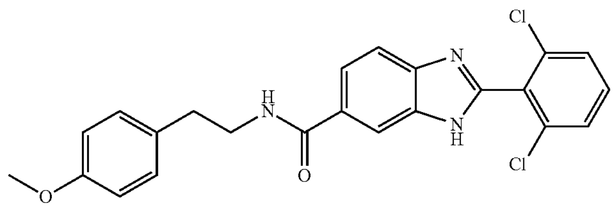 | 2-(2,6-Dichloro-phenyl)-3H-benzoimidazole-5-carboxylic acid [2-(4-methoxy-phenyl)-ethyl]-amide | 440 |
| 1-84 | 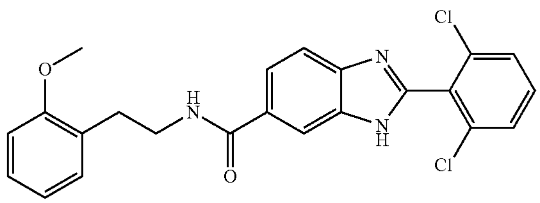 | 2-(2,6-Dichloro-phenyl)-3H-benzoimidazole-5-carboxylic acid [2-(2-methoxy-phenyl)-ethyl]-amide | 441 |
| 1-85 | 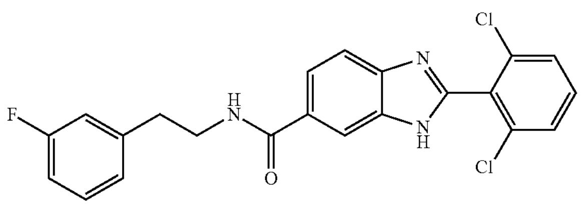 | 2-(2,6-Dichloro-phenyl)-3H-benzoimidazole-5-carboxylic acid [2-(3-fluoro-phenyl)-elhyl]-amide | 428 |
| 1-86 | 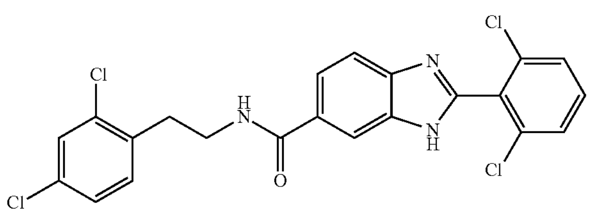 | 2-(2,6-Dichloro-phenyl)-3H-benzoimidazole-5-carboxylic acid [2-(2,4-dichloro-phenyl)-ethyl]-amide | 480 |
| 1-87 | 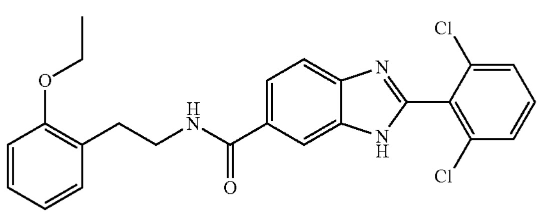 | 2-(2.6-Dichloro-phenyl)-3H-benzoimidazole-5-carboxylic acid [2-(2-ethoxy-phenyl)-ethyl]-amide | 455 |
| 1-88 | 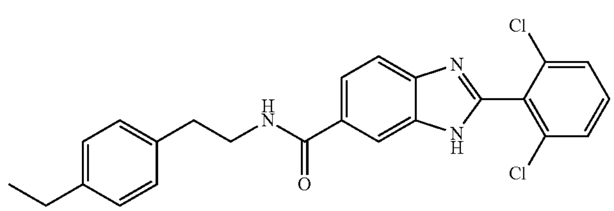 | 2-(2,6-Dichloro-phenyl)-3H-benzoimidazole-5-carboxylic acid [2-(4-ethyl-phenyl)-ethyl]-amide | 438 |

| Example | Structure | Chemical Name | MS found (M + 1) |
|---|---|---|---|
| 1-89 | 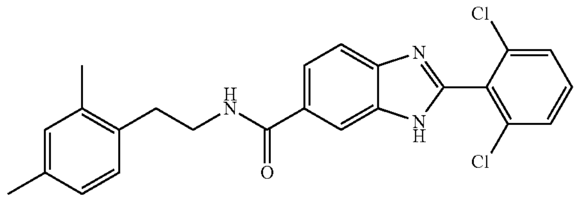 | 2-(2,6-Dichloro-phenyl)-3H-benzoimidazole-5-carboxylic acid [2-(2,4-dimethyl-phenyl)-ethyl]-amide | 438 |
| 1-90 | 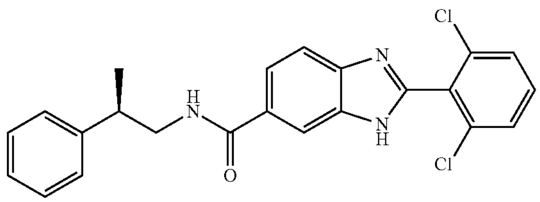 | (2,6-Dichloro-phenyl)-3H-benzoimidazole-5-carboxylic acid ((R)-2-phenyl-propyl)-amide | 424 |
| 1-91 | 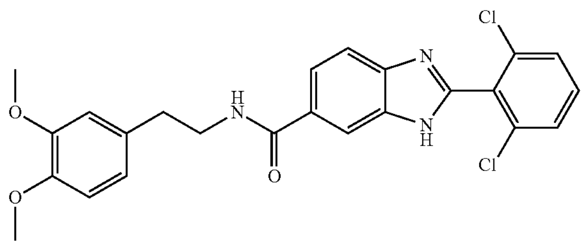 | 2-(2,6-Dichloro-pheny)-3H-benzoimidazole-5-carboxylic acid [2-(3,4-dimethoxy-phenyl)-ethyl]-amide | 470 |
| 1-92 | 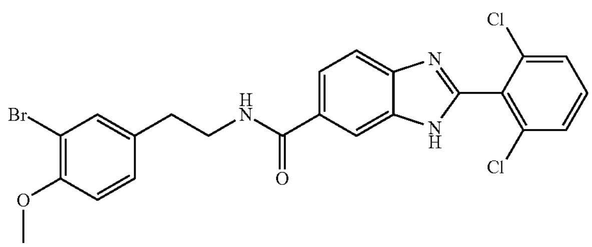 | 2-(2,6-Dichloro-phenyl)-3H-benzoimidazole-5-carboxylic acid [2-(3-bromo-4-methoxy-phenyl)-ethyl]-amide | 520 |
| 1-93 | 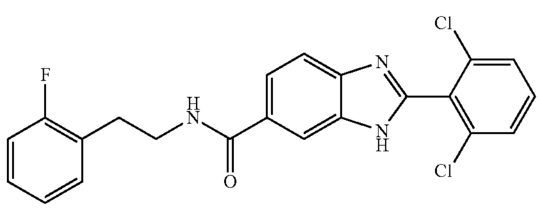 | 2-(2,6-Dichloro-phenyl)-3H-benzoimidazole-5-carboxylic acid [2-(2-fluoro-phenyl)-ethyl]-amide | 428 |
| 1-94 | 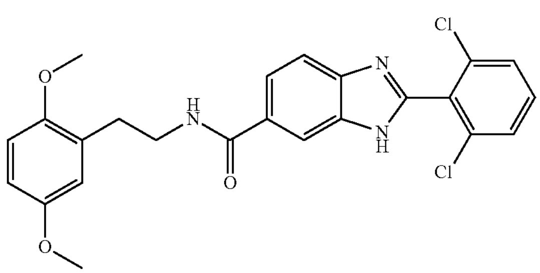 | (2,6-Dichloro-phenyl)-3H-benzoimidazole-5-carboxylic acid [2-(2,5-dimethoxy-phenyl)-ethyl]-amide | 470 |

-continued

| Example | Structure | Chemical Name | MS found (M + 1) |
|---|---|---|---|
| 1-95 | 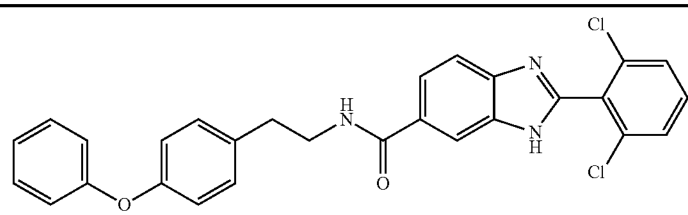 | 2-(2,6-Dichloro-phenyl)-3H-benzoimidazole-5-carboxylic acid [2-(4-phenoxy-phenyl)-ethyl]-amide | 502 |
| 1-96 | 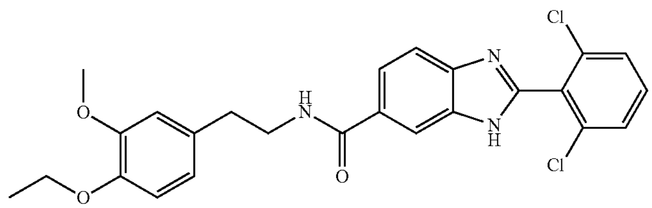 | 2-(2,6-Dichloro-phenyl)-3H-benzoimidazole-5-carboxylic acid [2-(4-ethoxy-3-methoxy-phenyl)-ethyl]-amide | 484 |
| 1-97 | 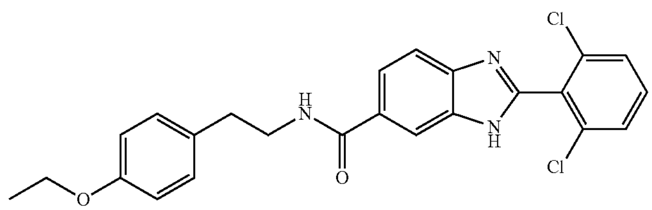 | 2-(2,6-Dichloro-phenyl)-3H-benzoimidazole-5-carboxylic acid [2-(4-ethoxy-phenyl)-ethyl]-amide | 454 |
| 1-98 | 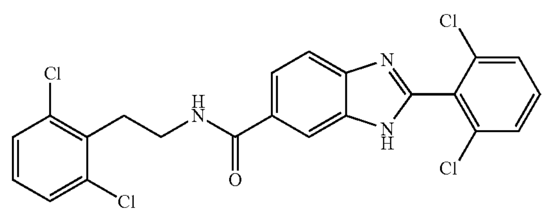 | 2-(2,6-Dichloro-phenyl)-3H-benzoimidazole-5-carboxylic acid [2-(2,6-dichloro-phenyl)-ethyl]-amide | 480 |
| 1-99 | 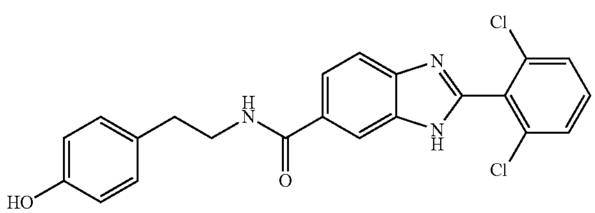 | 2-(2,6-Dichloro-phenyl)-3H-benzoimidazole-5-carboxylic acid [2-(4-hydroxy-phenyl)-ethyl]-amide | 426 |
| 1-100 | 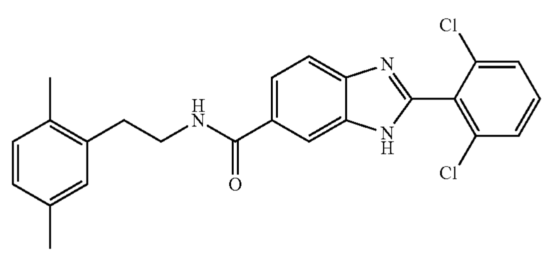 | 2-(2,6-Dichloro-phenyl)-3H-benzoimidazole-5-carboxylic acid [2-(2,5-dimethyl-phenyl)-ethyl]-amide | 438 |
| 1-101 | 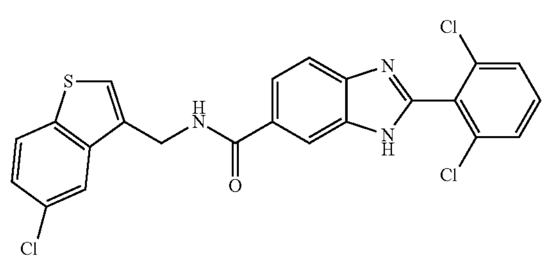 | 2-(2,6-Dichloro-phenyl)-3H-benzoimidazole-5-carboxylic acid (5-chloro-benzo[b]thiophen-3-ylmethyl)-amide | 488 |

| Example | Structure | Chemical Name | MS found (M + 1) |
|---|---|---|---|
| 1-102 | 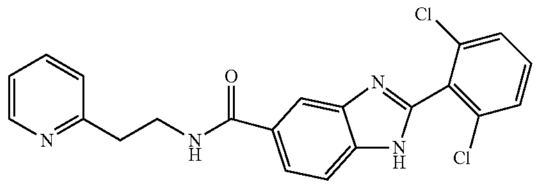 | 2-(2,6-Dichloro-phenyl)-1H-benzoimidazole-5-carboxylic acid [2-pyridin-2-yl-ethyl)-amide | 411.0 |
| 1-103 | 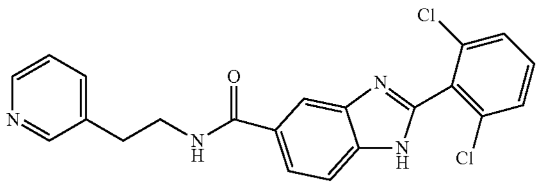 | 2-(2,6-Dichloro-phenyl)-1H-benzoimidazole-3-carboxylic acid (2-pyridin-3-yl-ethyl)-amide | 411.1 |
| 1-104 | 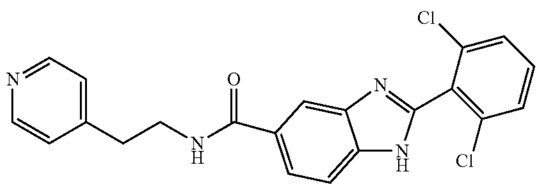 | 2-(2,6-Dichloro-phenyl)-1H-benzoimidazole-5-carboxylic acid (2-pyridin-4-yl-ethyl)-amide | 411.1 |

Example 1-105

2-(2,6-Dichloro-phenyl)-3H-benzoimidazole-5-carboxylic acid (3-chloro-phenyl)-methyl-amide

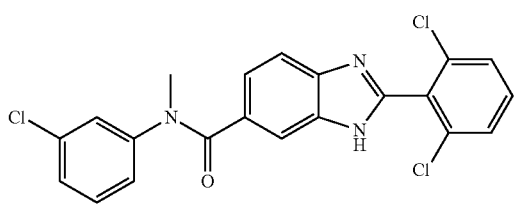

A solution of 2-(2,6-dichloro-phenyl)-3H-benzoimidazole-5-carboxylic acid (107.5 mg, 0.35 mmol). N-methyl-3-chloroaniline (50 mg, 0.35 mmol), BOP (186 mg, 0.42 mmol) and DIEA (0.091 mL, 0.53 mmol) in DMF (1 mL) was stirred at room temperature for 60 h. Then 1N NaOH aqueous solution was added. The aqueous layer was extracted with EtOAc, and the organic extracts were dried over $Na_2SO_4$, filtered and concentrated under reduced pressure. The crude product was purified by column chromatography ($SiO_2$, EtOAc:Hexane=20:80 to 80:10) and prep-HPLC later to give 2-(2,6-dichloro-phenyl)-3H-benzoimidazole-5-carboxylic acid (3-chloro-phenyl)-methyl-amide: MS (m/z) 432 (M+1); $^1$H NMR ($CDCl_3$, 400 MHz) δ 9.86 (s, 1H), 7.87 (s, 1H), 7.59 (d, 1H), 7.28-7.42 (m, 4H), 7.18 (s, 1H), 7.13 (t, 2H), 6.93 (t, 1H), 3.51 (s, 3H) (major tautomer).

Example 1-106

2-(2,6-Dichloro-phenyl)-3H-benzoimidazole-5-sulfonic acid (3,4-dimethyl-phenyl)-amide

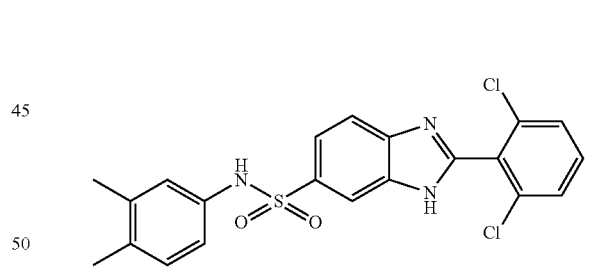

To a solution of 4-chloro-3-nitro-benzenesulfonyl chloride (0.51 g) in pyridine (2 mL) were added 3,4-dimethylaniline and dimethylaminopyridine (0.024 g). The reaction mixture was stirred overnight, concentrated under reduced pressure, and diluted with $CH_2Cl_2$. The mixture was washed with water, dried over $Na_2SO_4$, and concentrated in vacuo. The residue was purified by column chromatography ($SiO_2$, 1:3 EtOAc/Hexane) to give 4-chloro-N-(3,4-dimethyl-phenyl)-3-nitro-benzenesulfonamide.

To a suspension of 4-chloro-N-(3,4-dimethyl-phenyl)-3-nitro-benzenesulfonamide (0.22 g) in dioxane (2 mL) was added $NH_4OH$ (3 mL). The reaction mixture was heated to 95° C. for 8 h. The mixture was cooled to room temperature, diluted with water, and extracted with $CH_2Cl_2$. The extract was dried over $Na_2SO_4$ and concentrated in vacuo. Purification by column chromatography (SiO$_2$, 3:1 hexane/EtOAc) afforded 4-amino-N-(3,4-dimethyl-phenyl)-3-nitro-benzenesulfonamide.

To a solution of 4-amino-N-(3,4-dimethyl-phenyl)-3-nitro-benzenesulfonamide (0.12 g) in MeOH (5 mL) was added 10% Pd/C (0.04 g). The reaction mixture was stirred overnight under H$_2$ balloon. The mixture was filtered through a Celite pad, washed with MeOH, and concentrated in vacuo. The residue was purified by column chromatography (SiO$_2$, EtOAc) to give 3,4-diamino-N-(3,4-dimethyl-phenyl)-benzene-sulfonamide.

A freshly prepared solution of 3,4-diamino-N-(3,4-dimethyl-phenyl)-benzenesulfonamide in DMSO (0.2 M, 0.40 mL) was placed in a vial. To it was added 2,6-dichlorobenzaldehyde (0.2 M in toluene, 0.48 mL), followed by FeCl$_3$ (0.02 M in THF, 0.2 mL). The mixture was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give 2-(2,6-dichloro-phenyl)-3H-benzoimidazole-5-sulfonic acid (3,4-dimethyl-phenyl)-amide: MS (m/z) 446 (M+1).

Example 1-107

2-(2,6-Dichloro-phenyl)-3H-benzoimidazole-5-sulfonic acid (2-methyl-benzothiazolyl-5-yl)-amide

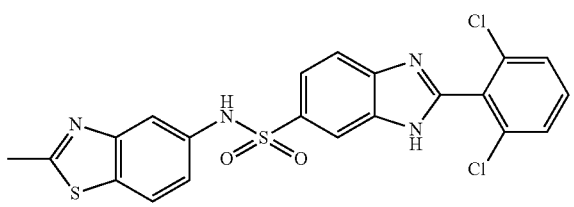

The similar procedure was repeated as described in Example 1-106, using appropriate starting materials to give 2-(2,6-dichloro-phenyl)-3H-benzoimidazole-5-sulfonic acid (2-methyl-benzothiazolyl-5-yl)-amide: MS (m/z) 489 (M+1).

Example 1-108

2-(2,6-Dimethyl-phenyl)-3H-benzoimidazole-5-carboxylic acid (3-chloro-phenyl)-amide

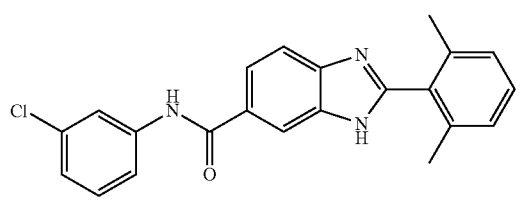

A solution of 4-amino-3-nitrobenzoic acid (0.5 g), 3-chloroaniline (0.29 mL), BOP (1.46 g) and DIEA (0.72 mL) in DMF (5 mL) was stirred at room temperature for 20 h. Then saturated NaHCO$_3$ aqueous solution was added. The aqueous layer was extracted with CH$_2$Cl$_2$, and the organic extracts were dried over Na$_2$SO$_4$, filtered and concentrated under reduced pressure. The crude product was purified by column chromatography (SiO$_2$, EtOAc:Hexane=12:88 to 100:0) to give 4-amino-N-(3-chloro-phenyl)-3-nitrobenzamide as a yellow solid: MS (m/z) 292 (M+1); $^1$H NMR (DMSO-d6, 400 MHz) δ 10.32 (s, 1H), 8.73 (s, 1H), 7.97 (d, 1H), 7.94 (s, 1H), 7.87 (s, 2H), 7.69 (d, 1H), 7.37 (t, 1H), 7.16 (d, 1H), 7.10 (d, 1H).

To a solution of 4-amino-N-(3-chloro-phenyl)-3-nitrobenzamide (590 mg) in EtOAc (200 mL) was added 10% Pd/C (100 mg). The reaction mixture was stirred overnight under H+ balloon. The reaction mixture was filtered through a Celite pad, washed with EtOAc. The solution was concentrated under reduced pressure. The crude product was purified by column chromatography (SiO$_2$, EtOAc:Hexane=20:80 to 100:0) to give of 3,4-diamino-N-(3-chloro-phenyl)-benzamide as a white solid: MS (m/z) 262 (M+1); $^1$H NMR (DMSO-d6, 400 MHz) δ 9.84 (s, 1H), 7.95 (t, 1H), 7.67 (d, 1H), 7.32 (t, 1H), 7.12 (m, 2H), 7.07 (dd, 1H), 6.54 (d, 1H), 5.12 (s, 2H), 4.63 (s, 2H).

A mixture of 3,4-diamino-N-(3-chloro-phenyl)-benzamide (0.1 mL in 0.2 M DMSO solution), 2,6-dimethyl-benzaldehyde (0.1 mL in 0.2 M toluene solution) and YB(SO$_3$CF$_3$)$_3$ (0.1 mL in 0.02M THF solution) was shaked at room temperature for 16 h. Then another 0.04 mL of 2,6-dimethyl benzaldehyde (0.2 M) toluene solution was added. The mixture was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give of 2-(2,6-dimethyl-phenyl)-3H-benzoimidazole-5-carboxylic acid (3-chloro-phenyl)-amide as white powder: MS (m/z) 376 (M+1).

Example 1-109

2-o-Tolyl-3H-benzoimidazole-5-carboxylic acid (3-chloro-phenyl)-amide

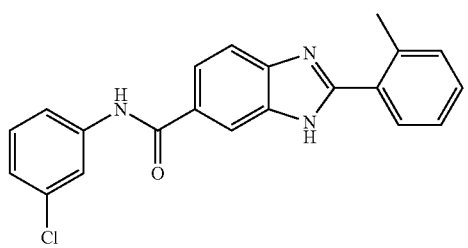

A mixture of 3,4-diamino-N-(3-chloro-phenyl)-benzamide (0.1 mL in 0.2 M DMSO solution), 2-methyl benzaldehyde (0.1 mL in 0.2 M toluene solution) and FeCl$_3$ (0.05 mL in 0.02M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give 2-o-tolyl-3H-benzoimidazole-5-carboxylic acid (3-chloro-phenyl)-amide as white powder: MS (m/z) 362 (M+1).

Example 1-110

{4-[6-(3-Chloro-phenylcarbamoyl)-1H-benzoimidazol-2-yl]-3,5-dimethyl-phenoxy}-acetic acid ethyl ester

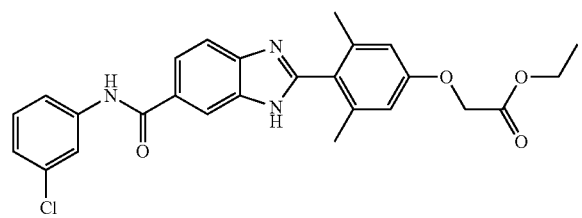

A mixture of 4-hydroxy-2,6-dimethyl-benzaldehyde (87 mg), ethyl chloroacetate (85 mg) and Cs$_2$CO$_3$ (375 mg) in acetone (4 mL) was stirred at room temperature for 16 h. The mixture was concentrated, diluted with water, and extracted with EtOAc. The organic extracts were washed with brine, dried over Na$_2$SO4, and concentrated under reduced pressure to give (4-formyl-3,5-dimethyl-phenoxy)-acetic acid ethyl ester: MS (m/z) 237 (M+1); $^1$H NMR (CDCl$_3$, 400 MHz) δ 10.48 (s, 1H), 6.59 (s, 2H), 4.66 (s, 2H), 4.29 (q, 2H), 2.60 (s, 6H), 3.29 (t, 3H).

A mixture of 3,4-diamino-N-(3-chloro-phenyl)-benzamide (0.1 mL in 0.2 M DMSO solution), (4-formyl-3,5-dimethyl-phenoxy)-acetic acid ethyl ester (0.1 mL in 0.2 M toluene solution) and FeCl$_3$ (0.05 mL in 0.02M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give {4-[6-(3-Chloro-phenylcarbamoyl)-1H-benzoimidazol-2-yl]-3,5-dimethyl-phenoxy}-acetic acid ethyl ester: MS (m/z) 478 (M+1).

Example 1-111

{4-[6-(3-Chloro-phenylcarbamoyl)-1H-benzoimidazol-2-yl]-3,5-dimethyl-phenoxy}-acetic acid

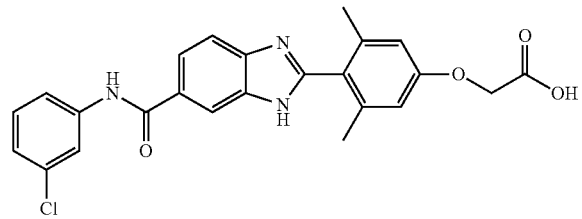

A solution of {4-[6-(3-Chloro-phenylcarbamoyl)-1H-benzoimidazol-2-yl]-3,5-dimethyl-phenoxy}-acetic acid ethyl ester (71.7 mg) in 2N LiOH aqueous solution (1 mL) and THF (1 mL) was stirred at room temperature for 16 h. The mixture was washed with Et$_2$O. The aqueous layer was acidified to pH 3 with 1N HCl aqueous solution, extracted with EtOAc, and the organic extracts were dried over Na$_2$SO$_4$, filtered and concentrated under reduced pressure to give {4-[6-(3-Chloro-phenylcarbamoyl)-1H-benzoimidazol-2-yl]-3,5-dimethyl-phenoxy}-acetic acid as white solid: MS (m/z) 444 (M+1); $^1$H NMR (MeOD, 400 MHz) δ 8.17 (s, 1H), 7.84 (d, 1H), 7.82 (s, 1H), 7.62 (d, 1H), 7.54 (d, 1H), 7.25 (t, 1H), 7.06 (dd, 1H), 6.70 (s, 2H), 4.59 (s, 2H), 2.06 (s, 6H).

Example 1-112

{4-[6-(3-Chloro-phenylcarbamoyl)-1H-benzoimidazol-2-yl]-3-methyl-phenyl}-carbamic acid ethyl ester

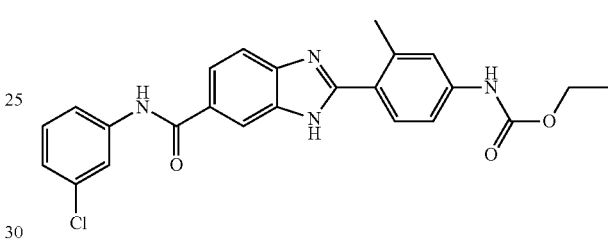

A mixture of methyl-4-bromo-3-methylbenzoate (400 mg) in 2N NaOH aqueous solution (3 mL) and THF (5 mL) was stirred at room temperature for 16 h. The mixture was washed with Et2O. The aqueous layer was acidified with 4N HCl aqueous solution, extracted with EtOAc. The organic extracts were dried over Na$_2$SO$_4$, filtered and concentrated under reduced pressure to give 4-bromo-3-methyl-benzoic acid as white powder: MS (m/z) 215 (M+1); $^1$H NMR (CD3OD, 400 MHz) δ 7.95 (s, 1H), 7.76 (d, 1H), 7.64 (d, 1H), 2.47 (s, 3H).

To a solution of 4-bromo-3-methyl-benzoic acid (300 mg) in 1,4-dioxane (5 mL) were added triethylamine (0.245 mL) and diphenylphosphory azide (0.316 mL). The mixture was stirred at room temperature for 16 h and then after adding EtOH (0.8 mL), the mixture was heated at 80° C. for 7 h. The reaction mixture was diluted with saturated NaHCO$_3$ aqueous solution. The aqueous layer was extracted with EtOAc, and the organic extracts were washed with brine, dried over Na$_2$SO$_4$, filtered and concentrated under reduced pressure. The crude product was purified by column chromatography (SiO2, EtOAc:Hexane=5:95 to 40:60) to give (4-bromo-3-methyl-phenyl)-carbamic acid ethyl ester as colorless oil: MS (m/z) 258 (M−1); $^1$H NMR (CDCl$_3$, 400 MHz) δ 7.42 (d, 1H), 7.30 (s, 1H), 7.08 (dd, 1H), 6.53 (s, 1H), 4.22 (q, 2H), 2.36 (s, 3H), 1.30 (t, 3H).

To a solution of (4-bromo-3-methyl-phenyl)-carbamic acid ethyl ester (210 mg) in THF (4 mL) was added n-BuLi (0.71 mL, 2.5 M solution in hexane) at −78° C. The mixture was stirred at −78° C. for 40 min, then DMF (0.31 mL) was added. The mixture was stirred at −78° C. for 40 min and then warmed up to room temperature. The reaction mixture was quenched with saturated NH$_4$Cl aqueous solution (11 mL) and extracted with EtOAc. The organic extracts were washed with brine, dried over Na$_2$SO$_4$, filtered and concentrated under reduced pressure. The crude product was purified by column chromatography (SiO$_2$, EtOAc:Hexane=5:95 to 40:60) to give (4-formyl-3-methyl-phenyl)-carbamic acid ethyl ester: MS (ESI): m/z 206 (M+1); $^1$H NMR (CDCl$_3$, 400 MHz) δ 10.14 (s, 1H), 7.75 (d, 1H), 7.39 (dd, 1H), 7.32 (s, 1H), 6.92 (s, 1H), 4.25 (q, 2H), 2.65 (s, 3H), 1.32 (t, 3H).

A mixture of 3,4-diamino-N-(3-chloro-phenyl)-benzamide (0.4 mL in 0.2 M DMSO solution), (4-formyl-3-methyl-phenyl)-carbamic acid ethyl ester (0.4 mL in 0.2 M toluene solution) and FeCl$_3$ (0.2 mL in 0.02M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give {4-[6-(3-Chloro-phenylcarbamoyl)-1H-benzoimidazol-2-yl]-3-methyl-phenyl}-carbamic acid ethyl ester: MS (m/z) 449 (M+1).

By employing the method of Example 1-108, 1-109, and 1-110, using appropriate starting materials, the following compounds were prepared:

| Example | Structure | Chemical Name | MS found (M + 1) |
|---|---|---|---|
| 1-113 | 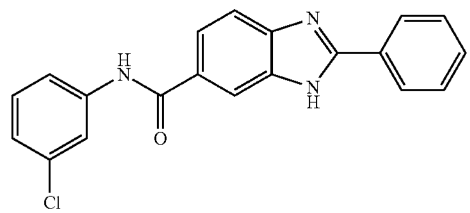 | 2-Phenyl-3H-benzoimidazole-5-carboxylic acid (3-chloro-phenyl)-amide | 348 |
| 1-114 | 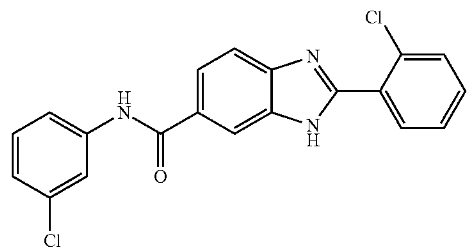 | 2-(2-Chloro-phenyl)-3H-benzoimidazole-5-carboxylic acid (3-chloro-phenyl)-amide | 382 |
| 1-115 | 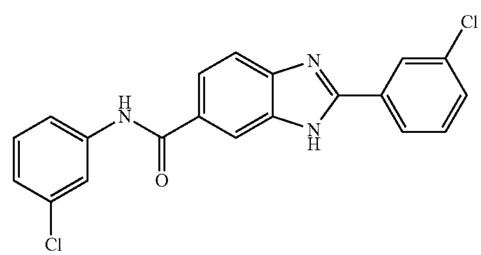 | 2-(3-Chloro-phenyl)-3H-benzoimidazole-5-carboxylic acid (3-chloro-phenyl)-amide | 382 |
| 1-116 | 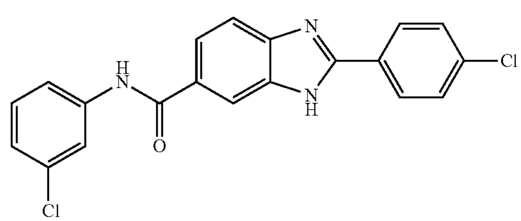 | 2-(4-Chloro-phenyl)-3H-benzoimidazole-5-carboxylic acid (3-chloro-phenyl)-amide | 382 |
| 1-117 | 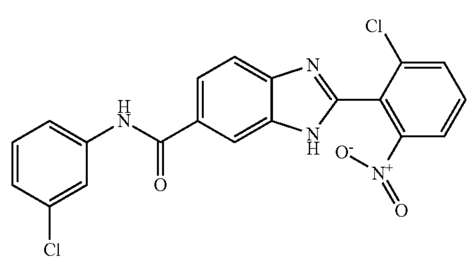 | 2-(2-Chloro-6-nitro-phenyl)-3H-benzoimidazole-5-carboxylic acid (3-chloro-phenyl)-amide | 427 |

-continued

| Example | Structure | Chemical Name | MS found (M + 1) |
|---|---|---|---|
| 1-118 | 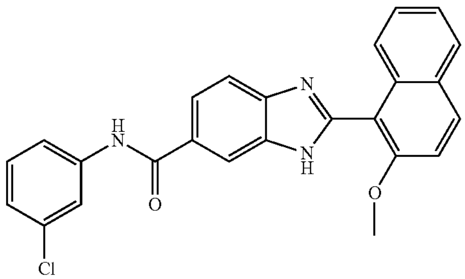 | 2-(2-Methoxy-naphthalen-1-yl)-3H-benzoimidazole-5-carboxylic acid (3-chloro-phenyl)-amide | 428 |
| 1-119 | 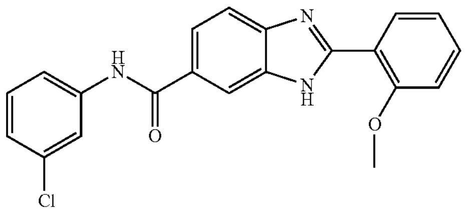 | 2-(2-Methoxy-phenyl)-3H-benzoimidazole-5-carboxylic acid (3-chloro-phenyl)-amide | 378 |
| 1-120 | 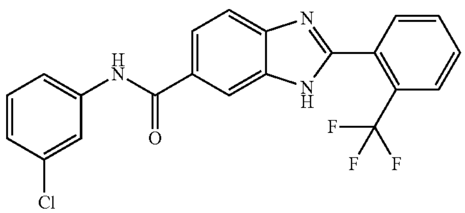 | 2-(2-Trifluoromethyl-phenyl)-3H-benzoimidazole-5-carboxylic acid (3-chloro-phenyl)-amide | 416 |
| 1-121 | 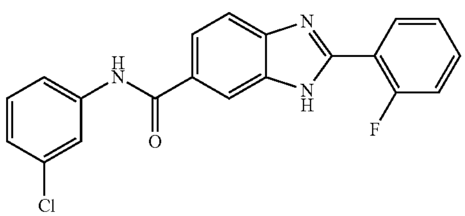 | 2-(2-Fluoro-phenyl)-3H-benzoimidazole-5-carboxylic (3-chloro-phenyl)-amide | 366 |
| 1-122 | 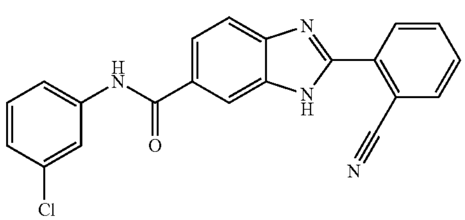 | 2-(2-Cyano-phenyl)-3H-benzoimidazole-5-carboxylic acid (3-chloro-phenyl)-amide | 373 |
| 1-123 | 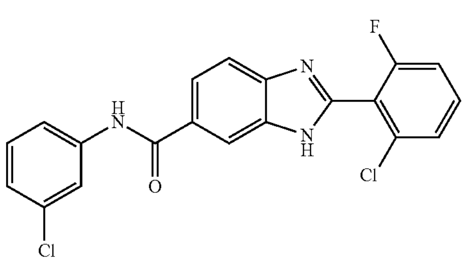 | 2-(2-Chloro-6-fluoro-phenyl)-3H-benzoimidazole-5-carboxylic acid (3-chloro-phenyl)-amide | 400 |

-continued

| Example | Structure | Chemical Name | MS found (M + 1) |
|---|---|---|---|
| 1-124 | 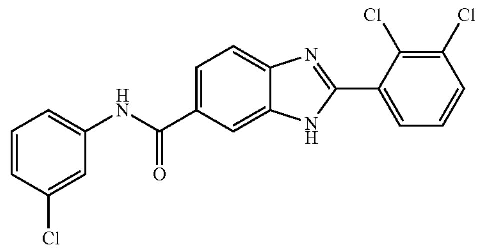 | 2-(2,3-Dichloro-phenyl)-3H-benzoimidazole-5-carboxylic acid (3-chloro-phenyl)-amide | 418 |
| 1-125 | 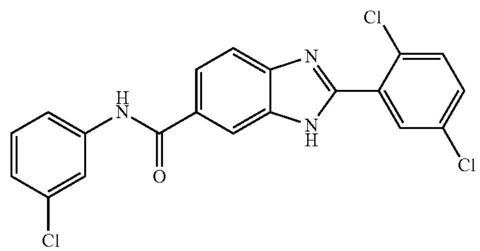 | 2-(2,5-Dichloro-phenyl)-3H-benzoimidazole-5-carboxylic acid (3-chloro-phenyl)-amide | 418 |
| 1-126 | 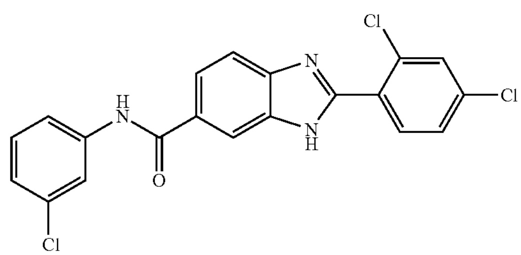 | 2-(2,4-Dichloro-phenyl)-3H-benzoimidazole-5-carboxylic acid (3-chloro-phenyl)-amide | 418 |
| 1-131 | 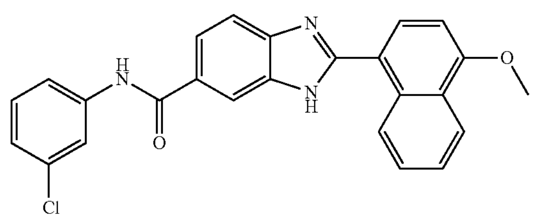 | 2-(4-Methoxy-naphthalen-1-yl)-3H-benzoimidazole-5-carboxylic acid (3-chloro-phenyl)-amide | 428 |
| 1-132 | 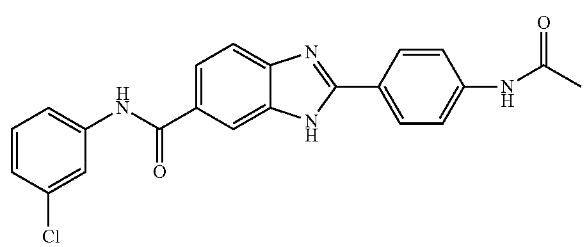 | 2-(4-Acetylamino-phenyl)-3H-benzoimidazole-5-carboxylic acid (3-chloro-phenyl)-amide | 405 |
| 1-133 | 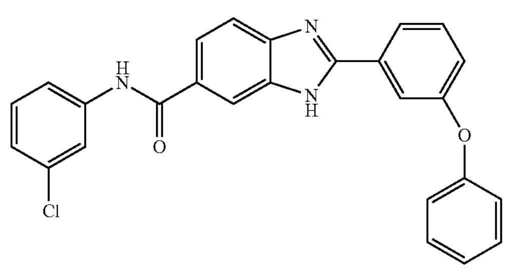 | 2-(3-Phenoxy-phenyl)-3H-benzoimidazole-5-carboxylic acid (3-chloro-phenyl)-amide | 440 |

-continued

| Example | Structure | Chemical Name | MS found (M + 1) |
|---|---|---|---|
| 1-134 | 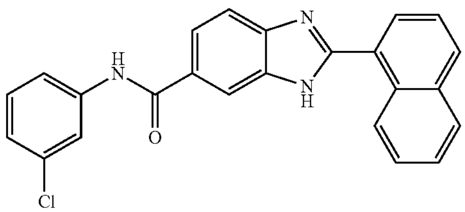 | 2-Naphthalen-1-yl-3H-benzoimidazole-5-carboxylic acid (3-chloro-phenyl)-amide | 398 |
| 1-136 | 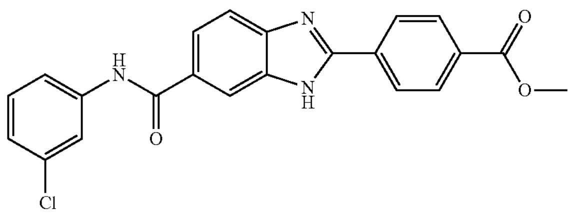 | 4-[6-(3-Chloro-phenylcarbamoyl)-1H-benzoimidazol-2-yl]-benzoic acid methyl ester | 406 |
| 1-137 | 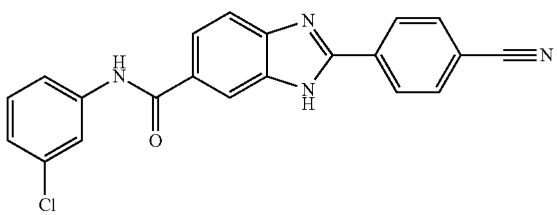 | 2-(4-Cyano-phenyl)-3H-benzoimidazole-5-carboxylic acid (3-chloro-phenyl)-amide | 373 |
| 1-138 | 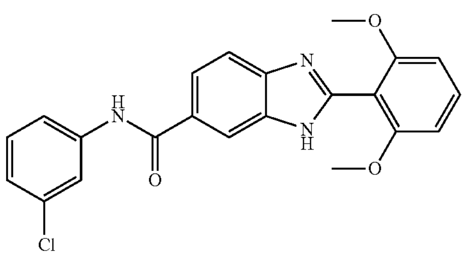 | 2-(2,6-Dimethoxy-phenyl)-3H-benzoimidazole-5-carboxylic acid (3-chloro-phenyl)-amide | 408 |
| 1-139 | 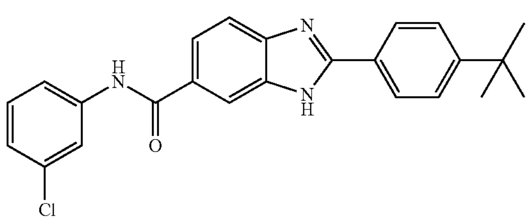 | 2-(4-tert-Butyl-phenyl)-3H-benzoimidazole-5-carboxylic acid (3-chloro-phenyl)-amide | 404 |
| 1-140 | 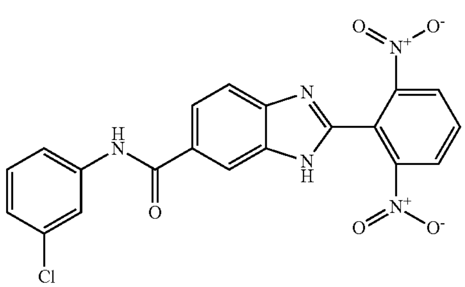 | 2-(2,6-Dinitro-phenyl)-3H-benzoimidazole-5-carboxylic acid (3-chloro-phenyl)-amide | 438 |

-continued

| Example | Structure | Chemical Name | MS found (M + 1) |
|---|---|---|---|
| 1-141 | 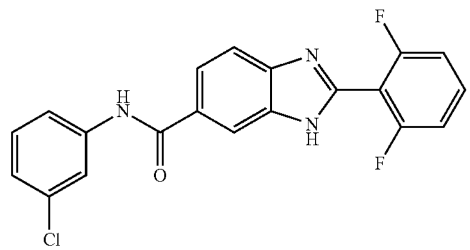 | 2-(2,6-Difluoro-phenyl)-3H-benzoimidazole-5-carboxylic acid (3-chloro-phenyl)-amide | 384 |
| 1-142 | 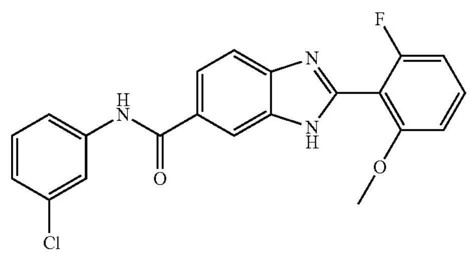 | 2-(2-Fluoro-6-methoxy-phenyl)-3H-benzoimidazole-5-carboxylic acid (3-chloro-phenyl)-amide | 396 |
| 1-143 | 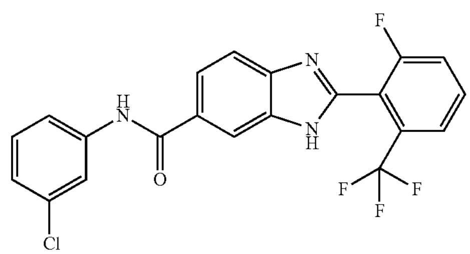 | 2-(2-Fluoro-6-trifluoromethyl-phenyl)-3H-benzoimidazole-5-carboxylic acid (3-chloro-phenyl)-amide | 434 |
| 1-144 | 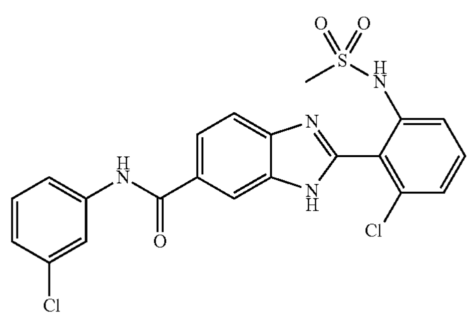 | 2-(2-Chloro-6-methanesulfonylamino-phenyl)-3H-benzoimidazole-5-carboxylic acid (3-chloro-phenyl)-amide | 475 |
| 1-145 | 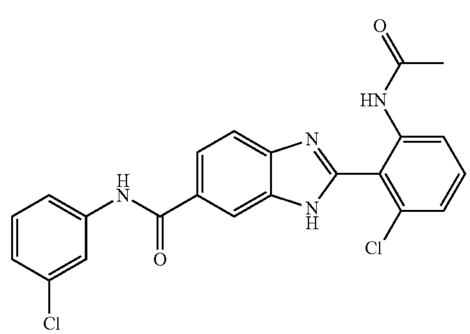 | 2-(2-Acetylamino-6-chloro-phenyl)-3H-benzoimidazole-5-carboxylic acid (3-chloro-phenyl)-amide | 439 |

| Example | Structure | Chemical Name | MS found (M + 1) |
|---|---|---|---|
| 1-146 | 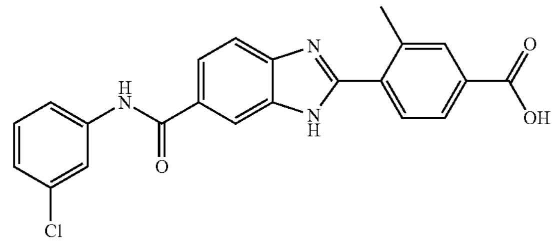 | 4-[6-(3-Chloro-phenylcarbamoyl)-1H-benzoimidazol-2-yl]-3-methyl-benzoic acid | 406 |
| 1-147 | 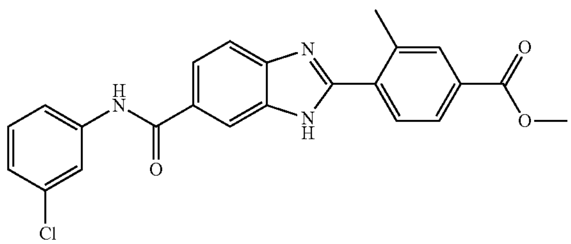 | 4-[6-(3-Chloro-phenylcarbamoyl)-1H-benzoimidazol-2-yl]-3-methyl-benzoic acid methyl ester | 420 |

Example 1-148

2-(4-Acetylamino-2,6-dimethyl-phenyl)-3H-benzoimidazole-5-carboxylic acid (3,4-dimethyl-phenyl)-amide

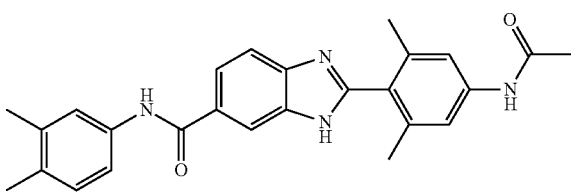

A suspension of 5-nitro-m-xylene (1.51 g) and 10% Pd/C (80 mg) in MeOH (50 mL) was stirred at room temperature under $H_2$ balloon for 16 h. The reaction mixture was filtered through a Celite pad, washed with EtOAc, concentrated under reduced pressure. The crude product was purified by column chromatography ($SiO_2$, EtOAc:Hexane=5:95 to 40:60) to give 3,5-dimethyl-phenylamine as a yellow oil: MS (m/z) 122 (M+1); $^1$H NMR ($CDCl_3$, 400 MHz) δ 6.41 (s, 1H), 6.33 (s, 2H), 3.52 (s, 2H), 2.22 (s, 6H).

To a solution of 3,5-dimethyl-phenylamine (400 mg) in THF (35 mL) was added n-BuLi (1.45 mL, 2.5 M solution in hexane) at −78° C. The mixture was stirred at −78° C. for 20 min, allowed to warm up to −40° C. for 5 min, and then was cooled down to −78° C. again. After 10 min, B(OMe)$_3$ (0.4 mL) was added dropwise. The mixture was stirred at −78° C. for 2.5 h, warmed up to 10° C. slowly, and then was cooled down to −78° C. again. Bromine (0.185 mL) was added dropwise to the mixture. The mixture was stirred at −78° C. for 1.5 h, and allowed to warm up to 0° C. for 1 h. The reaction was quenched with saturated $NaHCO_3$ aqueous solution and 20% $Na_2S_2O_3$ aqueous solution. The aqueous layer was extracted with EtOAc, and the organic extracts were washed with brine, dried over $Na_2SO_4$, filtered and concentrated under reduced pressure. The crude product was purified by column chromatography ($SiO_2$, EtOAc:Hexane=5:95 to 40:60) to give 4-bromo-3,5-dimethyl-phenylamine as a white solid: MS (m/z) 200 (M+1); $^1$H NMR ($CDCl_3$, 400 MHz) δ 6.43 (s, 2H), 3.52 (s, 2H), 2.31 (s, 6H).

To a solution of 4-bromo-3,5-dimethyl-phenylamine (130 mg) in $CH_2Cl_2$ (4 mL) was added acetic anhydride (0.123 mL) at 0° C. The mixture was allowed to warm up to room temperature and stirred for 2 h. The mixture was concentrated under reduced pressure. The crude product was purified by column chromatography ($SiO_2$, EtOAc:Hexane=10:90 to 60:40) to give N-(4-bromo-3,5-dimethyl-phenyl)-acetamide: MS (m/z) 244 (M+1); $^1$H NMR ($CDCl_3$, 400 MHz) δ 7.24 (s, 2H), 2.35 (s, 6H), 2.13 (s, 3H).

To a solution of N-(4-bromo-3,5-dimethyl-phenyl)-acetamide (150 mg) in THF (5 mL) was added n-BuLi (1.36 mL, 1.0 M solution in hexane) at −78° C. The mixture was stirred at −78° C. for 30 min, then warmed up to −40° C. for 5 min, then cooled down to at −78° C. again. After 20 min, DMF (0.24 mL) was added. The mixture was stirred at −78° C. for 30 min and then allowed to warm up to room temperature for 1 h. The reaction was quenched with saturated $NH_4Cl$ aqueous solution and extracted with EtOAc. The organic extracts were washed with brine, dried over $Na_2SO_4$, filtered and concentrated under reduced pressure to give N-(4-formyl-3,5-dimethyl-phenyl)-acetamide: MS (m/z) 192 (M+1).

A mixture of 3,4-diamino-N-(3,4-dimethyl-phenyl)-benzamide (0.8 mL in 0.2 M DMSO solution), N-(4-formyl-3,5-dimethyl-phenyl)-acetamide (0.8 mL in 0.2 M toluene solution) and $FeCl_3$ (0.4 mL in 0.02M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give 2-(4-acetylamino-2,6-dimethyl-phenyl)-3H-benzoimidazole-5-carboxylic acid (3,4-dimethyl-phenyl)-amide: MS (m/z) 427 (M+1).

Example 1-149

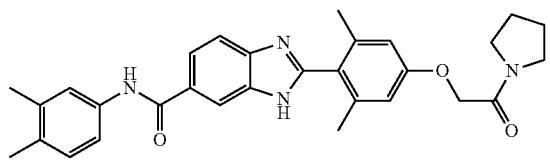

A mixture of 4-hydroxy-2,6-dimethyl-benzaldehyde (87 mg), 2-chloro-1-pyrrolidin-1-yl-ethanone (102 mg), and $Cs_2CO_3$ (375 mg, 1.15 mmol) in acetone (4 mL) was stirred at room temperature for 16 h. The mixture was concentrated, diluted with water, and extracted with EtOAc. The organic extracts were washed with brine, dried over $Na_2SO_4$, and concentrated under reduced pressure to give 2,6-dimethyl-4-(2-oxo-2-pyrrolidin-1-yl-ethoxy)-benzaldehyde: MS (m/z) 262 (M+1).

A mixture of 3,4-diamino-N-(3,4-dimethyl-phenyl)-benzamide (0.8 mL in 0.2 M DMSO solution), 2,6-dimethyl-4-(2-oxo-2-pyrrolidin-1-yl-ethoxy)-benzaldehyde (0.8 mL in 0.2 M toluene solution) and $FeCl_3$ (0.4 mL in 0.02M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge. United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give 2-[2,6-dimethyl-4-(2-oxo-2-pyrrolidin-1-yl-ethoxy)-phenyl]-3H-benzoimidazole-5-carboxylic acid (3,4-dimethyl-phenyl)-amide: MS (m/z) 497 (M+1).

Example 1-150

Toluene-4-sulfonic acid 4-[6-(3,4-dimethyl-phenylcarbamoyl)-1H-benzoimidazol-2-yl]-3,5-dimethyl-phenyl ester

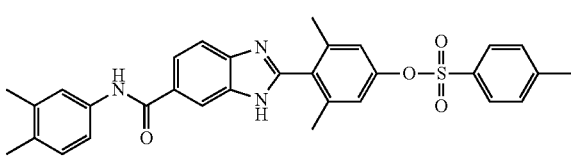

To a solution of 4-hydroxy-2,6-dimethyl-benzaldehyde (55 mg) in $CH_2Cl_2$ (1.5 mL) were added triethylamine (0.13 mL) and 4-methyl-benzenesulfonyl chloride (70 mg) at 0° C. The mixture was stirred for 16 h at room temperature, diluted with saturated $NaHCO_3$ aqueous solution, and extracted with $CH_2Cl_2$. The organic extracts were dried over $Na_2SO_4$ and concentrated under the reduced pressure to give N-(4-formyl-3,5-dimethyl-phenyl)-4-methyl-benzenesulfonylamide: MS (m/z) 305 (M+1).

To a solution of 3,4-diamino-N-(3,4-dimethyl-phenyl)-benzamide (102 mg) in DMSO (2 mL) were added 2,6-dimethyl-4-(2-oxo-2-pyrrolidin-1-yl-ethoxy)-benzaldehyde (116 mg) and $FeCl_3$ (1.2 mL in 0.02M THF solution). The mixture was stirred in open air at ambient temperature overnight. The mixture was then diluted by water and extracted with EtOAc. The extracts were dried over $Na_2SO_4$, filtered and concentrated under reduced pressure. The crude product was purified by column chromatography ($SiO_2$, EtOAc:Hexane=20:80 to 80:10) to give toluene-4-sulfonic acid 4-[6-(3,4-dimethyl-phenylcarbamoyl)-1H-benzoimidazol-2-yl]-3,5-dimethyl-phenyl ester: MS (m/z) 540 (M+1).

Example 1-151

2-[2,6-dimethyl-4-(2-pyrrolidin-1-yl-ethoxy)-phenyl]-3H-benzoimidazole-5-carboxylic acid (3,4-dimethyl-phenyl)-amide

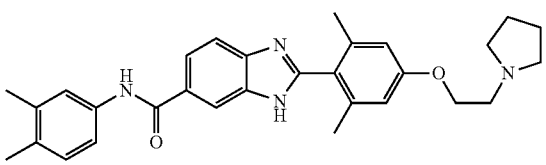

To a solution of 4-bromo-3,5-dimethylphenol (555 mg) were added 2-pyrrolidine-1-yl-ethanol (0.3 mL), PPh3 (721 mg), and DEAD (0.43 mL). The mixture was stirred room temperature for 16 h. The reaction mixture was concentrated. The residue was treated with $Et_2O$, filtered and the filtrated was concentrated under reduced pressure. The crude product was purified by column chromatography ($SiO_2$, EtOAc:Hexane=10:80 to 80:20) to give 1-[2-(4-bromo-3,5-dimethyl-phenoxy)-ethyl]-pyrrolidine as a white solid: MS (m/z) 300 (M+1).

To a solution of 1-[2-(4-bromo-3,5-dimethyl-phenoxy)-ethyl]-pyrrolidine (176 mg) in THF (5 mL) was added n-BuLi (1.36 mL, 1.0 M solution in hexane) at −78° C. The mixture was stirred at −78° C. for 30 min, allowed to warm up to −40° C. for 5 min, and then cooled down to at −78° C. After 20 min. DMF (0.24 mL) was added. The mixture was stirred at −78° C. for 30 min and then allowed to warm up to room temperature for 1 h. The reaction was quenched with saturated $NH_4Cl$ aqueous solution and extracted with EtOAc. The organic extracts were washed with brine, dried over $Na_2SO_4$, and concentrated under reduced pressure to give 2,6-dimethyl-4-(2-pyrrolidin-1-yl-ethoxy)-benzaldehyde: MS (m/z) 248 (M+1).

A mixture of 3,4-diamino-N-(3,4-dimethyl-phenyl)-benzamide (0.1 mL in 0.2 M DMSO solution), 2,6-dimethyl-4-(2-pyrrolidin-1-yl-ethoxy)-benzaldehyde (0.1 mL in 0.2 M toluene solution) and $FeCl_3$ (0.05 mL in 0.02M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give 2-[2,6-dimethyl-4-(2-pyrrolidin-1-yl-ethoxy)-phenyl]-3H-benzoimidazole-5-carboxylic acid (3,4-dimethyl-phenyl)-amide: MS (m/z) 483 (M+1).

Example 1-152

2-[2,6-Dimethyl-4-(1H-tetrazol-5-yl-methoxy)-phenyl]-3H-benzoimidazole-5-carboxylic acid (3,4-dimethyl-phenyl)-amide

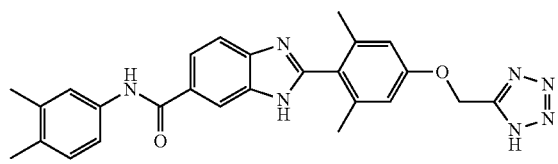

A mixture of 4-hydroxy-2,6-dimethyl-benzaldehyde (150 mg), chloroacetonitrile (0.1 mL), and $Cs_2CO_3$ (390 mg) in acetone (10 mL) was stirred at room temperature for 16 h. The mixture was concentrated, diluted with water, and extracted with EtOAc. The organic extracts were washed with brine, dried over $Na_2SO_4$, and concentrated in vacuo. Purification by column chromatography ($SiO_2$, 3:1 hexane/EtOAc) gave (4-formyl-3,5-dimethyl-phenoxy)-acetonitrile.

To a solution of (4-formyl-3,5-dimethyl-phenoxy)-acetonitrile (120 mg) in DMF (3 mL) were added sodium azide (62 mg) and ammonium chloride (51 mg). The reaction mixture was heated at 100° C. for 1 h. The mixture was then diluted by water and the whole was loaded onto a cartridge that contained C18 silica gel (reverse phase). Wash-to-waste (10 mL water) was followed by elute-to-collect (10 mL, acetonitrile) and, after evaporation of volatiles, 2,6-dimethyl-4-(1H-tetrazol-5-yl-methoxy)-benzaldehyde was obtained.

To a solution of 2,6-dimethyl-4-(1H-tetrazol-5-yl-methoxy)-benzaldehyde (50 mg) in DMSO (1 mL) were added 3,4-diamino-N-(3,4-dimethyl-phenyl)-benzamide (55 mg), $Yb(OTf)_3$ (13 mg), and $Cu(OTf)_2$ (8 mg). The reaction mixture was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-$Et_3N$) and, after evaporation of volatiles, the crude was further purified by silica gel column chromatography to give 2-[2,6-dimethyl-4-(1H-tetrazol-5-yl-methoxy)-phenyl]-3H-benzoimidazole-5-carboxylic acid (3,4-dimethyl-phenyl)-amide: MS (m/z) 468.16 (M+1).

By employing the method of Example 1-108, 1-109 1-110, 1-149, and 1-150, using appropriate starting materials, the following compounds were prepared:

| Example | Structure | Chemical Name | MS found (M + 1) |
|---|---|---|---|
| 1-153 | 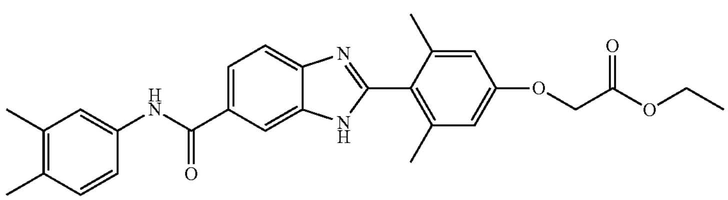 | {4-[6-(3,4-Dimethyl-phenylcarbamoyl)-1H-benzoimidazol-2-yl]-3,5-dimethyl-phenoxy}-acetic acid ethyl ester | 472 |
| 1-154 | 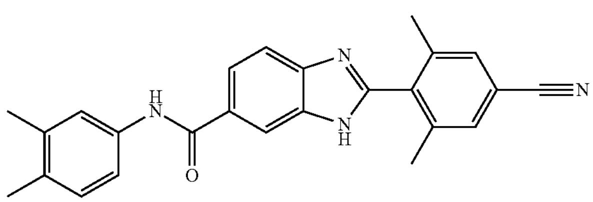 | 2-(4-Cyano-2,6-dimethyl-phenyl)-3H-benzoimidazole-5-carboxylic acid (3,4-dimethyl-phenyl)-amide | 395 |
| 1-155 | 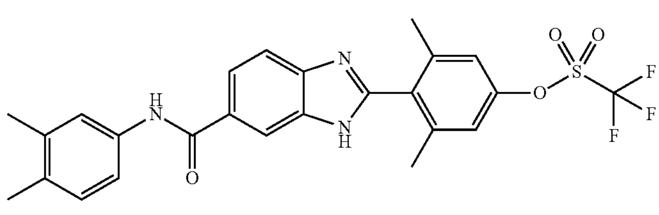 | Trifluoro-methanesulfonic acid [6-(3,4-dimethyl-phenylcarbamoyl)-1H-benzoimidazol-2-yl]-3,5-dimethyl-phenyl ester | 518 |
| 1-156 | 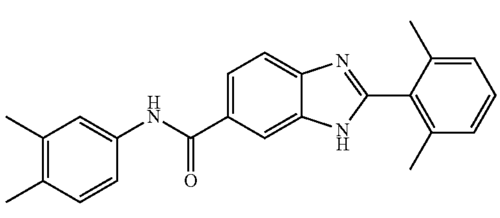 | 2-(2,6-Dimethyl-phenyl)-3H-benzoimidazole-5-carboxylic acid (3,4-dimethyl-phenyl)-amide | 370 |

| Example | Structure | Chemical Name | MS found (M + 1) |
|---|---|---|---|
| 1-157 | 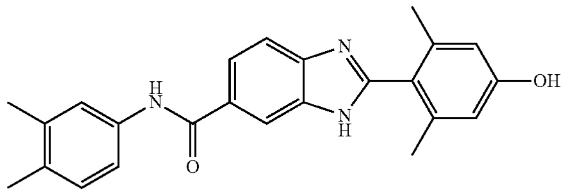 | 2-(4-Hydroxy-2,6-dimethyl-phenyl)-3H-benzoimidazole-5-carboxylic acid (3,4-dimethyl-phenyl)-amide | 386 |
| 1-158 | 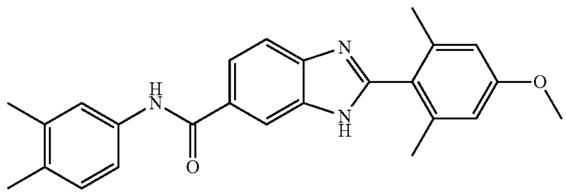 | 2-(4-Methoxy-2,6-dimethyl-phenyl)-3H-benzoimidazole-5-carboxylic acid (3,4-dimethyl-phenyl)-amide | 400 |
| 1-159 | 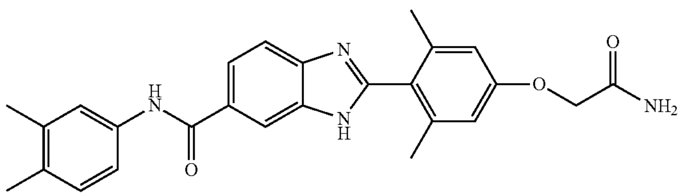 | 2-(4-Carbamoylmethoxy-2,6-dimethyl-phenyl)-3H-benzoimidazole-5-carboxylic acid (3,4-dimethyl-phenyl)-amide | 443 |
| 1-160 | 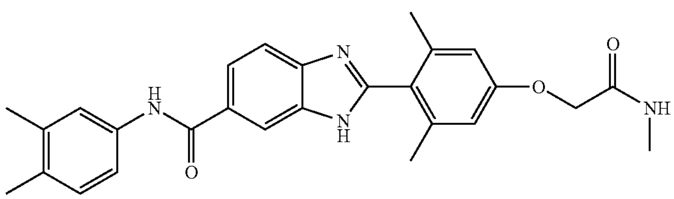 | 2-(2,6-Dimethyl-4-methylcarbamoylmethoxy-phenyl)-3H-benzoimidazole-5-carboxylic acid (3,4-dimethyl-phenyl)-amide | 457 |
| 1-161 | 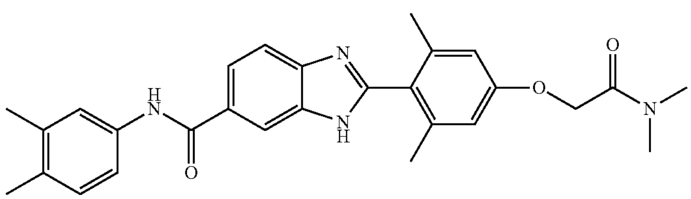 | 2-(4-Dimethylcarbamoylmethoxy-2,6-dimethyl-phenyl)-3H-benzoimidazole-5-carboxylic acid (3,4-dimethyl-phenyl)-amide | 471 |
| 1-162 | 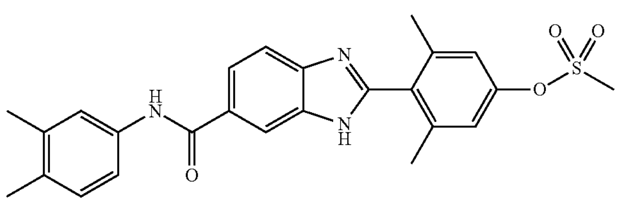 | Methanesulfonic acid 4-[6-(3,4-dimethyl-phenylcarbamoyl)-1H-benzoimidazol-2-yl]-3,5-dimethyl-phenyl ester | 464 |

Example 1-163

{4-[6-(3,4-Dimethyl-phenylcarbamoyl)-1H-benzoimidazol-2-yl]-3,5-dimethyl-phenoxy}-acetic acid

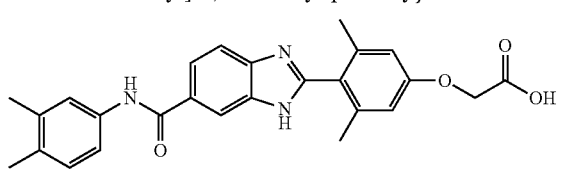

The similar procedure was repeated as described in example 1-111, using {-4-[6-(3,4-dimethyl-phenylcarbamoyl)-1H-benzoimidazol-2-yl]-3,5-dimethyl-phenoxy}-acetic acid ethyl ester, to give {4-[6-(3,4-dimethyl-phenylcarbamoyl)-1H-benzoimidazol-2-yl]-3,5-dimethyl-phenoxy}-acetic acid: MS (m/z) 444 (M+1): $^1$H NMR (MeOD, 400 MHz) δ 8.27 (s, 1H), 7.94 (dd, 1H), 7.73 (d, 1H), 7.49 (s, 1H), 7.45 (d, 1H), 7.15 (d, 1H), 6.82 (s, 2H), 4.72 (s, 2H), 2.28 (s, 3H), 2.21 (s, 3H), 2.17 (s, 6H).

Example 1-164

2-{2,6-Dimethyl-4-[2-(4-methyl-piperazin-1-yl)-2-oxo-ethoxy]-phenyl}-3H benzoimidazole-5-carboxylic acid (3,4-dimethyl-phenyl)-amide

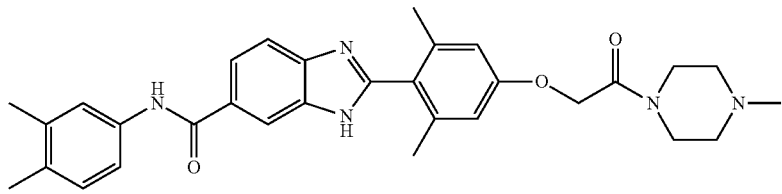

A solution of {4-[6-(3,4-dimethyl-phenylcarbamoyl)-1H-benzoimidazol-2-yl]-3,5-dimethyl-phenoxy}-acetic acid (53.2 mg), 1-methylpiperazine (12 mg), BOP (62 mg) and DIEA (0.031 mL) in DMF (0.5 mL) was stirred at room temperature for 16 h. Then 1N NaOH aqueous solution was added. The aqueous layer was extracted with EtOAc, and the organic extracts were dried over $Na_2SO_4$, filtered and concentrated under reduced pressure. The crude product was purified by column chromatography ($SiO_2$, EtOAc:Hexane=20:80 to 80:10) and prep-HPLC to give 2-{2,6-dimethyl-4-[2-(4-methyl-piperazin-1-yl)-2-oxo-ethoxy]-phenyl}-3H-benzoimidazole-5-carboxylic acid (3,4-dimethyl-phenyl)-amide: MS (m/z) 526 (M+1).

Example 1-165

4-[6-(3,4-Dimethyl-phenylcarbamoyl)-1H-benzoimidazol-2-yl]-3,5-dimethyl-benzoic acid

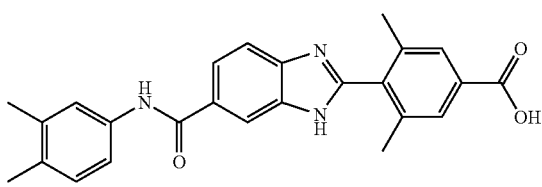

A mixture of 2-(4-cyano-2,6-dimethyl-phenyl)-3H-benzoimidazole-5-carboxylic acid (3,4-dimethyl-phenyl)-amide (60 mg) in 6N NaOH aqueous solution (1 mL) and EtOH (1 mL) was heated at 140° C. under microwave radiation for 50 min. The mixture was washed with $Et_2O$. The aqueous layer was acidified to pH 3 with 1N HCl aqueous solution, extracted with EtOAc, and the organic extracts were dried over $Na_2SO_4$, filtered and concentrated under reduced pressure. The crude product was purified by column chromatography ($SiO_2$, MeOH: $CH_2Cl_2$=3:97 to 10:90) to give 4-[6-(3,4-dimethyl-phenylcarbamoyl)-1H-benzoimidazol-2-yl]-3,5-dimethyl-benzoic acid as a white solid: MS (m/z) 414 (M+1); $^1$H NMR (MeOD, 400 MHz) δ 8.27 (s, 1H), 7.92 (d, 1H), 7.85 (s, 2H), 7.73 (d, 1H), 7.47 (s, 1H), 7.43 (d, 1H), 7.12 (d, 1H), 2.29 (s, 3H), 2.26 (s, 3H), 2.22 (s, 6H).

Example 1-166

2-[2,6-dimethyl-4-(4-methyl-piperazine-1-carbonyl)-phenyl]-3H-benzoimidazole-5-carboxylic acid (3,4-dimethyl-phenyl)-amide

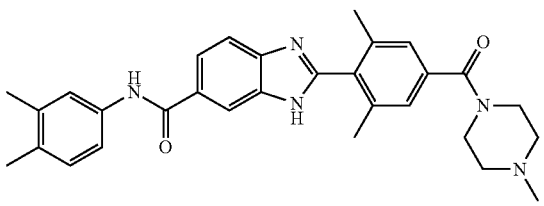

The similar procedure was repeated as described in example 1-164, using appropriate starting materials to give 2-[2,6-dimethyl-4-(4-methyl-piperazine-1-carbonyl)-phenyl]-3H-benzoimidazole-5-carboxylic acid (3,4-dimethyl-phenyl)-amide: MS (m/z) 497 (M+1); $^1$H NMR (MeOD, 400 MHz) δ 8.27 (s, 1H), 7.92 (d, 1H), 7.73 (s, 2H), 7.47 (s, 1H), 7.43 (dd, 1H), 7.25 (s, 2H), 7.12 (d, 1H), 2.37 (s, 3H), 2.29 (s, 3H), 2.26 (s, 3H), 2.20 (s, 6H).

Example 1-167

2-[2,6-Dimethyl-4-(2H-tetrazol-5-yl)-phenyl]-3H-benzoimidazole-5-carboxylic acid (3,4-dimethyl-phenyl)-amide

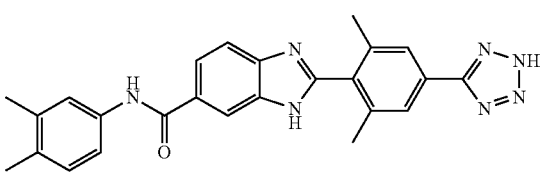

A mixture of 2-(4-Cyano-2,6-dimethyl-phenyl)-3H-benzoimidazole-5-carboxylic acid (3,4-dimethyl-phenyl)-amide (40 mg), $NaN_3$ (65 mg) and $NH_4Cl$ (54 mg) in DMF (1 mL) was heated at 120° C. under microwave radiation for 60 min. The mixture was concentrated under reduced pressure. The crude product was purified by reverse phase column chromatography (C18, $H_2O$:$CH_3CN$=100:0 to 70:30) to give 2-[2,6-dimethyl-4-(2H-tetrazol-5-yl)-phenyl]-3H-benzoimidazole-5-carboxylic acid (3,4-dimethyl-phenyl)-amide as a white solid: MS (m/z) 438 (M+1).

Example 1-168

[2-(2,6-Dichloro-phenyl)-3H-benzoimidazol-5-ylmethyl]-(3,4-dimethyl-phenyl)-amine

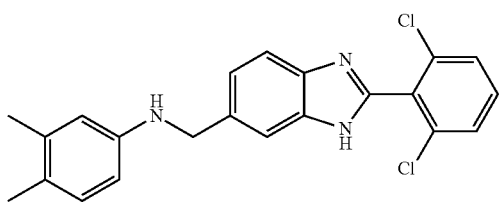

To a solution of 2-(2,6-dichloro-phenyl)-3H-benzoimidazole-5-carboxylic acid (3,4-dimethyl-phenyl)-amide (230 mg) in THF (2 mL) was added LiAlH$_4$ (1.12 mL, 1M THF solution) at 0° C. The mixture was stirred at 0° C. to room temperature for 16 h. Then to the mixture was added 3 mL of THF, 0.122 mL of water and 0.143 mL of 6N NaOH at 0° C., warmed up to room temperature and stirred for 30 min. The mixture was diluted with THF, filtered through celite, washed with THF. The filtrate was concentrated under reduced pressure. The crude product was purified by column chromatography (SiO$_2$, EtOAc:Hexane=10:80 to 100:0) to give 130 mg of the product (85% pure), and 30 mg of it was purified by prep-HPLC to give [2-(2,6-dichloro-phenyl)-3H-benzoimidazol-5-ylmethyl]-(3,4-dimethyl-phenyl)-amine: MS (m/z) 396 (M+1).

By employing the method of Example 1-108, 1-109 1-110, 1-149, and 1-150, using appropriate starting materials, the following compounds were prepared:

| Example | Structure | Chemical Name | MS found (M + 1) |
|---|---|---|---|
| 1-169 | 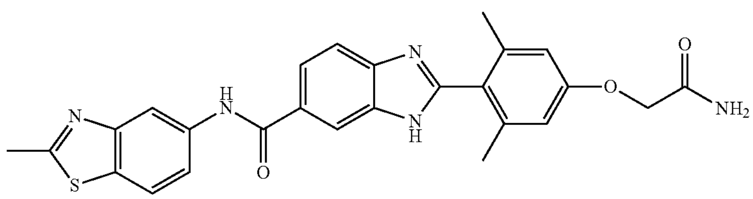 | 2-(4-Carbamoylmethoxy-2,6-dimethyl-phenyl)-3H-benzoimidazole-5-carboxylic acid (2-methyl-benzothiazol-5-yl)-amide | 488 |
| 1-170 | 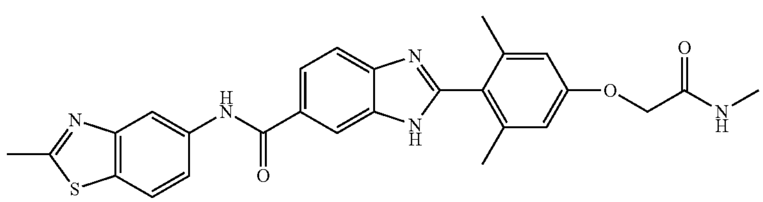 | 2-(2,6-Dimethy)-4-methylcarbamoylmethoxy-phenyl)-3H-benzoimidazole-5-carboxylic acid (2-methyl-benzothiazol-5-yl)-amide | 500 |
| 1-171 | 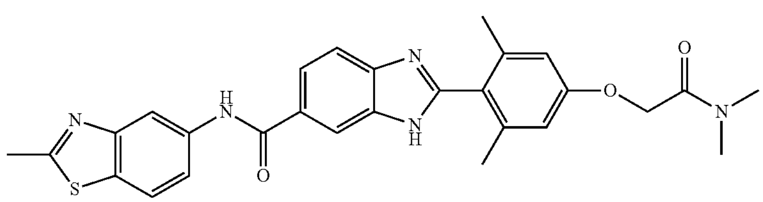 | 2-(4-Dimethylcarbamoylmethoxy-2,6-dimethyl-phenyl)-3H-benzoimidazole-5-carboxylic acid (2-methyl-benzothiazol-5-yl)-amide | 514 |
| 1-172 | 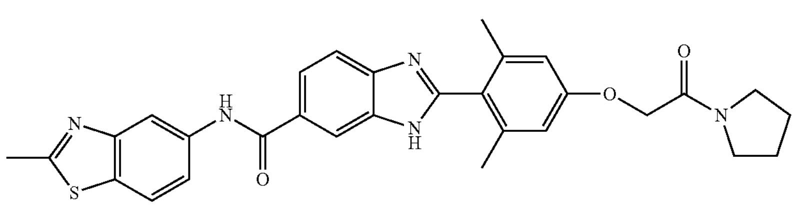 | 2-[2,6-Dimethyl-4-(2-oxo-2-pyrrolidin-1-yl-ethoxy)-phenyl]-3H-benzoimidazole-5-carboxylic acid (2-methyl-benzothiazol-5-yl)-amide | 540 |
| 1-173 | 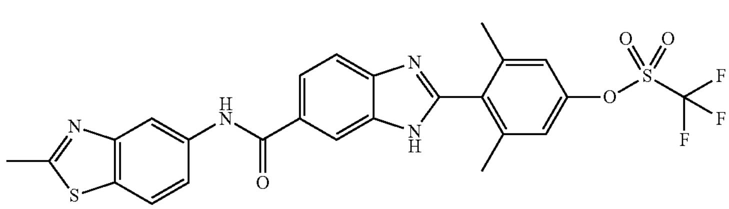 | Trifluoro-methanesulfonic acid 3,5-dimethyl-4-[6-(2-methyl-benzothiazol-5-ylcarbamoyl)-1H-benzoimidazol-2-yl]-phenyl ester | 561 |

| Example | Structure | Chemical Name | MS found (M + 1) |
|---|---|---|---|
| 1-174 | 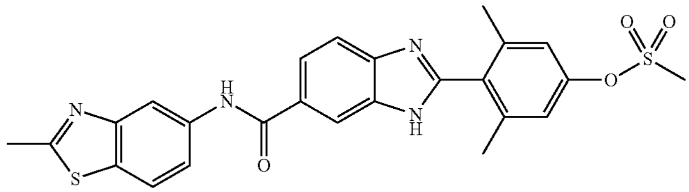 | Methanesulfonic acid 3,5-dimethyl-4-[6-(2-methyl-benzothiazol-5-ylcarbamoyl)-1H-benzoimidazol-2-yl]-phenyl ester | 507 |
| 1-175 | 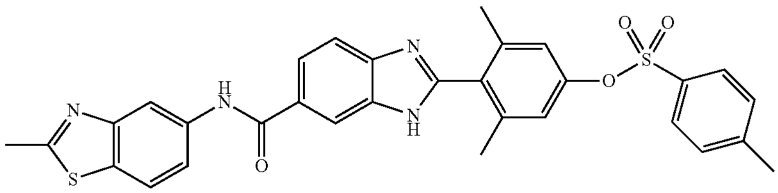 | Toluene-4-sulfonic acid 3,5-dimethyl-4-[6-(2-methyl-benzothiazol-5-ylcarbamoyl)-1H-benzoimidazol-2-yl]-phenyl ester | 583 |
| 1-176 | 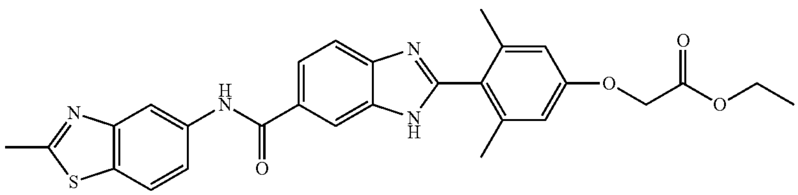 | {3,5-Dimethyl-4-[6-(2-methyl-benzothiazol-5-ylcarbamoyl)-1Hbenzoimidazol-2-yl]-phenoxy}-acetic acid ethyl ester | 517 |

Example 1-177

{3,5-dimethyl-4-[6-(2-methyl-benzothiazol-5-ylcarbamoyl)-1H-benzoimidazol-2-yl]-phenoxy}-acetic acid

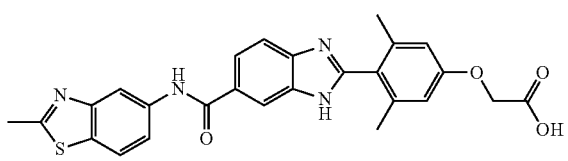

The similar procedure was repeated as described in example 1-111, using {3,5-dimethyl-4-[6-(2-methyl-benzothiazol-5-ylcarbamoyl)-1H-benzoimidazol-2-yl]-phenoxy}-acetic acid ethyl ester, to give {3,5-dimethyl-4-[6-(2-methyl-benzothiazol-5-ylcarbamoyl)-1H-benzoimidazol-2-yl]-phenoxy}-acetic acid: MS (m/z) 487 (M+1): $^1$H NMR (MeOD, 400 MHz) δ 8.44 (d, 1H), 8.32 (d, 1H), 7.99 (dd, 1H), 7.93 (d, 1H), 7.79 (d, 1H), 7.76 (d, 1H), 6.82 (s, 2H), 4.73 (s, 2H), 2.86 (s, 3H), 2.18 (s, 6H).

By employing methods analogous to Example 1-13 or standard peptide-coupling methods on the intermediate 2-(2,6-dichlorophenyl)-3H-benzoimidazole-5-carboxylic acid (EDCI/HOBt), using the appropriate starting materials, the following compounds were prepared:

| Example | Structure | Chemical Name | MS found (M + 1) | Retention time (min) Method |
|---|---|---|---|---|
| 1-178 | 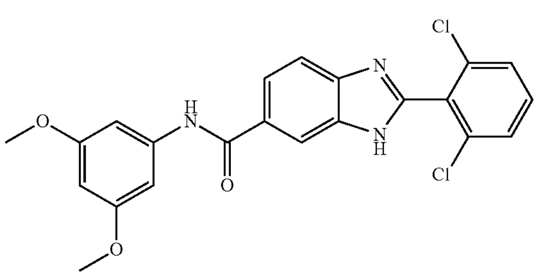 | 2-(2,6-Dichlorophenyl)-3H-benzoimidazole-5-carboxylic acid (3,5-dimethoxyphenyl)-amide | 442 | |

| Example | Structure | Chemical Name | MS found (M + 1) | Retention time (min) Method |
|---|---|---|---|---|
| 1-179 | 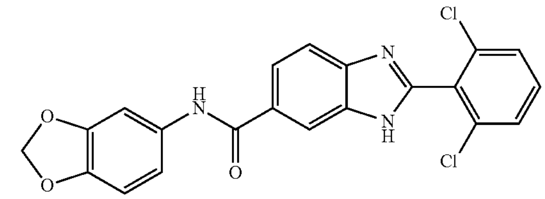 | 2-(2,6-Dichlorophenyl)-3H-benzoimidazole-5-carboxylic acid benzo[1,3]dioxol-5-ylamide | 426 | |
| 1-180 | 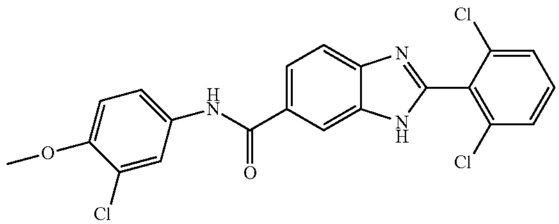 | 2-(2,6-Dichlorophenyl)-3H-benzoimidazole-5-carboxylic acid (3-chloro-4-methoxyphenyl)-amide | 447 | |
| 1-181 | 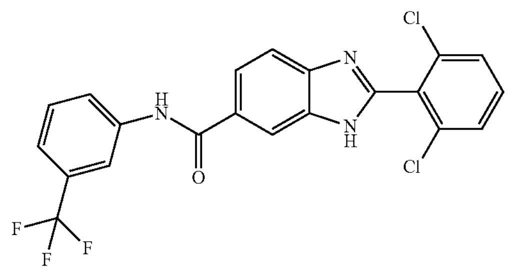 | 2-(2,6-Dichlorophenyl)-3H-benzoimidazole-5-carboxylic acid (3-trifluoromethylphenyl)-amide | 451 | |
| 1-182 | 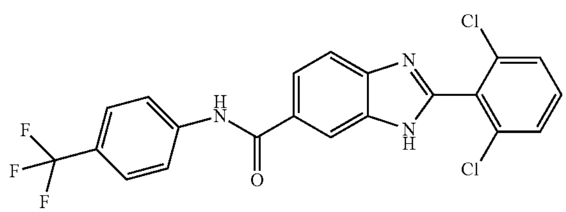 | 2-(2,6-Dichlorophenyl)-3H-benzoimidazole-5-carboxylic acid (4-trifluoromethylphenyl)-amide | 451 | |
| 1-183 | 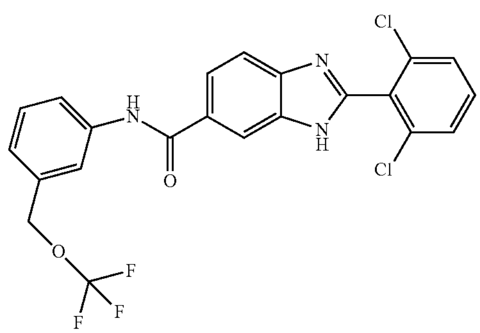 | 2-(2,6-Dichlorophenyl)-3H-benzoimidazole-5-carboxylic acid (3-trifluoromethoxyphenyl)-amide | 467 | |
| 1-184 | 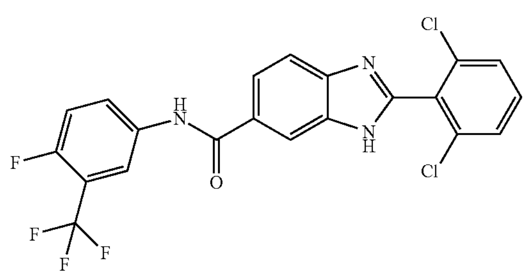 | 2-(2,6-Dichlorophenyl)-3H-benzoimidazole-5-carboxylic acid (4-fluoro-3-trifluoromethylphenyl)-amide | 469 | |

-continued

| Example | Structure | Chemical Name | MS found (M + 1) | Retention time (min) Method |
|---|---|---|---|---|
| 1-185 | 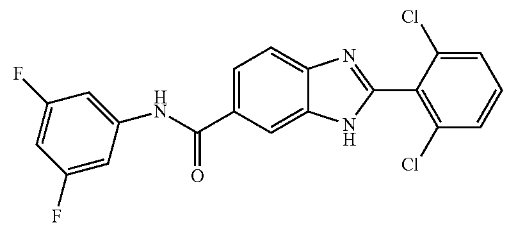 | 2-(2,6-Dichlorophenyl)-3H-benzoimidazole-5-carboxylic acid (3,5-difluorophenyl)-amide | 419 | |
| 1-186 | 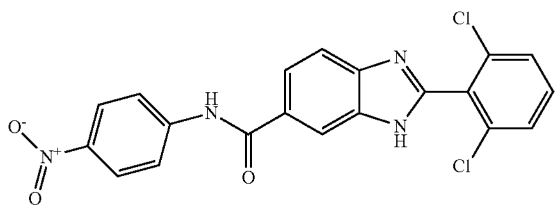 | 2-(2,6-Dichlorophenyl)-3H-benzoimidazole-5-carboxylic acid (4-nitrophenyl)-amide | 428 | |
| 1-187 | 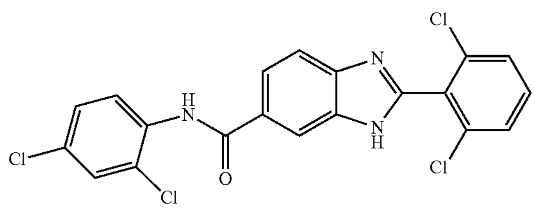 | 2-(2,6-Dichlorophenyl)-3H-benzoimidazole-5-carboxylic acid (2,4-dichlorophenyl)-amide | 452 | |
| 1-188 | 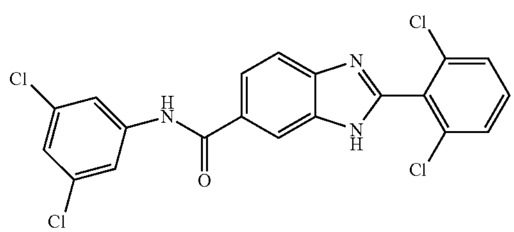 | 2-(2,6-Dichlorophenyl)-3H-benzoimidazole-5-carboxylic acid (3,5-dichlorophenyl)-amide | 451 | |
| 1-189 | 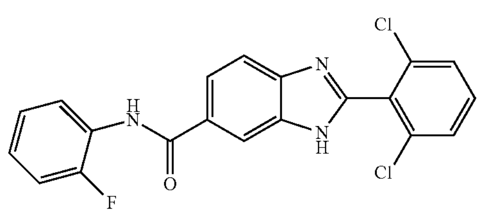 | 2-(2,6-Dichlorophenyl)-3H-benzoimidazole-5-carboxylic acid (2-fluorophenyl)-amide | 401 | |
| 1-190 | 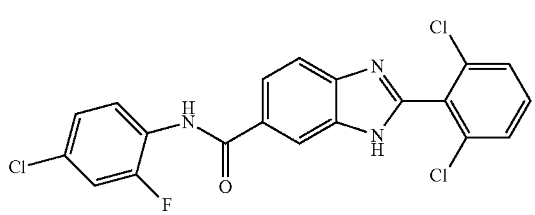 | 2-(2,6-Dichlorophenyl)-3H-benzoimidazole-5-carboxylic acid (4-chloro-2-fluorophenyl)-amide | 435 | |
| 1-191 | 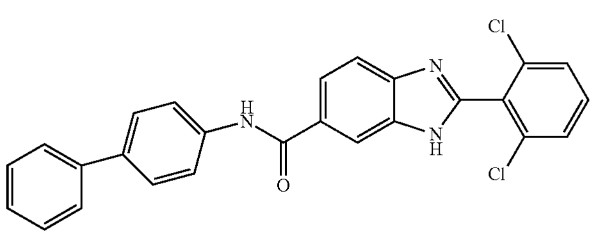 | 2-(2,6-Dichlorophenyl)-3H-benzoimidazole-5-carboxylic acid biphenyl-4-ylamide | 459 | |

-continued

| Example | Structure | Chemical Name | MS found (M + 1) | Retention time (min) Method |
|---|---|---|---|---|
| 1-192 | 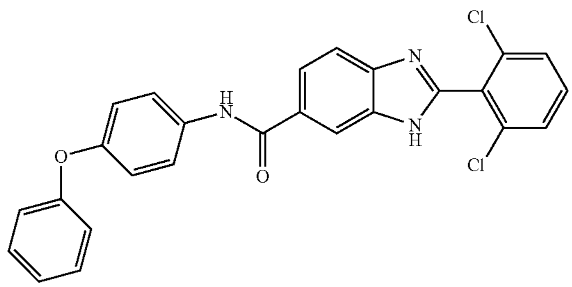 | 2-(2,6-Dichlorophenyl)-3H-benzoimidazole-3-carboxylic acid (4-phenoxyphenyl)-amide | 475 | |
| 1-193 | 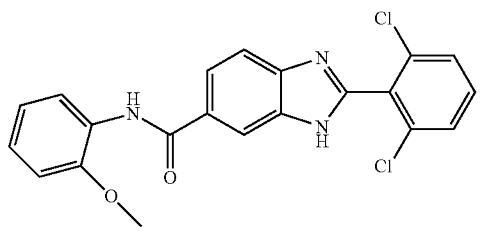 | 2-(2,6-Dichlorophenyl)-3H-benzoimidazole-5-carboxylic acid (2-methoxyphenyl)-amide | 413 | |
| 1-194 | 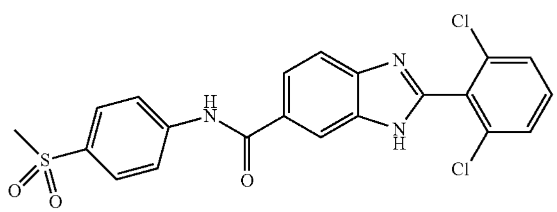 | 2-(2,6-Dichlorophenyl)-3H-benzoimidazole-5-carboxylic acid (4-methanesulfonylphenyl)-amide | 461 | |
| 1-195 | 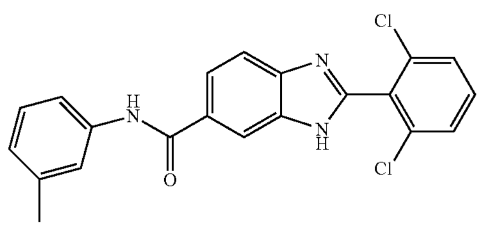 | 2-(2,6-Dichlorophenyl)-3H-benzoimidazole-5-carboxylic acid m-tolylamide | 397 | |
| 1-196 | 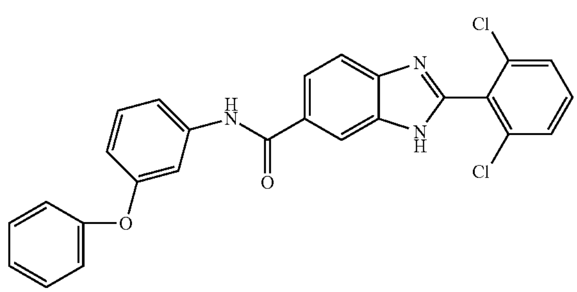 | 2-(2,6-Dichlorophenyl)-3H-benzoimidazole-5-carboxylic acid (3-phenoxyphenyl)-amide | 475 | |
| 1-197 | 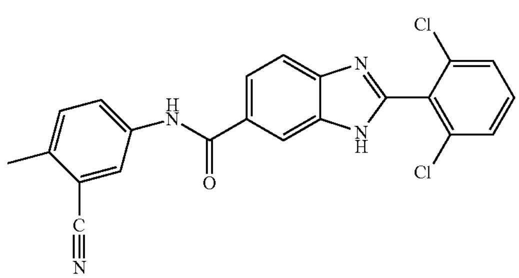 | 2-(2,6-Dichlorophenyl)-3H-benzoimidazole-5-carboxylic acid (3-cyano-4-methylphenyl)-amide | 422 | |

-continued

| Example | Structure | Chemical Name | MS found (M + 1) | Retention time (min) Method |
|---|---|---|---|---|
| 1-198 | 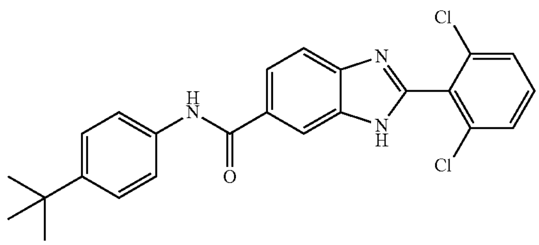 | 2-(2,6-Dichlorophenyl)-3H-benzoimidazole-5-carboxylic acid (4-tert-butylphenyl)-amide | 438 | |
| 1-199 | 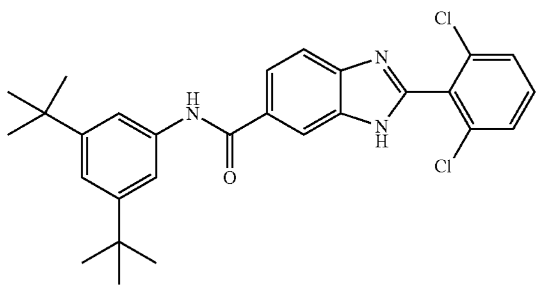 | 2-(2,6-Dichlorophenyl)-3H-benzoimidazole-5-carboxylic acid (3,5-di-tert-butylphenyl)-amide | 494 | |
| 1-201 | 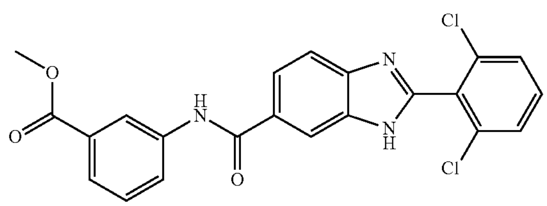 | 3-{[2-(2,6-Dichlorophenyl)-3H-benzoimidazole-5-carbonyl]-amino}-benzoic acid methyl ester | 440 | |
| 1-202 | 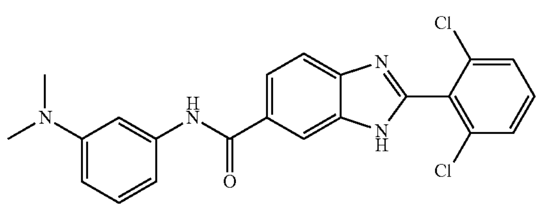 | 2-(2,6-Dichlorophenyl)-3H-benzoimidazole-5-carboxylic acid (3-dimethylaminophenyl)-amide | 425 | |
| 1-203 | 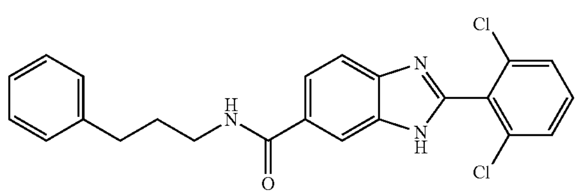 | 2-(2,6-Dichlorophenyl)-3H-benzoimidazole-5-carboxylic acid (3-phenylpropyl)-amide | 424 | |
| 1-204 | 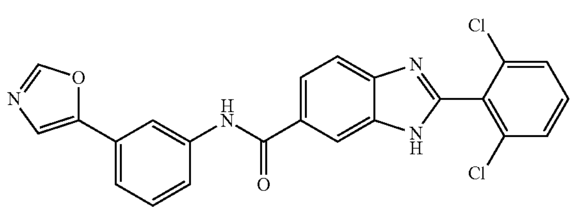 | 2-(2,6-Dichlorophenyl)-3H-benzoimidazole-5-carboxylic acid (3-oxazol-5-yl-phenyl)-amide | 449 | |

| Example | Structure | Chemical Name | MS found (M + 1) | Retention time (min) Method |
|---|---|---|---|---|
| 1-205 | 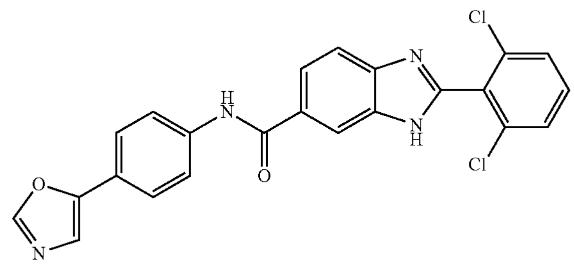 | 2-(2,6-Dichlorophenyl)-3H-benzoimidazole-5-carboxylic acid (4-oxazol-5-yl-phenyl)-amide | 449 | |
| 1-206 | 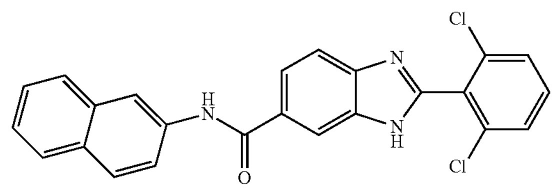 | 2-(2,6-Dichlorophenyl)-3H-benzoimidazole-5-carboxylic acid naphthalen-2-ylamide | 432 | |
| 1-207 | 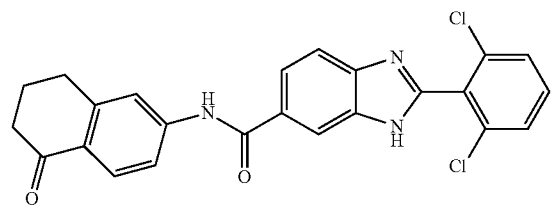 | 2-(2,6-Dichlorophenyl)-3H-benzoimidazole-5-carboxylic acid (5-oxo-5,6,7,8-tetrahydronaphthalen-2-yl)-amide | 450 | |
| 1-208 | 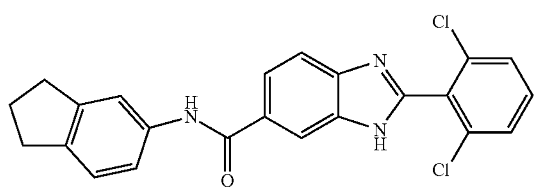 | 2-(2,6-Dichlorophenyl)-3H-benzoimidazole-5-carboxylic acid indan-5-ylamide | 423 | |
| 1-209 | 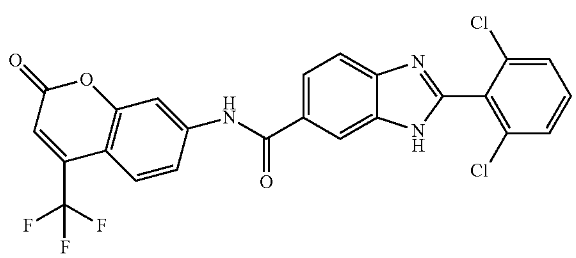 | 2-(2,6-Dichlorophenyl)-3H-benzoimidazole-5-carboxylic acid (2-oxo-4-trifluoromethyl-2H-chromen-7-yl)-amide | 518 | |
| 1-210 | 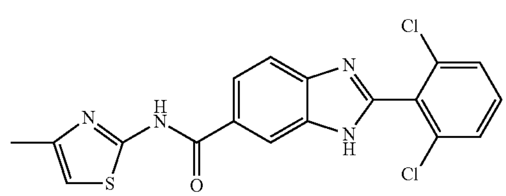 | 2-(2,6-Dichlorophenyl)-3H-benzoimidazole-5-carboxylic acid (4-methylthiazol-2-yl)-amide | 403 | |
| 1-211 | 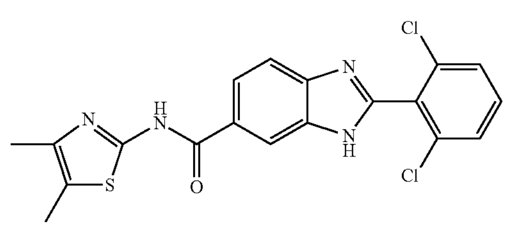 | 2-(2,6-Dichlorophenyl)-3H-benzoimidazole-5-carboxylic acid (4,5-dimethylthiazol-2-yl)-amide | 417 | |

| Example | Structure | Chemical Name | MS found (M + 1) | Retention time (min) Method |
|---|---|---|---|---|
| 1-212 | 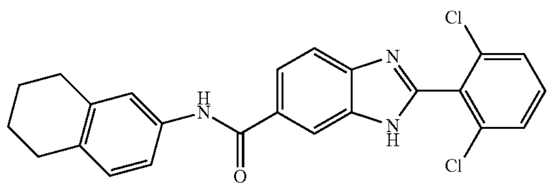 | 2-(2,6-Dichlorophenyl)-3H-benzoimidazole-5-carboxylic acid (5,6,7,8-tetrahydronaphthalen-2-yl)-amide | 436 | |
| 1-213 | 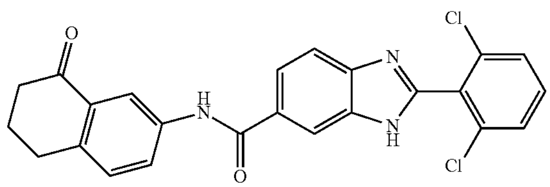 | 2-(2,6-Dichlorophenyl)-3H-benzoimidazole-5-carboxylic acid (8-oxo-5,6,7,8-tetrahydronaphthalen-2-yl)-amide | 450 | |
| 1-214 | 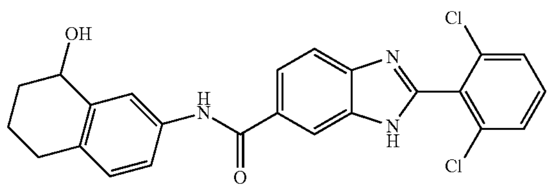 | 2-(2,6-Dichlorophenyl)-3H-benzoimidazole-5-carboxylic acid (8-hydroxy-5,6,7,8-tetrahydronaphthalen-2-yl)-amide | 452 | |
| 1-215 | 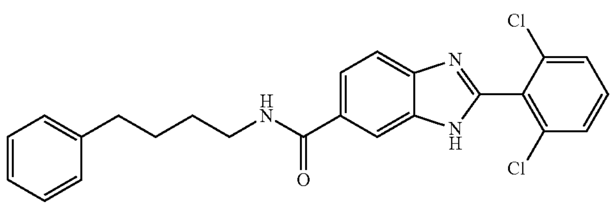 | 2-(2,6-Dichlorophenyl)-3H-benzoimidazole-5-carboxylic acid (4-phenylbutyl)-amide | 438 | |
| 1-216 | 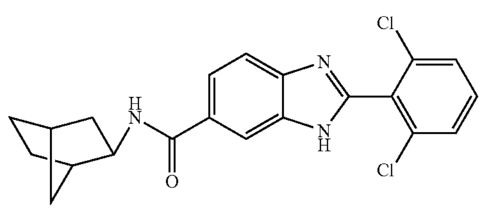 | 2-(2,6-Dichlorophenyl)-3H-benzoimidazole-5-carboxylic acid endo-bicyclo[2.2.1]hept-2-ylamide | 400 | |
| 1-217 | 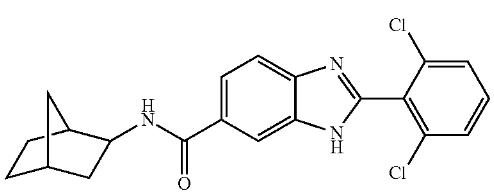 | 2-(2,6-Dichlorophenyl)-3H-benzoimidazole-5-carboxylic acid exo-bicyclo[2.2.1]hept-2-ylamide | 400 | |
| 1-218 | 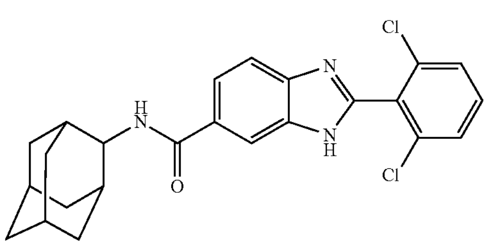 | 2-(2,6-Dichlorophenyl)-3H-benzoimidazole-5-carboxylic acid adamantan-2-ylamide | 440 | |

-continued

| Example | Structure | Chemical Name | MS found (M + 1) | Retention time (min) Method |
|---|---|---|---|---|
| 1-219 | 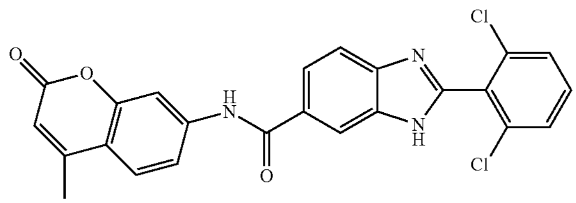 | 2-(2,6-Dichlorophenyl)-3H-benzoimidazole-5-carboxylic acid (4-methyl-2-oxo-2H-chromen-7-yl)-amide | 464 | |
| 1-220 | 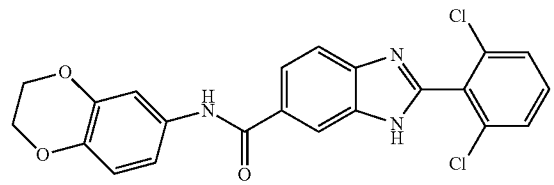 | 2-(2,6-Dichlorophenyl)-3H-benzoimidazole-5-carboxylic acid (2,3-dihydrobenzo[1,4]dioxin-6-yl)-amide | 440 | |
| 1-221 | 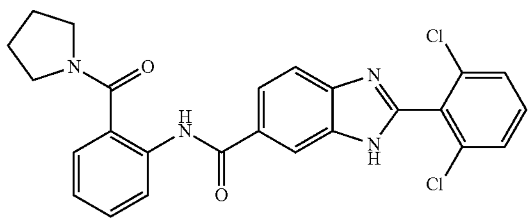 | 2-(2,6-Dichlorophenyl)-3H-benzoimidazole-5-carboxylic acid [2-(pyrrolidine-1-carbonyl)-phenyl]-amide | 479 | |
| 1-222 | 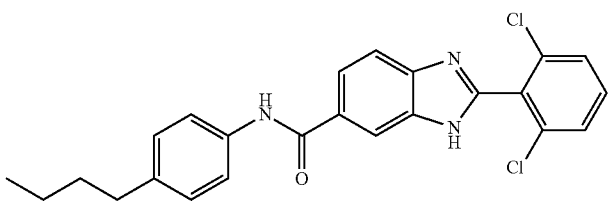 | 2-(2,6-Dichlorophenyl)-3H-benzoimidazole-5-carboxylic acid (4-butylphenyl)-amide | 438 | |
| 1-223 | 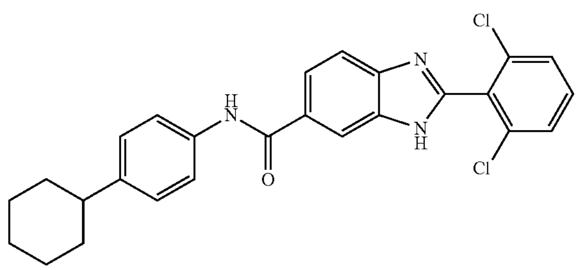 | 2-(2,6-Dichlorophenyl)-3H-benzoimidazole-5-carboxylic acid (4-cyclohexylphenyl)-amide | 464 | |
| 1-224 | 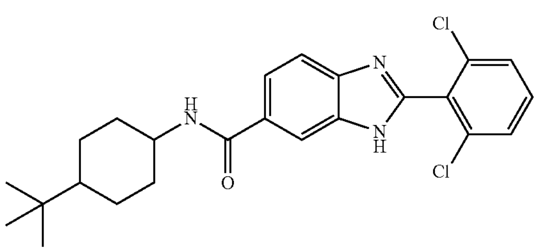 | 2-(2,6-Dichlorophenyl)-3H-benzoimidazole-5-carboxylic acid (4-tert-butylcyclohexyl)-amide | 444 | |
| 1-225 | 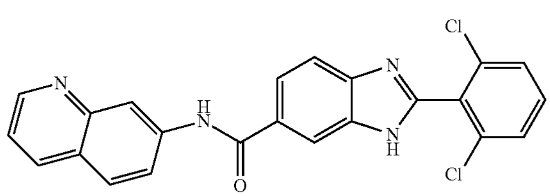 | 2-(2,6-Dichlorophenyl)-3H-benzoimidazole-5-carboxylic acid quinolin-7-ylamide | 433 | |

-continued

| Example | Structure | Chemical Name | MS found (M + 1) | Retention time (min) Method |
|---|---|---|---|---|
| 1-226 | 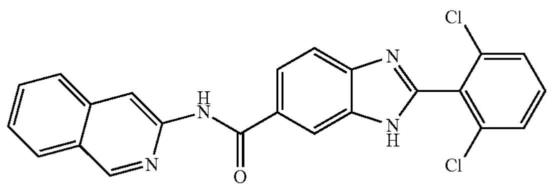 | 2-(2,6-Dichlorophenyl)-3H-benzoimidazole-5-carboxylic acid isoquinolin-3-ylamide | 433 | |
| 1-227 | 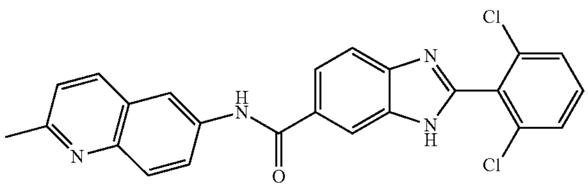 | 2-(2,6-Dichlorophenyl)-3H-benzoimidazole-5-carboxylic acid (2-methylquinolin-6-yl)-amide | 447 | |
| 1-228 | 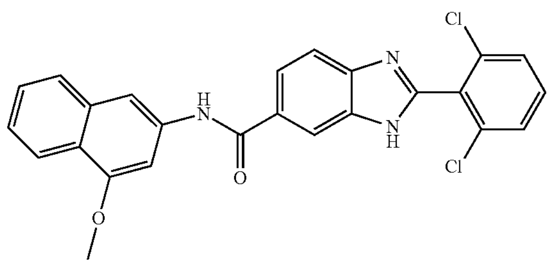 | 2-(2,6-Dichlorophenyl)-3H-benzoimidazole-5-carboxylic acid (4-methoxynaphthalen-2-yl)-amide | 462 | |
| 1-229 | 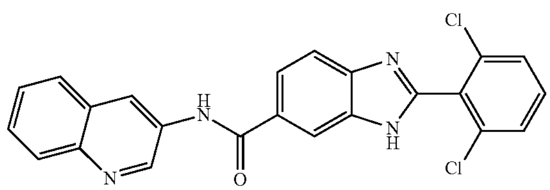 | 2-(2,6-Dichlorophenyl)-3H-benzoimidazole-5-carboxylic acid quinolin-3-ylamide | 433 | |
| 1-230 | 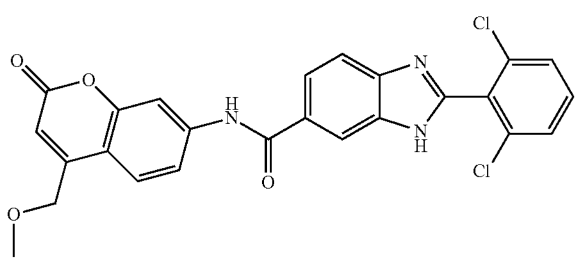 | 2-(2,6-Dichlorophenyl)-3H-benzoimidazole-5-carboxylic acid (4-methoxymethyl-2-oxo-2H-chromen-7-yl)-amide | 494 | |
| 1-231 | 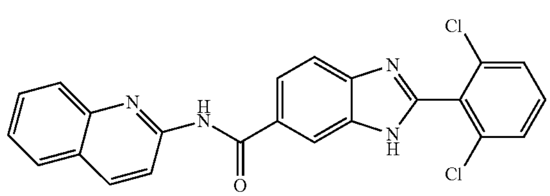 | 2-(2,6-Dichlorophenyl)-3H-benzoimidazole-5-carboxylic acid quinolin-2-ylamide | 433 | |
| 1-232 | 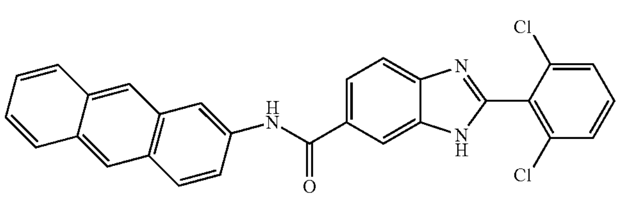 | 2-(2,6-Dichlorophenyl)-3H-benzoimidazole-5-carboxylic acid anthracen-2-ylamide | 482 | |

| Example | Structure | Chemical Name | MS found (M + 1) | Retention time (min) Method |
|---|---|---|---|---|
| 1-233 | 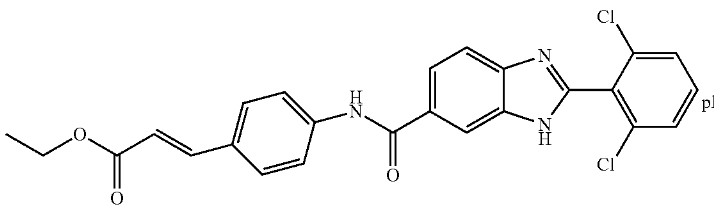 | (E)-3-(4-{[2-(2,6-Dichlorophenyl)-3H-benzoimidazole-5-carbonyl]-amino}-phenyl)-acrylic acid ethyl ester | 480 | |
| 1-234 | 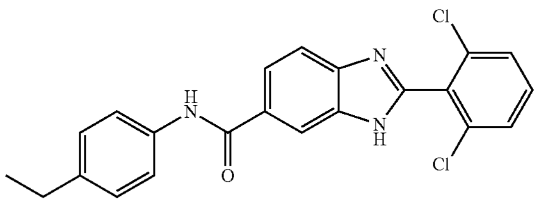 | 2-(2,6-Dichlorophenyl)-3H-benzoimidazole-5-carboxylic acid (4-ethylphenyl)-amide | 410 | |
| 1-235 | 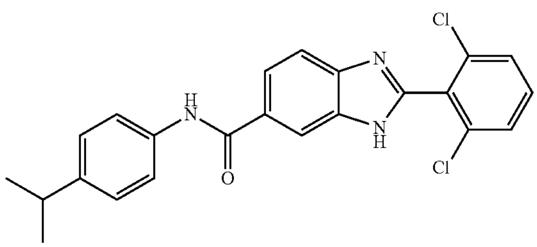 | 2-(2,6-Dichlorophenyl)-3H-benzoimidazole-5-carboxylic acid (4-isopropylphenyl)-amide | 424 | |
| 1-236 | 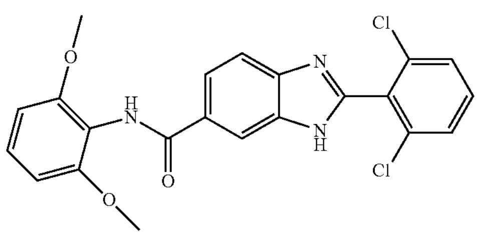 | 2-(2,6-Dichlorophenyl)-3H-benzoimidazole-5-carboxylic acid (2,6-dimethoxyphenyl)-amide | 442 | |
| 1-237 | 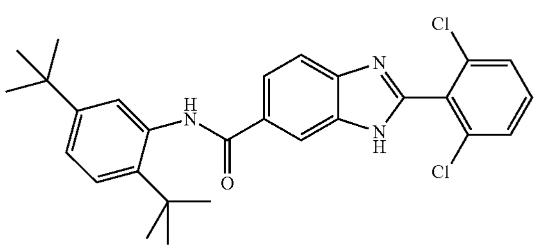 | 2-(2,6-Dichlorophenyl)-3H-benzoimidazole-5-carboxylic acid (2,5-di-tert-butylphenyl)-amide | 494 | |
| 1-238 | 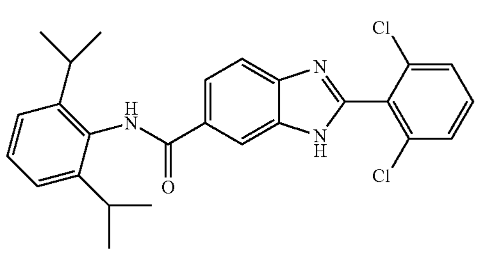 | 2-(2,6-Dichlorophenyl)-3H-benzoimidazole-5-carboxylic acid (2,6-diisopropylphenyl)-amide | 466 | |

-continued

| Example | Structure | Chemical Name | MS found (M + 1) | Retention time (min) Method |
|---|---|---|---|---|
| 1-239 | 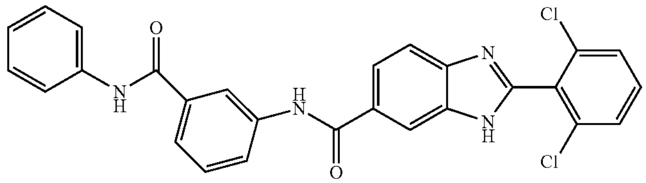 | 2-(2,6-Dichlorophenyl)-3H-benzoimidazole-5-carboxylic acid (3-phenylcarbamoylphenyl)-amide | 501 | |
| 1-240 | 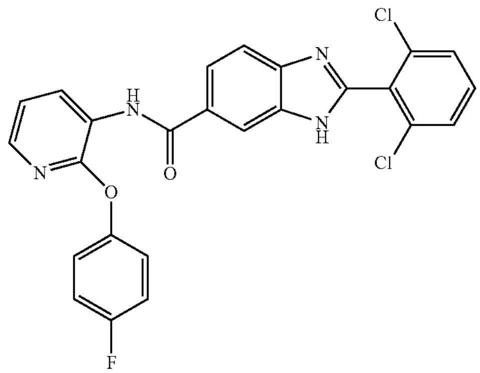 | 2-(2,6-Dichlorophenyl)-3H-benzoimidazole-5-carboxylic acid [2-(4-fluorophenoxy)-pyridin-3-yl]-amide | 493 | |
| 1-241 | 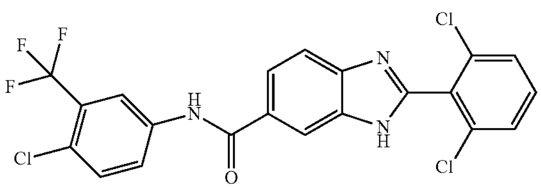 | 2-(2,6-Dichlorophenyl)-3H-benzoimidazole-5-carboxylic acid (4-chloro-3-trifluoromethylphenyl)-amide | 484 | |
| 1-242 | 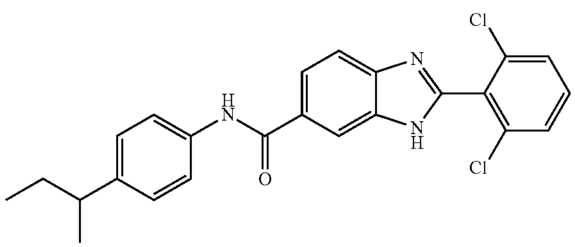 | 2-(2,6-Dichlorophenyl)-3H-benzoimidazole-5-carboxylic acid (4-sec-butylphenyl)-amide | 438 | |
| 1-243 | 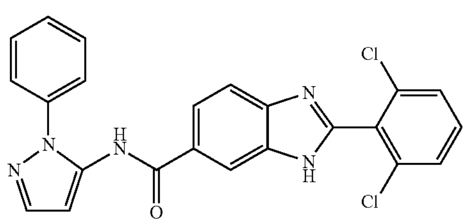 | 2-(2,6-Dichlorophenyl)-3H-benzoimidazole-5-carboxylic acid (2-phenyl-2H-pyrazol-3-yl)-amide | 447 | |
| 1-244 | 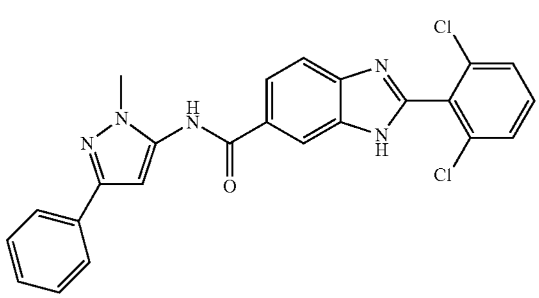 | 2-(2,6-Dichlorophenyl)-3H-benzoimidazole-5-carboxylic acid (2-methyl-5-phenyl-2H-pyrazol-3-yl)-amide | 461 | |

| Example | Structure | Chemical Name | MS found (M + 1) | Retention time (min) Method |
|---|---|---|---|---|
| 1-245 | 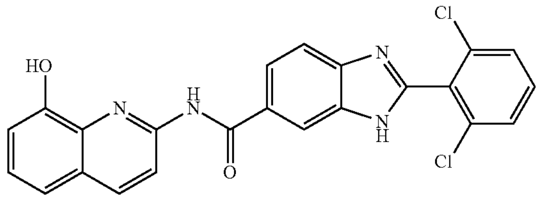 | 2-(2,6-Dichlorophenyl)-3H-benzoimidazole-5-carboxylic acid (8-hydroxyquinolin-2-yl)-amide | 449 | |
| 1-246 | 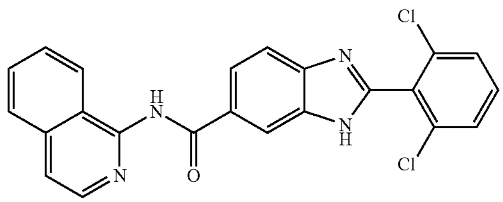 | 2-(2,6-Dichlorophenyl)-3H-benzoimidazole-5-carboxylic acid isoquinolin-1-ylamide | 433.0 | 1.33 Method 10 |
| 1-247 | 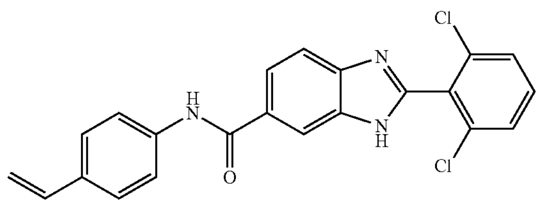 | 2-(2,6-Dichlorophenyl)-3H-benzoimidazole-5-carboxylic acid (4-vinylphenyl)-amide | 408 | 1.40 Method 10 |
| 1-248 | 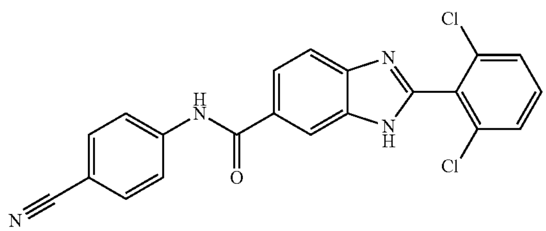 | 2-(2,6-Dichlorophenyl)-3H-benzoimidazole-5-carboxylic acid (4-cyanophenyl)-amide | 406 | 1.37 Method 10 |
| 1-249 | 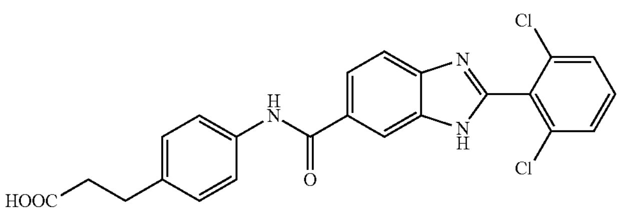 | 3-(4-{[2-(2,6-Dichlorophenyl)-3H-benzoimidazole-5-carbonyl]-amino}-phenyl)-propionic acid | 454 | 1.01 Method 10 |
| 1-250 | 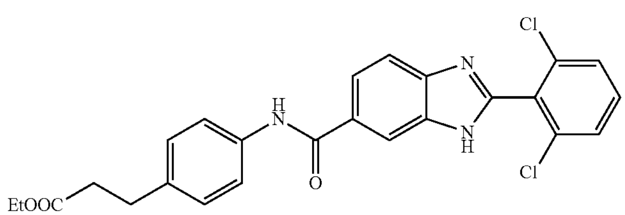 | 3-(4-{[2-(2,6-Dichlorophenyl)-3H-benzoimidazole-5-carbonyl]-amino}-phenyl)-propionic acid ethyl ester | 482 | 1.39 Method 10 |
| 1-251 | 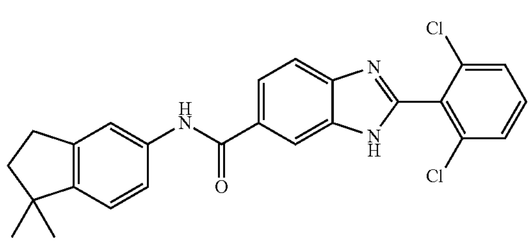 | 2-(2,6-Dichlorophenyl)-3H-benzoimidazole-5-carboxylic acid [1,1-dimethylindan-5-yl)-amide | 450.2 | |

| Example | Structure | Chemical Name | MS found (M + 1) | Retention time (min) Method |
|---|---|---|---|---|
| 1-252 | 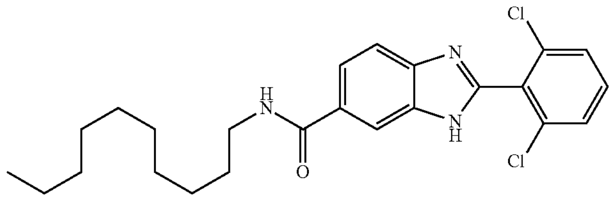 | 2-(2,6-Dichlorophenyl)-3H-benzimidazole-5-carboxylic acid decylamide | 446.2 | |
| 1-253 | 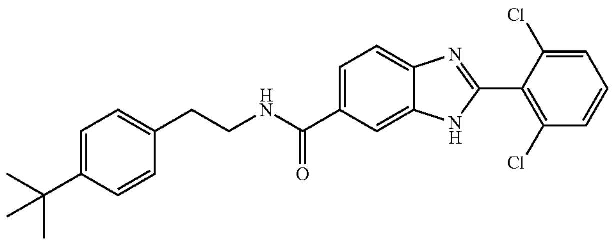 | 2-(2,6-Dichlorophenyl)-3H-benzoimidazole-5-carboxylic acid [2-(4-tert-butylphenyl)-ethyl] amide | 466.2 | |

Example 1-254

2-(2,3-Dimethylphenyl)-3H-benzoimidazole-5-carboxylic acid (3,4-dimethylphenyl)-amide

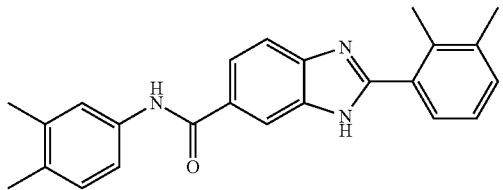

To a solution of 4-amino-3-nitro-benzoic acid (546 mg). EDCI (576 mg) and HOBt (405 mg) in DMF (8 mL) was added 3,4-dimethylaniline (363 mg) and the mixture was stirred at room temperature for 3 h. The mixture was poured into water and exreacted with EtOAc. The organic phase was washed with water (2×) and was dried over sodium sulfate. The solvent was concentrated to approximately 10 mL and the resulting precipitate was filtered, washed with EtOAc and dried under reduced pressure to give 4-amino-N-(3,4-dimethyl-phenyl)-3-nitro-benzamide as a yellow solid, mp=192-195° C.; MS (m/z) 284 (M−1).

A suspension of give 4-amino-N-(3,4-dimethyl-phenyl)-3-nitro-benzamide (560 mg) and platinum oxide (50 mg) in ethanol (50 mL) was hydrogenated at 50 psi for 3 h. The catalyst was filtered through Celite and the filtrate evaporated to give 3,4-diamino-N-(3,4-dimethylphenyl)-benzamide as a brownish foam; MS (m/z) 256 (M+1).

To a solution of 3,4-diamino-N-(3,4-dimethylphenyl)-benzamide (71 mg) and 2,3-dimethylbenzaldehyde (34 mg) in DMSO (1 mL) was added Yb(OTf)$_3$ and the mixture was stirred at room temperature for 4 h. Additional Yb(OTf)$_3$ was added and stirring was continued until starting material was consumed. Water was added and the mixture was extracted with EtOAc. The organic phase was washed with water and dried over sodium sulfate. The solvent was removed under reduced pressure and the residue was purified by flash chromatography using CH$_2$Cl$_2$/EtOAc (2:1) as eluent to furnish 2-(2,3-dimethylphenyl)-3H-benzoimidazole-5-carboxylic acid (3,4-dimethylphenyl)-amide as a beige solid, MS (m/z) 370 (M−1).

Example 1-255

2-(2,6-Dimethylphenyl)-3H-benzoimidazole-5-carboxylic acid naphthalen-2-ylamide

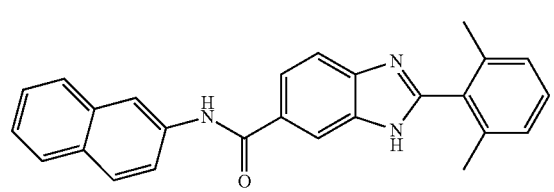

To a solution of 3,4-diaminobenzoic acid methyl ester (5.2 g) and 2,6-dimethylbenzaldehyde (4.2 g) in DMSO (50 mL) was added Yb(OTf)$_3$ (3.9 g). The mixture was stirred at room temperature for 18 h. The mixture was partioned between water and EtOAc and the aqueous layer was extracted with EtOAc. The combined organic layers were dried, filtered and concentrated to give 2-(2,6-dimethylphenyl)-3H-benzoimidazole-5-carboxylic acid methyl ester as a red solid; MS (ESI)m/z 281 (M+H).

To a stirred solution of 2-(2,6-dimethylphenyl)-3H-benzoimidazole-5-carboxylic acid methyl ester (8.5 g) in MeOH (80 mL) was added 1N NaOH (80 mL) and the solution was heated at 100° C. for 18 h. The mixture was washed with Et$_2$O and the aqueous layer was carefully acidified to pH=2-3 with 1N HCl and the resulting precipitate was filtered, washed with water and dried under reduced pressure to give 2-(2,6-dimethylphenyl)-3H-benzoimidazole-5-carboxylic acid as a red solid; MS (ESI)m/z 267 (M+H).

To a mixture of 2-(2,6-dimethylphenyl)-3H-benzoimidazole-5-carboxylic acid (8.0 g) in SOCl$_2$ (30 mL) was added 5 drops of DMF. After the suspension was stirred for 18 h, toluene (20 mL) was added and mixture was stirred for an additional 1 h. The suspension was filtered, washed with toluene and CH$_2$Cl$_2$. The white solid was dried under reduced pressure give 2-(2,6-dimethyl-phenyl)-3H-benzoimidazole-5-carbonyl chloride HCl salt; MS (ESI)m/z 267 (M+H).

To a stirred suspension of 2-(2,6-dimethylphenyl)-3H-benzoimidazole-5-carbonyl chloride HCl salt (160 mg) and naphthalen-2-ylamine (72 mg) was added DIPEA (0.27 mL). The resulting solution was stirred for at room temperature for 18 h then the mixture was partioned between water and EtOAc. The aqueous layer was extracted with EtOAc. The combined organic layers were dried, filtered and concentrated. The residue was purified by an amino column using hexanes/ethyl acetate (1:4) as eluent and gave 2-(2,6-dimethylphenyl)-3H-benzoimidazole-5-carboxylic acid naphthalen-2-ylamide as a white solid; MS (ESI)m/z 392 (M+H).

Example 1-256

2-(2,6-Dimethylphenyl)-3H-benzoimidazole-5-carboxylic acid (4-methyl-2-oxo-2H-chromen-7-yl)-amide

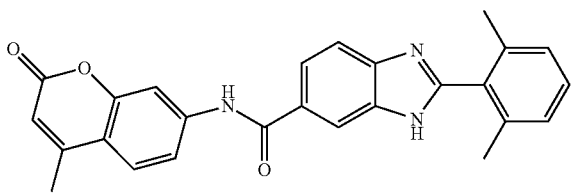

To a stirred suspension of 2-(2,6-dimethylphenyl)-3H-benzoimidazole-5-carbonyl chloride HCl salt (from Example 1-247) (160 mg) and 7-amino-4-methyl-chromen-2-one (87 mg) was added DIPEA (0.27 mL). The resulting solution was stirred at room temperature for 18 h. The mixture was partioned between water and EtOAc and the aqueous layer was extracted with EtOAc. The combined organic layers were dried, filtered and concentrated. The residue was purified by an amino column using hexanes/ethyl acetate (1:4) and gave 2-(2,6-dimethylphenyl)-3H-benzoimidazole-5-carboxylic acid (4-methyl-2-oxo-2H-chromen-7-yl)-amide as a white solid; MS (ESI)m/z 424 (M+H).

Example 1-257

2-(2-Chloro-6-methylphenyl)-3H-benzoimidazole-5-carboxylic acid (3,4-dimethylphenyl)-amide

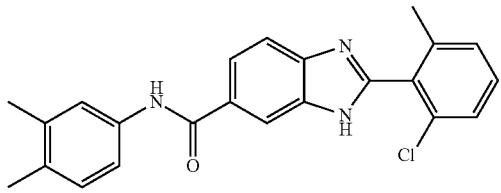

To a solution of 2-chloro-6-methylbenzaldehyde (107 mg) and 3,4-diamino-N-(3,4-dimethylphenyl)-benzamide (Example 5-1, step 6) (160 mg) in DMSO (1.5 mL) was added Yb(OTf)$_3$ (80 mg). The solution was stirred at room temperature for 18 h then an additional 40 mg of Yb(OTf)$_3$ was added the mixture was stirred at 70° C. for 24 h. The mixture was partioned between water and EtOAc. The aqueous layer was extracted with EtOAc. The combined organic layers were dried, filtered and concentrated. The residue was purified by flash chromatography using hexanes/ethyl acetate (5:1) and the product was isolated as a foam. MS (m/z) 390 (M+1), retention time=1.66 min, Method 10.

Example 1-258

2-(2-Chloro-6-trifluoromethylphenyl)-3H-benzoimidazole-5-carboxylic acid quinolin-2-ylamide

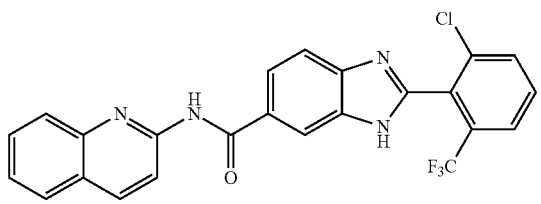

To a solution of 1-chloro-3-trifluoromethylbenzene (1.0 g, 5.54 mmol) in THF (15 mL) cooled to −78° C., under N$_2$ protection was added dropwise n-BuLi (3.81 mL of a 1.6 M solution in hexane, 6.1 mmol). After an hour, formic acid methyl ester (664.8 mg, 11.08 mmol) was added slowly to the solution. After the addition, the solution was warmed to ambient temperature slowly and stirred for 30 min. The reaction mixture was quenched with water and the aqueous layer was extracted with EtOAc. The organic layer was washed with water, brine, dried with MgSO$_4$ and filtered. The solvent was removed under reduced pressure and the residue was purified by flash chromatography using heptane/EtOAc (15:1) as eluent to give 2-chloro-6-trifluoromethylbenzaldehyde as a colorless oil.

To a stirred solution of 2-chloro-6-trifluoromethylbenzaldehyde (270 mg, 1.3 mmol) and 3,4-diaminobenzoic acid methyl ester (216 mg, 1.3 mmol) in DMSO (10 mL) was added Yb(OTf)$_3$ (161 mg, 0.26 mmol) and the solution was stirred at ambient temperature overnight. The reaction was quenched with water and the aqueous layer was extracted with EtOAc. The organic layer was washed with water, brine, dried with MgSO$_4$, and filtered. The solvent was removed under reduced pressure to give 2-(2-chloro-6-trifluoromethylphenyl)-3H-benzoimidazole-5-carboxylic acid methyl ester as a red oil. This was used directly in the next step.

To a stirred solution of 2-(2-chloro-6-trifluoromethylphenyl)-3H-benzoimidazole-5-carboxylic acid methyl ester (430 mg, 1.2 mmol) in MeOH (5 mL) was added 1N NaOH (5 mL). The solution was stirred at ambient temperature overnight and carefully acidified to pH 3 with 1N HCl. The resulting suspension was filtered and washed with water. The pale yellow solid was dried under reduced pressure give 2-(2-chloro-6-trifluoromethylphenyl)-3H-benzoimidazole-5-carboxylic acid.

To a stirred suspension of 2-(2-chloro-6-trifluoromethylphenyl)-3H-benzoimidazole-5-carboxylic acid (400 mg, 1.18 mmol) in SOCl$_2$ (10 mL) was added 3 drops of DMF and the suspension was stirred at ambient temperature overnight. The suspension was filtered and washed with CH$_2$Cl$_2$ and the white solid was dried in under reduced pressure to give 2-(2-chloro-6-trifluoromethylphenyl)-3H-benzoimidazole-5-carbonyl chloride.

To a stirred suspension of 2-(2-chloro-6-trifluoromethylphenyl)-3H-benzoimidazole-5-carbonyl chloride (394 mg, 1.0 mmol) and quinolin-2-ylamine (144 mg, 1.0 mmol) in THF (6 mL) was added DIPEA (0.53 ml, 3.0 mmol). The solution was heated at 60° C. for 2 days and the reaction was quenched with water and aqueous layer was extracted with EtOAc. The organic layer was washed with water, brine, dried with MgSO$_4$, and filtered. The solvent was removed under reduced pressure and the residue was purified by flash chromatography using heptane/EtOAc (1:4) as eluent to give 2-(2-chloro-6-trifluoromethylphenyl)-3H-benzoimidazole-5-carboxylic acid quinolin-2-ylamide as a white solid. $^1$H NMR (Methanol-d4, 400 MHz): δ 8.45 (d, 1H), 8.37 (d, 1H), 8.08 (d, 1H), 7.94 (m, 4H), 7.83 (m, 1H), 7.74 (m, 1H), 7.54 (m, 1H). MS (m/z) 467.1 (M+1); Retention time: 1.45 min (Method 10).

Example 1-259

2-(2,4-Dichloro-6-methoxyphenyl)-3H-benzoimidazole-5-carboxylic acid quinolin-2-ylamide

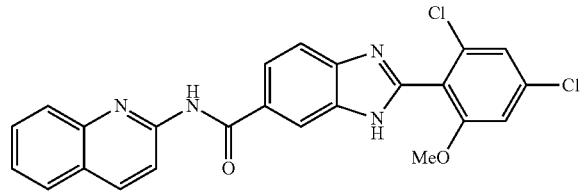

To a solution of 1,3-dichloro-5-methoxybenzene (1.0 g, 5.65 mmol) in THF (15 mL), cooled to −78° C., under N$_2$ protection, was added dropwise sec-BuLi (4.18 ml of a 1.4 M solution in hexane, 5.82 mmol). After 30 minutes, anhydrous DMF (0.65 ml, 8.48 mmol) was added slowly to the solution and the mixture was stirred for at −78° C. 1.5 h. The reaction mixture was quenched with water and the aqueous layer was extracted with EtOAc. The organic layer was washed with water, brine, dried with MgSO$_4$ and filtered. The solvent was removed under reduced pressure and the residue was purified by flash chromatography using heptane/EtOAc (10:1) as eluent to give 2,4-dichloro-6-methoxybenzaldehyde as a colorless oil.

The title compound was prepared using 2,4-dichloro-6-methoxybenzaldehyde analogous to Example 1-258. $^1$H NMR (Methanol-d4, 400 MHz): δ 8.44 (m, 3H), 8.04 (d, 1H), 7.92 (m, 2H), 7.74 (m, 2H), 7.54 (m, 1H), 7.29 (d, 1H), 7.24 (d, 1H), 3.84 (s, 3H). MS (m/z) 463.2 (M+1); Retention time: 1.45 min (Method 10).

Example 1-260

2-(3,5-Dichloro-pyridin-4-yl)-3H-benzoimidazole-5-carboxylic acid quinolin-2-ylamide

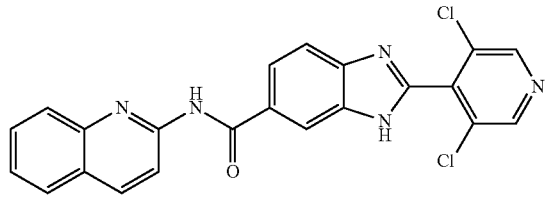

To a solution of 3,5-dichloropyridine (296 mg, 2.0 mmol) in THF (6 mL), cooled to −78° C., under N$_2$ protection, was added dropwise LDA (1.2 mL of a 1.8 M solution in THF, 2.2 mmol). After 30 min, a solution of formic acid methyl ester (240 mg, 4.0 mmol) in THF (1.0 mL) was added slowly to the solution. After 1.5 h, the reaction mixture was rapidly poured into a 0° C. sat. aqueous NaHCO$_3$ solution. The aqueous layer was extracted with EtOAc and the organic layer was washed with water, brine, dried with MgSO$_4$ and filtered. The solvent was removed under reduced pressure and the residue was purified by flash chromatography using heptane/EtOAc (5:1) as eluent to give 3,5-dichloro-pyridine-4-carbaldehyde as a white solid.

The title compound was prepared using 3,5-dichloro-pyridine-4-carbaldehyde analogous to Example 1-258. $^1$H NMR (Methanol-d4, 400 MHz): δ 8.82 (s, 2H), 8.52 (t, 2H), 8.32 (d, 1H), 8.14 (dd, 1H), 8.01 (t, 2H), 7.88 (d, 1H), 7.83 (m, 1H), 7.62 (m, 1H). MS (m/z) 434.0 (M+1); Retention time: 1.28 min (Method 10).

Example 1-261

2-(2,6-Dichlorophenyl)-3H-benzoimidazole-5-carboxylic acid [2-(4-chlorophenyl)-2-oxo-ethyl]-amide

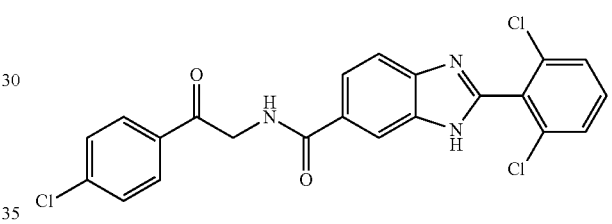

A mixture of 2-bromo-1-(4-chlorophenyl)-acetophenone (500 mg, 2.14 mmol) and sodium diformyl amide (244 mg, 2.57 mmol) in DMF (5 mL) was stirred at ambient temperature for 18 h. The mixture was poured into ethyl acetate, extracted once with water and five times with brine, dried, filtered, and the solvent was removed under reduced pressure. The residue was chromatographed using a gradient of 20-6% heptane/ethyl acetate to afford N,N-diformyl-2-amino-1-(4-chlorophenyl)-acetophenone.

A mixture of N,N-diformyl-2-amino-1-(4-chlorophenyl)-acetophenone (490 mg, 2.14 mmol) in 20 mL of 19:1 ethanol/conc. HCl was stirred at ambient temperature for 18 h. The solvent was removed under reduced pressure to give to afford 1-amino-2-(4-chlorophenyl)-acetophenone hydrochloride.

A mixture of 1-amino-2-(4-chlorophenyl)-acetophenone hydrochloride (320 mg, 1.55 mmol), 2-(2,6-dichlorophenyl)-3H-benzimidazole-5-carbonyl chloride hydrochloride (562 mg, 1.55 mmol) (from Example 1-13), and triethylamine (866 mL, 629 mg, 6.21 mmol) in THF (20 mL) was stirred at ambient temperature for 18 h. The mixture, was poured into ethyl acetate and was extracted with water and brine. The organic phase was dried, filtered, and the solvent was removed under reduced pressure. The residue was purified by chromatography using a gradient of 50-90% heptane/ethyl acetate to give 2-(2,6-dichlorophenyl)-3H-benzimidazole-5-carboxylic acid [2-(4-chlorophenyl)-2-oxo-ethyl]-amide. $^1$H-NMR (DMSO-d6, 400 MHz): δ 13.21 (s, 0.45H), 13.15 (s, 0.55H), 8.93 (m, 1H), 8.32 (s, 0.55H), 8.14 (s, 0.45H), 8.08 (d, J=8.6 Hz, 2H), 7.82 (m, 2H), 7.66 (m, 5H), 4.79 (d, J=5.4 Hz, 2H). MS (ESI) m/z 460.0 (M+H); retention time=1.31 min, (Method 10).

Example 1-262

2-(2,6-Dichlorophenyl)-3H-benzimidazole-5-carboxylic acid [2-(4-chlorophenyl)-1-methyl-2-oxoethyl]-amide

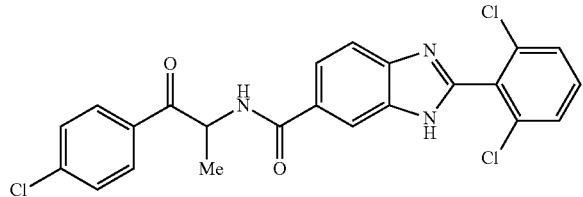

A stirred solution of p-chloropropiophenone (2.0 g, 11.9 mmol) in dichloromethane (35 mL) was treated with one drop of 48% HBr and one drop of bromine. When the color had discharged, bromine (608 µL, 1.90 g, 11.9 mmol) was added dropwise. The solution was stirred until 15 min after the color had fully discharged, then the mixture was concentrated under reduced pressure to give 2-bromo-1-(4-chlorophenyl)-propan-1-one.

A mixture of 2-bromo-1-(4-chlorophenyl)-propan-1-one and sodium diformyl amide (1.24 g, 13.0 mmol) in DMF (10 mL) was stirred at ambient temperature for 18 h. The solution was poured into ethyl acetate and extracted once with water and five times with brine. The solution was dried, filtered, and solvent removed under reduced pressure. The residue was purified by chromatography using a gradient of 20-50% heptane/ethyl acetate to give N,N-diformyl-2-amino-1-(4-chlorophenyl)-propiophenone.

A mixture of N,N-diformyl-2-amino-1-(4-chlorophenyl)-propiophenone (2.36 g, 9.85 mmol) in 40 mL of 19:1 ethanol/conc HCl was stirred at ambient temperature for 18 h. The solvent was removed under reduced pressure to afford 1-(4-chlorophenyl)-2-aminopropiophenone hydrochloride.

A mixture of 1-(4-chlorophenyl)-2-aminopropiophenone hydrochloride (365 mg, 1.66 mmol), 2-(2,6-dichlorophenyl)-3H-benzimidazole-5-carbonyl chloride hydrochloride (600 mg, 1.66 mmol) (from Example 1-13) and triethylamine (924 µL, 671 mg, 6.63 mmol) in THF (25 mL) was stirred at ambient temperature for 18 h. The solution was then poured into ethyl acetate and extracted with water and brine. The organic layer was dried, filtered, and the solvent was removed under reduced pressure. The residue was purified by chromatography using a gradient of 50-90% heptane/ethyl acetate to give 2-(2,6-dichlorophenyl)-3H-benzimidazole-5-carboxylic acid [2-(4-chlorophenyl)-1-methyl-2-oxoethyl]-amide. $^1$H-NMR (acetone-d6, 400 MHz): δ 8.57 (m, broad, 1H), 8.37 (m, 3H), 8.11 (m, broad, 1H), 7.83 (m, 5H), 5.92 (quintet, J=7.2 Hz, 1H), 1.75 (d, J=7.0 Hz, 3H). MS (ESI) m/z 473.9 (M+H).

Example 1-263

2-(2,6-Dichlorophenyl)-6,7-difluoro-3H-benzoimidazole-5-carboxylic acid quinolin-2-ylamide

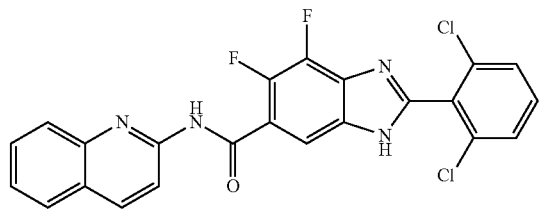

To a stirred solution of 4-amino-2,3-difluoro-5-nitrobenzoic acid methyl ester (500 mg, 2.2 mmol) in EtOH (20 ml) was added PtO$_2$ (50 mg, 10% w). The suspension was hydrogenated with a H$_2$ balloon overnight. The catalyst was filtered through Celite and washed with EtOH The solvent was removed under reduced pressure to give 4,5-diamino-2,3-difluorobenzoic acid methyl ester as a light yellow solid.

To a stirred solution of 4,5-diamino-2,3-difluorobenzoic acid methyl ester (404 mg, 2.0 mmol) and 2,6-dichlorobenzaldehyde in DMSO (15 mL) was added Yb(OTf)$_3$ (248 mg, 20%) and the solution was stirred at ambient temperature overnight. The reaction was quenched with water and the aqueous layer was extracted with EtOAc. The organic layer was washed with water, brine, dried with MgSO$_4$, and filtered. The solvent was removed under reduced pressure to give 2-(2,6-dichlorophenyl)-6,7-difluoro-3H-benzoimidazole-5-carboxylic acid methyl ester as a yellow solid.

To a stirred solution of 2-(2,6-dichlorophenyl)-6,7-difluoro-3H-benzoimidazole-5-carboxylic acid methyl ester (700 mg, 1.97 mmol) in MeOH (15 mL) was added 1N NaOH (10 mL). The solution was stirred at ambient temperature overnight and carefully acidified to pH 3 with 1N HCl. The resulting suspension was filtered and washed with water. The pale yellow solid was dried under reduced pressure to give 2-(2,6-dichlorophenyl)-6,7-difluoro-3H-benzoimidazole-5-carboxylic acid.

To a stirred suspension of 2-(2,6-dichlorophenyl)-6,7-difluoro-3H-benzoimidazole-5-carboxylic acid (570 mg, 1.67 mmol) in SOCl$_2$ (10 mL) was added 3 drops of DMF. The suspension was stirred at ambient temperature overnight. The solid was filtered and washed with CH$_2$Cl$_2$ and was dried under reduced pressure to give 2-(2,6-dichlorophenyl)-6,7-difluoro-3H-benzoimidazole-5-carbonyl chloride.

To a stirred suspension of 2-(2,6-dichlorophenyl)-6,7-difluoro-3H-benzoimidazole-5-carbonyl chloride (150 mg, 0.38 mmol) and quinolin-2-ylamine (55 mg, 0.38 mmol) in THF (10 mL) was added DIPEA (0.2 ml, 1.14 mmol) and the solution was heated at 60° C. for 4 days. The reaction was quenched with water and aqueous layer was extracted with EtOAc. The organic layer was washed with water, brine, dried with MgSO$_4$, and filtered. The solvent was removed under reduced pressure and the residue was purified by flash chromatography using a gradient of heptane/EtOAc (4:1 to 100% EtOAc) to give 2-(2,6-dichlorophenyl)-6,7-difluoro-3H-benzoimidazole-5-carboxylic acid quinolin-2-ylamide as a white solid. $^1$H NMR (DMSO-d6, 400 MHz): δ 13.67 (s, 1H), 11.26 (s, 1H), 8.47 (d, 1H), 8.41 (d, 1H), 7.98 (d, 1H), 7.87 (d, 1H), 7.81 (d, 1H), 7.77 (m, 4H), 7.56 (m, 1H). MS (m/z) 469.1 (M+1); Retention time: 1.51 min (Method 10).

The following compounds were prepared from 2-(2,6-dichlorophenyl)-3H-benzoimidazol-5-ylamine (from Example 1-6) using appropriate acid chlorides and DIPEA or from 3,4-diamino-N-(4-tert-butylphenyl)-benzamide (from Example 6-26) and an 2,6-dimethylbenzaldehyde in the presence of oxone.

| Example | Structure | Chemical Name | MS found (M + 1) | Retention time (min) Method |
|---|---|---|---|---|
| 1-264 | 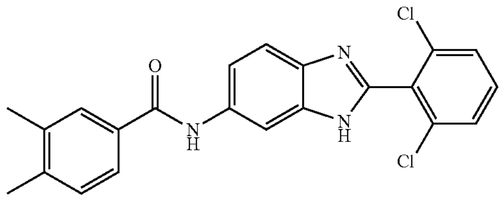 | N-[2-(2,6-dichlorophenyl)-3H-benzoimidazol-5-yl]-3,4-dimethylbenzamide | 410.1 | 1.37 Method 10 |
| 1-265 | 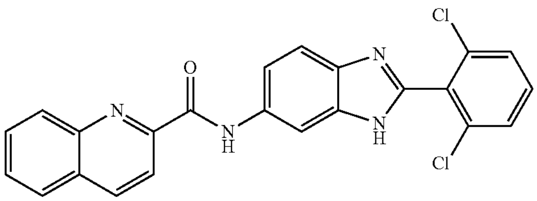 | quinoline-2-carboxylic acid [2-(2,6-dichlorophenyl)-3H-benzimidazol-5-yl]-amide | 433.1 | 1.44 Method 10 |
| 1-266 | 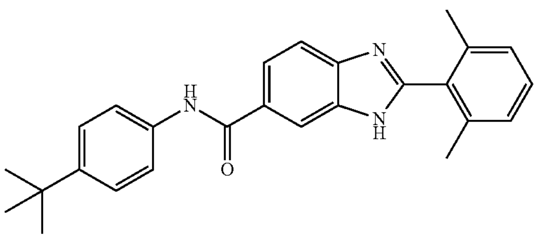 | 2-(2,6-dimethylphenyl)-3H-benzimidazole-5-carboxylic acid (4-tert-butylphenyl)-amide | 398.2 | 1.43 Method 10 |

Example 1-267

1-[2-(2,6-Dichlorophenyl)-3H-benzimidazol-5-yl]-3-(3,4-dimethylphenyl)-urea

Example 1-268

2-(2,4,6-Trichlorophenyl)-3H-benzoimidazole-5-carboxylic acid quinolin-2-ylamide

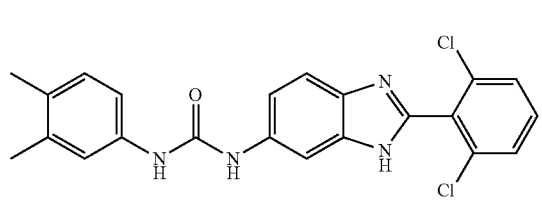

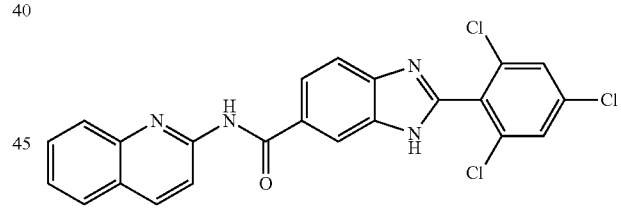

To a solution of 2-(2,6-dichlorophenyl)-3H-benzimidazol-5-ylamine (100 mg, 360 µmol) in THF (5 mL) was added 3,4-dimethylphenylisocyanate (51 µL, 54 mg., 360 µmols) and the mixture was stirred at ambient temperature for 18 h then was poured into ethyl acetate and extracted with water. The organic layer was dried, filtered, and solvent removed under reduced pressure to leave crude product that was purified by chromatography using a 50-90% gradient of heptane/ethyl acetate to give 1-[2-(2,6-dichlorophenyl)-3H-benzimidazol-5-yl]-3-(3,4-dimethylphenyl)-urea. $^1$H NMR (DMSO-d6, 400 MHz): δ 12.69 (s, broad, 1H), 8.69 (s, broad, 1H), 8.48 (s, 1H), 7.95 (s, broad, 1H), 7.67 (d, J=7.7 Hz, 2H), 7.60 (m, 2H), 7.26 (s, 1H), 7.20 (d, J=7.7 Hz, 1H) 7.03 (d, J=8.0 Hz, 2H), 2.20 (s, 3H), 2.16 (s, 3H); MS (m/z) 425.1 (M+1); Retention time=1.35 min (Method 10); High Resolution MS (M+1): theory 425.0936, measured 425.0951.

To a stirred solution of 2,4,6-trichlorobenzoic acid (451 mg, 2.0 mmol) in THF (15 mL) was added BH$_3$ (3 mL of a 1M solution in THF). After the addition, the solution was refluxed overnight. The reaction was quenched with water and the aqueous layer was extracted with EtOAc. The organic layer was washed with water, brine, dried with MgSO$_4$, and filtered. The solvent was removed under reduced pressure to give (2,4,6-trichlorophenyl)-methanol as a white solid.

To a stirred solution of (2,4,6-trichlorophenyl)-methanol (350 mg, 1.67 mmol) in CH$_2$Cl$_2$ (10 mL) was added Dess-Martin reagent (742 mg, 1.75 mmol). After the addition, the solution was stirred at ambient temperature for 2 h. The reaction was quenched with sat. NaHCO$_3$ and the aqueous layer was extracted with EtOAc. The organic layer was washed with water, brine, dried with MgSO$_4$, and filtered. The solvent was removed under reduced pressure to give 2,4,6-trichlorobenzaldehyde as a white solid.

To a stirred solution of 2,4,6-trichlorobenzaldehyde (150 mg, 0.72 mmol) and 3,4-diamino-N-quinolin-2-yl-benzamide (200 mg, 0.72 mmol) in DMSO (10 mL) was added FeCl$_3$ (23 mg, 0.14 mmol). The solution was stirred at ambient temperature for 2 days. The reaction was quenched with water and the aqueous layer was extracted with EtOAc. The organic layer was washed with water, brine, dried with MgSO$_4$, and filtered. The solvent was removed under reduced pressure and the residue was purified by flash chromatography using heptane/EtOAc (1/3) as eluent to give the title compound as a white solid. $^1$H NMR (Methanol-d4, 400 MHz): δ 8.45 (m, 3H), 8.08 (d, 1H), 7.93 (m, 2H), 7.85 (s, 1H), 7.76 (s, 2H), 7.75 (m, 1H), 7.55 (m, 1H). MS (m/z) 467.0 (M+1); Retention time: 1.48 min (Method 10).

Example 2-1

2-(4-Chloro-phenyl)-3-(2-hydroxyethyl)-3H-benzoimidazole-5-carboxylic acid (3,4-dimethyl-phenyl)-amide

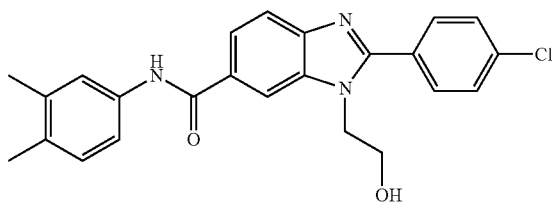

A solution of 3-fluoro-4-nitrobenzoic acid (2 g), 3,4-dimethylaniline (1.25 g), BOP (5.45 g) and DIEA (2.69 mL) in DMF (20 mL) was stirred at room temperature for 20 h. Then 1N NaOH aqueous solution was added (pH~12). The aqueous layer was extracted with EtOAc. The organic extracts were washed with brine, dried over Na$_2$SO$_4$, filtered and concentrated under reduced pressure. The crude product was washed with CH$_2$Cl$_2$/MeOH mixture, and the solid was filtered to give N-(3,4-dimethyl-phenyl)-3-fluoro-4-nitrobenzamide as a yellow solid: MS (m/z) 289 (M+1); $^1$H NMR (DMSO-d6, 400 MHz) δ 10.39 (s, 1H), 8.30 (t, 1H), 8.10 (d, 1H), 7.97 (d, 1H), 7.53 (s, 1H), 7.49 (d, 1H), 7.13 (d, 1H), 2.23 (s, 3H), 2.20 (s, 3H).

A mixture of N-(3,4-dimethyl-phenyl)-3-fluoro-4-nitrobenzamide (65 mg), 2-hydroxy-1-ethylamine (0.225 mL of 2M THF solution) in DMF (1 mL) was heated at 120° C. under microwave radiation for 5 min. Then saturated NaHCO$_3$ aqueous solution was added. The aqueous layer was extracted with EtOAc. The organic extracts were washed with brine, dried over Na$_2$SO$_4$, filtered and concentrated under reduced pressure to give N-(3,4-dimethyl-phenyl)-3-(2-hydroxy-ethylamino)-4-nitrobenzamide as a yellow oil: MS (m/z) 300 (M+1); $^1$H NMR (CDCl$_3$, 400 MHz) δ 8.24 (d, 1H), 8.06 (s, 1H), 7.78 (s, 1H), 7.42 (d, 2H), 7.35 (d, 1H), 7.13 (d, 1H), 6.95 (d, 1H), 3.09 (d, 3H), 2.28 (s, 3H), 2.25 (s, 3H), 1.58 (s, 1H).

To a solution of N-(3,4-dimethyl-phenyl)-3-(2-hydroxy-ethylamino)-4-nitro-benzamide (70 mg) in MeOH (20 mL) was added 10% Pd/C (10 mg). The reaction mixture was stirred under H$_2$ balloon at room temperature for 16 h. The reaction mixture was filtered through celite, washed with MeOH. The filtrate was concentrated under reduced pressure to give 4-amino-N-(3,4-dimethyl-phenyl)-3-(2-hydroxy-ethylamino)-benzamide as a grey solid; MS (m/z) 300 (M+1); $^1$H NMR (DMSO-d6, 400 MHz) δ 9.54 (s, 1H), 7.51 (s, 1H), 7.45 (d, 1H), 7.18 (d, 1H), 7.04 (d, 2H), 6.57 (d, 1H), 5.12 (s, 2H), 4.69 (t, 1H), 4.50 (t, 1H), 3.65 (q, 2H), 3.19 (q, 2H), 2.20 (s, 3H), 2.17 (s, 3H).

A mixture of 4-amino-N-(3,4-dimethyl-phenyl)-3-(2-hydroxy-ethylamino)-benzamide (0.1 mL in 0.2 M DMSO solution), 4-chlorobenzaldehyde (0.1 mL in 0.2 M toluene solution) and FeCl$_3$ (0.05 mL in 0.02 M THF solution) was stirred in open air at ambient temperature overnight. The mixture was then diluted by MeOH and the whole was loaded onto a solid phase extraction (SPE) cartridge that contained strong cation exchange (SCX) (1 g media in 6 mL cartridge, United Chemical Technology). Wash-to-waste (5 mL MeOH) was followed by elute-to-collect (5 mL 20:2:1 ethyl acetate-MeOH-Et3N) and, after evaporation of volatiles, the crude was further purified by silica gel column chromatography to give 2-(4-chlorophenyl)-3-(2-hydroxy-ethyl)-3H-benzoimidazole-5-carboxylicacid (3,4-dimethylphenyl)-amide: MS (m/z) 420 (M+1).

By employing the method of Example 2-1, using appropriate starting materials, the following compounds were prepared:

| Example | Structure | Chemical Name | MS found (M + 1) |
|---|---|---|---|
| 2-2 | 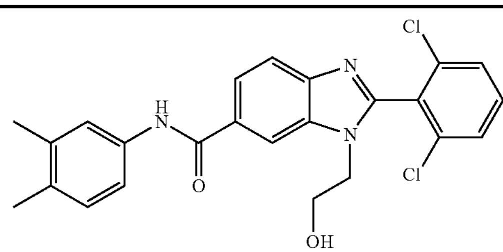 | 2-(2,6-Dichloro-phenyl)-3-(2-hydroxy-ethyl)-3H-benzoimidazole-5-carboxylic acid (3,4-dimethyl-phenyl)-amide | 454 |
| 2-3 | 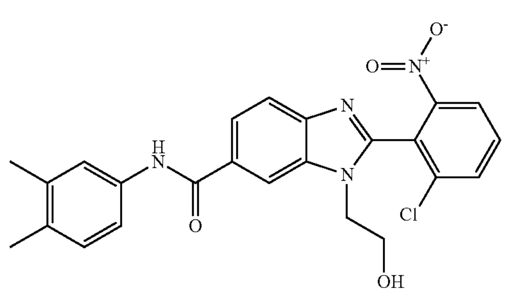 | 2-(2-Chloro-6-nitro-phenyl)-3-(2-hydroxy-ethyl)-3H-benzoimidazole-5-carboxylic acid (3,4-dimethyl-phenyl)-amide | 465 |

| Example | Structure | Chemical Name | MS found (M + 1) |
|---|---|---|---|
| 2-4 | 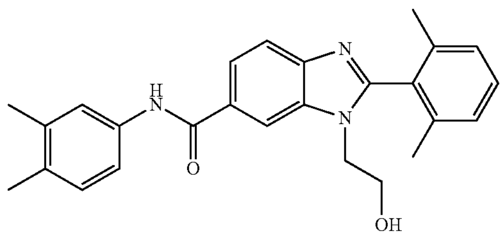 | 2-(2,6-Dimethyl-phenyl)-3-(2-hydroxy-ethyl)-3H-benzoimidazole-5-carboxylic acid (3,4-dimethyl-phenyl)-amide | 414 |
| 2-5 | 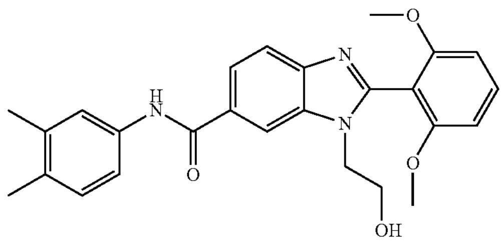 | 2-(2,6-Dimethoxy-phenyl)-3-(2-hydroxy-ethyl)-3H-benzoimidazole-5-carboxylic acid (3,4-dimethyl-phenyl)-amide | 446 |
| 2-6 | 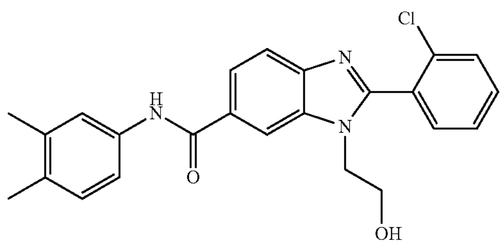 | 2-(2-Chloro-phenyl)-3-(2-hydroxy-ethyl)-3H-benzoimidazole-5-carboxylicacid (3,4-dimethyl-phenyl)-amide | 420 |

The following compounds are similarly prepared using the method of Example 2-1. The key intermediate, N-(3,4-dimethyl-phenyl)-3-methylamino-4-nitro-benzamide can be prepared by using methylamine instead of 2-hydroxy-1-ethylamine:

| Example | Structure | Chemical Name | MS found (M + 1) |
|---|---|---|---|
| 2-7 | 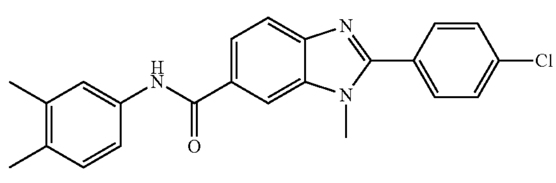 | 2-(4-Chloro-phenyl)-3-methyl-3H-benzoimidazole-5-carboxylic acid (3,4-dimethyl-phenyl)-amide | 390 |
| 2-8 | 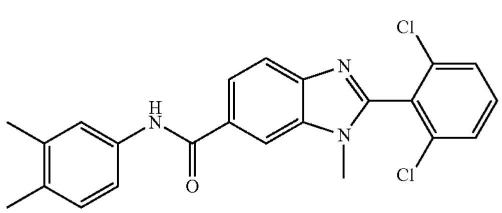 | 2-(2,6-Dichloro-phenyl)-3-methyl-3H-benzoimidazole-5-carboxylic acid (3,4-dimethyl-phenyl)-amide | 424 |

| Example | Structure | Chemical Name | MS found (M + 1) |
|---|---|---|---|
| 2-9 | 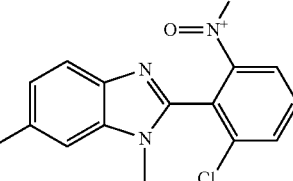 | 2-(2-Chloro-6-nitro-phenyl)-3-methyl-3H-benzoimidazole-5-carboxylic acid (3,4-dimethyl-phenyl)-amide | 435 |
| 2-10 | 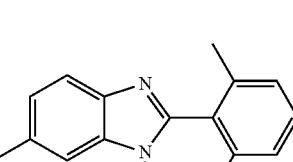 | 2-(2,6-Dimethyl-phenyl)-3-methyl-3H-benzoimidazole-5-carboxylic acid (3,4-dimethyl-phenyl)-amide | 384 |
| 2-11 | 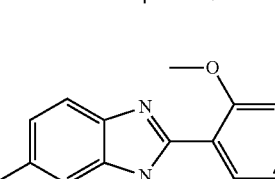 | 2-(2,6-Dimethoxy-phenyl)-3-methyl-3H-benzoimidazole-5-carboxylic acid (3,4-dimethyl-phenyl)-amide | 416 |
| 2-12 | 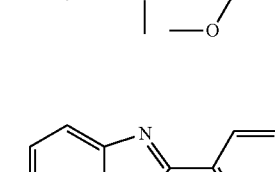 | 2-(2-Chloro-phenyl)-3-methyl-3H-benzoimidazole-5-carboxylic acid (3,4-dimethyl-phenyl)-amide | 390 |

Example 2-13

2-(2,6-Dichlorophenyl)-1-methyl-1H-benzoimidazole-5-carboxylic acid (3,4-dimethylphenyl)-amide

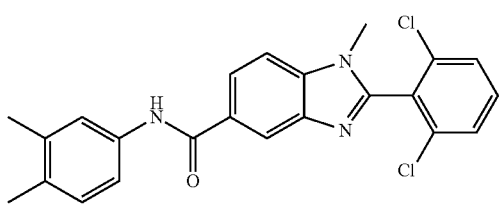

To a solution of 3-amino-4-methylaminobenzoic acid ethyl ester (388 mg) and 2,6-dichlorobenzaldehyde (350 mg) in DMSO (4 mL) was added Yb(OTf)$_3$ (50 mg) and the solution was stirred at room temperature for 24 h. More Yb(OTf)$_3$ was added and stirring was continued for 24 h. This process was repeated another two times. The reaction mixture was partioned between water and EtOAc. The aqueous layer was extracted with EtOAc. The combined organic layers were dried, filtered and concentrated. The residue was purified by flash chromatography using a gradient of ethyl acetate/CH$_2$Cl$_2$ (0% to 25%) to give 2-(2,6-dichlorophenyl)-1-methyl-1H-benzoimidazole-5-carboxylic acid ethyl ester as a beige solid, mp=164-166° C.; MS (m/z) 349 (M+1).

To a suspension of 2-(2,6-dichlorophenyl)-1-methyl-1H-benzoimidazole-5-carboxylic acid ethyl ester (400 mg) in EtOH (8 mL) was added 1.0 N NaOH (2.0 mL) and the mixture was stirred at 60° C. for 90 min. The ethanol was removed under reduced pressure and water (10 mL) was added. Any insoluble material was filtered and 2.0N HCl (2.0 mL) was added to the filtrate. The resulting precipitate was filtered, washed with water and dried under reduced pressure to give 2-(2,6-dichlorophenyl)-1-methyl-1H-benzoimidazole-5-carboxylic acid as a white solid, mp>250° C.; MS (m/z) 321 (M+1).

To a mixture of 2-(2,6-dichlorophenyl)-1-methyl-1H-benzoimidazole-5-carboxylic acid (100 mg), EDCI (59 mg) and HOBt (42 mg) in DMF (2 mL) was added 3,4-dimethylaniline (38 mg) and the mixture was stirred at room temperature for 18 h. The mixture was poured into water and was extracted with EtOAc. The organic phase was washed with water (3×) and dried over sodium sulfate. The solvent was removed under reduced pressure and the residue purified by flash chromatography using EtOAc/CH$_2$Cl$_2$ (1:5) as eluent to give 2-(2,6-dichlorophenyl)-1-methyl-1H-benzoimidazole-5-carboxylic acid (3,4-dimethylphenyl)-amide as a glasslike solid; MS (m/z) 424 (M+1); $^1$H NMR (CDCl$_3$, 400 MHz) δ 8.36 (s, 1H), 8.24 (s, 1H), 8.00 d, J=8.59 Hz, 1H), 7.52-7.39 (m, 6H), 7.10 (d, J=8.08 Hz, 1H), 3.65 (s, 3H), 2.28 (s, 3H), 2.25 (s, 3H).

Example 3-1

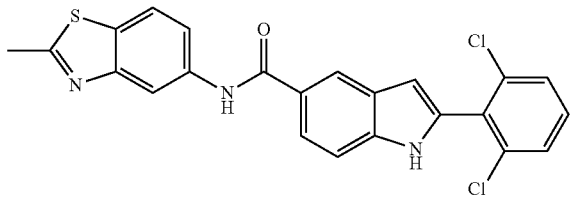

To a solution of 4-amino-benzoic acid methyl ester (1 g) in 10 mL of acetic acid and 10 mL of CH$_2$Cl$_2$ was added benzyltrimethylammonium dichloroiodate (2.763 g) at ambient temperature. The reaction mixture was heated at 55° C. for 1.5 h. The reaction mixture was concentrated to give the crude 4-amino-3-iodo-benzoic acid methyl ester: MS (m/z) 278.0 (M+1).

To a solution of the crude 4-amino-3-iodo-benzoic acid methyl ester in 20 mL of acetic acid was added acetic anhydride (1.25 mL). The reaction was heated at 60° C. for 1 h. The reaction mixture was quenched with water, extracted with ethyl acetate, dried over Na$_2$SO$_4$, and concentrated in vacuo. Purification by flash chromatography (SiO$_2$, 1:3 EtOAc/Hexane) afforded 4-acetylamino-3-iodo-benzoic acid methyl ester: MS (m/z) 320.0 (M+1).

To a solution of 4-acetylamino-3-iodo-benzoic acid methyl ester (0.17 g) in TMG (1.5 mL) and dioxane (1.5 mL) were added 1,3-dichloro-2-ethynyl-benzene (0.1 g), 10 mol % of Pd(PPh$_3$)$_2$Cl$_2$, and 10 mol % of CuI. The reaction mixture was heated to 100° C. overnight. The solvent were evaporated and the resulting mixture was purified by column chromatography (SiO$_2$, 2:3, EtOAc/Hexane) to give 2-(2,6-dichlorophenyl)-1H-indole-5-carboxylic acid methyl ester: MS (m/z) 320.0 (M+1).

A solution of 2-(2,6-dichloro-phenyl)-1H-indole-5-carboxylic acid methyl ester in 2N LiOH aqueous solution (1 mL) and THF (1 mL) was stirred at room temperature for 16 h. The mixture was washed with Et$_2$O. The aqueous layer was acidified with 1N HCl aqueous solution, extracted with Et$_2$O. The organic extracts were dried over Na$_2$SO$_4$, filtered and concentrated under reduced pressure to give 2-(2,6-dichlorophenyl)-1H-indole-5-carboxylic acid as a white solid: MS (m/z) 306.1 (M+1).

To a solution of 2-(2,6-dichloro-phenyl)-1H-indole-5-carboxylic acid (8.8 mg) in anhydrous DMF (0.5 mL) was added BOP (17.4 mg), diisopropylethylamine (0.014 mL), and 3,4-dimethylaniline (5.0 mg). The reaction mixture was stirred at 85° C. overnight, quenched with 1N NaOH aqueous solution at 0° C., extracted with EtOAc. The extracts were dried over Na$_2$SO$_4$, and concentrated in vacuo. The crude reaction mixture was purified by silica SPE eluting with EtOAc/Hexane to give 2-(2,6-dichloro-phenyl)-1H-indole-5-carboxylic acid (2-methyl-benzothiazol-5-yl)-amide: MS (m/z) 452.1 (M+1).

By employing the method of Example 3-1, using appropriate starting materials, the following compounds were prepared:

| Example | Structure | Chemical Name | MS found (M + 1) |
|---|---|---|---|
| 3-2 | 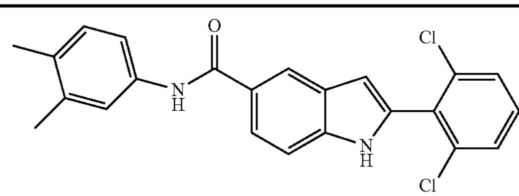 | 2-(2,6-Dichloro-phenyl)-1H-indole-5-carboxylic acid (3,4-dimethyl-phenyl)-amide | 409.3 |
| 3-3 | 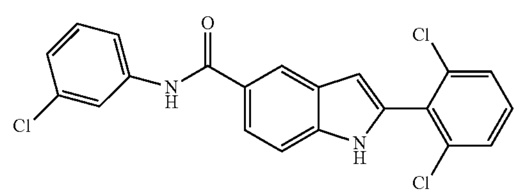 | 2-(2,6-Dichloro-phenyl)-1H-indole-5-carboxylic acid (3-chloro-phenyl)-amide | 417.0 |

Example 3-4

2-(2,6-Dimethylphenyl)-1H-indole-6-carboxylic acid (4-tert-butylphenyl)-amide

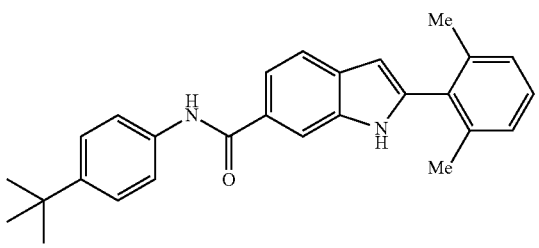

A mixture of methyl 3-aminobenzoate (5.0 g, 33.1 mmol) and benzyltrimethylammonium iodonium dichloride (11.51 g, 33.1 mmols) in acetic acid (20 mL) was stirred at ambient temperature for 18 h. The mixture was concentrated, then poured into ethyl acetate and extracted with aq. NaOH until washes remained basic. The washes were back-extracted with ethyl acetate and the combined ethyl acetate layers were dried, filtered, and the solvent was removed under reduced pressure. The residue was chromatographed on silica gel using a gradient of 0-40% heptane/ethyl acetate to afford methyl 3-amino-4-iodobenzoate.

A mixture of 2-bromo-m-xylene (3.50 mL, 2.52 g, 13.6 mmol), copper (I) iodide (52 mg, 270 µmol), triphenylphosphine (179 mg, 680 µmol), bis-(triphenylphosphine) palladium (II) chloride (191 mg, 270 µmol) and trimethylsilylacetylene (2.5 mL, 1.74 g, 17.7 mmol) in piperidine (18 mL) was heated at reflux for 6 h. The cooled mixture was diluted with hexane and filtered through Celite. The filtrate was extracted five times with water and once with brine, then dried, filtered, and the was solvent removed under reduced pressure. The residual oil of (2,6-dimethylphenylethynyl)-trimethylsilane was used in the next step without further purification.

To an ice cold solution of (2,6-dimethylphenylethynyl)-trimethylsilane from the previous step in THF (20 mL) was added tetrabutylammonium fluoride in THF (17 mL of 1 M solution) dropwise. After stirring 18 h, the solution was diluted with hexane and extracted with water and brine. The organic layer was dried, filtered, and solvent removed under reduced pressure. The residual oil was redissolved in hexane and filtered through a silica gel plug, then chromatographed using hexane as eluent to give 2,6-dimethylphenylacetylene.

A mixture of methyl 3-amino-4-iodobenzoate (920 mg, 3.32 mmol), 2,6-dimethylphenylacetylene (540 mg, 4.15 mmol),), bis-(triphenylphosphine) palladium (II) chloride (47 mg, 67 µmol), diethylamine (486 mg, 66 mmol), and copper (I) iodide (19 mg, 100 µmol) in DMF (10 mL) was heated at 120° C. in a microwave apparatus for 10 min. The mixture was poured into ethyl acetate and extracted six times with brine. The organic phase was dried, filtered, and the solvent was removed under reduced pressure to leave a residue that was chromatographed using a gradient of 0-30% heptane/ethyl acetate to afford methyl 3-amino-4-(2,6-dimethylphenylethynyl)-benzoate.

A mixture of methyl 3-amino-4-(2,6-dimethylphenylethynyl)-benzoate (150 mg, 540 µmol), trifluororacetic anhydride (82 µL, 124 mg, 590 µmol) and pyridine (48 µL, 47 mg, 590 µmol) in dichloromethane (10 mL) was stirred at ambient temperature for 18 h. Another 41 µL of anhydride and 24 µL of pyridine were added and stirred another 24 h. The solution was poured into ethyl acetate and extracted with water and brine. The organic phase was dried, filtered, and the solvent was removed under reduced pressure. The residue was chromatographed using a gradient of 10-40% heptane/ethyl acetate to afford methyl 4-(2,6-dimethylphenylethynyl)-3-(2,2,2-trifluoroacetylamino)-benzoate.

A mixture of methyl 4-(2,6-dimethylphenylethynyl)-3-(2,2,2-trifluoroacetylamino)-benzoate (103 mg, 270 µmol), copper (I) iodide (2 mg, 10 µmol), triphenylphosphine (6 mg, 23 µmol), and K$_3$PO$_4$ (117 mg, 550 µmol) in dioxane (2 mL) was heated at 115° C. in a microwave apparatus for 15 min. The solution was concentrated, then chromatographed using a gradient of 0-40% heptane/ethyl acetate to afford methyl 2-(2,6-dimethylphenyl)-1H-indole-6-carboxylate.

A mixture of methyl 2-(2,6-dimethylphenyl)-1H-indole-6-carboxylate (490 mg, 1.75 mmol) and 1N sodium hydroxide (3.5 mL, 3.5 mmol) in ethanol (25 mL) was heated at 80° C. for 18 h. The solution was poured into ethyl acetate and extracted with 1N HCl. The organic phase was dried, filtered, and solvent was removed under reduced pressure to afford 2-(2,6-dimethylphenyl)-1H-indole-6-carboxylic acid.

A mixture of 2-(2,6-dimethylphenyl)-1H-indole-6-carboxylic acid. (17 mg, 60 µmol), 4-tert.-butylaniline (10 µL, 9.4 mg, 63 µmol) and HATU (33 mg, 87 µmol) in DMF (3 mL) was stirred, initially at ambient temperature, then at 60° C. for 18 h. The mixture was poured into ethyl acetate and extracted once with water and five times with brine. The organic layer was dried, filtered, and solvent was removed under reduced pressure. The residual material was chromatographed using a gradient of 20-60% heptane/ethyl acetate to give 2-(2,6-dimethylphenyl)-1H-indole-6-carboxylic acid (4-tert-butylphenyl)-amide. $^1$H NMR (CDCl$_3$, 400 MHz) δ 8.54 (s, broad, 1H), 8.12 (s, 1H), 7.89 (s, 1H), 7.70 (d, J=8.3 Hz, 1H), 7.56 (m, 3H), 7.37 (d, J=8.7 Hz, 2H), 7.15 (d, J=7.6 Hz, 2H), 6.46 (s, 1H), 2.18 (s, 6H), 1.33 (s, 9H). MS (m/z) 397.2 (M+1).

Example 3-5

2-(2,6-Dichlorophenyl)-1H-indole-6-carboxylic acid (3,4-dimethylphenyl)-amide

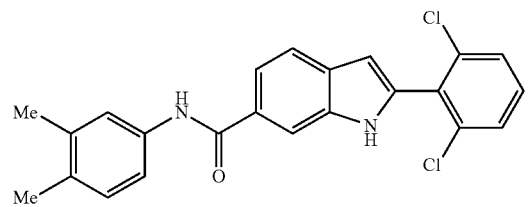

To a mixture of tosyl azide (2.70 g, 32 mmol) and K$_2$CO$_3$ (4.74 g, 34.3 mmol) in dry acetonitrile (20 mL) was added dropwise a solution of dimethyl 2-(oxopropyl)-phosphonate (1.89 mL, 2.27 g, 13.7 mmol) in acetonitrile (5 mL) then the mixture was stirred at ambient temperature for 3 h. To this mixture was added dropwise a solution of 2,6-dichlorobenzaldehyde (2.0 g, 11.4 mmol) in methanol (15 mL), and the resulting mixture stirred at ambient temperature for 18 h. The solvent was removed under reduced pressure, and the residue stirred with ethyl acetate and sat. ammonium chloride. This mixture was filtered to remove insolubles, and the filtrate separated. The aqueous phase was re-extracted with ethyl acetate, and the combined organic layers were dried, filtered, and the was solvent removed under reduced pressure. The residue was purified by chromatography using a gradient of 0-20% hexane/ethyl acetate to afford 2,6-dichlorophenylacetylene.

A mixture of methyl 3-amino-4-iodobenzoate (604 mg, 2.18 mmol) (from Example 3-4), 2,6-dichlorophenylacetylene (447 mg, 2.61 mmol), palladium (II) chloride bis(acetonitrile) (23 mg, 89 µmol), diethylamine (449 µL, 318 mg, 4.35 mmol), and copper (I) iodide (21 mg, 110 µmol) in acetonitrile (10 mL) was heated for 35 min at 120° C. in a microwave apparatus. The mixture was filtered, and the filtrate concentrated, then chromatographed using a gradient of 0-30% heptane/ethyl acetate to give methyl 3-amino-4-(2,6-dichlorophenylethynyl)-benzoate.

A mixture of methyl 3-amino-4-(2,6-dichlorophenylethynyl)-benzoate (450 mg, 1.41 mmol) and palladium (II) chloride bis(acetonitrile) (90 mg, 347 µmol) in acetonitrile (5 mL) was heated at 65° C. for 2 h. The solvent was removed on under reduced pressure and the residue was purified by chromatography using a gradient of 10-30% heptane/ethyl acetate to give methyl 2-(2,6-dichlorophenyl)-1H-indole-6-carboxylate.

A mixture of methyl 2-(2,6-dichlorophenyl)-1H-indole-6-carboxylate (160 mg, 500 μmol) and 1N NaOH (1.5 mL) in ethanol (25 mL) was heated at 80° C. for 18 h. The solution was cooled to ambient temperature, diluted with ethyl acetate, acidified with conc. HCl, and the layers separated. The aqueous phase was re-extracted with ethyl acetate, and the combined organic layers were dried, filtered, and the solvent was removed under reduced pressure to afford 2-(2,6-dichlorophenyl)-1H-indole-6-carboxylic acid. MS (m/z) 304.0 (M−1).

A mixture of 2-(2,6-dichlorophenyl)-1H-indole-6-carboxylic acid (150 mg, 490 μmol), 3,4-dimethylaniline (60 mg, 500 μmol), HATU (280 mg, 740 μmol), and triethylamine (137 μL, 99 mg, 980 μmol) in DMF (10 mL) was stirred 18 h at ambient temperature. The solution was decanted into ethyl acetate and extracted once with water and five times with brine, then dried, filtered, and the solvent removed under reduced pressure to leave an oil, which was purified by chromatography using a gradient of 10-50% heptane/ethyl acetate to give 2-(2,6-dichlorophenyl)-1H-indole-6-carboxylic acid (3,4-dimethylphenyl)-amide. $^1$H NMR (CDCl$_3$, 400 MHz) δ 8.53 (s, broad, 1H), 8.11 (s, 1H), 7.83 (s, 1H), 7.75 (d, J=8.2 Hz, 1H), 7.58 (d, J=8.3 Hz, 1H), 7.46 (m, 3H), 7.38 (dd, J=10.4, 2.1 Hz, 1H), 7.31 (m, 1H), 7.13 (d, J=8.2 Hz, 1H), 6.72 (s, 1H), 2.29 (s, 3H), 2.25 (s, 2H). MS (m/z) 409.1 (M+1); retention time=1.68 min (Method 10). High Resolution, MS (M+H): theory, 409.0874; measured 409.0867.

Example 3-6

2-(2,6-Dichlorophenyl)-1H-indole-6-carboxylic acid quinolin-2-ylamide

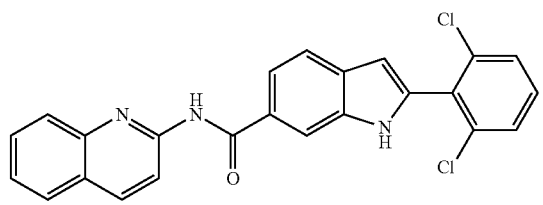

To 10 mL of ice-cold toluene was added 844 μL of 2 M trimethylaluminum in toluene then 2-aminoquinoline (233 mg, 1.62 mmol) was added in one portion and the mixture was stirred for 25 min. To this was added a solution of methyl 2-(2,6-dichlorophenyl)-1H-indole-6-carboxylate (470 mg, 1.47 mmol) (from Example 3-5) in toluene (7 mL) dropwise and the resulting solution was heated at 100° C. for 18 h. A second aliquot of trimethylaluminum was added and the mixture heated another 18 h, after which it was cooled to ambient temperature, quenched with 1N HCl, and basified by stirring with 8% NaHCO$_3$. This mixture was filtered, and the filtrate separated. The aqueous layer was re-extracted with ethyl acetate, and the combined organic layers were dried, filtered, and the solvent was removed under reduced pressure. The residue was chromatographed using a gradient of 20-50% heptane/ethyl acetate to give 2-(2,6-dichlorophenyl)-1H-indole-6-carboxylic acid quinolin-2-ylamide. $^1$H NMR (DMSO-d6, 400 MHz) δ 11.85 (s, 1H), 11.06 (s, 1H), 8.40 (s, 2H), 8.22 (s, 1H), 7.96 (d, J=8.8 Hz, 1H), 7.89 (d, J=8.3 Hz, 1H), 7.81 (dd, J=8.3, 1.5 Hz, 1H), 7.74 (td, J=6.8, 1.5 Hz, 1H), 7.70 (d, J=8.6 Hz, 1H), 7.88 (s, 1H), 7.66 (s, 1H), 7.53 (m, 2H), 6.62 (s, 1H). MS (m/z) 432.0 (M+1); retention time=1.57 min (Method 10).

Example 3-7

2-(2,6-Dimethylphenyl)-1H-indole-6-carboxylic acid quinolin-2-ylamide

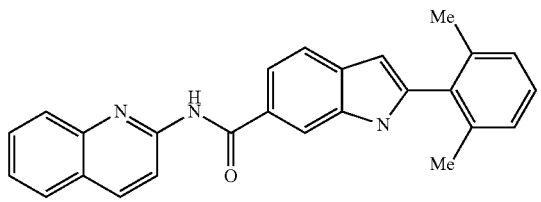

The title compound was prepared from methyl 2-(2,6-dimethylphenyl)-1H-indole-6-carboxylate and 2-aminoquinoline analogous to Example 3-6. $^1$H NMR (DMSO-d6, 400 MHz) δ 11.60 (s, 1H), 11.01 (s, 1H), 8.40 (s, 2H), 7.95 (d, J=7.83 Hz, 1H), 7.89 (d, J=8.46 Hz, 1H), 7.80 (d, J=9.60 Hz, 1H), 7.74 (t, 1H), 7.65 (d, J=8.34 Hz, 1H), 7.52 (t, 1H), 7.28 (m, 1H), 7.19 (d, J=7.45 Hz, 1H), 6.44 (s, 1H), 2.15 (s, 6H). MS (m/z) 392.2 (M+1).

Example 3-8

2-(2,6-Dichlorophenyl)-1H-indole-6-carboxylic acid (6-trifluoromethylpyridin-3-yl)-amide

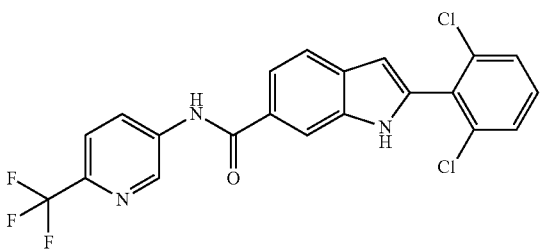

To a solution of 4-bromomethyl-3-nitrobenzoic acid (2.6 g, 10 mmol), MeOH (320 mg, 10 mmol) and DMAP (122 mg, 1 mmol) in methylene chloride (40 mL) was added DCC (2.06 g, 10 mmol) and the resulting mixture was stirred at ambient temperature for 2 h. The resulting precipitate was filtered and the filtrate evaporated under reduced pressure. The resulting oil was filtered through a plug of silica gel using methylene chloride as eluent. The solvent was removed under reduced pressure to give 4-bromomethyl-3-nitrobenzoic acid methyl ester as a pale-yellow oil.

A solution of 4-bromomethyl-3-nitrobenzoic acid methyl ester (1.89 g, 6.9 mmol) and Ph$_3$P (1.82 g, 6.9 mmol) in DMF (35 mL) was heated at 100° C. for 1 h then 2,6-dichlorobenzaldehyde (1.2 g, 6.9 mmol) was added followed by K$_2$CO$_3$ (1.9 g, 13.75 mmol). The resulting deep-red mixture was stirred at 100° C. for 18 h then was allowed to cool to ambient temperature. To this was added water and the mixture was extracted with EtOAc. The organic phase was washed with water (3×) and dried over sodium sulfate. The solvent was removed under reduced pressure and the residue was purified by chromatography using methylene chloride as eluent to give 4-[(E)-2-(2,6-dichlorophenyl)-vinyl]-3-nitrobenzoic acid methyl ester as a pale-yellow solid.

A mixture of 4-[(E)-2-(2,6-dichlorophenyl)-vinyl]-3-nitrobenzoic acid methyl ester (1.6 g, 4.5 mmol) and triethylphosphite (7.7 g, 6 equiv.) was heated at 162° C. for 3 h. Excess triethylphosphite was removed under reduced pressure and the redidual oil was purified by chromatography using methylene chloride as eluent to give methyl 2-(2,6-dichlorophenyl)-1H-indole-6-carboxylate as a white solid. ¹H NMR (DMSO-d6, 400 MHz) δ 11.88 (s, 1H), 8.05 (s, 1H), 7.71-7.65 (m, 4H), 7.65-7.53 (m, 1H), 6.63 (s, 1H), 3.87 (s, 3H). MS (m/z) 320.07 (M+1).

To 4 mL of ice-cold toluene was added 0.28 mL of 2 M trimethylaluminum in toluene then 6-trifluoromethyl-pyridin-3-ylamine (84 mg, 0.5 mmol) was added in one portion and the yellow solution was stirred for 30 min. To this was added a solution of methyl 2-(2,6-dichlorophenyl)-1H-indole-6-carboxylate (150 mg, 0.47 mmol) in toluene (5 mL) dropwise and the resulting solution was heated at 100° C. for 18 h. A second aliquot of trimethylaluminum was added and the mixture heated another 18 h, after which it was cooled to ambient temperature, quenched with 1N HCl. Water was added and the mixture was extracted with EtOAc (2×). The combined organic layers were dried over sodium sulfate, filtered, and the solvent was removed under reduced pressure. The residue was chromatographed using methylene chloride then 20% EtOAc/methylene chloride as eluent to give 2-(2,6-dichlorophenyl)-1H-indole-6-carboxylic acid (6-trifluoromethylpyridin-3-yl)-amide as a purple glass. MS (m/z) 449.9 (M+1); retention time=1.63 min (Method 10).

Example 3-9

2-(2,6-Dichlorophenyl)-1-ethoxy-1H-indole-6-carboxylic acid (3,4-dimethylphenyl)-amide

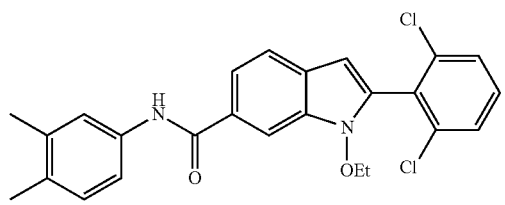

To a solution of 2-(2,6-dichlorophenyl)-1-ethoxy-1H-indole-6-carboxylic acid methyl ester (176 mg, 550 µmol) (obtained as a by-product from the triethylphosphite cyclization in Example 3-8) in ethanol (5 mL) was added 1N NaOH (1.1 mL, 1.1 mmol) and the mixture was heated at 80° C. for 2 h. The solution was decanted into water and extracted twice with ether. The aqueous phase was acidified with conc. HCl and extracted with ethyl acetate. The ethyl acetate layer was extracted with brine, dried, filtered, and the solvent was removed under reduced pressure to give 2-(2,6-dichlorophenyl)-1-ethoxy-1H-indole-6-carboxylic acid.

To a solution of 2-(2,6-dichlorophenyl)-1-ethoxy-1H-indole-6-carboxylic acid (230 mg, 660 µmol) in DMF (5 mL) was added HATU (375 mg, 990 µmol), triethylamine (137 µL, 99 mg, 980 µmol) and 3,4-dimethylaniline (80 mg, 660 µmol). After stirring the mixture for 72 h at ambient temperature, the solution was poured into ethyl acetate and extracted with water once and brine five times. The organic layer was dried, filtered, and solvent removed under reduced pressure. The residual material was chromatographed with a 10-60% gradient of heptane/ethyl acetate to afford 2-(2,6-dichlorophenyl)-1-ethoxy-1H-indole-6-carboxylic acid (3,4-dimethylphenyl)-amide. ¹H NMR (DMSO-d6, 400 MHz): δ 10.16 (s, 1H), 8.19 (s, 1H), 7.71 (m, 4H), 7.58 (m, 3H), 7.12 (d, J=8.2 Hz, 1H), 6.60 (s, 1H), 4.14 (q, J=7.1 Hz, 2H), 2.24 (s, 3H), 2.21 (s, 3H), 1.12 (t, J=7.1 Hz, 3H). MS (m/z) 453.0 (M+1); Retention time=1.72 min (Method 10). Anal. Calcd.: C, 66.23; H, 4.89; N, 6.18. Found: C, 66.34; H, 4.97; N, 6.06.

Example 3-10

2-(2,6-Dimethylphenyl)-1H-indole-6-carboxylic acid (3,4-dimethylphenyl)-amide

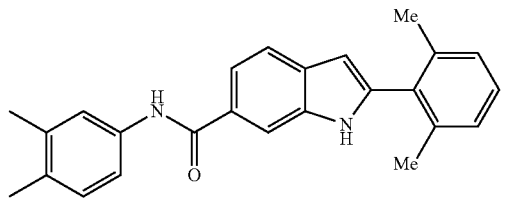

The title compound was prepared from 2-(2,6-dimethylphenyl)-1H-indole-6-carboxylic acid and 3,4-dimethylaniline analogous to Example 3-4. ¹H NMR (CDCl₃, 400 MHz): δ 8.38 (s, broad, 1H), 8.08 (s, 1H), 7.84 (s, broad, 1H), 7.69 (d, J=8.3 Hz, 1H), 7.56 (dd, J=8.3, 1.6 Hz, 1H), 7.45 (d, J=2.0 Hz, 1H), 7.37 (dd, J=8.1, 2.3 Hz, 1H), 7.25 (m, 1H), 7.12 (m, 3H), 6.46 (m, 1H), 2.27 (s, 3H), 2.24 (s, 3H), 2.17 (s, 61-1). MS (m/z) 369.2 (M+1), Retention time=1.73 min (Method 10).

Example 3-11

2-(2,6-Dichlorophenyl)-1H-indole-6-carboxylic acid thiazolo[5,4-b]pyridin-2-ylamide

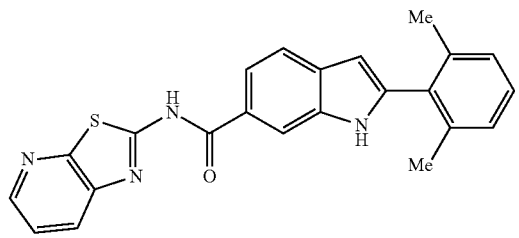

A mixture of 2-(2,6-dichlorophenyl)-1H-indole-6-carboxylic acid (362 mg, 1.18 mmol), thiazolo[5,4-b]pyridin-2-ylamine (179 mg, 1.18 mmol), EDCI (340 mg, 1.77 mmol) and HOBT (176 mg, 1.30 mmol) in THF (10 mL) was heated in a microwave apparatus at 150° C. for 3 h. The insolubles were filtered off and the filtrate was concentrated under reduced pressure. The residue was chromatographed using a 30-70% gradient of heptane/ethyl acetate to afford the title compound. ¹H NMR (DMSO-d6, 400 MHz): δ 12.95 (s, broad, 1H), 12.00 (s, broad, 1H), 8.51 (dd, J=4.7, 1.4 Hz, 1H), 8.34 (s, 1H), 8.16 (d, J=7.7 Hz, 1H), 7.88 (dd, J=8.5, 1.4 Hz, 1H), 7.76 (d, J=8.5 Hz, 1H), 7.68 (d, J=8.3 Hz, 2H), 7.54 (m, 2H), 6.66 (m, 1H). MS (m/z) 439.0 (M+1), Retention

Example 3-12

2-(2,6-Dichlorophenyl)-1H-indole-6-carboxylic acid (5-bromothiazolo[5,4-b]pyridin-2-yl)-amide

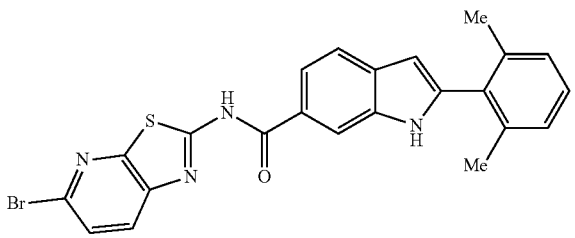

The title compound was prepared from 2-(2,6-dichlorophenyl)-1H-indole-6-carboxylic acid and 5-bromothiazolo[5,4-b]pyridin-2-ylamine (WO 2007041365) analogous to Example 3-11. $^1$H NMR (DMSO-d6, 400 MHz): δ 13.08 (s, broad, 1H), 12.01 (s, broad, 1H) 8.33 (s, 1H), 8.11 (d, J=8.5 Hz, 1H), 7.86 (dd, J=8.5, 1.5 Hz, 1H), 7.71 (m, 4H), 7.56 (m, 1H), 6.65 (d, J=1.3 Hz, 1H). MS (m/z) 518.9 (M+1), Retention time=1.58 min (Method 10). High Res. MS: theory 516.9292; measured 516.9277.

Example 3-13

2-(2,6-Dichloro-4-morpholin-4-yl-phenyl)-1H-indole-6-carboxylic acid quinolin-2-ylamide

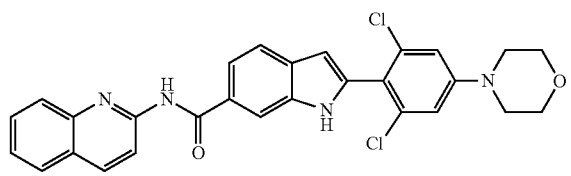

To a solution of 3,5-dichloroiodobenzene (272 mg, 1 mmol) in anhydrous THF (3 mL) was added morpholine (200 µL, 2 mmol), catalytic (+/−) BINAP (6 mol %), catalytic Pd$_2$(dba)$_3$ (3 mol %) and sodium tert-butoxide (192 mg, 2 mmol). The mixture was sparged with N$_2$ for 5 minutes, then the vial was sealed and heated at 80° C. for 18 h. The reaction mixture was directly purified via flash chromatography on silica gel, eluting with a 0-50% gradient of ethyl acetate/heptane to obtain 4-(3,5-dichlorophenyl)-morpholine as a white solid. $^1$H NMR (CDCl$_3$, 400 MHz) δ 6.84 (t, J=1.71 Hz, 1H), 6.75 (d, J=1.77 Hz, 2H), 3.81-3.87 (m, 4H), 3.13-3.19 (m, 4H). MS (m/z) 232.2 (M+1).

To a solution of to a solution of 4-(3,5-dichlorophenyl)-morpholine (1.60 g, 6.93 mmol) in dry THF (20 mL) under N$_2$ at −78° C. was added dropwise sec-BuLi (1.4M in cyclohexane, 5.44 mL). The solution was allow to stir for 30 min then DMF (2.68 mL, 34.7 mmol) was slowly added to the. Upon disappearance of the starting material by TLC, the reaction was warmed to 0° C. then was quench by addition of H$_2$O (15 mL). The mixture was extracted with EtOAc (150 mL), the organic phase was dried over Na$_2$SO$_4$ and the solvent was evaporate under reduced pressure. The resulting solid was triturated with Et$_2$O to yield 2,6-dichloro-4-morpholin-4-yl-benzaldehyde as an off white solid. 1H NMR (400 MHz, Acetonitrile-d3): δ 10.44 (s, 1H), 7.06 (s, 2H), 3.85-3.93 (m, 4H), 3.46-3.54 (m, 4H). MS (m/z) 260.0 (M+1).

A mixture of 4-bromomethyl-3-nitrobenzoic acid methyl ester (1.01 g, 3.68 mmol) (from Example 3-8) and triphenylphosphine (1.06 g, 4.05 mmol) in DMF (20 mL) under N$_2$ was heated at 95° C. Upon disappearance of the starting ester by TLC, 2,6-dichloro-4-morpholin-4-yl-benzaldehyde (1.15 g, 4.42 mmol) was added followed by K$_2$CO$_3$ (1.02 g, 7.36 mmol). The mixture was heated at 95° C. for 22.5 h then was allowed to cool to ambient temperature. The mixture was partitioned between EtOAc/DCM (700 mL) and Water (200 mL). The resulting orange precipitate was filtered and the organic phase was dried over Na$_2$SO$_4$ and concentrate under reduced pressure. The residue was triturated with EtOAc/Et$_2$O to yield additional orange solid. The combined orange solids provided 4-[(E)-2-(2,6-dichloro-4-morpholin-4-yl-phenyl)-vinyl]-3-nitrobenzoic acid methyl ester. $^1$H NMR (400 MHz, DMSO-d6): δ 8.46 (d, J=1.77 Hz, 1H), 8.24 (dd, J=8.27, 1.71 Hz, 1H), 8.11 (d, J=8.21 Hz, 1H), 7.49 (d, J=16.42 Hz, 1H), 7.33 (d, J=16.42 Hz, 1H), 7.10 (s, 2H), 3.91 (s, 3H), 3.67-3.73 (m, 4H), 3.22-3.27 (m, 4H). MS (m/z) 437.1 (M+1).

A suspension of 4-[(E)-2-(2,6-dichloro-4-morpholin-4-yl-phenyl)-vinyl]-3-nitrobenzoic acid methyl ester (1.25 g, 2.86 mmol) in triethylphosphite (10 mL) was heated at 160° C. for 1 h. The mixture was concentrated under reduced pressure and the residue was triturated to afford 2-(2,6-dichloro-4-morpholin-4-yl-phenyl)-1H-indole-6-carboxylic acid methyl ester as a light yellow solid. $^1$H NMR (400 MHz, DMSO-d6) δ 11.72 (d, J=1.52 Hz, 1H), 8.02 (d, J=1.01 Hz, 1H), 7.64 (s, 2H), 7.15 (s, 2H), 6.53 (dd, J=1.96, 0.82 Hz, 1H), 3.86 (s, 3H), 3.70-3.76 (m, 4H), 3.25-3.30 (m, 4H). MS (m/z) 405.1 (M+1).

A 2 M solution of AlMe$_3$ in toluene (0.74 mL, 1.48 mmol) was added to a flask charged with dry toluene (6 mL) at 0° C. under N$_2$. In one proportion quinolin-2-ylamine (0.213 g, 1.48 mmol) was added and the mixture was allow to stir for 50 min. The reaction was allowed to warm to ambient temperature over 15 min then a suspension of 2-(2,6-dichloro-4-morpholin-4-yl-phenyl)-1H-indole-6-carboxylic acid methyl ester (0.500 g, 1.23 mmol) in toluene was slowly added to the mixture at 0° C. Upon completing the addition the mixture was heated at 100° C. After 20 h an additional portion of AlMe$_3$/quinolin-2-ylamine solution (0.438 mmol) was added and heating was continued for an additional 3 h. The mixture was allowed to cool to ambient temperature and was concentrated under reduced pressure. The residue was partitioned between EtOAc (70 mL) and 1 N HCl (30 mL) and allowed to stir for 1 h. The resulting precipitate was filtered and dried under reduced pressure to afford 2-(2,6-dichloro-4-morpholin-4-yl-phenyl)-1H-indole-6-carboxylic acid quinolin-2-ylamide as a yellow solid. $^1$H NMR (400 MHz, DMSO-d6): δ 11.75 (s, 1H), 11.26 (s, broad, 1H), 8.50 (d, J=8.97 Hz, 1H), 8.34 (d, J=8.97 Hz, 1H), 8.20 (s, 1H), 8.00 (d, J=8.21 Hz, 1H), 7.97 (d, J=8.46 Hz, 1H), 7.76-7.82 (m, 2H), 7.68 (d, J=8.34 Hz, 1H), 7.57 (t, J=7.45 Hz, 1H), 7.17 (s, 2H), 6.54 (d, J=1.77 Hz, 1H), 3.71-3.77 (m, 4H), 3.24-3.32 (m, 4H). MS (m/z) 517.1 (M+1).

Example 3-14

3-{3,5-Dimethyl-4-[6-(quinolin-2-ylcarbamoyl)-1H-indol-2-yl]-phenyl}-propionic acid methyl ester

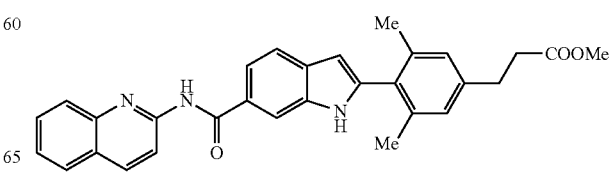

To a solution of 4-bromomethyl-3-nitrobenzoic acid (2.00 g, 7.69 mmol), benzyl alcohol (796 mL, 832 mg, 7.69 mmol) and 4-dimethylaminopyridine (9.4 mg, 77 μmol) in dichloromethane (5 mL) was added DCC (1.59 g, 7.71 mmol) and the mixture was stirred at ambient temperature for 3 h. The mixture was filtered and the solvent was removed under reduced pressure. The residue was purified by chromatography using a 0-30% gradient of heptane/ethyl acetate gave benzyl 4-bromomethyl-3-nitrobenzoate as an oil.

A mixture of benzyl 4-bromomethyl-3-nitrobenzoate (2.06 g, 5.88 mmol) and triphenylphosphine (1.54 g, 5.87 mmol) in DMF (10 mL) was heated at 100° C. for 1 h. To this solution was added methyl (E)-3-(4-formyl-3,5-dimethylphenyl)-acrylate (1.28 g., 5.86 mmol) and potassium carbonate (1.63 g, 11.8 mmol) and the mixture was heated and stirred at 100° C. for 18 h. The reaction was poured into ethyl acetate and extracted with water once and brine.five times. The organic layer was dried, filtered, and the solvent was removed under reduced pressure. The residue was purified by chromatography using a 0-40% gradient of heptane/ethyl acetate to give benzyl 4-{(E)-2-[4-((E)-2-methoxycarbonylvinyl)-2,6-dimethylphenyl]-vinyl}-3-nitrobenzoate.

A mixture of benzyl 4-{(E)-2-[4-((E)-2-methoxycarbonylvinyl)-2,6-dimethylphenyl]-vinyl}-3-nitrobenzoate (1.87 g, 3.97 mmol) and trimethylphosphite (5.0 mL, 5.26 g, 42 mmol) was heated at 110° C. for 3 h. The solvent was then removed under reduced pressure and the residue chromatographed using a 10-50% gradient of heptane/ethyl acetate to yield benzyl 2-[4-((E)-2-methoxycarbonylvinyl)-2,6-dimethylphenyl]-1H-indole-6-carboxylate.

A mixture of benzyl 2-[4-((E)-2-methoxycarbonylvinyl)-2,6-dimethylphenyl]-1H-indole-6-carboxylate (950 mg, 2.16 mmol) and 10% palladium on carbon (95 mg) in 100 mL of ethyl acetate/ethanol (1:1) was stirred under a hydrogen balloon for 18 h. The mixture was filtered through Celite to remove catalyst, and the solvent removed under reduced pressure to leave 2-[4-(2-methoxycarbonylethyl)-2,6-dimethylphenyl]-1H-indole-6-carboxylic acid. MS (m/z) 352.2 (M+1): Retention time=1.35 min (Method 10).

A mixture of 2-[4-(2-methoxycarbonylethyl)-2,6-dimethylphenyl]-1H-indole-6-carboxylic acid (600 mg, 1.71 mmol), 2-aminoquinoline (246 mg, 1.71 mmol), EDCI (491 mg, 2.56 mmol), HOBT (254 mg, 1.88 mmol) and 1-methyl-3-propylimidazolinium iodide (140 mg, 560 μmol) in THF (10 mL) was heated in a microwave apparatus at 150° C. for 3 h then the mixture was poured into ethyl acetate and extracted with water twice and brine once. The ethyl acetate layer was dried, filtered, and removed under reduced pressure, and the residual material was chromatographed using a 20-50% gradient of heptane/ethyl acetate to afford 3-{3,5-dimethyl-4-[6-(quinolin-2-ylcarbamoyl)-1H-indol-2-yl]-phenyl}-propionic acid methyl ester. ¹H NMR (DMSO-d6, 400 MHz): δ 11.56 (s, 1H), 11.00 (s, 1H), 8.39 (s, 2H), 8.16 (s, 1H), 7.95 (d, J=7.4 Hz, 1H), 7.88 (d, J=8.3 Hz, 1H), 7.79 (dd, J=8.3, 1.5 Hz, 1H), 7.73 (TD, J=7.0, 1.4 Hz, 1H), 7.63 (d, J=8.3 Hz, 1H), 7.52 (t, J=7.0 Hz, 1H), 7.05 (s, 2H), 6.41 (d, J=1.3 Hz, 1H), 3.62 (s, 3H), 2.85 (t, J=7.4 Hz, 2H), 2.67 (t, J=7.4 Hz, 2H), 2.12 (s, 6H). MS (m/z) 478.2 (M+1); Retention time=1.58 min (Method 10).

Example 3-15

3-{3,5-Dimethyl-4-[6-(quinolin-2-ylcarbamoyl)-1H-indol-2-yl]-phenyl}-propionic acid

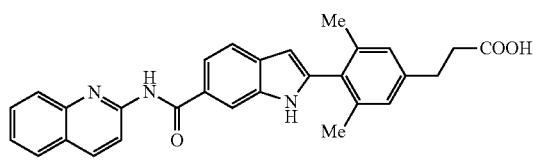

A mixture of 3-{3,5-dimethyl-4-[6-(quinolin-2-ylcarbamoyl)-1H-indol-2-yl]-phenyl}-propionic acid methyl ester (100 mg, 210 μmol) and lithium hydroxide monohydrate (26 mg, 620 μmol) in 5:5:2 THF/MeOH/H₂O (10 mL) was stirred at ambient temperature for 18 h. The solution was concentrated to remove the organic solvents, then was diluted with water and neutralized with one equivalent of 1N HCl. The mixture was stirred vigorously for 30 min and the precipitate was filtered and washed with water. The solid was triturated with water and refiltered, then dried at 50° C. under reduced pressure to give the title compound. ¹H NMR (DMSO-d6, 400 MHz): δ 12.15 (s, broad, 1H), 11.56 (s, 1H), 10.99 (s, 1H), 8.39 (s, 2H), 8.16 (s, 1H), 7.95 (d, J=7.4 Hz, 1H), 7.88 (d, J=8.3 Hz, 1H), 7.79 (dd, J=8.3, 1.4 Hz, 1H), 7.73 (m, 1H), 7.63 (d, J=8.2 Hz, 1H), 7.52 (t, J=7.1 Hz, 1H), 7.06 (s, 2H), 6.41 (d, J=1.4 Hz, 1H), 2.82 (t, J=7.4 Hz, 2H), 2.57 (t, J=7.6 Hz, 2H), 2.11 (s, 6H). MS (m/z) 464.3 (M+1); Retention time=1.36 min (Method 10).

Example 3-16

3-{4-[6-(4-tert-Butylphenylcarbamoyl)-1H-indol-2-yl]-3,5-dimethylphenyl}-propionic acid

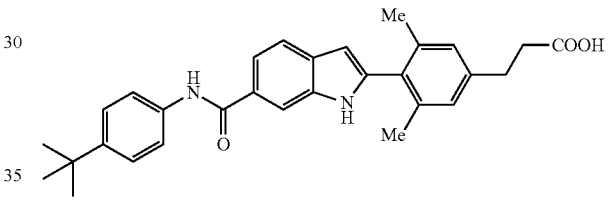

A mixture of 2-[4-(2-methoxycarbonylethyl)-2,6-dimethylphenyl]-1H-indole-6-carboxylic acid (100 mg, 280 μmol), 4-tert-butylaniline (45 μL, 290 μmol), EDCI (82 mg, 430 μmol) and HOBT (42 mg, 310 μmol) in THF (10 mL) was heated in a microwave apparatus at 150° C. for 3 h. The solvent was removed under reduced pressure and the residue was chromatographed using a 10-60% gradient of heptane/ethyl acetate to give 3-{4-[6-(4-tert-butylphenylcarbamoyl)-1H-indol-2-yl]-3,5-dimethylphenyl}-propionic acid methyl ester. MS (m/z) 484.3 (M+1); Retention time=1.50 min (Method 10).

A mixture of 3-{4-[6-(4-tert-butylphenylcarbamoyl)-1H-indol-2-yl]-3,5-dimethylphenyl}-propionic acid methyl ester and 1N NaOH (500 μL) in THF (5 mL) was heated at 50° C. for 18 h. The mixture was cooled and was neutralized with one equivalent of 1N HCl and partitioned between water and ethyl acetate. The ethyl acetate layer was dried, filtered, and the solvent removed under reduced pressure to leave an oil, which was twice taken up in ether and solvent removed under reduced pressure to give 3-{4-[6-(4-tert-butylphenylcarbamoyl)-1H-indol-2-yl]-3,5-dimethylphenyl}-propionic acid. ¹H NMR (Acetonitrile-d3, 400 MHz): δ 9.62 (s, 1H), 8.72 (s, 1H), 8.04 (s, 1H), 7.63 (m, 4H), 7.40 (d, J=8.7 Hz, 2H), 7.03 (s, 2H), 6.40 (s, 1H), 2.87 (t, J=7.6 Hz, 2H), 2.63 (t, J=7.7 Hz, 2H), 2.11 (s, 6H), 1.32 (s, 9H). MS (m/z) 469.3 (M+1); Retention time=1.50 min (Method 10).

Example 3-17

3-{3,5-Dichloro-4-[6-(quinolin-2-ylcarbamoyl)-1H-indol-2-yl]-phenyl}-propionic acid hydrochloride salt

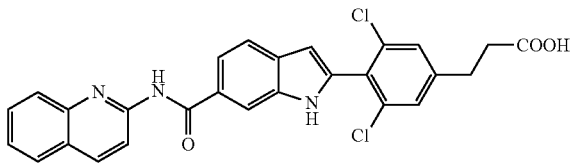

To a solution of 4-bromomethyl-3-nitrobenzoic acid methyl ester (1.64 g, 6.0 mmol) in DMF (15 mL) was added triphenylphosphine (1.57 g, 6.0 mmol) and the mixture was heated at 100° C. for 30 min. To this solution was added a solution of 3-(3,5-dichloro-4-formylphenyl)-propionic acid tert-butyl ester (1.50 g, 4.95 mmol) (from Example 6-25) in DMF (5 mL) in one portion, followed by pulverized potassium carbonate (1.37 g, 9.9 mmol) and the mixture was heated at 100° C. for 18 h. The reaction mixture was partitioned between ethyl acetate and water, washed with brine, dried with MgSO$_4$, filtered, and concentrated. The crude residue was purified by flash chromatography on silica gel, eluting with a gradient of 0-50% ethyl acetate/heptane to obtain 4-{(E)-2-[4-(2-tert-butoxycarbonylethyl)-2,6-dichlorophenyl]-vinyl}-3-nitrobenzoic acid methyl ester as a yellow solid. MS (m/z) 497.1 (M+18); $^1$H NMR (DMSO-d6, 400 MHz) δ 8.49 (d, J=1.64 Hz, 1H), 8.28 (dd, J=8.15, 1.58 Hz, 1H), 8.14 (d, J=8.21 Hz, 1H), 7.47 (s, 2H), 7.47 (d, J=16.7 Hz, 1H), 7.33 (d, J=16.4 Hz, 1H), 3.93 (s, 3H), 2.83 (t, J=7.33 Hz, 2H), 2.58 (t, J=7.33 Hz, 2H), 1.37 (s, 9H).

To a solution of 4-{(E)-2-[4-(2-tert-butoxycarbonylethyl)-2,6-dichlorophenyl]-vinyl}-3-nitrobenzoic acid methyl ester (1.29 g, 2.69 mmol) in THF (60 mL) was added potassium trimethylsilanolate (483 mg, 3.77 mmol) and the solution was stirred for 2 h. The precipitate was collected by filtration, then dried under vacuum for 18 h to obtain 4-{(E)-2-[4-(2-tert-butoxycarbonylethyl)-2,6-dichlorophenyl]-vinyl}-3-nitrobenzoic acid, potassium salt as yellow flakes. MS (m/z) 483.1 (M+18); $^1$H NMR (DMSO-d6, 400 MHz) δ 8.34 (d, J=1.39 Hz, 1H), 8.14 (dd, J=7.96, 1.14 Hz, 1H), 7.86 (d, J=8.08 Hz, 1H), 7.45 (s, 2H), 7.42 (d, J=16.42 Hz, 1H), 7.17 (d, J=16.42 Hz, 1H), 2.83 (t, J=7.26 Hz, 2H), 2.58 (t, J=7.39 Hz, 2H), 1.37 (s, 9H).

To 4-{(E)-2-[4-(2-tert-butoxycarbonylethyl)-2,6-dichlorophenyl]-vinyl}-3-nitrobenzoic acid potassium salt (280 mg, 0.56 mmol) in DCM (6 mL) was added diisopropylethylamine (292 µL, 1.68 mmol) and HATU (320 mg, 0.84 mmol) and the solution was stirred for 30 min. To this was added 2-aminoquinoline (96 mg, 0.66 mmol) and the mixture was stirred 18 h. The reaction mixture was partitioned between ethyl acetate and water, the organic layers were washed with brine, dried over MgSO$_4$, filtered, and concentrated. The crude residue was purified by flash chromatography on silica gel, eluting with a gradient of 0-50% ethyl acetate/heptane to obtain 3-(3,5-dichloro-4-{(E)-2-[2-nitro-4-(quinolin-2-ylcarbamoyl)-phenyl]-vinyl}-phenyl)-propionic acid tert-butyl ester as a white solid. MS (m/z) 592.1 (M+1); $^1$H NMR (DMSO-d6, 400 MHz) δ 11.58 (s, 1H), 8.74 (d, J=1.89 Hz, 1H), 8.43-8.48 (m, 2H), 8.36-8.41 (m, 1H), 8.16 (d, J=8.34 Hz, 1H), 7.99 (d, J=7.33 Hz, 1H), 7.91 (d, J=8.21 Hz, 1H), 7.77 (ddd, J=8.40, 6.95, 1.33 Hz, 1H), 7.56 (dd, J=15.03, 1.14 Hz, 1H), 7.49 (s, 2H), 7.48 (d, J=16.82 Hz, 1H), 7.36 (d, J=16.82 Hz, 1H), 2.85 (t, J=7.26 Hz, 2H), 2.59 (t, J=7.39 Hz, 2H) 1.38 (s, 9H).

To a solution of 3-(3,5-dichloro-4-{(E)-2-[2-nitro-4-(quinolin-2-ylcarbamoyl)-phenyl]-vinyl}-phenyl)-propionic acid tert-butyl ester (200 mg, 0.34 mmol) was added triethylphosphite (300 µL) and the mixture was stirred at 160° C. for 3 h. The solvent was removed under reduced pressure and the residue was taken up in toluene and concentrated twice. The crude material was purified by flash chromatography on silica gel, eluting with a gradient of 2-100% ethyl acetate/heptane to obtain 3-{3,5-dichloro-4-[6-(quinolin-2-ylcarbamoyl)-1H-indol-2-yl]-phenyl}-propionic acid tert-butyl ester as a yellow solid. MS (m/z) 560.2 (M+1); $^1$H NMR (DMSO-d6, 400 MHz) δ 11.81 (d, J=1.52 Hz, 1H), 11.04 (s, 1H), 8.39 (s, 2H), 8.20 (s, 1H), 7.94 (d, J=1.14 Hz, 1H), 7.88 (d, J=8.08 Hz, 1H), 7.80 (dd, J=8.34, 1.52 Hz, 1H), 7.73 (ddd, J=8.37, 6.92, 1.39 Hz, 1H), 7.68 (d, J=8.46 Hz, 1H), 7.55 (s, 2H), 7.52 (t, J=6.95 Hz, 1H), 6.57 (d, J=1.39 Hz, 1H), 2.90 (t, J=7.33 Hz, 2H), 2.62 (t, J=7.45 Hz, 2H), 1.40 (s, 9H).

To a solution of 3-{3,5-dichloro-4-[6-(quinolin-2-ylcarbamoyl)-1H-indol-2-yl]-phenyl}-propionic acid tert-butyl ester (139 mg, 0.25 mmol) in DCM (1 mL) was added HCl (4M in 1,4-dioxane, 1 mL) and the solution was stirred for 2 h, after which more HCl (4M in 1,4-dioxane, 2 mL) was added. The mixture was stirred for 18 h then the solvent was removed under reduced pressure and the remaining solid was triturated with ether to obtain the title compound as a yellow solid. MS (m/z) 504.1 (M+1); $^1$H NMR (DMSO-d6, 400 MHz) δ 11.83 (s, 1H), 11.14 (s, broad, 1H), 8.44 (d, J=9.17 Hz, 1H), 8.36 (d, J=8.98 Hz, 1H), 7.97 (dd, J=8.21, 0.88 Hz, 1H) 8.21 (s, 1H), 7.92 (d, J=8.34 Hz, 1H), 7.80 (dd, J=8.40, 1.58 Hz, 1H), 7.76 (td, J=7.71, 1.39 Hz, 1H), 7.69 (d, J=8.34 Hz, 1H), 7.53 (m, 1H) 7.56 (s, 2H), 6.59 (dd, J=1.89, 0.76 Hz, 1H), 2.91 (t, J=7.39 Hz, 2H), 2.63-2.68 (m, 2H).

Example 3-18

2-(2,6-Dichloro-4-hydroxyphenyl)-1H-indole-6-carboxylic acid quinolin-2-ylamide

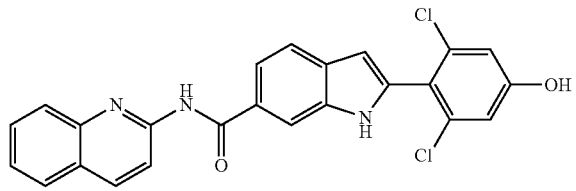

To a solution of 3,5-dichlorophenol (10.0 g, 61.3 mmol) in DMF (120 mL) at 0° C. was added 9.19 g (135 mmol) of imidazole and the dark yellow solution was allowed to stir at 0° C. for 10 min. To this was added TBDMS-Cl (10.18 g, 67.5 mmol) and the solution went from pale yellow to clear in 1 min. The solution was allowed to stir from 0° C. to ambient temperature over 18 h. The mixture was cooled to 0° C. then water (120 mL) was added and stirred for 10 min. The mixture was extracted with EtOAc, washed with water, brine, and dried with Na$_2$SO$_4$. The solvent was removed under reduced pressure and the residue was purified on silica gel using EtOAc/heptane (0 to 1:9) as eluent to give 4-(tert-butyldimethylsilanyloxy)-2,6-dichlorobenzaldehyde as a clear liquid. $^1$H NMR (DMSO-d6, 400 MHz): δ 6.99 (t, J=1.83 Hz, 1H), 6.70 (d, J=1.89 Hz, 2H), 0.73 (s, 9H), 0.00 (s, 6H).

To a solution of 4-(tert-butyldimethylsilanyloxy)-2,6-dichlorobenzaldehyde (15.51 g, 55.9 mmol) in THF (80 mL) at −78° C. was added sec-butyllithium (41.14 mL, 57.6 mmol) dropwise over 25 min and the mixture was allowed to stir at −78° C. for 1.5 h. To the mostly yellow suspension was added DMF (6.47 mL, 83.9 mmol) and the yellow solution was allowed to stir at −78° C. for 5 h. To the reaction mixture was added MeOH (1 mL) and 1N HCl (60 mL) and allowed to warm to ambient temperature for 18 h. The brown solution was brought to pH 4, extracted with EtOAc, washed with water, brine, and dried with $Na_2SO_4$. A solid precipitated from the organic layer and was filtered and rinsed with DCM to give 2,6-dichloro-4-hydroxybenzaldehyde as white solid. MS (m/z) 191.0 (M+1); $^1$H NMR (DMSO-d6, 400 MHz) δ 11.45 (s, 1H), 10.24 (s, 1H), 6.93 (s, 2H).

To a mixture of 2,6-dichloro-4-hydroxybenzaldehyde (1.00 g, 5.24 mmol) and $K_2CO_3$ (1.45 g, 10.5 mmol) in THF (25 mL) under $N_2$ was added dropwise1-bromomethyl-4-methoxybenzene (1.10 mL, 7.85 mmol). The reaction was heated at 65° C. for 3 h, at 45° C. overnight then at 65° C. for 3 hr. The reaction was allowed to cool to ambient temperature then was filtered and the filtrate concentrated under reduced pressure. The concentrate was diluted with EtOAc (150 mL) and extracted with water (30 mL). The organic phase was dried over $Na_2SO_4$ and evaporated. The residue was purified by silica gel chromatography using a gradient of 5-15% EtOAc/heptane as eluent to afford 2,6-dichloro-4-(4-methoxybenzyloxy)-benzaldehyde as a white solid. MS (m/z) 311.0 (M+1); $^1$H NMR (DMSO-d6, 400 MHz) δ 10.28 (s, 1H), 7.40 (d, J=8.59 Hz, 2H), 7.29 (s, 2H), 6.97 (d, J=8.72 Hz, 2H), 5.19 (s, 2H), 3.76 (s, 3H).

2-[2,6-dichloro-4-(4-methoxybenzyloxy)-phenyl]-1H-indole-6-carboxylic acid quinolin-2-ylamide was prepared from 2,6-dichloro-4-(4-methoxybenzyloxy)-benzaldehyde and 4-bromomethyl-3-nitrobenzoic acid methyl ester analogous to Example 3-13. MS (m/z) 568.2 (M+1); $^1$H NMR (DMSO-d6, 400 MHz) δ 11.79 (d, J=1.26 Hz, 1H), 11.22 (s, broad, 1H), 8.47 (d, J=9.09 Hz, 1H), 8.34 (d, J=9.09 Hz, 1H), 8.21 (s, 1H), 7.92-8.03 (m, 2H), 7.75-7.83 (m, 2H), 7.69 (d, J=8.46 Hz, 1H), 7.53-7.59 (m, 1H), 7.39-7.45 (m, 2H), 7.34 (s, 2H), 6.96-7.02 (m, 2H), 6.54-6.58 (m, 1H), 5.18 (s, 2H), 3.77 (s, 3H).

To a suspension of 2-[2,6-dichloro-4-(4-methoxybenzyloxy)-phenyl]-1H-indole-6-carboxylic acid quinolin-2-ylamide (200 mg, 0.352 mmol) in DCM (7.5 mL) and MeOH (2.5 mL) was added 4 M HCl in dioxane (7.5 mL) and the mixture was stirred for 2.5 hr. The reaction was concentrated under reduced pressured and the concentrate partitioned between EtOAc (150 mL) and sat $NaHCO_3$ (30 mL). The organic phase was dried over $Na_2SO_4$ and the solvent evaporated. The residue was triturated with DCM to afford the title compound as an orange solid. MS (m/z) 448.1 (M+1); $^1$H NMR (DMSO-d6, 400 MHz) δ 11.72 (d, J=1.14 Hz, 1H), 11.04 (s, 1H), 10.68 (s, 1H), 8.36-8.43 (m, 2H), 8.18 (s, 1H), 7.96 (d, J=8.08 Hz, 1H), 7.89 (d, J=8.34 Hz, 1H), 7.79 (dd, J=8.34, 1.26 Hz, 1H), 7.74 (dd, J=15.35, 1.20 Hz, 1H), 7.66 (d, J=8.34 Hz, 1H), 7.52 (t, J=7.52 Hz, 1H), 7.02 (s, 2H), 6.53 (d, J=1.77 Hz, 1H).

Example 4-1

2-(2,6-dichloro-phenyl)-benzooxazole-6-carboxylic acid (2-o-tolyl-ethyl)-amide

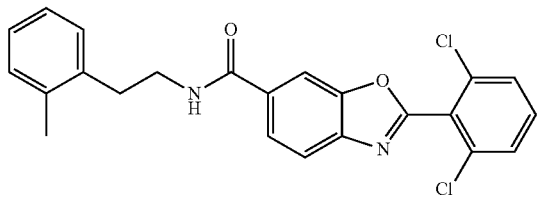

To a solution of 4-amino-3-hydroxy-benzoic acid methyl ester (2.0 g) in MeOH (100 mL) was added 2,6-dichlorobenzaldehyde (2.1 g). The reaction mixture was heated at 45° C. overnight, and then concentrated in vacuo. The residue was dissolved in THF (10 mL) and dichloromethane (90 mL). To the mixture solution was added 2,3-dichloro-5,6-dicyano-1,4-benzoquinone (2.72 g). The reaction mixture was stirred for 1 h, diluted with $NaHCO_3$ aqueous solution, extracted with EtOAc, and washed with brine. The extracts were dried over $Na_2SO_4$ and concentrated in vacuo. Purification by column chromatography ($SiO_2$, 2:3 EtOAc/Hexane) gave 2-(2,6-dichlorophenyl)-benzooxazole-6-carboxylic acid methyl ester: MS (m/z) 321.9 (M+1).

To a solution of 2-(2,6-dichlorophenyl)-benzooxazole-6-carboxylic acid methyl ester (1.6 g) in EtOH (13 mL) was added 4N NaOH aqueous solution (6.2 mL). The reaction was stirred at 80° C. for 0.5 h. The reaction mixture was concentrated, diluted with water, and treated with $Et_2O$. The aqueous layer was acidified with 1N HCl aqueous solution. The precipitate was filtered, washed with water, and dried in vacuo to give 2-(2,6-dichloro-phenyl)-benzooxazole-6-carboxylic acid as a white solid: MS (m/z) 308.0 (M+1).

To a solution of 2-(2,6-dichloro-phenyl)-benzooxazole-6-carboxylic acid (8.9 mg) in anhydrous DMF (0.5 mL) was added BOP (17.4 mg), diisopropylethylamine (0.014 mL), and 2-o-tolyl-ethylamine (5.5 mg). The reaction mixture was stirred at 85° C. overnight, quenched with 1N NaOH aqueous solution at 0° C., extracted with EtOAc. The extracts were dried over $Na_2SO_4$ and concentrated in vacuo. The crude reaction mixture was purified by silica SPE eluting with EtOAc/Hexane to give 2-(2,6-dichlorophenyl)-benzooxazole-6-carboxylic acid (2-o-tolyl-ethyl)-amide: MS (m/z) 425.1 (M+1).

By employing the method of Example 4-1, using appropriate starting materials, the following compounds were prepared:

| Example | Structure | Chemical Name | MS found (M + 1) |
|---------|-----------|---------------|------------------|
| 4-2 | 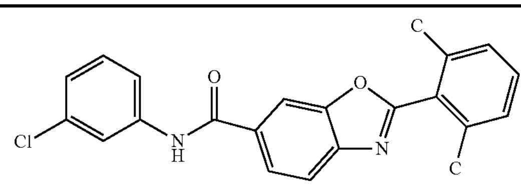 | 2-(2,6-Dichloro-phenyl)-benzooxazole-6-carboxylic acid (3-chloro-phenyl)-amide | 419.0 |

-continued

| Example | Structure | Chemical Name | MS found (M + 1) |
|---|---|---|---|
| 4-3 | 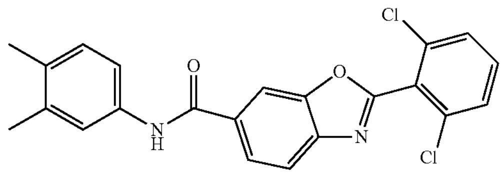 | 2-(2,6-Dichloro-phenyl)-benzooxazole-6-carboxylic acid (3,4-dimethyl-phenyl)-amide | 411.1 |
| 4-4 | 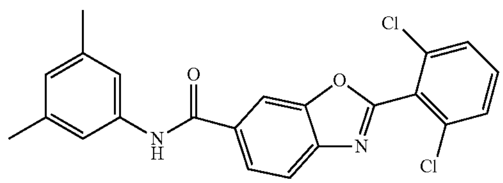 | 2-(2,6-Dichloro-phenyl)-benzooxazole-6-carboxylic acid (3,5-dimethyl-phenyl)-amide | 411.1 |
| 4-5 | 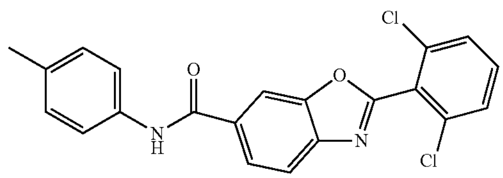 | 2-(2,6-Dichloro-phenyl)-benzooxazole-6-carboxylic acid p-tolylamide | 397.1 |
| 4-6 | 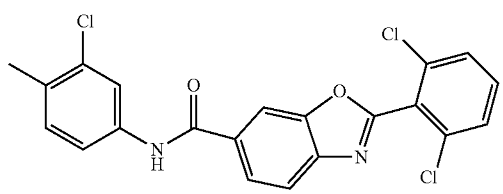 | 2-(2,6-Dichloro-phenyl)-benzooxazole-6-carboxylic acid (3-chloro-4-methyl-phenyl)-amide | 433.0 |
| 4-7 | 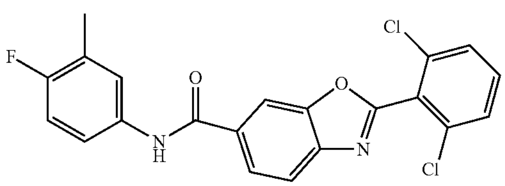 | 2-(2,6-Dichloro-phenyl)-benzooxazole-6-carboxylic acid (4-fluoro-3-methyl-phenyl)-amide | 415.0 |
| 4-8 | 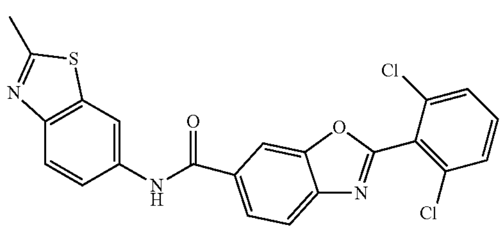 | 2-(2,6-Dichloro-phenyl)-benzooxazole-6-carboxylic acid (2-methyl-benzothiazol-6-yl)-amide | 454.0 |
| 4-9 | 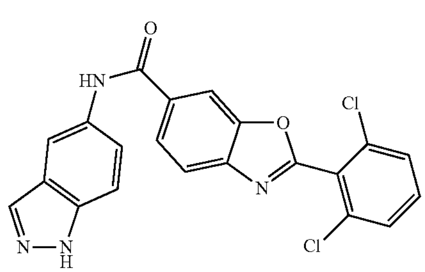 | 2-(2,6-Dichloro-phenyl)-benzooxazole-6-carboxylic acid (1H-indazol-5-yl)-amide | 423.0 |

-continued

| Example | Structure | Chemical Name | MS found (M + 1) |
|---|---|---|---|
| 4-10 | 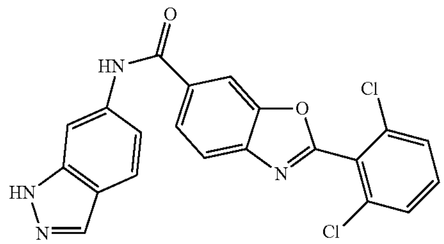 | 2-(2,6-Dichloro-phenyl)-benzooxazole-6-carboxylic acid (1H-indazol-6-yl)-amide | 423.0 |
| 4-11 | 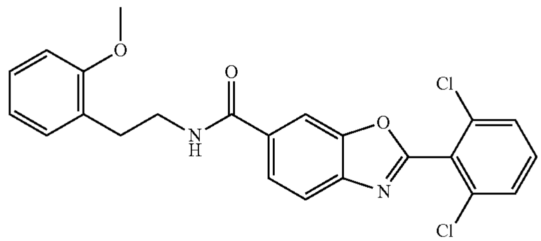 | 2-(2,6-Dichloro-phenyl)-benzooxazole-6-carboxylic acid [2-(2-methoxy-phenyl)-ethyl]-amide | 441.1 |
| 4-12 | 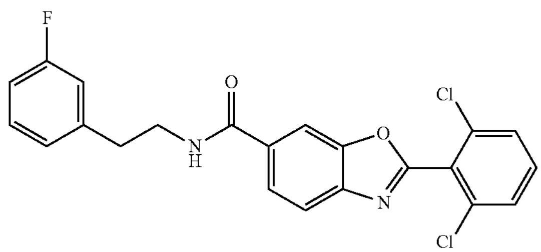 | 2-(2,6-Dichloro-phenyl)-benzooxazole-6-carboxylic acid [2-(3-fluoro-phenyl)-ethyl]-amide | 429.1 |
| 4-13 | 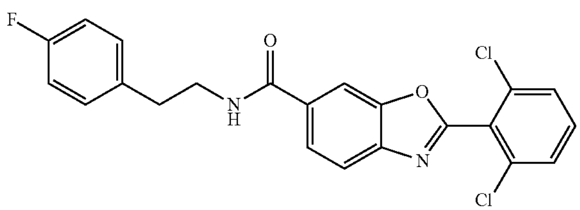 | 2-(2,6-Dichloro-phenyl)-benzooxazole-6-carboxylic acid [2-(4-fluoro-phenyl)-ethyl]-amide | 429.1 |
| 4-14 | 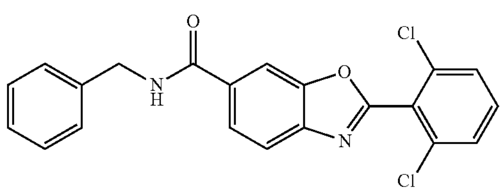 | 2-(2,6-Dichloro-phenyl)-benzooxazole-6-carboxylic acid benzylamide | 397.1 |
| 4-15 | 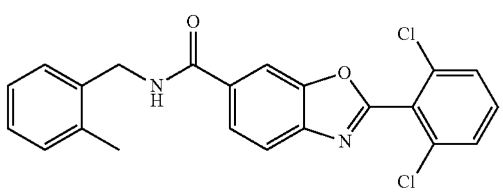 | 2-(2,6-Dichloro-phenyl)-benzooxazole-6-carboxylic acid 2-methyl-benzylamide | 411.0 |
| 4-16 | 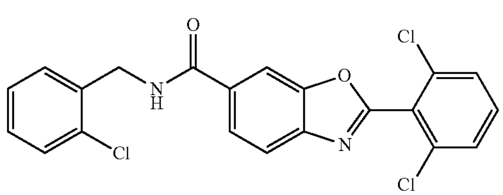 | 2-(2,6-Dichloro-phenyl)-benzooxazole-6-carboxylic acid 2-chloro-benzylamide | 433.0 |

| Example | Structure | Chemical Name | MS found (M + 1) |
|---|---|---|---|
| 4-17 | 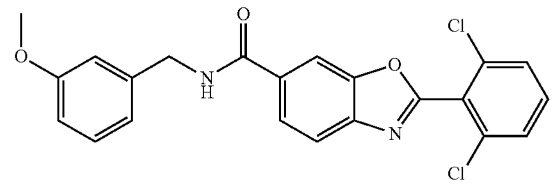 | 2-(2,6-Dichloro-phenyl)-benzooxazole-6-carboxylic acid 3-methoxy-benzylamide | 427.0 |
| 4-18 | 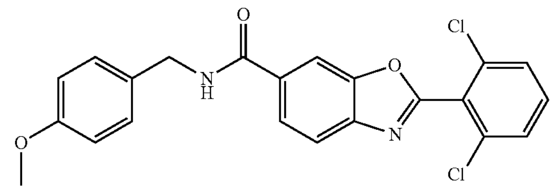 | 2-(2,6-Dichloro-phenyl)-benzooxazole-6-carboxylic acid 4-methoxy-benzylamide | 427.0 |

The following compounds was prepared in the same way as described for Example 4-1. The starting material is 3-amino-4-hydroxy-benzoic acid instead of 4-amino-3-hydroxy-benzoic acid:

| Example | Structure | Chemical Name | MS found (M + 1) |
|---|---|---|---|
| 4-19 | 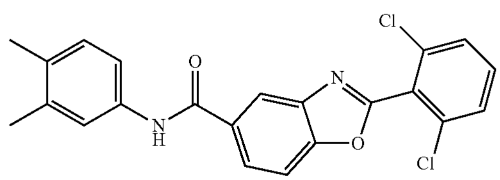 | 2-(2,6-Dichlorophenyl)-benzooxazole-5-carboxylic acid (3,4-dimethylphenyl)-amide | 411.0 |
| 4-20 | 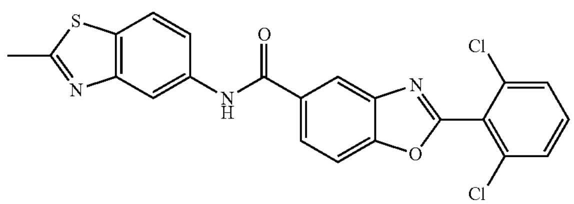 | 2-(2,6-Dichlorophenyl)-benzooxazole-5-carboxylic acid (2-methylbenzothiazol-5-yl)-amide | 454.0 |
| 4-21 | 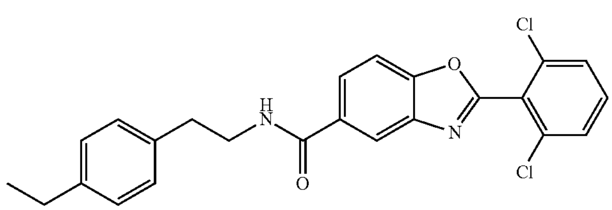 | 2-(2,6-Dichlorophenyl)-benzooxazole-5-carboxylic acid [2-(4-ethylphenyl)-ethyl]-amide | 439 |
| 4-22 | 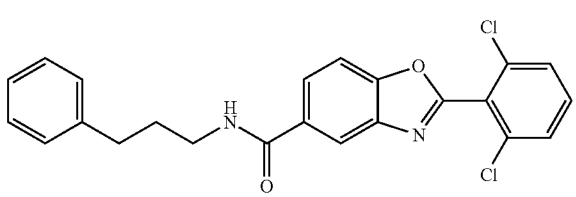 | 2-(2,6-Dichlorophenyl)-benzooxazole-5-carboxylic acid (3-phenylpropyl)-amide | 425 |

Example 4-23

2-(4-Dimethylcarbamoylmethoxy-2,6-dimethylphenyl)-benzooxazole-5-carboxylic acid (3,4-dimethylphenyl)-amide

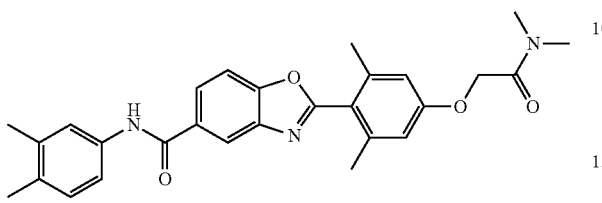

To a mixture of 4-hydroxy-3-nitrobenzoic acid (732 mg), EDCI (768 mg) and HOBt (540 mg) in DMF (8 mL) was added 3,4-dimethylaniline (484 mg) and the mixture was stirred at room temperature for 18 h. The mixture was poured into water and was extracted with EtOAc. The organic phase was washed with water (3×) and dried over sodium sulfate. The solvent was concentrated until crystallization occurred. The mixture was cooled to room temperature and the solid filtered, washed with EtOAc and dried under reduced pressure to give N-(3,4-dimethyl-phenyl)-4-hydroxy-3-nitrobenzamide as a pale-yellow solid, mp=209-212° C.; MS (m/z) 285 (M−1).

A solution of N-(3,4-dimethyl-phenyl)-4-hydroxy-3-nitrobenzamide (700 mg) in ethanol (50 mL) was hydrogenated over PtO$_2$ at 40 psi for 3 h. The catalyst was filtered through Celite and the filtrate evaporated to give 3-amino-N-(3,4-dimethylphenyl)-4-hydroxy-benzamide as an off-white solid, mp=220-223° C.; MS (m/z) 255 (M−1).

To a solution of 4-hydroxy-2,6-dimethylbenzaldehyde (100 mg) and 2-chloro-N,N-dimethylacetamide (89 mg) in DMF (2 mL) was added K$_2$CO$_3$ (185 mg) and the mixture was stirred at room temperature for 48 h. The mixture was poured into water and extracted with EtOAc. The organic phase was washed with water (3×) and dried over sodium sulfate. The solvent was removed under reduced pressure and the residue was purified by flash chromatography using 30% EtOAc/CH$_2$Cl$_2$ as eluent to give 2-(4-formyl-3,5-dimethylphenoxy)-N,N-dimethylacetamide as a solid.

A mixture of 3-amino-N-(3,4-dimethylphenyl)-4-hydroxy-benzamide (70 mg) and 2-(4-formyl-3,5-dimethylphenoxy)-N,N-dimethylacetamide (64 mg) in MeOH (5 mL) was stirred at 45° C. for 24 h. The MeOH was removed under reduced pressure and the residue was dissolved in CH$_2$Cl$_2$ (5 mL). To this solution was added DDQ (68 mg) and the dark mixture was stirred at room temperature for 6 h. The majority of the solvent was removed under reduced pressure and EtOAc was added. The solution was washed with NaHCO$_3$ solution and water then was dried over sodium sulfate. The solvent was removed under reduced pressure and the residue was purified by flash chromatography using EtOAc/CH$_2$Cl$_2$ (1:2) as eluent to give 2-(4-dimethylcarbamoylmethoxy-2,6-dimethylphenyl)-benzooxazole-5-carboxylic acid (3,4-dimethylphenyl)-amide as a brownish solid, mp=207-209° C.; MS (m/z) 470 (M−1); $^1$H NMR (DMSO-d$_6$, 400 MHz) δ 10.18 (s, 1H), 8.46 (s, 1H), 8.04 (d, J=10.36 Hz, 1H), 7.90 (d, J=8.34 Hz, 1H), 7.60 (s, 1H), 7.53 (d, J=8.08 Hz, 1H), 7.11 (d, J=8.34 Hz, 1H), 6.83 (s, 2H), 4.89 (s, 2H), 3.02 (s, 3H), 2.87 (s, 3H), 2.27 (s, 6H), 2.24 (s, 3H), 2.21 (s, 3H).

Example 5-1

{4-[5-(3,4-Dimethyl-phenylcarbamoyl)-1H-benzoimidazol-2-yl]-3,5-dimethyl-phenylamino}-acetic acid methyl ester

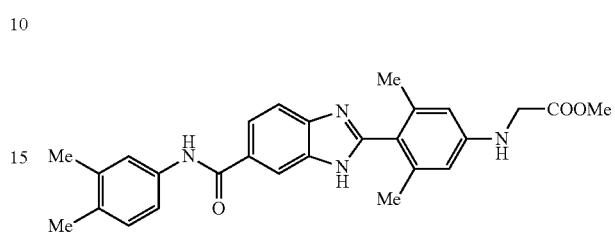

To a solution of 3,5-dimethylphenylamine (7.26 g) in 200 mL of CH$_2$Cl$_2$, cooled in an ice bath, was added trifluoroacetic anhydride (12.5 mL) slowly. After the addition, the solution was stirred at room temperature for 15 min then Br$_2$ (2.93 mL) was added slowly while maintaining room temperature with a water bath. The solution was stirred at room temperature for 3.5 h then was quenched with 10% Na$_2$S$_2$O$_3$. The aqueous layer was extracted with CH$_2$Cl$_2$. The combined organic layers were dried and filtered. Removal of the solvent under reduced pressure gave an orange solid which was purified by recrystallization (1:1 hexanes/ethyl ether) to give N-(4-bromo-3,5-dimethylphenyl)-2,2,2-trifluoroacetamide as a white solid. MS (ESI)m/z 297 (M+H).

To a solution of N-(4-bromo-3,5-dimethylphenyl)-2,2,2-trifluoroacetamide (592 mg) in THF (10 mL) at −78° C. was added MeLi/LiBr (1.5M in Et$_2$O, 1.87 mL) slowly. After 5 min, sec-BuLi (1.4M. in cyclohexane, 2.0 mL) was added slowly to the solution at −78° C. After 5 min DMF (0.31 mL) was added to the solution drowise at −78° C. then the mixture was warmed to room temperature. After 30 min the reaction mixture was partioned between water and CH$_2$Cl$_2$. The aqueous layer was extracted with CH$_2$Cl$_2$ and the combined organic layers were dried and filtered. Removal of the solvent under reduced pressure to gave a yellow solid which was purified by flash chromatography using hexanes/ethyl acetate (5:1) as eluent which gave 2,2,2-trifluoro-N-(4-formyl-3,5-dimethyl-phenyl)-acetamide as a light yellow solid. MS (ESI) m/z 246 (M+H).

To a solution of 2,2,2-trifluoro-N-(4-formyl-3,5-dimethylphenyl)-acetamide (1.0 g) in MeOH (20 mL) was added 1N NaOH (16.3 mL). After 4 hrs at room temperature, the suspension was filtered and washed with water. The solid was dried under reduced pressure to give 4-amino-2,6-dimethylbenzaldehyde as a light yellow solid. MS (ESI)m/z 150 (M+H).

To a solution of 4-amino-2,6-dimethylbenzaldehyde (600 mg) and bromoacetic acid methyl ester (0.4 mL) in DMF (20 mL) was added K$_2$CO$_3$ (1.4 g) and the suspension was heated at 80° C. After 1 h, additional bromoacetic acid methyl ester (0.4 mL) was added and this process was continued until the starting material was consumed (check by LC/MS). The reaction mixture was partioned between water and EtOAc. The aqueous layer was extracted with EtOAc. The combined organic layers were dried, filtered and concentrated and the residue was purified by flash chromatography using hexanes/ethyl acetate (2:1) to give (4-formyl-3,5-dimethylphenylamino)-acetic acid methyl ester as a yellow solid. MS (ESI) m/z 222 (M+H).

To a solution of 4-amino-3-nitrobenzoic acid (1.82 g) in DMF (20 mL) was added HOBT (1.49 g) and EDCI (2.1 g). After stirring at room temperature for 10 min, 3,4-dimethylphenylamine (1.2 g) and DIPEA (5.3 mL) were added. The solution was stirred at room temperature for 18 h then the mixture was partioned between water and EtOAc The aqueous layer was extracted with EtOAc. The combined organic layers were washed with water, brine, dried, filtered and concentrated. The residue was purified by recrystallization from EtOAc and gave 4-amino-N-(3,4-dimethylphenyl)-3-nitrobenzamide as a yellow solid. MS (ESI)m/z 286 (M+H).

A solution of 4-amino-N-(3,4-dimethylphenyl)-3-nitrobenzamide (2.0 g) in EtOH (40 mL) was hydrogenated at 1 atm over $PtO_2$ (200 mg, 10% w) for 18 hrs. The catalyst was filtered through Celite and the solvent was removed under reduced pressure to afford 3,4-diamino-N-(3,4-dimethylphenyl)-benzamide as a yellow solid. MS (ESI)m/z 256 (M+H).

To a solution of (4-formyl-3,5-dimethylphenylamino)-acetic acid methyl ester (800 mg) and 3,4-diamino-N-(3,4-dimethylphenyl)-benzamide (694 mg) in DMSO (15 mL) was added $Yb(OTf)_3$ (390 mg) and $Cu(OTf)_2$ (228 mg). The solution was stirred at room temperature for 18 h then the reaction mixture was partioned between water and EtOAc The aqueous layer was extracted with EtOAc. The combined organic layers were dried, filtered and concentrated. The residue was purified by flash chromatography (amino-column) using hexanes/ethyl acetate (1:4) to give {4-[5-(3,4-dimethylphenylcarbamoyl)-1H-benzoimidazol-2-yl]-3,5-dimethylphenylamino}-acetic acid methyl ester as a light yellow solid. MS (ESI)m/z 457 (M+H); $^1$H NMR (MeOD, 400 MHz) δ 8.21 (s, 1H), 7.85 (dd, 1H), 7.67 (s, 1H), 7.47 (d, 1H), 7.42 (dd, 1H), 7.12 (d, 1H), 6.42 (s, 2H), 3.97 (s, 2H), 3.75 (s, 3H), 2.29 (s, 3H), 2.26 (s, 3H), 2.09 (s, 6H).

Example 5-2

{4-[5-(3,4-Dimethylphenylcarbamoyl)-1H-benzoimidazol-2-yl]-3,5-dimethylphenylamino}-acetic acid

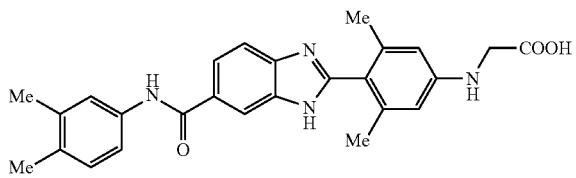

To a stirred solution of {4-[5-(3,4-dimethylphenylcarbamoyl)-1H-benzoimidazol-2-yl]-3,5-dimethyl-phenylamino}-acetic acid methyl ester (160 mg) in MeOH (5 mL) was added 1N NaOH (5 mL) and the mixture was stirred at room temperature for 18 h. The solution was washed with $Et_2O$ and the aqueous layer was carefully acidified to pH=2-3 with 1N HCl. The resulting suspension was filtered, washed with water and dried to give {4-[5-(3,4-dimethylphenylcarbamoyl)-1H-benzoimidazol-2-yl]-3,5-dimethylphenylamino}-acetic acid as a white solid. MS (ESI)m/z 443 (M+H). $^1$H NMR (MeOD, 400 MHz) δ 8.22 (s, 1H), 7.91 (dd, 1H), 7.70 (d, 1H), 7.46 (d, 1H), 7.42 (dd, 1H), 7.12 (d, 1H), 6.44 (s, 2H), 3.91 (s, 2H), 2.29 (s, 3H), 2.26 (s, 3H), 2.10 (s, 6H).

Example 5-3

2-[4-(2-Hydroxyethylamino)-2,6-dimethylphenyl]-1H-benzoimidazole-5-carboxylic acid (3,4-dimethylphenyl)-amide

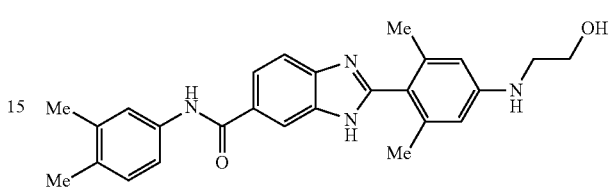

To a solution of {4-[5-(3,4-dimethylphenylcarbamoyl)-1H-benzoimidazol-2-yl]-3,5-dimethylphenylamino}-acetic acid methyl ester (80 mg) in THF (5 mL), cooled at 0° C. in an ice bath, was added $LiAlH_4$ (1M in THF, 0.26 mL) dropwise. The mixture was warmed to room temperature. After 1 hr, the reaction was quenched with 2 drops of water and filtered. The organic layer was dried, filtered and concentrated. The residue was purified by flash chromatography using hexanes/ethyl acetate (1:4) to afford 2-[4-(2-hydroxyethylamino)-2,6-dimethylphenyl]-1H-benzoimidazole-5-carboxylic acid (3,4-dimethyl-phenyl)-amide as a light yellow solid. MS (ESI)m/z 429 (M+H). $^1$H NMR (MeOD, 400 MHz) δ 8.20 (s, 1H), 7.87 (dd, 1H), 7.67 (s, 1H), 7.48 (d, 1H), 7.43 (dd, 1H), 7.13 (d, 1H), 6.47 (s, 2H), 3.74 (t, 2H), 3.27 (t, 2H), 2.30 (s, 3H), 2.26 (s, 3H), 2.09 (s, 6H).

Example 6-1

3-{4-[5-(3,4-Dimethylphenylcarbamoyl)-1H-benzoimidazol-2-yl]-3,5-dimethylphenyl}-propionic acid tert-butyl ester

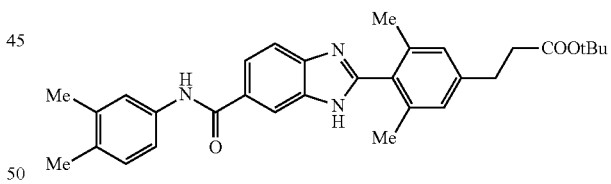

A solution of $NaNO_2$ (102 mg) in water (1 mL) was added to an ice cold mixture of 4-amino-2,6-dimethylbenzaldehyde (Example 5-1, step 3) (220 mg) and 48% $HBF_4$ (0.5 mL). After 30 min at 0° C., tert-butyl acrylate (0.43 mL) and $Pd(OAc)_2$ (10 mg) were added and the mixture was heated to 80° C. (or in a water bath) for 30 min. The suspension was filtered through Celite, washed with $CH_2Cl_2$ and the filtrate extracted with $CH_2Cl_2$. The combined organic layers were dried, filtered and concentrated. The residue was purified by flash chromatography using hexanes/ethyl acetate (7:1) and gave 3-(4-formyl-3,5-dimethylphenyl)-acrylic acid tert-butyl ester.

A solution of 3-(4-formyl-3,5-dimethylphenyl)-acrylic acid tert-butyl ester (210 mg) in $CH_2Cl_2$ (8 mL) was hydrogenated at 1 atm over 10% Pd/C (21 mg) for 4 h. The catalyst was filtered and the filtrate concentrated to give 3-(4-formyl- 3,5-dimethylphenyl)-propionic acid tert-butyl ester as a yellow solid. MS (ESI)m/z 286 (M+H).

To a solution of 3-(4-formyl-3,5-dimethylphenyl)-propionic acid tert-butyl ester (200 mg) and 3,4-diamino-N-(3,4-dimethylphenyl)-benzamide (Example 5-1, step 6) (194 mg) in DMSO (10 mL) was added Yb(OTf)3 (93 mg). The solution was stirred at room temperature for 18 h then the mixture was partioned between water and EtOAc. The aqueous layer was extracted with EtOAc. The combined organic layers were dried, filtered and concentrated. The residue was purified by flash chromatography (amino-column) using hexanes/ethyl acetate (1:4) and gave 3-{4-[5-(3,4-dimethylphenylcarbamoyl)-1H-benzoimidazol-2-yl]-3,5-dimethylphenyl}-propionic acid tert-butyl ester as a red solid. MS (ESI)m/z 498 (M+H). $^1$H NMR (Acetone-$d_6$, 400 MHz) δ 11.73 (s, 1H), 9.39 (s, 1H), 8.30 (s, 1H), 7.94 (t, 1H), 7.69 (m, 3H), 7.12 (s, 1H), 7.07 (s, 2H), 2.90 (t, 2H), 2.58 (t, 2H), 2.28 (s, 3H), 2.25 (s, 3H), 2.16 (s, 6H), 1.45 (s, 9H).

Example 6-2

3-{4-[5-(3,4-Dimethylphenylcarbamoyl)-1H-benzoimidazol-2-yl]-3,5-dimethylphenyl}-propionic acid

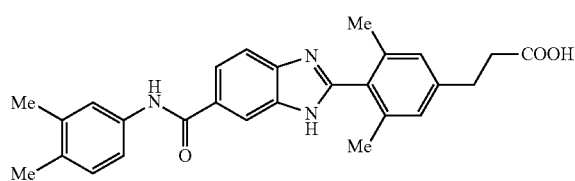

To a stirred solution of 3-{4-[5-(3,4-dimethylphenylcarbamoyl)-1H-benzoimidazol-2-yl]-3,5-dimethylphenyl}-propionic acid tert-butyl ester (120 mg) in MeOH (5 mL) was added 1N NaOH solution (5 mL). The mixture was stirred at room temperature for 18 h then the aqueous layer was carefully acidified to pH=2-3 with 1N HCl. The resulting suspension was filtered, washed with water and dried to give 3-{4-[5-(3,4-dimethylphenylcarbamoyl)-1H-benzoimidazol-2-yl]-3,5-dimethylphenyl}-propionic acid as red solid. MS (ESI)m/z 442 (M+H). $^1$H NMR (MeOD, 400 MHz) δ 8.37 (s, 1H), 8.14 (d, 1H), 7.90 (d, 1H), 7.48 (s, 1H), 7.44 (dd, 1H), 7.21 (s, 2H), 7.14 (d, 1H), 2.97 (t, 2H), 2.67 (t, 2H), 2.30 (s, 3H), 2.27 (s, 3H), 2.10 (s, 6H).

Example 6-3

3-{4-[6-(3,4-Dimethylphenylcarbamoyl)-1H-benzoimidazol-2-yl]-3,5-dimethylphenyl}-propionic acid methyl ester

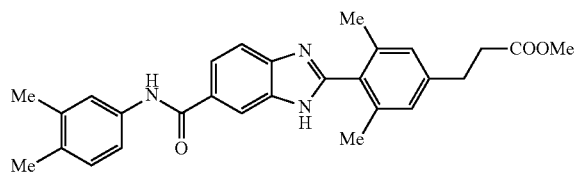

The title compound was prepared from 3,4-diamino-N-(3,4-dimethylphenyl)-benzamide and 3-(4-formyl-3,5-dimethylphenyl)-propionic acid methyl ester (from Example 6-17) analogous to Example 6-1. $^1$H NMR (Methanol-d4, 400 MHz): δ 8.32 (d, 1H), 7.91 (d, 1H), 7.79 (dd, 1H), 7.48 (s, 1H), 7.45 (dd, 1H), 7.15 (d, 1H), 7.08 (s, 2H), 3.67 (s, 3H), 2.97 (t, 2H), 2.71 (t, 2H), 2.30 (s, 3H), 2.27 (s, 3H), 2.15 (s, 6H). MS (m/z) 456.1 (M+1); Retention time: 1.44 min (Method 10).

Example 6-4

3-{4-[6-(5,6-Dimethylpyridin-2-ylcarbamoyl)-1H-benzimidazol-2-yl]-3,5-dimethylphenyl}-propionic acid

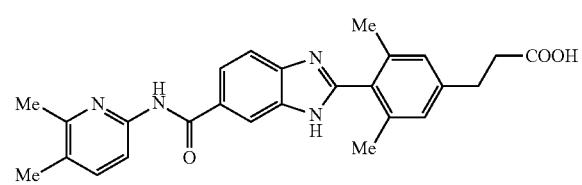

To DMF (20 mL) were added HATU (2.87 g, 7.55 mmol), 4-amino-3-nitrobenzoic acid (916 mg, 5.03 mmol), triethylamine (1.05 mL, 762 mmol) and 5-amino-2,3-dimethyllutidine (615 mg, 5.03 mmol) [J. Het. Chem. 31, 1641 (1994)]. The mixture was stirred at ambient temperature for 1 h, then at 80° C. for 18 h. The solution was decanted into ethyl acetate and extracted once with water and five times with brine, then dried, filtered, and the solvent was removed under reduced pressure. The residue was purified by chromatography using a gradient of 80-100% heptane/ethyl acetate to give 4-amino-N-(5,6-dimethylpyridin-2-yl)-3-nitrobenzamide. MS (m/z) 287.0 (M+1).

A mixture of 4-amino-N-(5,6-dimethylpyridin-2-yl)-3-nitrobenzamide (470 mg, 1.64 mmol) and of 5% platinum on carbon (60 mg) in 50 mL of ethyl acetate/ethanol (1:1) was stirred in under a hydrogen balloon. When the reaction was complete by LC/MS, the mixture was filtered through Celite to remove catalyst, and the filtrate was removed under reduced pressure to afford 3,4-diamino-N-(5,6-dimethylpyridin-2-yl)-benzamide.

The title compound was prepared from 3,4-diamino-N-(5,6-dimethylpyridin-2-yl)-benzamide and 3-(4-formyl-3,5-dimethylphenyl)-propionic acid methyl ester (from Example 6-17) analogous to the final two steps of Example 6-17. $^1$H-NMR (DMSO-d6, 400 MHz): δ 10.58 (s, 0.5H), 10.53 (s, 0.5H), 8.41 (s, 0.5H), 8.23 (s, 0.5H), 7.92 (m, 2.5H), 7.72 (d, J=8.6 Hz, 0.5H), 7.56 (m, 2H), 7.08 (s, 2H), 2.84 (t, J=7.4 Hz, 2H), 2.58 (t, J=7.4 Hz, 2H), 2.41 (s, 3H), 2.24 (s, 3H), 2.09 (s, 6H). MS (m/z) 392.3 (M−1); Retention time=1.09 min (Method 10).

Example 6-5

{3,5-Dichloro-4-[6-(3,4-dimethylphenylcarbamoyl)-1H-benzoimidazol-2-yl]-phenoxy}-acetic acid methyl ester

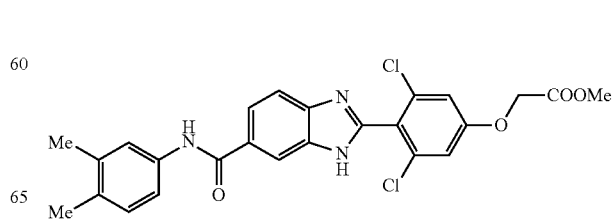

A solution of 3,5-dichlorophenol (1.63 g, 10 mmol) and imidazole (1.50 g, 22 mmol) in DMF (10 mL) was cooled to 0° C. then TBDMSCl (1.66 g, 11 mmol) was added. After the addition, the solution was warmed up to ambient temperature and stirred for 10 min. The solution was re-cooled to 0° C. and the mixture was quenched with water. The aqueous layer was extracted with Et$_2$O and the combined organic layers were washed with water, brine, dried with MgSO$_4$ and filtered. The solvent was removed under reduced pressure and the residue was purified by flash chromatography using heptane/EtOAc (15:1) as eluent to give tert-butyl-(3,5-dichlorophenoxy)-dimethylsilane as a pale yellow solid.

To a solution of tert-butyl-(3,5-dichlorophenoxy)-dimethylsilane (2.7 g, 9.8 mmol) in THF (20 mL) at −78° C., under a N$_2$ atmosphere, was added dropwise sec-BuLi (7.2 mL of a 1.4 M solution in cyclohexane, 10.1 mmol). After 30 min, anhydrous DMF (1.2 mL, 15.2 mmol) was added slowly to the solution. After the addition, the solution was stirred at −78° C. for 1.5 h then 20 mL of 1N HCl was added and the aqueous layer was warmed to ambient temperature. The aqueous layer was extracted with EtOAc and the organic layer was washed with water, brine, dried with MgSO$_4$ and filtered. The solvent was removed under reduced pressure to give 2,6-dichloro-4-hydroxybenzaldehyde as a pale yellow solid.

To a solution of 2,6-dichloro-4-hydroxybenzaldehyde (1.9 g, 10 mmol) and bromoacetic acid methyl ester (1.1 ml, 11 mmol) in DMF (20 ml) was added K$_2$CO$_3$ (2.8 g, 20 mmol). The suspension was stirred at ambient temperature overnight then the reaction mixture was partoned between water and EtOAc. The aqueous layer was extracted with EtOAc and the combined organic layers were dried with MgSO$_4$, filtered and concentrated. Purification by flash chromatography using heptane/EtOAc (8:1) as eluent gave (3,5-dichloro-4-formylphenoxy)-acetic acid methyl ester as a white solid.

To a solution of (3,5-dichloro-4-formylphenoxy)-acetic acid methyl ester (524 mg, 2.0 mmol) and 3,4-diamino-N-(3,4-dimethyl-phenyl)-benzamide (510 mg, 2.0 mmol) (Example 5-1, step 6) in DMSO (15 mL) was added Yb(OTf)$_3$ (248 mg, 0.4 mmol) and the solution was stirred at ambient temperature overnight. The mixture was partioned between water and EtOAc and the aqueous layer was extracted with EtOAc. The combined organic layers were washed with water, brine, dried with MgSO$_4$, filtered and concentrated. Purification by HPLC (0-80% MeCN/water) gave {3,5-dichloro-4-[6-(3,4-dimethylphenylcarbamoyl)-1H-benzoimidazol-2-yl]-phenoxy}-acetic acid methyl ester as a white solid. MS (m/z) 498.1 (M+1); $^1$H-NMR (Methanol-d4, 400 MHz): δ 8.36 (d, 1H), 8.09 (dd, 1H), 7.87 (dd, 1H), 7.49 (d, 1H), 7.46 (dd, 1H), 7.31 (s, 2H), 7.16 (d, 1H), 4.93 (s, 2H), 3.83 (s, 3H), 2.31 (s, 3H), 2.28 (s, 3H).

Example 6-6

{3,5-Dichloro-4-[6-(3,4-dimethyl-phenylcarbamoyl)-1H-benzoimidazol-2-yl]-phenoxy}-acetic acid

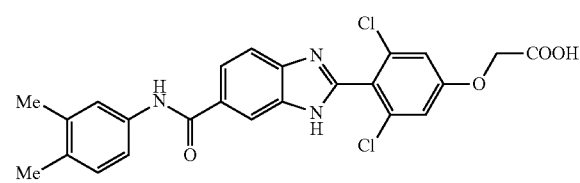

To a solution of {3,5-dichloro-4-[6-(3,4-dimethylphenylcarbamoyl)-1H-benzoimidazol-2-yl]-phenoxy}-acetic acid methyl ester (85 mg, 0.17 mmol) in MeOH (3 mL) was added 1N NaOH (3 mL) and the solution was stirred at ambient temperature for 3 h. The solution was carefully acidified to pH 3-4 with 1N HCl and the resulting suspension was filtered, washed with water, was dried under reduced pressure to give the title compound. $^1$H NMR (Methanol-d4, 400 MHz): δ 8.29 (d, 1H), 7.96 (dd, 1H), 7.76 (dd, 1H), 7.49 (d, 1H), 7.45 (dd, 1H), 7.23 (s, 2H), 7.15 (d, 1H), 4.84 (s, 2H), 2.30 (s, 3H), 2.27 (s, 3H). MS (m/z) 484.1 (M+1); retention time: 1.18 min (Method 10).

Example 6-7

{3-Chloro-4-[6-(3,4-dimethylphenylcarbamoyl)-1H-benzoimidazol-2-yl]-phenoxy}-acetic acid methyl ester

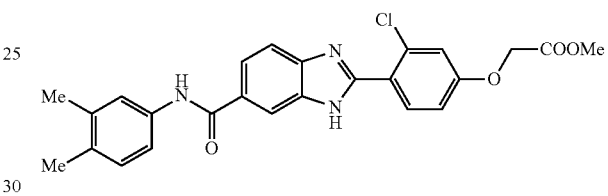

The title compound was obtained as a by-product from the final step of Example 6-5. $^1$H NMR (Methanol-d4, 400 MHz): δ 8.34 (s, 1H), 8.10 (d, 1H), 7.88 (q, 2H), 7.47 (d, 1H), 7.41 (dd, 1H), 7.34 (d, 1H), 7.21 (dd, 1H), 7.14 (d, 1H), 4.91 (s, 2H), 3.81 (s, 3H), 2.29 (s, 3H), 2.26 (s, 3H). MS (m/z) 464.2 (M+1); Retention time: 1.38 min (Method 10).

Example 6-8

{3-Chloro-4-[6-(3,4-dimethylphenylcarbamoyl)-1H-benzoimidazol-2-yl]-phenoxy}-acetic acid

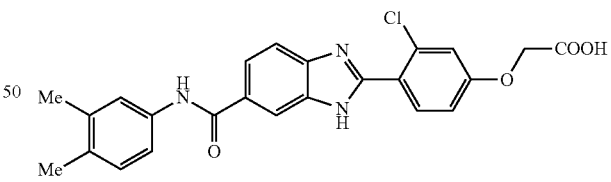

To a solution of {3-chloro-4-[6-(3,4-dimethylphenylcarbamoyl)-1H-benzoimidazol-2-yl]-phenoxy}-acetic acid methyl ester (100 mg, 0.21 mmol) in MeOH (3 mL) was added 1N NaOH (3 mL) and the solution was stirred at ambient temperature for 3 h. The solution was carefully acidified to pH 3-4 with 1N HCl and the suspension was filtered, washed with water, and the white solid was dried in vacuum oven to give the title compound. $^1$H NMR (Methanol-d4, 400 MHz): δ 8.26 (s, 1H), 7.92 (dd, 1H), 7.84 (d, 2H), 7.74 (d, 1H), 7.48 (dd, 1H), 7.44 (dd, 1H), 7.23 (dd, 1H), 7.14 (m, 2H), 4.80 (s, 2H), 2.30 (s, 3H), 2.27 (s, 3H). MS (m/z) 450.2 (M+1) Retention time: 1.19 min (Method 10).

Example 6-9

{3,5-Dimethyl-4-[6-(quinolin-2-ylcarbamoyl)-1H-benzoimidazol-2-yl]-phenoxy}-acetic acid methyl ester

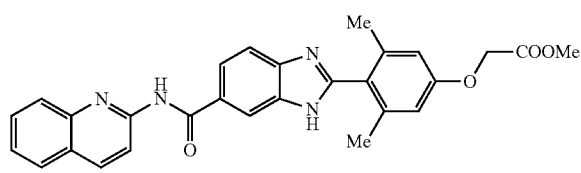

A solution of 4-bromo-3,5-dimethylphenol (2.1 g, 10 mmol) and imidazole (1.50 g, 22 mmol) in DMF (15 mL) was cooled to 0° C. then TBDMSCl (1.66 g, 11 mmol) was added. After the addition, the solution was warmed up to ambient temperature and was stirred for 10 min. The solution was recooled to 0° C. and the reaction was quenched with water. The aqueous layer was extracted with Et$_2$O and the organic layer was washed with water, brine, dried with MgSO$_4$ and filtered. The solvent was removed under reduced pressure and the residue was purified by flash chromatography using heptane/EtOAc (10:1) to give (4-bromo-3,5-dimethylphenoxy)-tert-butyl-dimethylsilane as a pale yellow solid.

To a solution of (4-bromo-3,5-dimethylphenoxy)-tert-butyl-dimethylsilane (3.1 g, 9.8 mmol) in THF (30 mL) at −78° C. under N$_2$ protection was added dropwise methyllithium/LiBr (9.3 ml of a 1.5 M solution in Et$_2$O, 14 mmol). After 5 min of stirring, sec-BuLi (10 mL of a 1.4 M solution in cyclohexane, 14 mmol) was added slowly to the reaction solution at −78° C. After 5 min, anhydrous DMF (1.5 mL, 20 mmol) was added slowly then the solution was warmed to 25° C. After 30 min, the reaction mixture was quenched with water. The aqueous layer was extracted with CH$_2$Cl$_2$ and the combined organic layers were washed with water, brine, dried with MgSO$_4$ and filtered. The solvent was removed under reduced pressure and the residue was purified by flash chromatography using heptane/EtOAc (6:1) to give 4-(tert-butyldimethyl-silanyloxy)-2,6-dimethylbenzaldehyde as a yellow oil.

To a stirred solution of 4-(tert-butyldimethyl-silanyloxy)-2,6-dimethylbenzaldehyde (2.4 g, 9 mmol) in THF (10 mL) was added TBAF (10 mL of a 1.0 M solution in THF). After an hour at ambient temperature, the reaction mixture was quenched with water and the aqueous layer was extracted with EtOAc. The organic layer was washed with water, brine, dried with MgSO$_4$ and filtered. The solvent was removed under reduced pressure to give 4-hydroxy-2,6-dimethylbenzaldehyde as a yellow oil.

To a solution of 4-hydroxy-2,6-dimethylbenzaldehyde (1.3 g, 8.6 mmol) and bromoacetic acid methyl ester (0.98 ml, 10.3 mmol) in DMF (20 mL) was added K$_2$CO$_3$ (1.8 g, 12.9 mmol). The suspension was stirred at ambient temperature overnight then the reaction mixture was partioned between water and EtOAc. The aqueous layer was extracted with EtOAc and the organic layer was dried with MgSO$_4$, filtered and concentrated. Purification by flash chromatography using heptane/EtOAc (5:1) as eluent gave (4-formyl-3,5-dimethylphenoxy)-acetic acid methyl ester as a yellow solid.

To a solution of 3,4-diamino-N-quinolin-2-yl-benzamide (770 mg, 2.77 mmol) and (4-formyl-3,5-dimethylphenoxy)-acetic acid methyl ester (615 mg, 2.77 mmol) in DMSO (10 mL) was added Yb(OTf)$_3$ (344 mg, 0.55 mmol) and the mixture was stirred at ambient temperature overnight. The reaction mixture was partioned between water and EtOAc and the aqueous layer was extracted with EtOAc. The combined organic layers were dried with MgSO$_4$, filtered and concentrated. Purification by flash chromatography using heptane/EtOAc (1:4) as eluent gave {3,5-dimethyl-4-[6-(quinolin-2-ylcarbamoyl)-1H-benzoimidazol-2-yl]-phenoxy}-acetic acid methyl ester as a white solid. MS (m/z) 481.4 (M+1); $^1$H NMR (Methanol-d4, 400 MHz): δ 8.45 (m, 3H), 8.04 (d, 1H), 7.92 (d, 2H), 7.75 (m, 2H), 7.54 (m, 1H), 6.80 (s, 2H), 4.78 (s, 2H), 3.81 (s, 3H), 2.17 (s, 6H).

Example 6-10

{3,5-Dimethyl-4-[6-(quinolin-2-ylcarbamoyl)-1H-benzoimidazol-2-yl]-phenoxy}-acetic acid

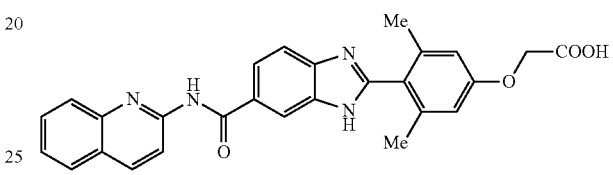

To a solution of {3,5-dimethyl-4-[6-(quinolin-2-ylcarbamoyl)-1H-benzoimidazol-2-yl]-phenoxy}-acetic acid methyl ester (200 mg, 0.41 mmol) in MeOH (5 mL) was added NaOH (1N, 5 ml) and the solution was stirred at ambient temperature for 3 h. The solution was carefully acidified to pH 3-4 with 1N HCl and the suspension was filtered, washed with water, and the white solid was dried in vacuum oven to give the title compound. $^1$H NMR (DMSO-d6, 400 MHz): δ 13.02 (s, 1H), 11.13 (s, 1H), 8.44 (m, 3H), 8.04 (d, 1H), 7.98 (d, 1H), 7.91 (d, 1H), 7.77 (m, 2H), 7.56 (m, 1H), 6.81 (s, 2H), 4.76 (s, 2H), 2.13 (s, 6H). MS (m/z) 467.2 (M+1); Retention time: 1.03 min (Method 10).

Example 6-11

2-[4-((R)-2,2-Dimethyl-[1,3]dioxolan-4-ylmethoxy)-2,6-dimethylphenyl]-3H-benzoimidazole-5-carboxylic acid (3,4-dimethylphenyl)-amide

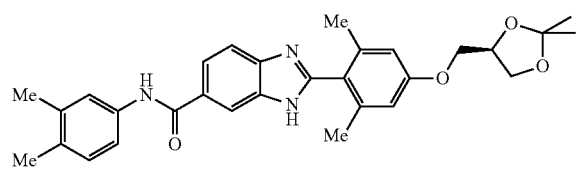

To a solution of 4-hydroxy-2,6-dimethylbenzaldehyde (150 mg, 1.0 mmol) and ((R)-2,2-dimethyl-[1,3]dioxolan-4-yl)-methanol (132 mg, 1.0 mmol) in THF (10 mL) was added PPh$_3$-resin (553 mg, 2.13 mmol/g) and DEAD (0.54 mL of a 40% solution, 1.2 mmol) and the suspension was stirred at ambient temperature overnight. The reaction mixture was filtered and partioned between water and EtOAc. The aqueous layer was extracted with EtOAc and the organic layer was dried with MgSO$_4$, filtered and concentrated. Purification by flash chromatography using heptane/EtOAc (2:1) as eluent gave 4-((R)-2,2-dimethyl-[1,3]dioxolan-4-ylmethoxy)-2,6-dimethylbenzaldehyde as a white solid.

To a solution of 4-((R)-2,2-dimethyl-[1,3]dioxolan-4-yl-methoxy)-2,6-dimethylbenzaldehyde (145 mg, 0.55 mmol) and 3,4-diamino-N-(3,4-dimethylphenyl)-benzamide (153 mg, 0.55 mmol) in DMSO (8 mL) was added Yb(OTf)$_3$ (68 mg, 0.11 mmol) and the mixture was stirred at ambient temperature overnight. The reaction mixture was partioned between water and EtOAc and the aqueous layer was extracted with EtOAc. The organic layer was washed with water, brine, dried with MgSO$_4$, filtered and concentrated. Purification by flash chromatography using heptane/EtOAc (1:2) as eluent gave 2-[4-((R)-2,2-dimethyl-[1,3]dioxolan-4-ylmethoxy)-2,6-dimethylphenyl]-3H-benzoimidazole-5-carboxylic acid (3,4-dimethylphenyl)-amide as a pale yellow solid $^1$H NMR (Methanol-d4, 400 MHz): δ 8.30 (d, 1H), 7.90 (d, 1H), 7.77 (dd, 1H), 7.47 (s, 1H), 7.44 (dd, 1H), 7.13 (d, 1H), 6.79 (s, 2H), 4.51 (m, 1H), 4.19 (q, 1H), 4.07 (d, 2H), 3.91 (q, 1H), 2.29 (s, 3H), 2.26 (s, 3H), 2.15 (s, 6H), 1.44 (s, 3H), 1.38 (s, 3H). MS (m/z) 500.3 (M+1); Retention time: 1.51 min (Method 10).

Example 6-12

2-[4-((S)-2,3-Dihydroxy-propoxy)-2,6-dimethylphenyl]-3H-benzoimidazole-5-carboxylic acid (3,4-dimethylphenyl)-amide

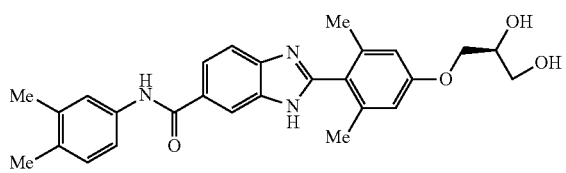

To a solution of 2-[4-((R)-2,2-dimethyl-[1,3]dioxolan-4-ylmethoxy)-2,6-dimethylphenyl]-3H-benzoimidazole-5-carboxylic acid (3,4-dimethylphenyl)-amide (120 mg, 0.24 mmol) in MeOH (3 mL) was added 1N HCl (3 mL) and the solution was stirred at ambient temperature for 3 h. The solution was basified to pH 10 with 1N NaOH and the mixture was partioned between water and EtOAc. The aqueous layer was extracted with EtOAc and the organic layer was washed with water, brine, dried with MgSO$_4$, filtered and concentrated. Purification by HPLC gave the title compound as a white solid. $^1$H NMR (Methanol-d4, 400 MHz): δ 8.22 (s, 1H), 7.90 (dd, 1H), 7.70 (d, 1H), 7.47 (s, 1H), 7.44 (dd, 1H), 7.13 (d, 1H), 6.80 (s, 2H), 4.11 (m, 1H), 4.03 (m, 2H), 3.72 (m, 2H), 2.29 (s, 3H), 2.26 (s, 3H), 2.14 (s, 6H). MS (m/z) 460.1 (M+1); Retention time: 1.23 min (Method 10).

Example 6-13

2-[4-((S)-2,2-Dimethyl-[1,3]dioxolan-4-ylmethoxy)-2,6-dimethylphenyl]-3H-benzoimidazole-5-carboxylic acid (3,4-dimethylphenyl)-amide

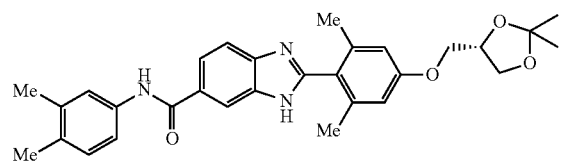

The title compound was prepared analogous to Example 6-11 using ((S)-2,2-dimethyl-[1,3]dioxolan-4-yl)-methanol. $^1$H NMR (Methanol-d4, 400 MHz): δ 8.30 (d, 1H), 7.91 (d, 1H), 7.77 (dd, 1H), 7.48 (s, 1H), 7.44 (dd, 1H), 7.14 (d, 1H), 6.80 (s, 2H), 4.50 (m, 1H), 4.20 (q, 1H), 4.08 (d, 2H), 3.92 (q, 1H), 2.30 (s, 3H), 2.26 (s, 3H), 2.15 (s, 6H), 1.44 (s, 3H), 1.39 (s, 3H). MS (m/z) 500.3 (M+1); Retention time: 1.51 min (Method 10).

Example 6-14

2-[4-((R)-2,3-Dihydroxy-propoxy)-2,6-dimethylphenyl]-3H-benzoimidazole-5-carboxylic acid (3,4-dimethylphenyl)-amide

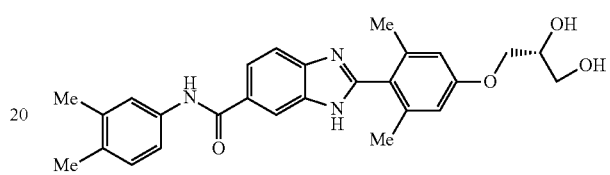

The title compound was prepared analogous to Example 6-12. $^1$H NMR (Methanol-d4, 400 MHz): δ 8.30 (d, 1H), 7.90 (d, 1H), 7.77 (dd, 1H), 7.47 (s, 1H), 7.44 (dd, 1H), 7.14 (d, 1H), 6.81 (s, 2H), 4.12 (m, 1H), 4.02 (m, 2H), 3.70 (m, 2H), 2.29 (s, 3H), 2.26 (s, 3H), 2.15 (s, 6H). MS (m/z) 460.1 (M+1); Retention time: 1.24 min (Method 10).

Example 6-15

2-[4-((R)-2,2-Dimethyl-[1,3]dioxolan-4-ylmethoxy)-2,6-dimethylphenyl]-3H-benzoimidazole-5-carboxylic acid quinolin-2-ylamide

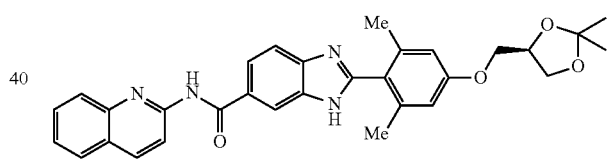

The title compound was prepared analogous to Example 6-11 using 3,4-diamino-N-quinolin-2-yl-benzamide. $^1$H NMR (Methanol-d4, 400 MHz): δ 8.45 (m, 3H), 8.03 (d, 1H), 7.93 (d, 2H), 7.75 (m, 2H), 7.55 (t, 1H), 6.81 (s, 2H), 4.50 (m, 1H), 4.21 (q, 1H), 4.09 (d, 2H), 3.93 (q, 1H), 2.17 (s, 6H), 1.45 (s, 3H), 1.39 (s, 3H). MS (m/z) 523.1 (M+1); Retention time: 1.50 min (Method 10).

Example 6-16

2-[4-((S)-2,3-Dihydroxypropoxy)-2,6-dimethylphenyl]-3H-benzoimidazole-5-carboxylic acid quinolin-2-ylamide

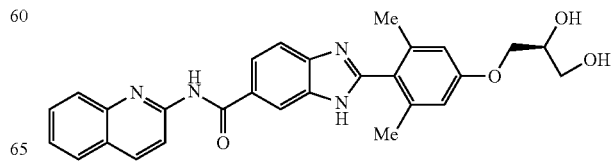

The title compound was prepared analogous to Example 6-12. $^1$H NMR (Methanol-d4, 400 MHz): δ 8.46 (m, 3H), 8.04 (dd, 1H), 7.93 (d, 2H), 7.75 (m, 2H), 7.55 (m, 1H), 6.83 (s, 2H), 4.14 (m, 1H), 4.05 (m, 2H), 3.72 (m, 2H), 2.17 (s, 6H). MS (m/z) 483.5 (M+1); Retention time: 1.22 min (Method 10).

Example 6-17

3-{3,5-Dimethyl-4-[6-(quinolin-2-ylcarbamoyl)-1H-benzoimidazol-2-yl]-phenyl}-propionic acid

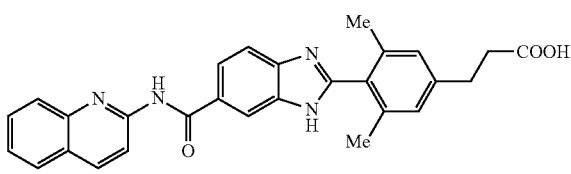

A solution of 3,5-dimethylaniline (7.26 g, 60 mmol) in CH$_2$Cl$_2$ (200 mL) was cooled in an water bath then trifluoroacetic anhydride (12.51 mL, 90 mmol) was added slowly. After the addition, the solution was stirred at 25° C. for 15 min then bromine (2.93 mL, 57 mmol) was added slowly to the solution while maintaining the ambient temperature of the water bath. The solution was stirred at 25° C. for 3 h then was quenched with 10% Na$_2$S$_2$O$_3$. The aqueous layer was extracted with CH$_2$Cl$_2$ and the combined organic layers were washed with water, brine, dried with MgSO$_4$ and filtered. The solvent was removed under reduced pressure to give an orange solid which was recrystallized from hexanes/Et$_2$O (1:1) to give N-(4-bromo-3,5-dimethylphenyl)-2,2,2-trifluoroacetamide as a white solid.

A solution of N-(4-bromo-3,5-dimethylphenyl)-2,2,2-trifluoroacetamide (14.0 g, 47.3 mmol) in THF (200 mL) was cooled to −78° C. Under a nitrogen atmosphere, methyllithium/LiBr (44.1 mL of a 1.5 M solution in Et$_2$O, 66.2 mmol) was added slowly to the solution. After 5 min of stirring, sec-BuLi (47.3 mL of a 1.4 M solution in cyclohexane, 66.2 mmol) was added slowly to the reaction keeping the temperature at −78° C. After 5 min, anhydrous DMF (25.5 mL, 331 mmol) was added slowly to the solution. After the addition, the solution was warmed to 25° C. and after 30 min the reaction mixture was quenched with water. The aqueous layer was extracted with CH$_2$Cl$_2$ and the combined organic layers were washed with water, brine, dried with MgSO$_4$ and filtered. The solvent was removed under reduced pressure to give 2,2,2-trifluoro-N-(4-formyl-3,5-dimethylphenyl)-acetamide as a yellow solid.

A suspension of the above 2,2,2-trifluoro-N-(4-formyl-3,5-dimethylphenyl)-acetamide was taken up in MeOH (30 mL) and 1N NaOH (30 mL) was stirred at ambient temperature overnight. Water (200 mL) was added and the resulting solid was filtered, washed with water, and dried to give 4-amino-2,6-dimethylbenzaldehyde. The aqueous layer was extracted with EtOAc and the combined organic layers were washed with water, brine, dried with MgSO$_4$, and filtered. The solvent was removed under reduced pressure and the residue was purified by flash chromatography using heptane/EtOAc (4:1) as eluent to give additional product.

The above 4-amino-2,6-dimethylbenzaldehyde (1.0 g, 6.71 mmol) was taken up in enough 42% HBF$_4$ until the suspension stirred well and then was cooled to 0° C. A solution of NaNO$_2$ (463 mg, 6.71 mmol) in water (5 mL) was added slowly and after 30 min at 0° C., MeOH (20 mL) was added followed by Pd(OAc)$_2$ (229 mg) and methyl acrylate (1.16 g, 13.42 mmol). The reaction mixture was heated at 80° C. for 30 min then the suspension was filtered through Celite and washed with CH$_2$Cl$_2$. The combined organic layers were washed with water, brine, dried with MgSO$_4$, and filtered. The solvent was removed under reduced pressure and the residue was purified by flash chromatography using a 10/1 to 5/1 gradient of heptane/EtOAc to give 3-(4-formyl-3,5-dimethylphenyl)-acrylic acid methyl ester as a light yellow solid.

To a solution of 3-(4-formyl-3,5-dimethylphenyl)-acrylic acid methyl ester (900 mg, 4.1 mmol) in CH$_2$Cl$_2$ (20 mL) was added 10% Pd/C (90 mg) and the mixture was hydrogenated at one atm overnight. The catalyst was filtered through Celite and was washed with CH$_2$Cl$_2$. The solvent was removed under reduced pressure and the residue was purified by flash chromatography using heptane/EtOAc (5:1) to give 3-(4-formyl-3,5-dimethylphenyl)-propionic acid methyl ester as a light yellow oil.

To a solution of 4-amino-3-nitrobenzoic acid (3.64 g, 20 mmol) in DMF (35 mL) was added HOBT (4.05 g, 30 mmol) and EDCI (5.75 g, 30 mmol). After the addition, the solution was stirred at 25° C. for 10 min then 2-aminoquinoline (2.88 g, 20 mmol) was added followed by the addition of DIPEA (10.69 mL, 60 mmol). The solution was stirred at 25° C. for 3 h then EtOAc was added and stirred for a while. Water was added and the EtOAc layer was separated and the aqueous layer was extracted with EtOAc. The combined organic layers were washed with water, brine, dried with MgSO$_4$ and filtered. The solvent was removed under reduced pressure to 4-amino-3-nitro-N-quinolin-2-yl-benzamide as a yellow solid.

A suspension of the above 4-amino-3-nitro-N-quinolin-2-yl-benzamide (5 g, 16.2 mmol) in EtOH (50 mL) was hydrogenated at one atm over PtO$_2$ (250 mg) for 4 h (the suspension will become a clear when the reaction is complete). The catalyst was filtered through Celite and washed with EtOH. The solvent was removed under reduced pressure to give 3,4-diamino-N-quinolin-2-yl-benzamide as a red solid.

To a mixture of 3,4-diamino-N-quinolin-2-yl-benzamide (1.0 g, 3.92 mmol) and 3-(4-formyl-3,5-dimethyl-phenyl)-propionic acid methyl ester (1.09 g, 3.92 mmol) in DMF (10 mL) and water (1 mL) was added oxone (1.62 g, 2.63 mmol) and the mixture was stirred atambient temperature for 20 min. The mixture was quenched with water and the aqueous layer was extracted with EtOAc. The combined organic layers were washed with water, brine, dried with MgSO$_4$, and filtered. The solvent was removed under reduced pressure and the residue was purified by flash chromatography using heptane/EtOAc (1:3) to give 3-{4-[6-(quinolin-2-ylcarbamoyl)-1H-benzoimidazol-2-yl]-phenyl}-propionic acid methyl ester as a pale yellow solid. $^1$H NMR (Methanol-d4, 400 MHz): δ 8.45 (d, 1H), 8.38 (d, 1H), 8.29 (s, 1H), 8.04 (d, 1H), 7.93 (d, 2H), 7.83 (s, 1H), 7.75 (m, 1H), 7.55 (m, 1H), 7.09 (s, 2H), 3.67 (s, 3H), 2.97 (t, 2H), 2.71 (t, 2H), 2.16 (s, 6H). MS (m/z) 479.2 (M+1); Retention time: 1.48 min (Method 10).

The above 3-{4-[6-(quinolin-2-ylcarbamoyl)-1H-benzoimidazol-2-yl]-phenyl}-propionic acid methyl ester was taken up in MeOH (5 mL) then 1N NaOH (5 mL) was added. The solution was stirred at ambient temperature for 3 h then the solution was carefully acidified to pH 3-4 with 1N HCl. The suspension was filtered, washed with water, and dried under reduced pressure to give 3-{4-[6-(quinolin-2-ylcarbamoyl)-1H-benzoimidazol-2-yl]-phenyl}-propionic acid. $^1$H NMR (MeOD, 400 MHz): δ 8.45-8.43 (d, J=8.97 Hz, 1H), 8.38-8.36 (d, J=8.97 Hz, 2H), 8.04-8.01 (dd, J=1.77 Hz, 8.59 Hz, 1H), 7.92-7.90 (d, J=8.34 Hz, 2H), 7.77-7.71 (m, 2H), 7.54-7.51 (t, J=7.83 Hz, 1H), 7.1 (s, 2H), 2.96-2.92 (t, J=7.45 Hz, 2H), 2.65-2.62 (t, J=7.71 Hz, 2H), 2.16 (s, 6H). MS (ESI) m/z 465.1 (M+H).

Example 6-18

3-{3,5-Dimethyl-4-[6-(naphthalen-2-ylcarbamoyl)-1H-benzoimidazol-2-yl]-phenyl}-propionic acid

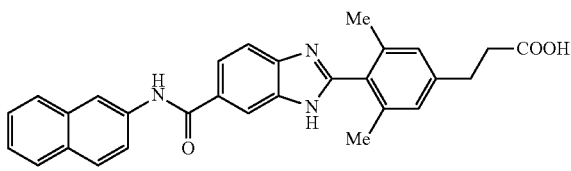

The title compound was prepared analogous to Example 6-17 using 2-aminonaphthalene. $^1$H NMR (Methanol-d4, 400 MHz): δ 8.36 (m, 2H), 8.06 (d, 1H), 7.90 (m, 5H), 7.50 (m, 2H), 7.14 (s, 2H), 2.98 (t, 2H), 2.68 (t, 2H), 2.19 (s, 6H). MS (m/z) 464.5 (M+1); Retention time: 1.11 min (Method 10).

Example 6-19

3-{4-[6-(Isoquinolin-1-ylcarbamoyl)-1H-benzoimidazol-2-yl]-3,5-dimethylphenyl}-propionic acid

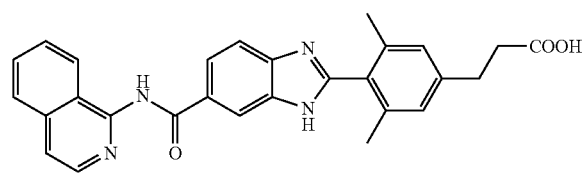

To a solution of 4-amino-3-nitrobenzoic acid (546 mg), EDCI (576 mg) and HOBt (405 mg) in DMF (7 mL) was added isoquinolin-1-ylamine (432 mg) and the mixture was stirred at ambient temperature for 18 h. Water was added and the orange precipitate was filtered to give 4-amino-N-isoquinolin-1-yl-3-nitrobenzamide.

A suspension of give 4-amino-N-isoquinolin-1-yl-3-nitrobenzamide and platinum oxide (330 mg) in MeOH (100 mL) was hydrogenated at 40 psi for 18 h. The catalyst was filtered from the solution through Celite and the filtrate evaporated to give 3,4-diamino-N-isoquinolin-1-yl-benzamide as a thick oil. MS (ESI) m/z 279.1 (M+H).

A solution of 3,4-diamino-N-isoquinolin-1-yl-benzamide (200 mg) and 3-(4-formyl-3,5-dimethylphenyl)-propionic acid methyl ester (189 mg) (from Example 6-17) in 5 mL DMF/0.5 mL water was stirred at ambient temperature for 15 min then oxone (292 mg) was added and stirring was continued for 1 h. Water was added and the mixture was extracted with EtOAc. The organic phase was dried over sodium sulfate and the solvent was removed under reduced pressure. The residue was purified by flash chromatography using 5% MeOH/methylene chloride as eluent to give 3-{4-[6-(Isoquinolin-1-ylcarbamoyl)-1H-benzoimidazol-2-yl]-3,5-dimethylphenyl}-propionic acid methyl ester. MS (ESI)m/z 479.1 (M+H), retention time=1.33 min, Method 10.

To a solution of 3-{4-[6-(isoquinolin-1-ylcarbamoyl)-1H-benzoimidazol-2-yl]-3,5-dimethylphenyl}-propionic acid methyl ester (85 mg) in MeOH (2 mL) was added 0.5 mL of 1.0 N NaOH and the mixture was stirred at ambient temperature for 18 h. To this solution was added 0.5 mL of 1.0 N HCl then the solvent was removed under reduced pressure. Water was added and the mixture was extracted with EtOAc. The organic phase was dried over sodium sulfate and the solvent was removed under reduced pressure. The residue was triturated with MeCN to give 3-{4-[6-(isoquinolin-1-ylcarbamoyl)-1H-benzoimidazol-2-yl]-3,5-dimethylphenyl}-propionic acid as a tan solid. MS (ESI) m/z 465.1 (M+H), retention time=1.01 min, Method 10.

Example 6-20

{3,5-Dichloro-4-[6-(quinolin-2-ylcarbamoyl)-1H-benzoimidazol-2-yl]-phenoxy}-acetic acid methyl ester

The title compound was prepared from 3,4-diamino-N-quinolin-2-yl-benzamide (from Example 6-17) and (3,5-dichloro-4-formylphenoxy)-acetic acid methyl ester (from Example 6-5) analogous to Example 6-17. $^1$H NMR (Methanol-d4, 400 MHz): δ 8.44 (m, 3H), 8.06 (d, 1H), 7.92 (d, 2H), 7.74 (m, 2H), 7.54 (m, 1H), 7.23 (s, 2H), 4.89 (s, 2H), 3.82 (s, 3H). MS (m/z) 521.2 (M+1); Retention time: 1.42 min (Method 10).

Example 6-21

{3,5-Dichloro-4-[6-(quinolin-2-ylcarbamoyl)-1H-benzoimidazol-2-yl]-phenoxy}-acetic acid

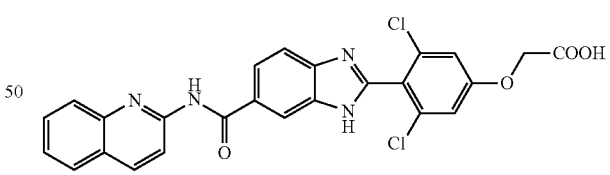

To a solution of {3,5-dichloro-4-[6-(quinolin-2-ylcarbamoyl)-1H-benzoimidazol-2-yl]-phenoxy}-acetic acid methyl ester (100 mg, 0.19 mmol) in MeOH (3 mL) was added 1N NaOH (3 mL) and the solution was stirred at ambient temperature for 3 h. The solution was carefully acidified to pH 3-4 with 1N HCl and the suspension was filtered, washed with water, and the pale yellow solid was dried in vacuum oven to give the title compound. $^1$H NMR (Methanol-d4, 400 MHz): δ 11.14 (s, 1H), 8.46 (s, 1H), 8.43 (q, 2H), 8.02 (dd, 1H), 7.97 (d, 1H), 7.91 (d, 1H), 7.76 (m, 2H), 7.55 (m, 1H), 7.32 (s, 2H), 4.93 (s, 2H). MS (m/z) 507.3 (M+1); Retention time: 1.11 min (Method 10).

Example 6-22

2-(2,6-Dichloro-4-dimethylcarbamoylmethoxyphenyl)-3H-benzoimidazole-5-carboxylic acid quinolin-2-ylamide

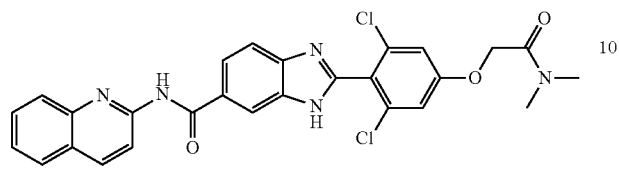

To a solution of 2,6-dichloro-4-hydroxybenzaldehyde (250 mg, 1.31 mmol) and 2-chloro-N,N-dimethylacetamide (238 mg, 1.97 mmol) in DMF (10 mL) was added $CsCO_3$ (854 mg, 2.62 mmol) and the suspension was stirred at ambient temperature overnight. The reaction mixture was partioned between water and EtOAc and the aqueous layer was extracted with EtOAc. The combined organic layers were dried with $MgSO_4$, filtered and concentrated. The material was purified by flash chromatography using heptane/EtOAc (1:3) as eluent to give 2-(3,5-dichloro-4-formylphenoxy)-N,N-dimethyl-acetamide as a yellow solid.

The title compound was prepared from 3,4-diamino-N-quinolin-2-yl-benzamide (from Example 6-17) and 2-(3,5-dichloro-4-formylphenoxy)-N,N-dimethyl-acetamide analogous to Example 6-17. $^1$H NMR (Methanol-d4, 400 MHz): δ 8.83 (d, 1H), 8.56 (d, 1H), 8.20 (t, 1H), 8.18 (t, 1H), 8.14 (d, 1H), 8.02 (m, 2H), 7.90 (d, 1H), 7.79 (t, 1H), 7.28 (s, 2H), 5.02 (s, 2H), 3.09 (s, 3H), 3.01 (s, 3H). MS (m/z) 534.2 (M+1); Retention time: 1.28 min (Method 10).

Example 6-23

{3,5-Dichloro-4-[6-(quinolin-2-ylcarbamoyl)-1H-benzoimidazol-2-yl]-phenoxymethyl}-phosphonic acid diethylester

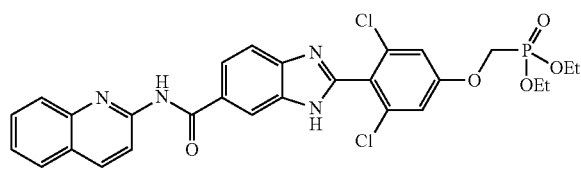

To a solution of 2,6-dichloro-4-hydroxy-benzaldehyde (190 mg, 1.0 mmol) and hydroxymethyl-phosphonic acid diethyl ester (278 mg, 1.0 mmol) in THF (8 mL) was added $PPh_3$-resin (553 mg, 2.13 mmol/g) and DEAD (0.54 ml of 40% solution, 1.2 mmol). The suspension was stirred at ambient temperature overnight then the reaction mixture was filtered and partioned between water and EtOAc. The aqueous layer was extracted with EtOAc and the combined organic layers were dried with $MgSO_4$, filtered and concentrated. Purification by flash chromatography using heptane/EtOAc (1:3) gave (3,5-dichloro-4-formylphenoxymethyl)-phosphonic acid diethyl ester as a colorless oil.

The title compound was prepared from 3,4-diamino-N-quinolin-2-yl-benzamide (from Example 6-17) and (3,5-dichloro-4-formylphenoxymethyl)-phosphonic acid diethyl ester analogous to Example 6-17. $^1$H NMR (Methanol-d4, 400 MHz): δ 8.77 (d, 1H), 8.54 (d, 1H), 8.17 (t, 1H), 8.16 (t, 1H), 8.12 (d, 1H), 8.07 (d, 1H), 7.99 (m, 1H), 7.86 (d, 1H), 7.77 (m, 1H), 7.38 (s, 2H), 4.62 (d, 2H), 4.30 (m, 4H), 1.42 (t, 6H). MS (m/z) 599.5 (M+1); Retention time: 1.40 min (Method 10).

Example 6-24

{3,5-Dichloro-4-[6-(quinolin-2-ylcarbamoyl)-1H-benzoimidazol-2-yl]-phenoxymethyl}-phosphonic acid

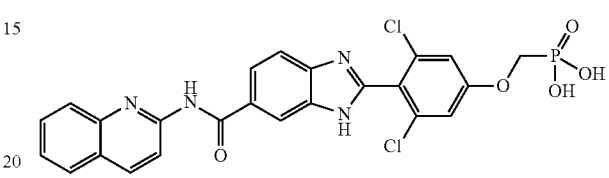

To a solution of {3,5-dichloro-4-[6-(quinolin-2-ylcarbamoyl)-1H-benzoimidazol-2-yl]-phenoxymethyl}-phosphonic acid diethylester (50 mg, 0.083 mmol) in $CH_2Cl_2$ (5 mL) was added TMSBr (0.11 ml, 0.83 mmol) and the solution was stirred at ambient temperature overnight. The solvent was removed under reduced pressure and the residue was purified by HPLC to give the title compound as a white solid. $^1$H NMR (Methanol-d4, 400 MHz): δ 8.84 (d, 1H), 8.56 (d, 1H), 8.21 (d, 2H), 8.15 (d, 1H), 8.03 (m, 2H), 7.90 (d, 1H), 7.80 (t, 1H), 7.37 (s, 2H), 4.49 (d, 2H). MS (m/z) 543.3 (M+1); Retention time: 1.10 min. (method 10).

Example 6-25

3-{3,5-Dichloro-4-[6-(quinolin-2-ylcarbamoyl)-1H-benzoimidazol-2-yl]-phenyl}-propionic acid

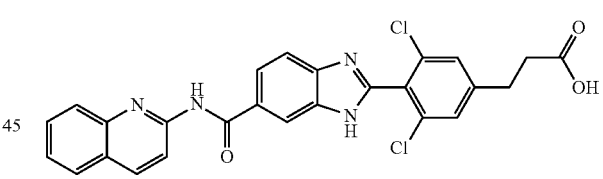

A mixture of 3,5-dichloro-iodobenzene (5 g, 18 mmol), tert butyl acrylate (6.5 mL, 2.5 eq), tetrabutyl ammonium chloride hydrate (5.1 g, 1 eq), potassium acetate (5.4 g, 3 eq) and palladium (II) acetate (~200 mg, 30 mol %) in DMF (50 mL) was stirred at ambient temperature for 5 h. The reaction mixture was reduced in vacuo and partitioned between water and ethyl acetate. The ethyl acetate fractions were dried over magnesium sulphate and filtered through a small plug of silica gel using 10% ethyl aceate/n-heptanes as eluent to afford 3-(3,5-dichlorophenyl)-acrylic acid tert butyl ester as a white solid. $^1$H-NMR (DMSO-d6, 400 MHz): δ 7.81 (d, J=1.77 Hz, 2H), 7.59 (t, J=1.89 Hz, 1H), 7.49 (d, J=16.04 Hz, 1H), 6.69 (d, J=16.04 Hz, 1H), 1.46 (s, 9H).

A solution of 3-(3,5-dichlorophenyl)-acrylic acid tert butyl ester (4 g, 14 mmol) in ethanol (100 mL) under nitrogen atmosphere was charged with platinum oxide (800 mg). A balloon of hydrogen was attached and the mixture was stirred vigorously at ambient temperature over night. After removal of excess hydrogen, the catalyst was removed by filtering mixture through a pad of Celite and the resulting solution was evaporated to afford 3-(3,5-dichlorophenyl)-propionic acid tert-butyl ester as an oil. $^1$H-NMR (CDCl$_3$, 400 MHz): δ 7.18 (s, 1H), 7.08 (s, 2H), 2.85 (s, 2H), 2.52 (s, 2H), 1.41 (s, 9H).

To a solution of 3-(3,5-dichlorophenyl)-propionic acid tert butyl ester (1 g, 3.6 mmol) in THF (50 mL) at −78° C. was added dropwise s-butyllithium (1.4 M cyclohexanes; 5.7 mL, 2.2 eq). The resulting red-colored homogeneous solution was stirred under nitrogen at −78° C. for 1 h, at which time DMF (560 mL, 2 eq) was added. After 30 minutes, the reaction was quenched with saturated ammonium chloride solution at. The mixture was allowed to reach ambient temperature and the volatiles were removed under reduced pressure. The residue was partitioned between water and ethyl acetate and the combined organic fractions were dried over magnesium sulfate and the solvent was removed under reduced pressure. The residue was purified by chromatography using 20% ethyl acetate/n-heptanes as eluent to give 3-(3,5-dichloro-4-formylphenyl)-propionic acid tert-butyl ester. $^1$H-NMR (CDCl$_3$, 400 MHz): δ 10.45 (s, 1H), 7.23 (s, 2H), 2.90 (t, J=7.45 Hz, 2H), 2.55 (t, J=7.45 Hz, 2H), 1.35-1.44 (m, 10H).

A mixture of 3-(3,5-dichloro-4-formylphenyl)-propionic acid tert butyl ester (440 mg, 0.8 mmol), 3,4-diamino-N-quinolin-2-yl-benzamide (403 mg, 1 eq) and oxone (600 mg, 0.67 eq) in DMF (10 mL)/H$_2$O (1 mL) was stirred vigorously open to air for 1 h. The mixture was partitioned between water and ethyl acetate. The ethyl acetate fractions were dried over magnesium sulphate and the solvent was removed under reduced pressure. The residue was purified by silica gel chromatography to give 3-{3,5-dichloro-4-[6-(quinolin-2-ylcarbamoyl)-1H-benzoimidazol-2-yl]-phenyl}-propionic acid tert-butyl ester as an orange foam. $^1$H-NMR (CDCl$_3$, 400 MHz): δ 8.60 (d, J=8.97 Hz, 1H), 8.38 (s, 1H), 8.21-8.29 (m, 1H), 7.95 (dd, J=8.34, 1.26 Hz, 1H), 7.82-7.91 (m, 2H), 7.71 (ddd, J=8.37, 6.98, 1.33 Hz, 2H), 7.47-7.56 (m, 1H), 7.17-7.24 (m, 2H), 2.85 (t, J=7.33 Hz, 2H), 2.50-2.57 (m, 2H), 1.42-1.48 (m, 10H).

A solution of 3-(3,5-dichloro-4-[6-(quinolin-2-ylcarbamoyl)-1H-benzoimidazol-2-yl]-phenyl)-propionic acid tert butyl ester (440 mg, 0.8 mmol) in 4 M HCl in dioxane (25 mL) was stirred at ambient temperature 6 h. The solution was evaporated to half volume and diluted with diethyl ether to give 3-(3,5-dichloro-4-[6-(quinolin-2-ylcarbamoyl)-1H-benzoimidazol-2-yl]-phenyl)-propionic acid as an HCl salt. $^1$H-NMR (DMSO-d6, 400 MHz): δ 11.91 (s, 1H), 8.67 (d, J=9.09 Hz, 1H), 8.61 (s, 1H), 8.35 (d, J=9.09 Hz, 1H), 8.05-8.14 (m, 4H), 7.87 (t, J=7.77 Hz, 2H), 7.62-7.67 (m, 4H), 2.94 (t, J=7.33 Hz, 2H), 2.68 (t, J=7.39 Hz, 2H). MS (ESI) m/z 505.0 (M+H).

To DMF (10 mL) was added HATU (3.61 g, 9.50 mmol), 4-amino-3-nitrobenzoic acid (1.15 g, 6.32 mmol), triethylamine (1.32 mL, 958 mg, 9.47 mmol), and 4-tert-butylaniline (1.0 mL, 945 mg, 6.33 mmol). The mixture was stirred at ambient temperature for 18 h then was poured into ethyl acetate and extracted once with water and five times with brine. The organic phase was dried, filtered, and the solvent removed under reduced pressure. The residue was purified by chromatography using gradient of a 30-70% heptane/ethyl acetate to afford 4-amino-N-(4-tert-butylphenyl)-3-nitrobenzamide. MS (ESI) m/z 314.1 (M+H); retention time 1.50 min (Method 10), which was used directly in the next step.

A mixture of 4-amino-N-(4-tert-butylphenyl)-3-nitrobenzamide from the previous step and 100 mg of 5% platinum on carbon in 50 mL of 1:1 ethyl acetate/ethanol was reduced under a hydrogen balloon. The reaction was filtered through Celite to remove catalyst and the solvent was removed under reduced pressure to afford 3,4-diamino-N-(4-tert-butylphenyl)-benzamide.

A mixture of 3,4-diamino-N-(4-tert-butylphenyl)-benzamide (200 mg, 710 µmol), 3-(4-formyl-3,5-dimethylphenyl)-propionic acid methyl ester (190 mg, 860 µmols) (from Example 6-17) and oxone (286 mg, 470 µmols) in a solution of 5 mL DMF/0.5 mL water was stirred at ambient temperature for 1 h. The mixture was poured into ethyl acetate and extracted once with water and five times with brine. The organic phase was dried, filtered, and the solvent was removed under reduced pressure. The residue was purified by chromatography using a gradient of 50-90% heptane/ethyl acetate to afford 3-{4-[6-(4-tert-butylphenylcarbamoyl)-1H-benzimidazol-2-yl]-3,5-dimethylphenyl}-propionic acid methyl ester. $^1$H-NMR (CDCl$_3$, 400 MHz): δ 8.51 (s, broad, 1H), 8.07 (s, broad, 1H), 7.58 (d, J=8.5 Hz, 1H), 7.53 (d, J=8.1 Hz, 2H), 7.31 (d, J=8.6 Hz, 2H), 6.82 (s, 2H), 3.63 (s, 3H), 2.89 (t, J=7.4 Hz, 2H), 2.63 (t, J=7.4 Hz, 2H), 1.92 (s, 6H), 1.30 (s, 9H). MS (ESI) m/z 484.3 (M+H).

A mixture of 3-{4-[6-(4-tert-butylphenylcarbamoyl)-1H-benzimidazol-2-yl]-3,5-dimethylphenyl}-propionic acid methyl ester (310 mg, 640 mmols) and 3.2 mL of 1N sodium hydroxide in MeOH (1.6 mL) was stirred until the reaction was complete. The solution was neutralized to pH 4-5 with 1N hydrochloric acid and the resulting precipitate was filtered, washed with water, and dried under reduced pressure to afford 3-{4-[6-(4-tert-butylphenylcarbamoyl)-1H-benzimidazol-2-yl]-3,5-dimethylphenyl}-propionic acid. $^1$H-NMR (DMSO-d6, 400 MHz): δ 12.17 (s, broad, 1H), 10.22 (s, 1H), 8.29 (s, broad, 1H), 7.89 (d, J=8.5 Hz, 2H), 7.74 (d, J=9.0 Hz, 2H), 7.72 (m, 1H), 7.37 (d, J=9.0 Hz, 2H), 7.10 (s, 2H), 2.85 (t, J=7.3 Hz, 2H,), 2.59 (t, =7.3 Hz, 2H), 2.10 (s, 6H). MS (ESI) m/z 470.2 (M+H). High resolution MS (M+H): theory 470.2444, measured 470.2434.

Example 6-26

3-{4-[6-(4-tert-Butylphenylcarbamoyl)-1H-benzimidazol-2-yl]-3,5-dimethylphenyl}-propionic acid

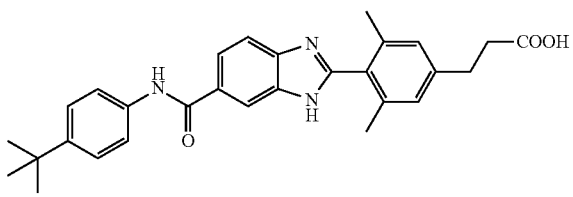

Example 6-27

(E)-3-{4-[6-(4-tert-Butylphenylcarbamoyl)-1H-benzimidazol-2-yl]-3,5-dimethylphenyl}-acrylic acid

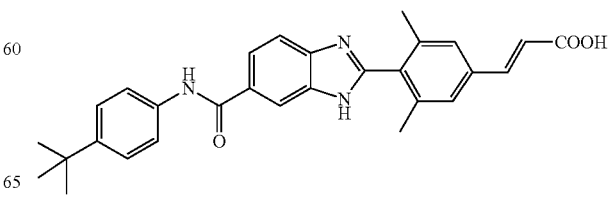

To a solution of 3,4-diamino-N-(4-tert-butylphenyl)-benzamide (1.83 g, 6.46 mmol) and 3-(4-formyl-3,5-dimethylphenyl)-propionic acid methyl ester (1.55 g, 7.10 mmol) (from Example 6-17) in DMF (25 mL) and water (2.5 mL) was added oxone (2.66 g, 4.33 mmols) and the mixture was stirred at ambient temperature for 1 h. The mixture was poured into ethyl acetate, extracted once with water and five times with brine, and the organic layer was dried, filtered, and the solvent was removed under reduced pressure. The residue was chromatographed using a 50-90% gradient of heptane/ethyl acetate to give methyl (E)-3-{4-[6-(4-tert-butylphenyl-carbamoyl)-1H-benzimidazol-2-yl]-3,5-dimethylphenyl}-acrylate.

A mixture of methyl (E)-3-{4-[6-(4-tert-butylphenylcarbamoyl)-1H-benzimidazol-2-yl]-3,5-dimethylphenyl}-acrylate (200 mg, 420 µmol), 1N NaOH (520 µL), and methanol (260 µL) was diluted with 3 mL of water/methanol (2:1) and stirred at ambient temperature for 18 h. The solution was then quenched with 1N HCl (520 µL), filtered, and the precipitate washed with water and dried, to yield (E)-3-{4-[6-(4-tert-butylphenylcarbamoyl)-1H-benzimidazol-2-yl]-3,5-dimethylphenyl}-acrylic acid. $^1$H-NMR (DMSO-d6, 400 MHz): δ 8.31 (s, broad, 1H), 7.87 (d, J=8.3 Hz, 1H), 7.74 (d, J=8.7 Hz, 2H), 7.67 (m, 1H), 7.58 (m, 3H), 7.37 (d, J=8.7 Hz, 2H), 6.63 (d, J=16.2 Hz, 1H), 2.15 (s, 6H), 1.29 (s, 9H). MS (ESI) m/z 468.2 (M+H): Retention time=1.24 min (Method 10).

Example 6-28

{4-[6-(4-tert-Butylphenylcarbamoyl)-1H-benzoimidazol-2-yl]-3,5-dimethylphenoxy}-acetic acid

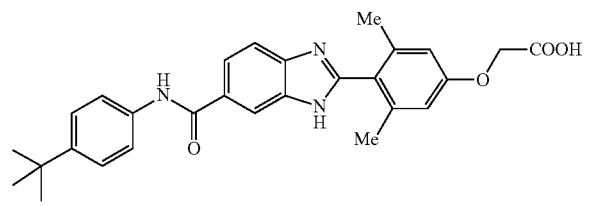

To a solution (4-formyl-3,5-dimethylphenoxy)-acetic acid methyl ester (2.4 g) (from Example 6-9) and 3,4-diaminobenzoic acid (2.0 g) in DMSO (30 mL) under air at ambient temperature was added FeCl$_3$ (150 mg) and the resulting brown reaction mixture was stirred at the same temperature overnight. The reaction was monitored by LC/MS which indicated completion. The reaction mixture was then decanted into 400 mL of stirred water and the resulting precipitate was collected by filtration and washed with water. The crude product was dried in the suction funnel for 4 h to give 2-(4-methoxycarbonylmethoxy-2,6-dimethylphenyl)-3H-benzoimidazole-5-carboxylic acid. MS (ESI) m/z 355.04 (M+H); Retention time=0.79 min (Method 10).

To a solution of 2-(4-methoxycarbonylmethoxy-2,6-dimethylphenyl)-3H-benzoimidazole-5-carboxylic acid (0.3 g, 0.847 mmol) in DMF (6 mL) was added t-butylaniline (0.1338 mL, 0.847 mmol), EDCI (0.1953 g, 1.02 mmol) and HOBt (0.1374 g, 1.02 mmol). The brown solution was stirred at ambient temperature for 18 h. The mixture was extracted with EtOAc, then washed with water, brine, and dried with Na$_2$SO$_4$. The solvent was removed under reduced pressure and the residue purified on silica gel using MeCN/methylene chloride (1:1) to give {4-[6-(4-tert-butylphenylcarbamoyl)-1H-benzoimidazol-2-yl]-3,5-dimethylphenoxy}-acetic acid methyl ester.

To a solution of {4-[6-(4-tert-butylphenylcarbamoyl)-1H-benzoimidazol-2-yl]-3,5-dimethylphenoxy}-acetic acid methyl ester (0.1727 g, 0.356 mmol) in tetrahydrofuran (5 mL) was added LiOH (1 mL of a 4M solution) and the mixture was stirred at ambient temperature for 18 h. The solvent was removed under reduced pressure and the residue was taken up in water, brought to pH 4 and the solid filtered to the title compound. $^1$H-NMR (DMSO-d6, 400 MHz): δ 12.97 (s, broad, 1H), 12.72 (d, J=24.76 Hz, 1H), 10.11 (d, J=15.16 Hz, 1H), 10.11 (d, J=15.16 Hz, 1H), 8.31 (s, 0.5H), 8.06 (s, 0.5H), 7.75-7.81 (m, 1H), 7.63-7.71 (m, 2.5H), 7.51 (d, J=8.34 Hz, 0.5H,) 7.30 (d, J=8.59 Hz, 2H), 6.71 (s, 2H), 4.68 (s, 2H), 2.03 (s, 6H), 1.22 (s, 9H). MS (m/z) 472.2 (M+1).

Example 6-29

3-{4-[6-(4-tert-Butylphenylcarbamoyl)-1H-benzoimidazol-2-yl]-3,5-dimethylphenyl}-2,2-dimethyl-propionic acid

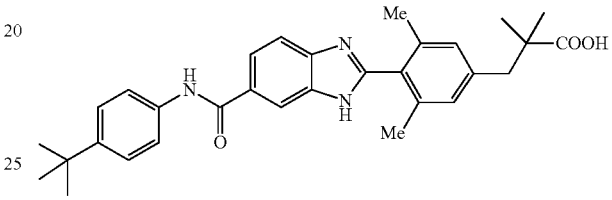

To a stirred solution of 3-(4-formyl-3,5-dimethylphenyl)-propionic acid methyl ester, (2.2 g, 10 mmol) and ethane-1, 2-diol (1.86 g, 30 mmol) in toluene (50 mL) was added p-TsOH.H$_2$O (38 mg, 0.2 mmol) and the solution was refluxed using a Dean-Stark apparatus overnight. The solvent was removed under reduced pressure and the residue was purified by flash chromatography using heptane/EtOAc (5:1) as eluent to give 3-(4-[1,3]dioxolan-2-yl-3,5-dimethylphenyl)-propionic acid methyl ester as a colorless oil.

To a solution of 3-(4-[1,3]dioxolan-2-yl-3,5-dimethylphenyl)-propionic acid methyl ester (2.0 g, 7.55 mmol) in THF (30 mL) cooled to −78° C. under N$_2$ protection, was added slowly LDA (16.8 mL of a 1.8 M solution in THF, 30.2 mmol). After 30 min, MeI (4.29 g, 30.2 mmol) was added slowly to the solution. The solution was stirred at −78° C. for 30 min then the reaction mixture was quenched with water. The aqueous layer was extracted with EtOAc and the organic layer was washed with water, brine, dried with MgSO$_4$ and filtered. The solvent was removed under reduced pressure and the residue was purified by flash chromatography using heptane/EtOAc (5:1) as eluent to give 3-(4-[1,3]dioxolan-2-yl-3,5-dimethylphenyl)-2,2-dimethylpropionic acid methyl ester as a colorless oil.

To a stirred solution of 3-(4-[1,3]dioxolan-2-yl-3,5-dimethylphenyl)-2,2-dimethylpropionic acid methyl ester (1.7 g, 5.8 mmol) in acetone (20 mL) and water (0.3 mL) was added Amberlyst-15 (233 mg). The suspension was stirred at ambient temperature overnight and the suspension was filtered and washed with acetone. The solvent was removed under reduced pressure and the residue was purified by flash chromatography using heptane/EtOAc (5:1) to give 3-(4-formyl-3,5-dimethylphenyl)-2,2-dimethylpropionic acid methyl ester as a pale-yellow oil.

The title compound was prepared from 3,4-diamino-N-(4-tert-butylphenyl)-benzamide and 3-(4-formyl-3,5-dimethylphenyl)-2,2-dimethylpropionic acid methyl ester analogous to Example 6-26. $^1$H NMR (Methanol-d4, 400 MHz): δ 8.26 (s, 1H), 7.93 (d, 1H), 7.72 (m, 1H), 7.65 (m, 2H), 7.44 (m, 2H), 7.05 (s, 2H), 2.89 (s, 2H), 2.15 (s, 6H), 1.35 (s, 9H), 1.2 (s, 6H). MS (m/z) 498.2 (M+1); Retention time: 1.47 min (Method 10).

Example 6-30

3-{3,5-Dimethyl-4-[6-(quinolin-2-ylcarbamoyl)-1H-benzoimidazol-2-yl]-phenyl}-2,2-dimethyl-propionic acid

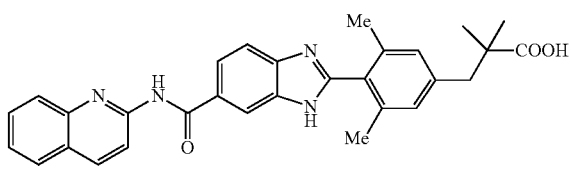

The title compound was prepared from 3,4-diamino-N-quinolin-2-yl-benzamide (from Example 6-17) and 3-(4-formyl-3,5-dimethylphenyl)-2,2-dimethylpropionic acid methyl ester analogous to Example 6-26. $^1$H NMR (Methanol-d4, 400 MHz): δ 8.45 (d, 1H), 8.38 (d, 2H), 8.04 (dd, 1H), 7.93 (m, 2H), 7.77 (m, 2H), 7.55 (m, 1H), 7.06 (s, 2H), 2.89 (s, 2H), 2.16 (s, 6H), 1.2 (s, 6H). MS (m/z) 493.2 (M+1); Retention time: 1.25 min (Method 10).

Example 6-31

3-{3,5-Dimethyl-4-[5-(6-trifluoromethyl-pyridin-3-ylcarbamoyl)-1H-benzoimidazol-2-yl]-phenyl}-2,2-dimethylpropionic acid

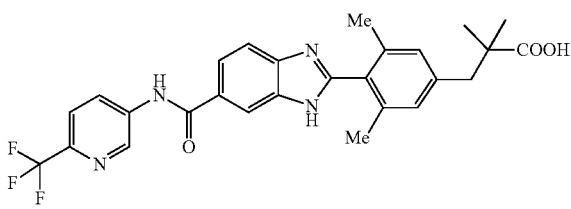

The title compound was prepared from 3,4-diamino-N-(6-trifluoromethylpyridin-3-yl)-benzamide (from Example 6-36) and 3-(4-formyl-3,5-dimethylphenyl)-2,2-dimethyl-propionic acid methyl ester analogous to Example 6-29. $^1$N NMR (400 MHz, MeOD): δ 9.20 (s, 1H), 8.68 (d, 1H), 8.43 (s, 1H), 8.10 (d, 1H), 7.98 (d, 1H), 7.85 (d, 1H), 7.19 (s, 2H), 3.00 (s, 2H), 2.27 (s, 6H), 1.29 (s, 6H). MS (m/z) 511.2 (M+1); Retention time: 1.20 min (Method 10).

Example 6-32

(2-{3,5-Dimethyl-4-[6-(quinolin-2-ylcarbamoyl)-1H-benzoimidazol-2-yl]-phenyl}-ethyl)-phosphonic acid

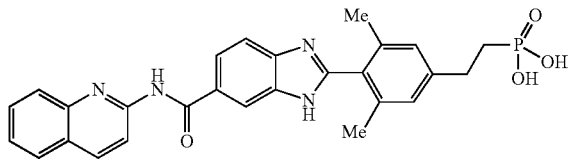

4-Amino-2,6-dimethylbenzaldehyde (149 mg, 1.0 mmol)) was taken up in enough 42% HBF$_4$ until the suspension stirred well and then was cooled to 0° C. To this was added a solution of NaNO$_2$ (69 mg, 1.0 mmol) in water (0.5 mL) slowly. After 30 minutes at 0° C., MeOH (3 mL) was added and followed by Pd(OAc)$_2$ (7.5 mg) and vinylphosphonic acid diethyl ester (197 mg, 1.2 mmol). The reaction mixture was heated at 80° C. for 30 min and the suspension was filtered through Celite, washed with CH$_2$Cl$_2$, and the filtrate was extracted with CH$_2$Cl$_2$. The organic layer was washed with water, brine, dried with MgSO$_4$, and filtered. The solvent was removed under reduced pressure and the residue was purified by flash chromatography using heptane/EtOAc (4:1 then followed by 100% EtOAc) to give [(E)-2-(4-formyl-3,5-dimethylphenyl)-vinyl]-phosphonic acid diethyl ester as a colorless oil.

To a solution of 3,4-diamino-N-quinolin-2-yl-benzamide (186 mg., 0.67 mmol) and [(E)-3-(4-formyl-3,5-dimethylphenyl)-allyl]-phosphonic acid diethyl ester (200 mg., 0.67 mmol) in DMF (8 mL) and water (0.8 mL) was added oxone (277 mg, 0.45 mmol) and the mixture was stirred at ambient temperature for 30 min. The reaction was quenched with water and sat. NaHCO$_3$ and the suspension was extracted with EtOAc. The organic layer was washed with water, brine, dried with MgSO$_4$ and filtered. The solvent was removed under reduced pressure to give ((E)-2-{3,5-dimethyl-4-[6-(quinolin-2-ylcarbamoyl)-1H-benzoimidazol-2-yl]-phenyl}-vinyl)-phosphonic acid diethyl ester as red solid.

A solution of ((E)-2-{3,5-dimethyl-4-[6-(quinolin-2-ylcarbamoyl)-1H-benzoimidazol-2-yl]-phenyl}-vinyl)-phosphonic acid diethyl ester (300 mg, 0.54 mmol) in EtOH (20 mL) was hydrogenated at one atm over Pd/C (225 mg) for 3 hours. The catalyst was filtered through Celite and was washed with EtOH. The solvent was removed under reduced pressure to give (2-{3,5-dimethyl-4-[6-(quinolin-2-ylcarbamoyl)-1H-benzoimidazol-2-yl]-phenyl}-ethyl)-phosphonic acid diethyl ester as a red solid.

To a solution of (2-{3,5-dimethyl-4-[6-(quinolin-2-ylcarbamoyl)-1H-benzoimidazol-2-yl]-phenyl}-ethyl)-phosphonic acid diethyl ester (270 mg, 0.49 mmol) in CH$_2$Cl$_2$ (10 mL) was added TMSBr (0.64 ml, 4.9 mmol) and the solution was stirred at ambient temperature overnight. The solvent was removed under reduced pressure and the residue was purified by HPLC to give (2-{3,5-dimethyl-4-[6-(quinolin-2-ylcarbamoyl)-1H-benzoimidazol-2-yl]-phenyl}-ethyl)-phosphonic acid as a white solid. $^1$H NMR (Methanol-d4, 400 MHz): δ 8.45 (m, 3H), 8.08 (dd, 1H), 7.94 (m, 2H), 7.81 (dd, 1H), 7.77 (m, 1H), 7.56 (m, 1H), 7.13 (s, 2H), 2.95 (m, 2H), 2.18 (s, 6H), 2.01 (m, 2H). MS (m/z) 501.1 (M+1): Retention time: 1.12 min (Method 10).

Example 6-33

(3-{3,5-Dimethyl-4-[6-(quinolin-2-ylcarbamoyl)-1H-benzoimidazol-2-yl]-phenyl}-propyl)-phosphonic acid diethyl ester

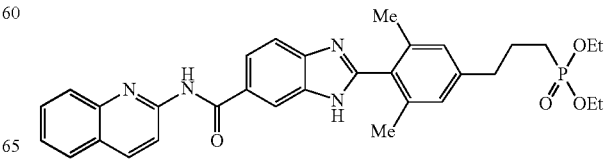

4-Amino-2,6-dimethylbenzaldehyde (3.0 g, 20.1 mmol) was taken up in enough 42% HBF$_4$ until the suspension stirred well and then was cooled to 0° C. To this was added a solution of NaNO$_2$ (1.39 g, 20.1 mmol) in water (10 mL) slowly. After 30 min at 0° C., MeOH (50 mL) was added followed by Pd(OAc)$_2$ (677 mg) and diethyl allylphosphonate (5.38 g, 30.2 mmol). The reaction mixture was heated to 80° C. for 30 min and the suspension was filtered through Celite, washed with CH$_2$Cl$_2$, and the filtrate was extracted with CH$_2$Cl$_2$. The combined organic layers were washed with water, brine, dried with MgSO$_4$, and filtered. The solvent was removed under reduced pressure and the residue was purified by flash chromatography using a gradient of heptane/EtOAc (10:1 to 5:1 then followed by 100% EtOAc) to give [(E)-3-(4-formyl-3,5-dimethylphenyl)-allyl]-phosphonic acid diethyl ester as a light yellow oil.

The title compound was prepared from 3,4-diamino-N-quinolin-2-yl-benzamide and [(E)-3-(4-formyl-3,5-dimethylphenyl)-allyl]-phosphonic acid diethyl ester analogous to Example 6-32 (steps 2 and 3). $^1$H NMR (Methanol-d4, 400 MHz): δ 8.46 (d, 1H), 8.39 (d, 1H), 8.30 (s, 1H), 8.05 (d, 1H), 7.93 (d, 2H), 7.83 (s, 1H), 7.76 (m, 1H), 7.55 (m, 1H), 7.09 (s, 2H), 4.14 (m, 4H), 2.78 (t, 2H), 2.18 (s, 6H), 1.96 (m, 2H), 1.85 (m, 2H), 1.34 (t, 6H). MS (m/z) 571.4 (M+1); Retention time: 1.41 min (Method 10).

Example 6-34

(3-{3,5-Dimethyl-4-[6-(quinolin-2-ylcarbamoyl)-1H-benzoimidazol-2-yl]-phenyl}-propyl)-phosphonic acid

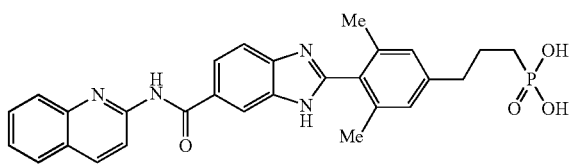

The title compound was prepared from 3,4-diamino-N-quinolin-2-yl-benzamide and [(E)-3-(4-formyl-3,5-dimethylphenyl)-allyl]-phosphonic acid diethyl ester analogous to Example 6-32. $^1$H NMR (Methanol-d4, 400 MHz): δ 8.42 (m, 3H), 8.05 (dd, 1H), 7.94 (dd, 2H), 7.79 (dd, 1H), 7.77 (m, 1H), 7.56 (m, 1H), 7.09 (s, 2H), 2.75 (t, 2H), 2.18 (s, 6H), 2.00 (m, 2H), 1.69 (m, 2H). MS (m/z) 543.2 (M+1); Retention time: 1.13 min (Method 10).

Example 6-35

(3-{3,5-Dimethyl-4-[6-(quinolin-2-ylcarbamoyl)-1H-benzoimidazol-2-yl]-phenyl}-propyl)-phosphonic acid monoethyl ester

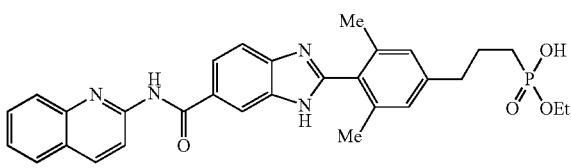

To a solution of (3-{3,5-dimethyl-4-[6-(quinolin-2-ylcarbamoyl)-1H-benzoimidazol-2-yl]-phenyl}-propyl)-phosphonic acid diethyl ester (40 mg, 0.07 mmol) in CH$_2$Cl$_2$ (5 mL) was added TMSBr (0.045 mL, 0.35 mol). The solution was stirred at ambient temperature until monohydrolysis occurred (5 h). The solvent was removed under reduced pressure and the residue was purified by HPLC to give the title compound as a white solid. $^1$H NMR (Methanol-d4, 400 MHz): δ 8.41 (m, 3H), 8.08 (dd, 1H), 7.94 (dd, 2H), 7.81 (d, 1H), 7.77 (m, 1H), 7.56 (m, 1H), 7.10 (s, 2H), 3.97 (m, 2H), 2.75 (t, 2H), 2.18 (s, 6H), 1.97 (m, 2H), 1.68 (m, 2H), 1.29 (t, 3H). MS (m/z) 543.2 (M+1); Retention time: 1.17 min (method 10).

Example 6-36

(3-{3,5-Dimethyl-4-[6-(6-trifluoromethyl-pyridin-3-ylcarbamoyl)-1H-benzoimidazol-2-yl]-phenyl}-propyl)-phosphonic acid

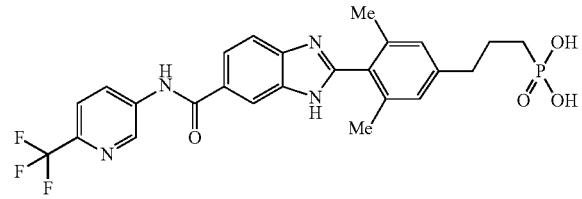

To a solution of 6-trifluoromethylpyridin-3-ylamine (1.0 g, 6.17 mmol) and 4-amino-3-nitrobenzoic acid (1.12 g, 6.17 mmol) in DMF (25 mL) was added HATU (3.5 g, 9.23 mmol) followed by NEt$_3$ (1.77 ml, 9.23 mmol). The reaction mixture was stirred at ambient temperature overnight. The reaction was quenched with water and extracted with EtOAc. The organic layer was washed with water, brine, dried with MgSO$_4$, and filtered. The solvent was removed under reduced pressure and the residue was purified by flash chromatography using a heptane/EtOAc (1:1 then followed by 100% EtOAc) to give 4-amino-3-nitro-N-(6-trifluoromethylpyridin-3-yl)-benzamide as a red solid.

A suspension of 4-amino-3-nitro-N-(6-trifluoromethylpyridin-3-yl)-benzamide (500 mg, 1.53 mmol) in THF (20 mL) was hydrogenated at one atm over Pt/C (50 mg) for 3 hours. The catalyst was filtered through Celite and washed with THF. The solvent was removed under reduced pressure to give 3,4-diamino-N-(6-trifluoromethylpyridin-3-yl)-benzamide as a yellow solid.

The title compound was prepared from 3,4-diamino-N-(6-trifluoromethylpyridin-3-yl)-benzamide and [(E)-3-(4-formyl-3,5-dimethylphenyl)-allyl]-phosphonic acid diethyl ester analogous to Example 6-32. $^1$H NMR (Methanol-d4, 400 MHz): δ 9.09 (d, 1H), 8.57 (dd, 1H), 8.34 (dd, 1H), 8.00 (dd, 1H), 7.87 (d, 1H), 7.76 (dd, 1H), 7.09 (s, 2H), 2.76 (t, 2H), 2.16 (s, 6H), 2.00 (m, 2H), 1.71 (m, 2H). MS (m/z) 533.1 (M+1); Retention time: 1.13 min (Method 10).

Example 6-37

(3-{4-[6-(4-tert-Butyl-phenylcarbamoyl)-1H-benzoimidazol-2-yl]-3,5-dimethyl-phenyl}-propyl)-phosphonic acid

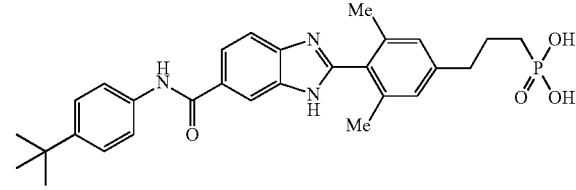

The title compound was prepared from 3,4-diamino-N-(4-tert-butylphenyl)-benzamide (from Example 6-26) and [(E)-3-(4-formyl-3,5-dimethylphenyl)-allyl]-phosphonic acid diethyl ester analogous to Example 6-32. ¹H NMR (Methanol-d4, 400 MHz): δ 8.25 (dd, 1H), 7.92 (dd, 1H), 7.72 (dd, 1H), 7.63 (m, 2H), 7.42 (m, 2H), 7.06 (s, 2H), 2.73 (t, 2H), 2.14 (s, 6H), 1.95 (m, 2H), 1.69 (m, 2H), 1.33 (s, 9H). MS (m/z) 520.2 (M+1); Retention time: 1.19 min (Method 10).

Example 6-38

3-{3,5-Dichloro-4-[6-(6-trifluoromethylpyridin-3-ylcarbamoyl)-1H-benzoimidazol-2-yl]-phenyl}-propionic acid

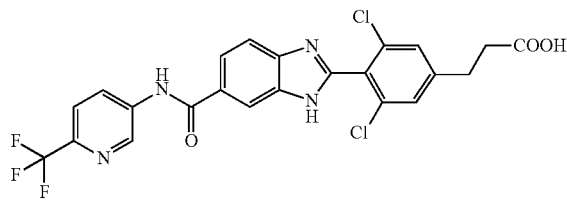

The title compound was prepared from 3,4-diamino-N-(6-trifluoromethylpyridin-3-yl)-benzamide (from Example 6-36) and 3-(3,5-dichloro-4-formylphenyl)-propionic acid tert butyl ester analogous to Example 6-25. 1H NMR (MeOD, 400 MHz): δ 9.07 (d, 1H), 8.54 (dd, 1H), 8.35 (s, 1H), 7.99 (dd, 1H), 7.84 (dd, 1H), 7.76 (d, 1H), 7.52 (s, 2H), 3.01 (t, 2H), 2.69 (t, 2H); MS (m/z) 523.01 (M+1), Retention time=1.06 min (Method 10).

Example 7-1

2-(2,6-Dimethylphenyl)-1,3-dioxo-2,3-dihydro-1H-isoindole-5-carboxylic acid (3,4-dimethylphenyl)-amide

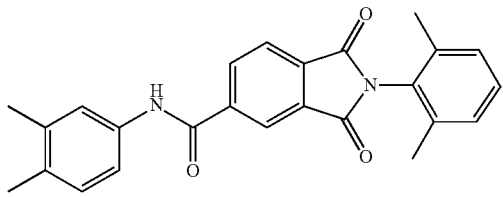

To a solution of 2,6-dimethylaniline (1.21 g) in DMF (15 mL) was added 1,3-dioxo-1,3-dihydroisobenzofuran-5-carboxylic acid (1.92 g) and the mixture was stirred at room temperature for 18 h. The mixture was poured into water and the resulting precipitate was filtered, washed with water and dried under reduced pressure. The solid was suspended in HOAc (25 mL) and the mixture was heated at 110° C. for 4 h. The resulting solution was cooled and the solvent was removed under reduced pressure to give 2-(2,6-dimethylphenyl)-1,3-dioxo-2,3-dihydro-1H-isoindole-5-carboxylic acid as an off-white solid, mp=210-213° C.; MS (m/z) 294 (M−1).

To a mixture of 2-(2,6-dimethylphenyl)-1,3-dioxo-2,3-dihydro-1H-isoindole-5-carboxylic acid (130 mg), EDCI (85 mg) and HOBt (60 mg) in DMF (3 mL) was added 3,4-dimethylaniline (53 mg) and the mixture was stirred at room temperature for 24 h. The mixture was poured into water and was extracted with EtOAc. The organic phase was washed with water (3×) and dried over sodium sulfate. The solvent was removed under reduced pressure and the residue purified by flash chromatography using CH₂Cl₂ as eluent to give 2-(2,6-dimethylphenyl)-1,3-dioxo-2,3-dihydro-1H-isoindole-5-carboxylic acid (3,4-dimethylphenyl)-amide as a pale-yellow solid, mp=223-225° C.; MS (m/z) 397 (M−1); ¹H NMR (CDCl₃, 400 MHz) δ 8.38 (s, 1H), 8.09 (d, J=8.34 Hz, 1H), 7.81 (s, 1H), 7.45 (s, 1H), 7.37-7.15 (m, 5H), 2.30 (s, 3H), 2.27 (s, 3H), 1.54 (s, 6H).

Example 7-2

2-(2,6-Dichlorophenyl)-1,3-dioxo-2,3-dihydro-1H-isoindole-5-carboxylic acid (3,4-dimethylphenyl)-amide

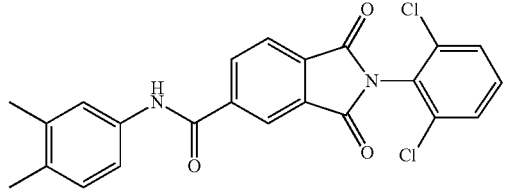

To a solution of 2,6-dichlorolaniline (1.62 g) in DMF (15 mL) was added 1,3-dioxo-1,3-dihydroisobenzofuran-5-carboxylic acid (1.92 g) and the mixture was stirred at 100° C. for 96 h. The mixture was cooled to room temperature and was poured into water. The resulting precipitate was filtered, washed with water and dried under reduced pressure. The solid was suspended in HOAc (10 mL) and the mixture was heated at 110° C. for 4 h. The resulting solution was cooled and the solvent was removed under reduced pressure to give crude 2-(2,6-dichlorophenyl)-1,3-dioxo-2,3-dihydro-1H-isoindole-5-carboxylic acid as a yellowish solid; MS (m/z) 334 (M−1).

To a mixture of 2-(2,6-dichlorophenyl)-1,3-dioxo-2,3-dihydro-1H-isoindole-5-carboxylic acid (403 mg), EDCI (121 mg) and HOBt (135 mg) in DMF (8 mL) was added 3,4-dimethylaniline (53 mg) and the mixture was stirred at room temperature for 24 h. The mixture was poured into water and was extracted with EtOAc. The organic phase was washed with water (3×) and dried over sodium sulfate. The solvent was removed under reduced pressure and the residue crystallized from EtOAc to give 2-(2,6-dichlorophenyl)-1,3-dioxo-2,3-dihydro-1H-isoindole-5-carboxylic acid (3,4-dimethylphenyl)-amide as a pale-yellow solid, mp=238-240° C.; MS (m/z) 439 (M−1); ¹H NMR DMSO-d₆, 400 MHz) δ 10.49 (s, 1H), 8.62 (s, 1H), 8.50 (d, J=7.83 Hz, 1H), 8.24 (d, J=7.58 Hz, 1H), 7.80 (s, 1H), 7.78 (s, 1H), 7.67 (t, 1H), 7.59 (s, 1H), 7.53 (d, J=8.08 Hz, 1H), 2.24 (s, 3H), 2.21 (s, 3H).

Example 8-1

(3,4-Dimethylphenyl)-{1-[2-(2,6-dimethylphenyl)-3H-benzoimidazol-5-yl]-2,2,2-trifluoroethyl}-amine

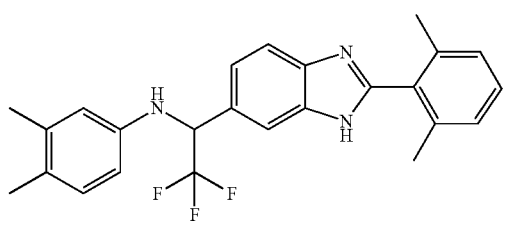

To a solution of 2-(2,6-dimethylphenyl)-3H-benzoimidazole-5-carboxylic acid methyl ester (930 mg) (Example 1-255, step 1) in THF (10 mL) was added 16.6 mL of a 1M solution of LiAlH$_4$ in ether dropwise. The mixture was stirred at ambient temperature for 18 h then approximately 4 mL of saturated sodium sulfate solution was added dropwide. Ethyl acetate was added to the mixture and the solvent decanted from any insoluble material. The organic solution was dried over sodium sulfate and the solvent was removed under reduced pressure to give [2-(2,6-dimethylphenyl)-3H-benzoimidazol-5-yl]-methanol as a foam.

A mixture of [2-(2,6-dimethylphenyl)-3H-benzoimidazol-5-yl]-methanol (750 mg) and MnO$_2$ (5 g) in THF (10 mL) was stirred at ambient temperature for 4 h. The mixture was filtered through Celite and the filtrate evaporated to give 2-(2,6-dimethyl-phenyl)-3H-benzoimidazole-5-carbaldehyde as an oil. MS (ESI)m/z 251 (M+H).

To a solution of 2-(2,6-dimethylphenyl)-3H-benzoimidazole-5-carbaldehyde as an oil (590 mg) and Boc$_2$O (515 mg) in THF (5 mL) was added DMAP (25 mg) and the mixture was stirred at ambient temperature for 18 h. The solvent was removed under reduced pressure and the residue was purified by flash chromatography using 10% EtOAc/methylene chloride as eluent to give 2-(2,6-dimethylphenyl)-6-formyl-benzoimidazole-1-carboxylic acid tert-butyl ester as an oil.

To 2-(2,6-dimethylphenyl)-6-formyl-benzoimidazole-1-carboxylic acid tert-butyl ester (565 mg) was added 16 mL of a 0.5 M solution of trifluoromethyltrimethylsilane in THF. When a solution formed the mixture was cooled to −30° C. then a solution of TBAF (1.76 mL of a 1.0M solution in THF) was added dropwise. The mixture was stirred at −30° C. for 45 min then was allowed to warm to 5° C. The mixture was extracted with EtOAc (2×) and the combined organic layers were dried over sodium sulfate. The solvent was removed under reduced pressure and the resulting foam was purified by flash chromatography using 10% EtOAc/methylene chloride as eluent to give 2-(2,6-dimethyl-phenyl)-6-(2,2,2-trifluoro-1-hydroxyethyl)-benzoimidazole-1-carboxylic acid tert-butyl ester as a waxy solid. MS (ESI)m/z 421 (M+H).

In addition to the above material, the de-Boc analog 1-[2-(2,6-dimethylphenyl)-3H-benzoimidazol-5-yl]-2,2,2-trifluoroethanol was also isolated. MS (ESI)m/z 321.1 (M+H), retention time=3.80 min, Method 10.

To a solution of 2-(2,6-dimethylphenyl)-6-(2,2,2-trifluoro-1-hydroxyethyl)-benzoimidazole-1-carboxylic acid tert-butyl ester (475 mg) in methylene chloride (15 mL) was added Dess-Martin reagent (527 mg) and the mixture was stirred at ambient temperature for 18 h. The mixture was washed with water and sodium bicarbonate solution then was dried over sodium sulfate. The solvent was removed under reduced pressure to give 2-(2,6-dimethylphenyl)-6-(2,2,2-trifluoroacetyl)-benzoimidazole-1-carboxylic acid tert-butyl ester as a gummy solid. The material was used directly in the next reaction.

To a solution of 2-(2,6-dimethylphenyl)-6-(2,2,2-trifluoroacetyl)-benzoimidazole-1-carboxylic acid tert-butyl ester (617 mg) and 3,4-dimethylaniline (118 mg) in toluene (10 mL) was added 4 Å molecular sieves and pTos-OH (50 mg) then the mixture was stirred at 120° C. for 18 h. The sieves were filtered and the filtrate evaporated under reduced pressure to give 1-[2-(2,6-dimethylphenyl)-3H-benzoimidazol-5-yl]-2,2,2-trifluoro-ethanone as an oil.

To a solution of 1-[2-(2,6-dimethylphenyl)-3H-benzoimidazol-5-yl]-2,2,2-trifluoro-ethanone (710 mg), 3,4-dimethylaniline (150 mg) and diisopropylethylamine (150 mg) in methylene chloride (15 mL) was added dropwise 1.1 mL of a 1.0M solution of TiCl$_4$ in methylene chloride. The mixture was stirred at ambient temperature for 10 min then was washed with NaHCO$_3$ solution. The organic phase was dried over sodium sulfate and the solvent was removed under reduced pressure. The residue was purified by flash chromatography using 10% EtOAc/methylene chloride as eluent to give (3,4-dimethyl-phenyl)-[1-[2-(2,6-dimethylphenyl)-3H-benzoimidazol-5-yl]-2,2,2-trifluoroeth-(Z)-ylidene]-amine as an oil. This was used directly in the next reaction.

To a solution of (3,4-dimethyl-phenyl)-[1-[2-(2,6-dimethylphenyl)-3H-benzoimidazol-5-yl]-2,2,2-trifluoroeth-(Z)-ylidene]-amine in MeOH (3 mL) was added sodium borohydride (25 mg) and the mixture was stirred at ambient temperature for 1 h. The MeOH was removed under reduced pressure and EtOAc was added to the residue. The mixture was washed with NaHCO$_3$ solution and the organic layer was dried over sodium sulfate. The solvent was removed under reduced pressure and the residue was purified by flash chromatography using 10% EtOAc/methylene chloride as eluent to give, (3,4-Dimethylphenyl)-{1-[2-(2,6-dimethylphenyl)-3H-benzoimidazol-5-yl]-2,2,2-trifluoroethyl}-amine as a white solid. MS (ESI)m/z 424.0 (M+H), retention time=1.63 min, Method 10.

The table below shows the DGAT1 inhibitory activity of representative compounds of the invention.

| Example Number | IC$_{50}$ (µM) |
| --- | --- |
| 1-11 | 6.9 |
| 4-15 | 6.8 |
| 1-136 | 12 |
| 1-124 | 0.23 |

We claim:

1. A compound of formula (I)

designated as the ALPHA group, or a compound of formula (III)

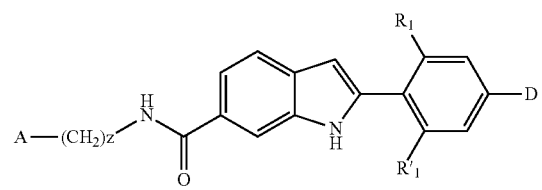

designated as the GAMMA group,
wherein
A is a substituted or unsubstituted heterocyclyl, wherein A is linked to L1 via a carbon member of the ring when A is a ring,

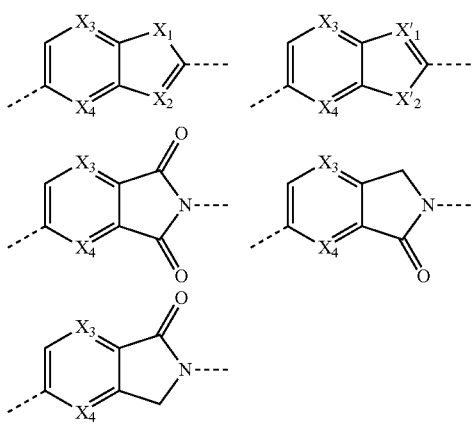

Z is an integer from 0 to 2,
R$_1$ is selected from cyano, lower alkylsulfonylamino, alkanoylamino, halogen, lower alkyl, trifluoromethyl, lower alkoxy, lower alkylamino, lower dialkylamino, and NO$_2$,
R'$_1$ is selected from halogen, trifluoromethyl, aryloxy, lower alkyl, lower alkoxy, lower alkylamino, lower dialkylamino, and NO$_2$,
D is selected from hydrogen, halogen, hydroxyl, cyano, alkanoylamino, carboxy, carbamoyl, —O-L$_2$-E, —S-L$_2$-E', —C(O)—O-L$_2$-E, -L$_2$-E'', and —NR$_6$-L$_2$-E',
L$_2$ is —(CH$_2$)$_{n'}$—(CR$_5$R$_{5'}$)$_{p'}$—(CH$_2$)$_{m'}$—
E is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, —SO$_2$—OH, sulfamoyl, sulfonylcarbamoyl, sulfonyloxy, sulfonamido, —C(O)—O—R—PRO, substituted or unsubstituted aryl, substituted or unsubstituted heterocyclyl, or substituted or unsubstituted heteroaryl, and when n'+m'+p' is equal to zero, E is not sulfonyloxy or sulfonamido,
E' is;
  alkyl, acyl, alkoxycarbonyl, cycloalkoxycarbonyl, aryloxycarbonyl, heterocyclyloxycarbony, carboxy, carbamoyl, sulfonylcarbamoyl, sulfonyl, —SO$_2$—OH, sulfamoyl, sulfonamido, phosphonic acid, phosphonate, sulfonyloxy, —C(O)—O—R—PRO, substituted or unsubstituted aryl, substituted or unsubstituted heterocyclyl, or substituted or unsubstituted heteroaryl, and when n'+m'+p' is equal to zero, E' is not sulfamoyl, sulfonamido, phosphonic acid, phosphonate, or sulfonyloxy,
E'' is;
  alkyl, acyl, alkoxycarbonyl, phosphonic acid, phosphonate, cycloalkoxycarbonyl, aryloxycarbonyl, heterocyclyloxycarbony, carboxy, carbamoyl, sulfonyl, sulfamoyl, sulfonyloxy, sulfonamido, —SO$_2$—OH, sulfonylcarbamoyl, —C(O)—O—R—PRO, substituted or unsubstituted aryl, substituted or unsubstituted heterocyclyl, or substituted or unsubstituted heteroaryl,
m', n' and p' are, independently from each other, an integer from 0 to 4,
m'+n'+p' is between 0 and 12, —R$_5$ and R$_{5'}$ are, independently from each other, hydrogen, halogen, hydroxyl, lower alkoxy, or lower alkyl, or R$_5$ and R$_{5'}$ are joined together to form a spiro residue of the formula

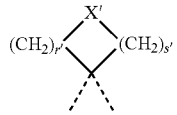

wherein;
  X' is NR$_x$, O, S or CR$_x$R$_{x''}$
  r' and s' are, independently from each other, zero or an integer from 1 to 3,
  R$_x$ is hydrogen or lower alkyl,
  R$_{x'}$ is hydrogen, halogen, hydroxyl, alkoxy, or lower alkyl,
  R$_{x''}$ is hydrogen or lower alkyl; or
a stereoisomer, enantiomer or tautomer or a pharmaceutically acceptable salt thereof.

2. The compound according to claim 1, wherein A is a substituted or unsubstituted 5 or 6-membered monocyclic heterocyclyl, or a 9 or 10-membered bicyclic heterocyclyl group.

3. The compound according to claim 1, wherein A is a substituted or unsubstituted monocyclic heteroaryl, selected from a substituted or unsubstituted imidazole, pyrazole, triazole, thiazole, pyridine, pyridine N-oxide, pyridazine, pyrimidine, triazine or pyrazine residue.

4. The compound according to claim 1, wherein A is a substituted or unsubstituted bicyclic heterocyclyl, selected from substituted or unsubstituted benzimidazole, benzopyrrole, benzoxazole, benzothiazole, oxazolopyridine, thiazolopyridine, imidazolopyridine, indole, quinoline, isoquinoline, benzofuran, benzothiophene, indazole, cinnoline, quinazoline, coumarin, quinoxaline or phthalazine residue.

5. The compound according to claim 1, wherein A is a substituted or unsubstituted benzothiazole.

6. The compound according to claim 1, wherein A is selected from the group consisting of:

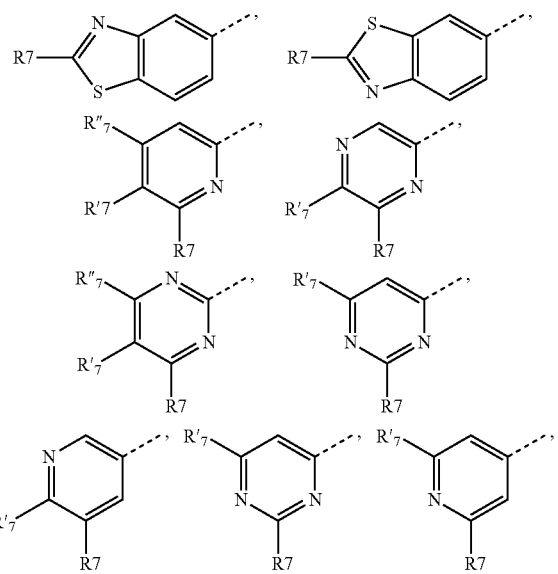

-continued

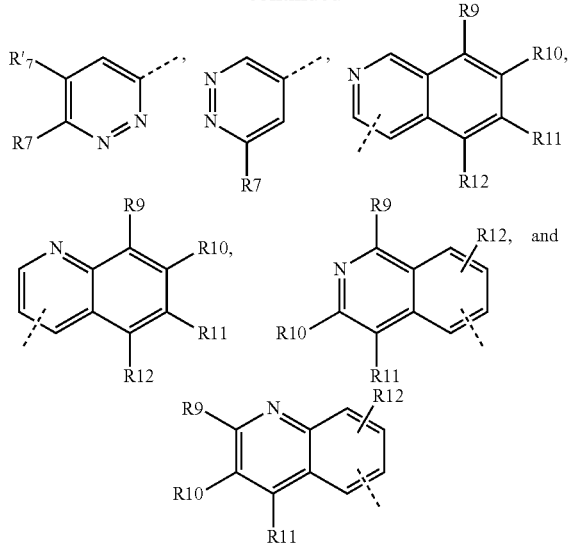

wherein,
R₇, R'₇ and R"₇ are, independently hydrogen, optionally substituted alkyl; hydroxyl, protected hydroxyl; halo; oxo; optionally substituted amino; optionally substituted alkoxy; cycloalkyl; carboxy; heterocyclooxy; alkoxycarbonyl; mercapto; nitro; cyano; sulfamoyl; alkanoyloxy; aroyloxy; arylthio; optionally substituted aryloxy; alkylthio; formyl; carbamoyl; optionally substituted aralkyl; optionally substituted aryl, or optionally substituted phenyl,
and
and
R₉, R₁₀, R₁₁ and R₁₂ are, independently hydrogen, optionally substituted alkyl, trifluoromethyl, trifluoromethoxy, cycloalkyl, halo, hydroxy, alkoxy, acyl, alkanoyloxy, alkanoyl, optionally substituted phenyl, optionally substituted aryloxy, optionally substituted amino, thiol, alkylthio, arylthio, nitro, cyano, carboxy, alkoxycarbonyl, carbamoyl, alkylthiono, sulfonyl, sulfonamido, or optionally substituted heterocyclyl.

7. The compound according to claim 6, wherein one or two of the substituents R₇, R'₇ and R"₇ is not hydrogen.

8. The compound according to claim 1, wherein the moiety D is hydrogen, lower alkanoylamino, or carboxy.

9. A pharmaceutical composition, comprising:
the compound according to claim 1, and
a pharmaceutical acceptable carrier or excipient.

10. A method of treating type II diabetes in a patient in need thereof, comprising:
administering to a patient in need thereof a therapeutically effective amount of the compound according to claim 1.

11. A compound selected from:
[2-(2-Chloro-phenyl)-3H-benzoimidazol-5-yl]carbamic acid ethyl ester;
[2-(4-Methoxy-2-methyl-phenyl)-3H-benzoimidazol-5-yl]carbamic acid ethyl ester;
[2-(2,6-Dimethyl-phenyl)-3H-benzoimidazol-5-yl]carbamic acid ethyl ester;
[2-(2,4-Dichloro-phenyl)-3H-benzoimidazol-5-yl]carbamic acid ethyl ester;
[2-(2,3-Dichloro-phenyl)-3H-benzoimidazol-5-yl]carbamic acid ethyl ester;
N-[2-(2,6-Dichloro-phenyl)-3H-benzoimidazol-5-yl]-butyramide;
N-[2-(2,6-Dichloro-phenyl)-3H-benzoimidazol-5-yl]-3-methyl-butyramide;
N-[2-(2,6-Dichloro-phenyl)-3H-benzoimidazol-5-yl]-2-ethoxy-acetamide;
N-[2-(2,6-Dichloro-phenyl)-3H-benzoimidazol-5-yl]-2-phenyl-acetamide;
N-[2-(2,6-Dichloro-phenyl)-3H-benzoimidazol-5-yl]-3-methyl-benzamide;
N-[2-(2,6-Dichloro-phenyl)-3H-benzoimidazol-5-yl]-2,4,6-trimethyl-benzenesulfonamide;
2-(2,6-Dichloro-phenyl)-3H-benzoimidazole-5-carboxylic acid propylamide;
2-(2,6-Dichloro-phenyl)-3H-benzoimidazole-5-carboxylic acid butylamide;
2-(2,6-Dichloro-phenyl)-3H-benzoimidazole-5-carboxylic acid benzylamide;
2-(2,6-Dichloro-phenyl)-3H-benzoimidazole-5-carboxylic acid (2-methoxy-ethyl)-amide;
2-(2,6-Dichloro-phenyl)-3H-benzoimidazole-5-carboxylic acid isopropylamide;
2-(2,6-Dichloro-phenyl)-3H-benzoimidazole-5-carboxylic acid cyclohexylamide;
2-(2,6-Dichloro-phenyl)-3H-benzoimidazole-5-carboxylic acid isobutyl-methyl-amide;
2-(2,6-Dichloro-phenyl)-3H-benzoimidazole-5-carboxylic acid diethylamide;
2-(2,6-Dichloro-phenyl)-3H-benzoimidazole-5-carboxylic acid benzyl-methyl-amide;
2-(2,6-Dichloro-phenyl)-3H-benzoimidazole-5-carboxylic acid ((R)-1-phenyl-ethyl)-amide;
2-(2,6-Dichloro-phenyl)-3H-benzoimidazole-5-carboxylic acid ((S)-1-phenyl-ethyl)-amide;
2-(2,6-Dichloro-phenyl)-3H-benzoimidazole-5-carboxylic acid (1,2,3,4-tetrahydro-naphthalen-1-yl)-amide;
2-(2,6-Dichloro-phenyl)-3H-benzoimidazole-5-carboxylic acid (Rindan-1-yl)-amide;
2-(2,6-Dichloro-phenyl)-3H-benzoimidazole-5-carboxylic acid (biphenyl-3-ylmethyl)-amide;
2-(2,6-Dichloro-phenyl)-3H-benzoimidazole-5-carboxylic acid (biphenyl-4-ylmethyl)-amide;
2-(2,6-Dichloro-phenyl)-3H-benzoimidazole-5-carboxylic acid 2-methyl-benzylamide;
2-(2,6-Dichloro-phenyl)-3H-benzoimidazole-5-carboxylic acid phenethyl-amide;
2-(2,6-Dichloro-phenyl)-3H-benzoimidazole-5-carboxylic acid (2-o-tolyl-ethyl)-amide;
2-(2,6-Dichloro-phenyl)-3H-benzoimidazole-5-carboxylic acid phenylamide;
2-(2,6-Dichloro-phenyl)-3H-benzoimidazole-5-carboxylic acid o-tolylamide;
2-(2,6-Dichloro-phenyl)-3H-benzoimidazole-5-carboxylic acid (3-chloro-phenyl)-amide;
2-(2,6-Dichloro-phenyl)-3H-benzoimidazole-5-carboxylic acid (4-chloro-phenyl)-amide;
2-(2,6-Dichloro-phenyl)-3H-benzoimidazole-5-carboxylic acid (4-dimethylcarbamoyl-phenyl)-amide;
2-(2,6-Dichloro-phenyl)-3H-benzoimidazole-5-carboxylic acid (3-methoxy-phenyl)-amide;
2-(2,6-Dichloro-phenyl)-3H-benzoimidazole-5-carboxylic acid (4-methoxy-phenyl)-amide;
2-(2,6-Dichloro-phenyl)-3H-benzoimidazole-5-carboxylic acid (3-isopropoxy-phenyl)-amide;
2-(2,6-Dichloro-phenyl)-3H-benzoimidazole-5-carboxylic acid (3-ethoxy-phenyl)-amide;
2-(2,6-Dichloro-phenyl)-3H-benzoimidazole-5-carboxylic acid (3,4-dimethyl-phenyl)-amide;

2-(2,6-Dichloro-phenyl)-3H-benzoimidazole-5-carboxylic acid (3,5-dimethyl-phenyl)-amide;
2-(2,6-Dichloro-phenyl)-3H-benzoimidazole-5-carboxylic acid p-tolylamide;
2-(2,6-Dichloro-phenyl)-3H-benzoimidazole-5-carboxylic acid (3-cyano-phenyl)-amide;
2-(2,6-Dichloro-phenyl)-3H-benzoimidazole-5-carboxylic acid (3-acetyl-phenyl)-amide;
2-(2,6-Dichloro-phenyl)-3H-benzoimidazole-5-carboxylic acid (4-fluoro-phenyl)-amide;
2-(2,6-Dichloro-phenyl)-3H-benzoimidazole-5-carboxylic acid (4-cyano-phenyl)-amide;
2-(2,6-Dichloro-phenyl)-3H-benzoimidazole-5-carboxylic acid (3-chloro-4-fluoro-phenyl)-amide;
2-(2,6-Dichloro-phenyl)-3H-benzoimidazole-5-carboxylic acid (3,4-dichloro-phenyl)-amide;
2-(2,6-Dichloro-phenyl)-3H-benzoimidazole-5-carboxylic acid (4-fluoro-3-methyl-phenyl)-amide;
2-(2,6-Dichloro-phenyl)-3H-benzoimidazole-5-carboxylic acid (3-chloro-4-methyl-phenyl)-amide;
2-(2,6-Dichloro-phenyl)-3H-benzoimidazole-5-carboxylic acid (3,4-difluoro-phenyl)-amide;
2-(2,6-Dichloro-phenyl)-3H-benzoimidazole-5-carboxylic acid (3,4-dimethoxy-phenyl)-amide;
2-(2,6-Dichloro-phenyl)-3H-benzoimidazole-5-carboxylic acid (1H-indazol-5-yl)-amide;
2-(2,6-Dichloro-phenyl)-3H-benzoimidazole-5-carboxylic acid (1H-indazol-6-yl)-amide;
2-(2,6-Dichloro-phenyl)-3H-benzoimidazole-5-carboxylic acid (2-methyl-benzothiazol-6-yl)-amide;
2-(2,6-Dichloro-phenyl)-3H-benzoimidazole-5-carboxylic acid (2-methyl-benzothiazol-5-yl)-amide;
2-(2,6-Dichloro-phenyl)-3H-benzoimidazole-5-carboxylic acid quinoli6-ylamide;
2-(2,6-Dichloro-phenyl)-1H-benzoimidazole-5-carboxylic acid pyridin-2-ylamide;
2-(2,6-Dichloro-phenyl)-1H-benzoimidazole-5-carboxylic acid (6-chloro-pyridin-2-yl)-amide;
2-(2,6-Dichloro-phenyl)-1H-benzoimidazole-5-carboxylic acid (6-methyl-pyridin-2-yl)-amide;
2-(2,6-Dichloro-phenyl)-1H-benzoimidazole-5-carboxylic acid quinoxalin-6-ylamide;
2-(2,6-Dichloro-phenyl)-1H-benzoimidazole-5-carboxylic acid (6-chloro-pyridin-3-yl)-amide;
2-(2,6-Dichloro-phenyl)-1H-benzoimidazole-5-carboxylic acid pyridin-3-ylamide;
2-(2,6-Dichloro-phenyl)-1H-benzoimidazole-5-carboxylic acid (5-chloro-pyridin-2-yl)-amide;
2-(2,6-Dichloro-phenyl)-1H-benzoimidazole-5-carboxylic acid (5-methyl-pyridin-2-yl)-amide;
2-(2,6-Dichloro-phenyl)-1H-benzoimidazole-5-carboxylic acid (4-methyl-pyridin-2-yl)-amide;
2-(2,6-Dichloro-phenyl)-1H-benzoimidazole-5-carboxylic acid (6-chloro-pyridazin-3-yl)-amide;
2-(2,6-Dichloro-phenyl)-1H-benzoimidazole-5-carboxylic acid pyrazin-2-ylamide;
2-(2,6-Dichloro-phenyl)-1H-benzoimidazole-5-carboxylic acid (4-methyl-pyrimidin-2-yl)-amide;
2-(2,6-Dichloro-phenyl)-1H-benzoimidazole-5-carboxylic acid pyridazin-3-ylamide;
2-(2,6-Dichloro-phenyl)-1H-benzoimidazole-5-carboxylic acid (6-chloro-pyrazin-2-yl)-amide;
2-(2,6-Dichloro-phenyl)-1H-benzoimidazole-5-carboxylic acid (5-chloro-pyrimidin-2-yl)-amide;
2-(2,6-Dichloro-phenyl)-1H-benzoimidazole-5-carboxylic acid pyrimidin-4-ylamide;
2-(2,6-Dichloro-phenyl)-1H-benzoimidazole-5-carboxylic acid [3-(2H-tetrazol-5-yl)-phenyl]-amide;
2-(2,6-Dichloro-phenyl)-3H-benzoimidazole-5-carboxylic acid [2-(3-chloro-phenyl)-ethyl]-amide;
2-(2,6-Dichloro-phenyl)-3H-benzoimidazole-5-carboxylic acid [2-(4-bromo-phenyl)-ethyl]-amide;
2-(2,6-Dichloro-phenyl)-3H-benzoimidazole-5-carboxylic acid [2-(4-fluoro-phenyl)-ethyl]-amide;
2-(2,6-Dichloro-phenyl)-3H-benzoimidazole-5-carboxylic acid [2-(3,4-dimethyl-phenyl)-ethyl]-amide;
2-(2,6-Dichloro-phenyl)-3H-benzoimidazole-5-carboxylic acid [2-(3-ethoxy-phenyl)-ethyl]-amide;
2-(2,6-Dichloro-phenyl)-3H-benzoimidazole-5-carboxylic acid [2-(4-methoxy-phenyl)-ethyl]-amide;
2-(2,6-Dichloro-phenyl)-3H-benzoimidazole-5-carboxylic acid [2-(2-methoxy-phenyl)-ethyl]-amide;
2-(2,6-Dichloro-phenyl)-3H-benzoimidazole-5-carboxylic acid [2-(3-fluoro-phenyl)-ethyl]-amide;
2-(2,6-Dichloro-phenyl)-3H-benzoimidazole-5-carboxylic acid [2-(2,4-dichloro-phenyl)-ethyl]-amide;
2-(2,6-Dichloro-phenyl)-3H-benzoimidazole-5-carboxylic acid [2-(2-ethoxy-phenyl)-ethyl]-amide;
2-(2,6-Dichloro-phenyl)-3H-benzoimidazole-5-carboxylic acid [2-(4-ethyl-phenyl)-ethyl]-amide;
2-(2,6-Dichloro-phenyl)-3H-benzoimidazole-5-carboxylic acid [2-(2,4-dimethyl-phenyl)-ethyl]-amide;
2-(2,6-Dichloro-phenyl)-3H-benzoimidazole-5-carboxylic acid ((R)-2-phenyl-propyl)-amide;
2-(2,6-Dichloro-phenyl)-3H-benzoimidazole-5-carboxylic acid [2-(3,4-dimethoxy-phenyl)-ethyl]-amide;
2-(2,6-Dichloro-phenyl)-3H-benzoimidazole-5-carboxylic acid [2-(3-bromo-4-methoxy-phenyl)-ethyl]-amide;
2-(2,6-Dichloro-phenyl)-3H-benzoimidazole-5-carboxylic acid [2-(2-fluoro-phenyl)-ethyl]-amide;
2-(2,6-Dichloro-phenyl)-3H-benzoimidazole-5-carboxylic acid [2-(2,5-dimethoxy-phenyl)-ethyl]-amide;
2-(2,6-Dichloro-phenyl)-3H-benzoimidazole-5-carboxylic acid [2-(4-phenoxy-phenyl)-ethyl]-amide;
2-(2,6-Dichloro-phenyl)-3H-benzoimidazole-5-carboxylic acid [2-(4-ethoxy-3-methoxy-phenyl)-ethyl]-amide;
2-(2,6-Dichloro-phenyl)-3H-benzoimidazole-5-carboxylic acid [2-(4-ethoxy-phenyl)-ethyl]-amide;
2-(2,6-Dichloro-phenyl)-3H-benzoimidazole-5-carboxylic acid [2-(2,6-dichloro-phenyl)-ethyl]-amide;
2-(2,6-Dichloro-phenyl)-3H-benzoimidazole-5-carboxylic acid [2-(4-hydroxy-phenyl)-ethyl]-amide;
2-(2,6-Dichloro-phenyl)-3H-benzoimidazole-5-carboxylic acid [2-(2,5-dimethyl-phenyl)-ethyl]-amide;
2-(2,6-Dichloro-phenyl)-3H-benzoimidazole-5-carboxylic acid (5-chloro-benzo[b]thiophen-3-ylmethyl)-amide;
2-(2,6-Dichloro-phenyl)-1H-benzoimidazole-5-carboxylic acid (2-pyridin-2-yl-ethyl)-amide;
2-(2,6-Dichloro-phenyl)-1H-benzoimidazole-5-carboxylic acid (2-pyridin-3-yl-ethyl)-amide;
2-(2,6-Dichloro-phenyl)-1H-benzoimidazole-5-carboxylic acid (2-pyridin-4-yl-ethyl)-amide;
2-(2,6-Dichloro-phenyl)-3H-benzoimidazole-5-carboxylic acid (3-chloro-phenyl)-methyl-amide;
2-(2,6-Dichloro-phenyl)-3H-benzoimidazole-5-sulfonic acid (3,4-dimethyl-phenyl)-amide;
2-(2,6-Dichloro-phenyl)-3H-benzoimidazole-5-sulfonic acid (2-methyl-benzothiazolyl-5-yl)-amide;
2-(2,6-Dimethyl-phenyl)-3H-benzoimidazole-5-carboxylic acid (3-chloro-phenyl)-amide;
{4-[6-(3-Chloro-phenylcarbamoyl)-1H-benzoimidazol-2-yl]-3,5-dimethyl-phenoxy}-acetic acid ethyl ester;

{4-[6-(3-Chloro-phenylcarbamoyl)-1H-benzoimidazol-2-yl]-3,5-dimethyl-phenoxy}-acetic acid;
2-(2-Chloro-6-nitro-phenyl)-3H-benzoimidazole-5-carboxylic acid (3-chloro-phenyl)-amide;
2-(2,6-Dimethoxy-phenyl)-3H-benzoimidazole-5-carboxylic acid (3-chloro-phenyl)-amide;
2-(2,6-Dinitro-phenyl)-3H-benzoimidazole-5-carboxylic acid (3-chloro-phenyl)-amide;
2-(2,6-Difluoro-phenyl)-3H-benzoimidazole-5-carboxylic acid (3-chloro-phenyl)-amide;
2-(2-Fluoro-6-methoxy-phenyl)-3H-benzoimidazole-5-carboxylic acid (3-chloro-phenyl)-amide;
2-(2-Fluoro-6-trifluoromethyl-phenyl)-3H-benzoimidazole-5-carboxylic acid (3-chloro-phenyl)-amide;
2-(2-Chloro-6-methanesulfonylamino-phenyl)-3H-benzoimidazole-5-carboxylic acid (3-chloro-phenyl)-amide;
2-(2-Acetylamino-6-chloro-phenyl)-3H-benzoimidazole-5-carboxylic acid (3-chloro-phenyl)-amide;
2-(4-Acetylamino-2,6-dimethyl-phenyl)-3H-benzoimidazole-5-carboxylic acid (3,4-dimethyl-phenyl)-amide;
2-[2,6-dimethyl-4-(2-oxo-2-pyrrolidin-1-yl-ethoxy)-phenyl]-3H-benzoimidazole-5-carboxylic acid (3,4-dimethyl-phenyl)-amide;
Toluene-4-sulfonic acid 4-[6-(3,4-dimethyl-phenylcarbamoyl)-1H-benzoimidazol-2-yl]-3,5-dimethyl-phenyl ester;
2-[2,6-dimethyl-4-(2-pyrrolidin-1-yl-ethoxy)-phenyl]-3H-benzoimidazole-5-carboxylic acid (3,4-dimethyl-phenyl)-amide;
2-[2,6-Dimethyl-4-(1H-tetrazol-5-yl-methoxy)-phenyl]-3H-benzoimidazole-5-carboxylic acid (3,4-dimethyl-phenyl)-amide;
{4-[6-(3,4-Dimethyl-phenylcarbamoyl)-1H-benzoimidazol-2-yl]-3,5-dimethyl-phenoxy}-acetic acid ethyl ester;
2-(4-Cyano-2,6-dimethyl-phenyl)-3H-benzoimidazole-5-carboxylic acid (3,4-dimethyl-phenyl)-amide;
Trifluoro-methanesulfonic acid 4-[6-(3,4-dimethyl-phenylcarbamoyl)-1H-benzoimidazol-2-yl]-3,5-dimethyl-phenyl ester;
2-(2,6-Dimethyl-phenyl)-3H-benzoimidazole-5-carboxylic acid (3,4-dimethyl-phenyl)-amide;
2-(4-Hydroxy-2,6-dimethyl-phenyl)-3H-benzoimidazole-5-carboxylic acid (3,4-dimethyl-phenyl)-amide;
2-(4-Methoxy-2,6-dimethyl-phenyl)-3H-benzoimidazole-5-carboxylic acid (3,4-dimethyl-phenyl)-amide;
2-(4-Carbamoylmethoxy-2,6-dimethyl-phenyl)-3H-benzoimidazole-5-carboxylic acid (3,4-dimethyl-phenyl)-amide;
2-(2,6-Dimethyl-4-methylcarbamoylmethoxy-phenyl)-3H-benzoimidazole-5-carboxylic acid (3,4-dimethyl-phenyl)-amide;
2-(4-Dimethylcarbamoylmethoxy-2,6-dimethyl-phenyl)-3H-benzoimidazole-5-carboxylic acid (3,4-dimethyl-phenyl)-amide;
Methanesulfonic acid 4-[6-(3,4-dimethyl-phenylcarbamoyl)-1H-benzoimidazol-2-yl]-3,5-dimethyl-phenyl ester;
{4-[6-(3,4-Dimethyl-phenylcarbamoyl)-1H-benzoimidazol-2-yl]-3,5-dimethyl-phenoxy}-acetic acid;
2-{2,6-Dimethyl-4-[2-(4-methyl-piperazin-1-yl)-2-oxo-ethoxy]-phenyl}-3H benzoimidazole-5-carboxylic acid (3,4-dimethyl-phenyl)-amide;
4-[6-(3,4-Dimethyl-phenylcarbamoyl)-1H-benzoimidazol-2-yl]-3,5-dimethyl-benzoic acid;
2-[2,6-dimethyl-4-(4-methyl-piperazine-1-carbonyl)-phenyl]-3H-benzoimidazole-5-carboxlic acid (3,4-dimethyl-phenyl)-amide;
2-[2,6-Dimethyl-4-(2H-tetrazol-5-yl)-phenyl]-3H-benzoimidazole-5-carboxylic acid (3,4-dimethyl-phenyl)-amide;
[2-(2,6-Dichloro-phenyl)-3H-benzoimidazol-5-ylmethyl]-(3,4-dimethyl-phenyl)-amine;
2-(4-Carbamoylmethoxy-2,6-dimethyl-phenyl)-3H-benzoimidazole-5-carboxylic acid (2-methyl-benzothiazol-5-yl)-amide;
2-(2,6-Dimethyl-4-methylcarbamoylmethoxy-phenyl)-3H-benzoimidazole-5-carboxylic acid (2-methyl-benzothiazol-5-yl)-amide;
2-(4-Dimethylcarbamoylmethoxy-2,6-dimethyl-phenyl)-3H-benzoimidazole-5-carboxylic acid (2-methyl-benzothiazol-5-yl)-amide;
2-[2,6-Dimethyl-4-(2-oxo-2-pyrrolidin-1-yl-ethoxy)-phenyl]-3H-benzoimidazole-5-carboxylic acid(2-methyl-benzothiazol-5-yl)-amide;
2-(2,6-Dichlorophenyl)-3H-benzoimidazole-5-carboxylic acid (3,5-dimethoxyphenyl)-amide;
2-(2,6-Dichlorophenyl)-3H-benzoimidazole-5-carboxylic acid benzo[1,3]dioxol-5-ylamide;
2-(2,6-Dichlorophenyl)-3H-benzoimidazole-5-carboxylic acid (3-chloro-4-methoxyphenyl)-amide;
2-(2,6-Dichlorophenyl)-3H-benzoimidazole-5-carboxylic acid (3-trifluoromethylphenyl)-amide;
2-(2,6-Dichlorophenyl)-3H-benzoimidazole-5-carboxylic acid (4-trifluoromethylphenyl)-amide;
2-(2,6-Dichlorophenyl)-3H-benzoimidazole-5-carboxylic acid (3-trifluoromethoxyphenyl)-amide;
2-(2,6-Dichlorophenyl)-3H-benzoimidazole-5-carboxylic acid (4-fluoro-3-trifluoromethylphenyl)-amide;
2-(2,6-Dichlorophenyl)-3H-benzoimidazole-5-carboxylic acid (3,5-difluorophenyl)-amide;
2-(2,6-Dichlorophenyl)-3H-benzoimidazole-5-carboxylic acid (4-nitrophenyl)-amide;
2-(2,6-Dichlorophenyl)-3H-benzoimidazole-5-carboxylic acid (2,4-dichlorophenyl)-amide;
2-(2,6-Dichlorophenyl)-3H-benzoimidazole-5-carboxylic acid (3,5-dichlorophenyl)-amide;
2-(2,6-Dichlorophenyl)-3H-benzoimidazole-5-carboxylic acid (2-fluorophenyl)-amide;
2-(2,6-Dichlorophenyl)-3H-benzoimidazole-5-carboxylic acid (4-chloro-2-fluorophenyl)-amide;
2-(2,6-Dichlorophenyl)-3H-benzoimidazole-5-carboxylic acid biphenyl-4-ylamide;
2-(2,6-Dichlorophenyl)-3H-benzoimidazole-5-carboxylic acid (4-phenoxyphenyl)-amide;
2-(2,6-Dichlorophenyl)-3H-benzoimidazole-5-carboxylic acid (2-methoxyphenyl)-amide;
2-(2,6-Dichlorophenyl)-3H-benzoimidazole-5-carboxylic acid (4-methanesulfonylphenyl)-amide;
2-(2,6-Dichlorophenyl)-3H-benzoimidazole-5-carboxylic acid m-tolylamide;
2-(2,6-Dichlorophenyl)-3H-benzoimidazole-5-carboxylic acid (3-phenoxyphenyl)-amide;
2-(2,6-Dichlorophenyl)-3H-benzoimidazole-5-carboxylic acid (3-cyano-4-methylphenyl)-amide;
2-(2,6-Dichlorophenyl)-3H-benzoimidazole-5-carboxylic acid (4-tert-butylphenyl)-amide;
2-(2,6-Dichlorophenyl)-3H-benzoimidazole-5-carboxylic acid (3,5-di-tert-butylphenyl)-amide;
3-{[2-(2,6-Dichlorophenyl)-3H-benzoimidazole-5-carbonyl]-amino}-benzoic acid methyl ester;

2-(2,6-Dichlorophenyl)-3H-benzoimidazole-5-carboxylic acid (3-dimethylaminophenyl)-amide;
2-(2,6-Dichlorophenyl)-3H-benzoimidazole-5-carboxylic acid (3-phenylpropyl)-amide;
2-(2,6-Dichlorophenyl)-3H-benzoimidazole-5-carboxylic acid (3-oxazol-5-yl-phenyl)-amide;
2-(2,6-Dichlorophenyl)-3H-benzoimidazole-5-carboxylic acid (4-oxazol-5-yl-phenyl)-amide;
2-(2,6-Dichlorophenyl)-3H-benzoimidazole-5-carboxylic acid naphthalen-2-ylamide;
2-(2,6-Dichlorophenyl)-3H-benzoimidazole-5-carboxylic acid (5-oxo-5,6,7,8-tetrahydronaphthalen-2-yl)-amide;
2-(2,6-Dichlorophenyl)-3H-benzoimidazole-5-carboxylic acid indan-5-ylamide;
2-(2,6-Dichlorophenyl)-3H-benzoimidazole-5-carboxylic acid (2-oxo-4-trifluoromethyl-2H-chromen-7-yl)-amide;
2-(2,6-Dichlorophenyl)-3H-benzoimidazole-5-carboxylic acid (4-methylthiazol-2-yl)-amide;
2-(2,6-Dichlorophenyl)-3H-benzoimidazole-5-carboxylic acid (4,5-dimethylthiazol-2-yl)-amide;
2-(2,6-Dichlorophenyl)-3H-benzoimidazole-5-carboxylic acid (5,6,7,8-tetrahydronaphthalen-2-yl)-amide;
2-(2,6-Dichlorophenyl)-3H-benzoimidazole-5-carboxylic acid (8-oxo-5,6,7,8-tetrahydronaphthalen-2-yl)-amide;
2-(2,6-Dichlorophenyl)-3H-benzoimidazole-5-carboxylic acid (8-hydroxy-5,6,7,8-tetrahydronaphthalen-2-yl)-amide;
2-(2,6-Dichlorophenyl)-3H-benzoimidazole-5-carboxylic acid (4-phenylbutyl)-amide;
2-(2,6-Dichlorophenyl)-3H-benzoimidazole-5-carboxylic acid endo-bicyclo[2.2.1]hept-2-ylamide;
2-(2,6-Dichlorophenyl)-3H-benzoimidazole-5-carboxylic acid exo-bicyclo[2.2.1]hept-2-ylamide;
2-(2,6-Dichlorophenyl)-3H-benzoimidazole-5-carboxylic acid adamantan-2-ylamide;
2-(2,6-Dichlorophenyl)-3H-benzoimidazole-5-carboxylic acid (4-methyl-2-oxo-2H-chromen-7-yl)-amide;
2-(2,6-Dichlorophenyl)-3H-benzoimidazole-5-carboxylic acid (2,3-dihydrobenzo[1,4]dioxin-6-yl)-amide;
2-(2,6-Dichlorophenyl)-3H-benzoimidazole-5-carboxylic acid [2-(pyrrolidine-1-carbonyl)-phenyl]-amide;
2-(2,6-Dichlorophenyl)-3H-benzoimidazole-5-carboxylic acid (4-butylphenyl)-amide;
2-(2,6-Dichlorophenyl)-3H-benzoimidazole-5-carboxylic acid (4-cyclohexylphenyl)-amide;
2-(2,6-Dichlorophenyl)-3H-benzoimidazole-5-carboxylic acid (4-tert-butylcyclohexyl)-amide;
2-(2,6-Dichlorophenyl)-3H-benzoimidazole-5-carboxylic acid quinolin-7-ylamide;
2-(2,6-Dichlorophenyl)-3H-benzoimidazole-5-carboxylic acid isoquinolin-3-ylamide;
2-(2,6-Dichlorophenyl)-3H-benzoimidazole-5-carboxylic acid (2-methylquinolin-6-yl)-amide;
2-(2,6-Dichlorophenyl)-3H-benzoimidazole-5-carboxylic acid (4-methoxynaphthalen-2-yl)-amide;
2-(2,6-Dichlorophenyl)-3H-benzoimidazole-5-carboxylic acid quinolin-3-ylamide;
2-(2,6-Dichlorophenyl)-3H-benzoimidazole-5-carboxylic acid (4-methoxymethyl-2-oxo-2H-chromen-7-yl)-amide;
2-(2,6-Dichlorophenyl)-3H-benzoimidazole-5-carboxylic acid quinolin-2-ylamide;
2-(2,6-Dichlorophenyl)-3H-benzoimidazole-5-carboxylic acid anthracen-2-ylamide;
(E)-3-(4-{[2-(2,6-Dichlorophenyl)-3H-benzoimidazole-5-carbonyl]-amino}-phenyl)-acrylic acid ethyl ester;
2-(2,6-Dichlorophenyl)-3H-benzoimidazole-5-carboxylic acid (4-ethylphenyl)-amide;
2-(2,6-Dichlorophenyl)-3H-benzoimidazole-5-carboxylic acid (4-isopropylphenyl)-amide;
2-(2,6-Dichlorophenyl)-3H-benzoimidazole-5-carboxylic acid (2,6-dimethoxyphenyl)-amide;
2-(2,6-Dichlorophenyl)-3H-benzoimidazole-5-carboxylic acid (2,5-di-tert-butylphenyl)-amide;
2-(2,6-Dichlorophenyl)-3H-benzoimidazole-5-carboxylic acid (2,6-diisopropylphenyl)-amide;
2-(2,6-Dichlorophenyl)-3H-benzoimidazole-5-carboxylic acid (3-phenylcarbamoylphenyl)-amide;
2-(2,6-Dichlorophenyl)-3H-benzoimidazole-5-carboxylic acid [2-(4-fluorophenoxy)-pyridin-3-yl]-amide;
2-(2,6-Dichlorophenyl)-3H-benzoimidazole-5-carboxylic acid (4-chloro-3-trifluoromethylphenyl)-amide;
2-(2,6-Dichlorophenyl)-3H-benzoimidazole-5-carboxylic acid (4-sec-butylphenyl)-amide;
2-(2,6-Dichlorophenyl)-3H-benzoimidazole-5-carboxylic acid (2-phenyl-2H-pyrazol-3-yl)-amide;
2-(2,6-Dichlorophenyl)-3H-benzoimidazole-5-carboxylic acid (2-methyl-5-phenyl-2H-pyrazol-3-yl)-amide;
2-(2,6-Dichlorophenyl)-3H-benzoimidazole-5-carboxylic acid (8-hydroxyquinolin-2-yl)-amide;
2-(2,3-Dimethylphenyl)-3H-benzoimidazole-5-carboxylic acid (3,4-dimethylphenyl)-amide;
2-(2,6-Dimethylphenyl)-3H-benzoimidazole-5-carboxylic acid naphthalen-2-ylamide;
2-(2,6-Dimethylphenyl)-3H-benzoimidazole-5-carboxylic acid (4-methyl-2-oxo-2-chromen-7-yl)-amide;
2-(2,6-Dichloro-phenyl)-3-(2-hydroxy-ethyl)-3H-benzoimidazole-5-carboxylic acid (3,4-dimethyl-phenyl)-amide;
2-(2-Chloro-6-nitro-phenyl)-3-(2-hydroxy-ethyl)-3H-benzoimidazole-5-carboxylic acid (3,4-dimethyl-phenyl)-amide;
2-(2,6-Dimethyl-phenyl)-3-(2-hydroxy-ethyl)-3H-benzoimidazole-5-carboxylic acid (3,4-dimethyl-phenyl)-amide;
2-(2,6-Dimethoxy-phenyl)-3-(2-hydroxy-ethyl)-3H-benzoimidazole-5-carboxylic acid (3,4-dimethyl-phenyl)-amide;
2-(2,6-Dichloro-phenyl)-3-methyl-3H-benzoimidazole-5-carboxylic acid (3,4-dimethyl-phenyl)-amide;
2-(2-Chloro-6-nitro-phenyl)-3-methyl-3H-benzoimidazole-5-carboxylic acid (3,4-dimethyl-phenyl)-amide;
2-(2,6-Dimethyl-phenyl)-3-methyl-3H-benzoimidazole-5-carboxylic acid (3,4-dimethyl-phenyl)-amide;
2-(2,6-Dimethoxy-phenyl)-3-methyl-3H-benzoimidazole-5-carboxylic acid (3,4-dimethyl-phenyl)-amide;
2-(2,6-Dichlorophenyl)-1-methyl-1H-benzoimidazole-5-carboxylic acid (3,4-dimethylphenyl)-amide;
{4-[5-(3,4-Dimethyl-phenylcarbamoyl)-1H-benzoimidazol-2-yl]-3,5-dimethyl-phenylamino}-acetic acid methyl ester;
{4-[5-(3,4-Dimethylphenylcarbamoyl)-1H-benzoimidazol-2-yl]-3,5-dimethylphenylamino}-acetic acid;
2-[4-(2-Hydroxyethylamino)-2,6-dimethylphenyl]-1H-benzoimidazole-5-carboxylic acid (3,4-dimethyl-phenyl)-amide;
3-{4-[5-(3,4-Dimethylphenylcarbamoyl)-1H-benzoimidazol-2-yl]-3,5-dimethylphenyl}-propionic acid tert-butyl ester;
3-{4-[5-(3,4-dimethylphenylcarbamoyl)-1H-benzoimidazol-2-yl]-3,5-dimethylphenyl}-propionic acid;
2-(2,6-Dichlorophenyl)-3H-benzoimidazole-5-carboxylic acid isoquinolin-1-ylamide;

2-(2,6-Dichlorophenyl)-3H-benzoimidazole-5-carboxylic acid (4-vinylphenyl)-amide;
2-(2,6-Dichlorophenyl)-3H-benzoimidazole-5-carboxylic acid (4-cyanophenyl)-amide;
3-(4-{[2-(2,6-Dichlorophenyl)-3H-benzoimidazole-5-carbonyl]-amino}-phenyl)-propionic acid;
3-(4-{[2-(2,6-Dichlorophenyl)-3H-benzoimidazole-5-carbonyl]-amino}-phenyl)-propionic acid ethyl ester;
2-(2,6-Dichlorophenyl)-3H-benzoimidazole-5-carboxylic acid (1,1-dimethylindan-5-yl)-amide;
2-(2,6-Dichlorophenyl)-3H-benzimidazole-5-carboxylic acid decylamide;
2-(2,6-Dichlorophenyl)-3H-benzimidazole-5-carboxylic acid [2-(4-tert-butylphenyl)-ethyl]amide;
2-(2-Chloro-6-methylphenyl)-3H-benzoimidazole-5-carboxylic acid (3,4-dimethylphenyl)-amide;
2-(2-Chloro-6-trifluoromethylphenyl)-3H-benzoimidazole-5-carboxylic acid quinolin-2-ylamide;
2-(2,6-Dichlorophenyl)-3H-benzoimidazole-5-carboxylic acid [2-(4-chlorophenyl)-2-oxo-ethyl]-amide;
2-(2,6-Dichlorophenyl)-3H-benzoimidazole-5-carboxylic acid [2-(4-chlorophenyl)-1-methyl-2-oxoethyl]-amide;
2-(2,6-Dichlorophenyl)-6,7-difluoro-3H-benzoimidazole-5-carboxylic acid quinolin-2-ylamide;
N-[2-(2,6-Dichlorophenyl)-3H-benzoimidazol-5-yl]-3,4-dimethylbenzamide;
Quinoline-2-carboxylic acid [2-(2,6-dichlorophenyl)-3H-benzimidazol-5-yl]-amide;
2-(2,6-Dimethylphenyl)-3H-benzimidazole-5-carboxylic acid (4-tert-butylphenyl)-amide;
1-[2-(2,6-Dichlorophenyl)-3H-benzimidazol-5-yl]-3-(3,4-dimethylphenyl)-urea;
3-{4-[5-(3,4-Dimethylphenylcarbamoyl)-1H-benzoimidazol-2-yl]-3,5-dimethylphenyl}-propionic acid;
3-{4-[6-(3,4-Dimethylphenylcarbamoyl)-1H-benzoimidazol-2-yl]-3,5-dimethylphenyl}-propionic acid methyl ester;
3-{4-[6-(5,6-Dimethylpyridin-2-ylcarbamoyl)-1H-benzimidazol-2-yl]-3,5-dimethylphenyl}-propionic acid;
{3,5-Dichloro-4-[6-(3,4-dimethylphenylcarbamoyl)-1H-benzoimidazol-2-yl]-phenoxy}-acetic acid methyl ester;
{3,5-Dichloro-4-[6-(3,4-dimethyl-phenylcarbamoyl)-1H-benzoimidazol-2-yl]-phenoxy}-acetic acid;
{3,5-Dimethyl-4-[6-(quinolin-2-ylcarbamoyl)-1H-benzoimidazol-2-yl]-phenoxy}-acetic acid methyl ester;
{3,5-Dimethyl-4-[6-(quinolin-2-ylcarbamoyl)-1H-benzoimidazol-2-yl]-phenoxy}-acetic acid;
2-[4-((R)-2,2-Dimethyl-[1,3]dioxolan-4-ylmethoxy)-2,6-dimethylphenyl]-3H-benzoimidazole-5-carboxylic acid (3,4-dimethylphenyl)-amide;
2-[4-((S)-2,3-Dihydroxy-propoxy)-2,6-dimethylphenyl]-3H-benzoimidazole-5-carboxylic acid (3,4-dimethylphenyl)-amide;
2-[4-((S)-2,2-Dimethyl-[1,3]dioxolan-4-ylmethoxy)-2,6-dimethylphenyl]-3H-benzoimidazole-5-carboxylic acid (3,4-dimethylphenyl)-amide;
2-[4-((R)-2,3-Dihydroxy-propoxy)-2,6-dimethylphenyl]-3H-benzoimidazole-5-carboxylic acid (3,4-dimethylphenyl)-amide;
2-[4-((R)-2,2-Dimethyl-[1,3]dioxolan-4-ylmethoxy)-2,6-dimethylphenyl]-3H-benzoimidazole-5-carboxylic acid quinolin-2-ylamide;
2-[4-((S)-2,3-Dihydroxypropoxy)-2,6-dimethylphenyl]-3H-benzoimidazole-5-carboxylic acid quinolin-2-ylamide;
3-{3,5-Dimethyl-4-[6-(naphthalen-2-ylcarbamoyl)-1H-benzoimidazol-2-yl]-phenyl}-propionic acid;
3-{4-[6-(Isoquinolin-1-ylcarbamoyl)-1H-benzoimidazol-2-yl]-3,5-dimethylphenyl}-propionic acid;
{3,5-Dichloro-4-[6-(quinolin-2-ylcarbamoyl)-1H-benzoimidazol-2-yl]-phenoxy}-acetic acid methyl ester;
{3,5-Dichloro-4-[6-(quinolin-2-ylcarbamoyl)-1H-benzoimidazol-2-yl]-phenoxy}-acetic acid;
2-(2,6-Dichloro-4-dimethylcarbamoylmethoxyphenyl)-3H-benzoimidazole-5-carboxylic acid quinolin-2-ylamide;
{3,5-Dichloro-4-[6-(quinolin-2-ylcarbamoyl)-1H-benzoimidazol-2-yl]-phenoxymethyl}-phosphonic acid diethylester;
{3,5-Dichloro-4-[6-(quinolin-2-ylcarbamoyl)-1H-benzoimidazol-2-yl]-phenoxymethyl}-phosphonic acid;
3-{3,5-Dichloro-4-[6-(quinolin-2-ylcarbamoyl)-1H-benzoimidazol-2-yl]-phenyl}-propionic acid;
3-{4-[6-(4-tert-Butylphenylcarbamoyl)-1H-benzimidazol-2-yl]-3,5-dimethylphenyl}-propionic acid;
(E)-3-{4-[6-(4-tert-Butylphenylcarbamoyl)-1H-benzimidazol-2-yl]-3,5-dimethylphenyl}-acrylic acid;
{4-[6-(4-tert-Butylphenylcarbamoyl)-1H-benzoimidazol-2-yl]-3,5-dimethylphenoxy}-acetic acid;
3-{4-[6-(4-tert-Butylphenylcarbamoyl)-1H-benzoimidazol-2-yl]-3,5-dimethylphenyl}-2,2-dimethylpropionic acid;
3-{3,5-Dimethyl-4-[6-(quinolin-2-ylcarbamoyl)-1H-benzoimidazol-2-yl]-phenyl}-2,2-dimethyl-propionic acid;
3-{3,5-Dimethyl-4-[5-(6-trifluoromethyl-pyridin-3-ylcarbamoyl)-1H-benzoimidazol-2-yl]-phenyl}-2,2-dimethylpropionic acid;
(2-{3,5-Dimethyl-4-[6-(quinolin-2-ylcarbamoyl)-1H-benzoimidazol-2-yl]-phenyl}-ethyl)-phosphonic acid;
(3-{3,5-Dimethyl-4-[6-(quinolin-2-ylcarbamoyl)-1H-benzoimidazol-2-yl]-phenyl}-propyl)-phosphonic acid diethyl ester;
(3-{3,5-Dimethyl-4-[6-(quinolin-2-ylcarbamoyl)-1H-benzoimidazol-2-yl]-phenyl}-propyl)-phosphonic acid;
(3-{3,5-Dimethyl-4-[6-(quinolin-2-ylcarbamoyl)-1H-benzoimidazol-2-yl]-phenyl}-propyl)-phosphonic acid monoethyl ester;
(3-{3,5-Dimethyl-4-[6-(6-trifluoromethyl-pyridin-3-ylcarbamoyl)-1H-benzoimidazol-2-yl]-phenyl}-propyl)-phosphonic acid;
(3-{4-[6-(4-tert-Butyl-phenylcarbamoyl)-1H-benzoimidazol-2-yl]-3,5-dimethyl-phenyl}-propyl)-phosphonic acid;
3-{3,5-Dichloro-4-[6-(6-trifluoromethylpyridin-3-ylcarbamoyl)-1H-benzoimidazol-2-yl]-phenyl}-propionic acid;
(3,4-Dimethylphenyl)-{1-[2-(2,6-dimethylphenyl)-3H-benzoimidazol-5-yl]-2,2,2-trifluoroethyl}-amine;
3-{3,5-Dimethyl-4-[6-(quinolin-2-ylcarbamoyl)-1H-benzoimidazol-2-yl]-phenyl}-propionic acid;
or any pharmaceutically acceptable salt thereof.

* * * * *